(12) United States Patent
Yang et al.

(10) Patent No.: US 10,398,689 B2
(45) Date of Patent: Sep. 3, 2019

(54) BENZOPIPERIDINE DERIVATIVE, PREPARATION METHOD THEREOF AND MEDICAL USE THEREOF

(71) Applicants: Jiangsu Hengrui Medicine Co., Ltd., Lianyungang, Jiangsu (CN); Shanghai Hengrui Pharmaceutical Co., Ltd., Shanghai (CN)

(72) Inventors: Fanglong Yang, Shanghai (CN); Ling Zhang, Shanghai (CN); Chunfei Wang, Shanghai (CN); Mingxun He, Shanghai (CN); Qiyue Hu, Shanghai (CN); Feng He, Shanghai (CN); Weikang Tao, Shanghai (CN); Piaoyang Sun, Jiangsu (CN)

(73) Assignees: Jiangsu Hengrui Medicine Co., Ltd., Lianyungang, Jiangsu (CN); Shanghai Hengrui Pharmaceutical Co., Ltd., Shanghai (CN)

( * ) Notice: Subject to any disclaimer, the term of this patent is extended or adjusted under 35 U.S.C. 154(b) by 0 days.

(21) Appl. No.: 16/061,676

(22) PCT Filed: Dec. 2, 2016

(86) PCT No.: PCT/CN2016/108367
§ 371 (c)(1),
(2) Date: Jun. 13, 2018

(87) PCT Pub. No.: WO2017/107754
PCT Pub. Date: Jun. 29, 2017

(65) Prior Publication Data
US 2018/0318284 A1    Nov. 8, 2018

(30) Foreign Application Priority Data

Dec. 22, 2015    (CN) .......................... 2015 1 0975923

(51) Int. Cl.
| | | |
|---|---|---|
| *A61K 31/4725* | (2006.01) | |
| *C07D 401/04* | (2006.01) | |
| *A61P 35/00* | (2006.01) | |

(52) U.S. Cl.
CPC .......... *A61K 31/4725* (2013.01); *A61P 35/00* (2018.01); *C07D 401/04* (2013.01)

(58) Field of Classification Search
None
See application file for complete search history.

(56) References Cited

U.S. PATENT DOCUMENTS

| | | |
|---|---|---|
| 5,455,252 A | 10/1995 | Wilhelm et al. |
| 2001/0039285 A1 | 11/2001 | Cameron et al. |
| 2010/0197651 A1 | 8/2010 | Taniguchi et al. |

FOREIGN PATENT DOCUMENTS

| | | |
|---|---|---|
| EP | 1113007 A1 | 7/2001 |
| WO | 2014106848 A1 | 7/2014 |
| WO | 2014133361 A1 | 9/2014 |
| WO | 2014135834 A1 | 9/2014 |
| WO | 2014141292 A2 | 9/2014 |
| WO | 2014151899 A1 | 9/2014 |
| WO | 2014165723 A3 | 10/2014 |
| WO | 2014191726 A1 | 12/2014 |
| WO | 2015092634 A1 | 6/2015 |
| WO | 2017107754 A1 | 6/2017 |

OTHER PUBLICATIONS

Ye et al., "Metal Nanoparticles Catalyzed Selective Carbon-Carbon Bond Activation in the Liquid Phase", Journal of the American Chemical Society,138(27). pp. 8533-8537, 2016.

(Continued)

*Primary Examiner* — Heidi Reese
(74) *Attorney, Agent, or Firm* — Panitch Schwarze Belisario & Nadel LLP

(57) ABSTRACT

The present invention relates to a benzopiperidine derivative, a preparation method thereof and a medical use thereof. In particular, the present invention relates to a benzopiperidine derivative as shown by general formula (I), a preparation method thereof and a pharmaceutical composition containing the derivative, as well as a use thereof as an estrogen receptor modulator in the prevention and/or treatment of estrogen receptor-mediated or dependent diseases or conditions. Preferably, the disease is breast cancer. The substituents in the general formula (I) are the same as those defined in the description.

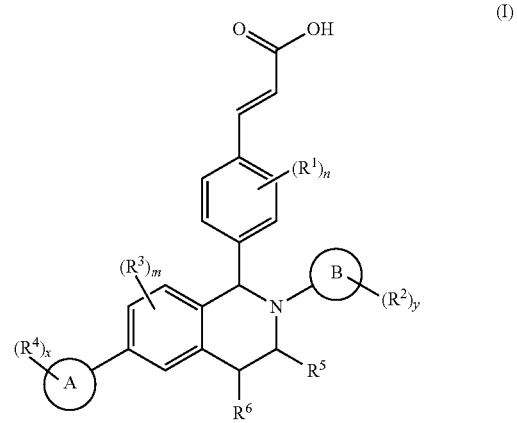

24 Claims, No Drawings

(56) References Cited

OTHER PUBLICATIONS

Wallace, et al., "Cyclopropylboronic Acid: Synthesis and Suzuki Cross-Coupling Reactions", Tetrahedron Letters vol. 43, pp. 6987-6900, Jul. 30, 2002.
Altau e t al., "Some Derivatives of Ethylbenzene", Journal of Chemical and Engineering Data, vol. 8, No. 1, pp. 122-130, Jan. 1963.
Scott et al., "Tetrahydroisoquinoline Phenols: Selective Estrogen Receptor Downregulator Antagonists with Oral Bioavailabillity in Rat", ACS Medicinal Chemistry Lettes, vol. 7, No. 1, pp. 94-99, Dec. 19, 2015.

BENZOPIPERIDINE DERIVATIVE, PREPARATION METHOD THEREOF AND MEDICAL USE THEREOF

CROSS-REFERENCE TO RELATED APPLICATION

This application is a Section 371 of International Application No. PCT/CN2016/108367, filed Dec. 2, 2016, which was published in the Chinese language on Jun. 29, 2017, under International Publication No. WO 2017/107754 A1, which claims priority under 35 U.S.C. § 119(b) to Chinese Application No. 201510975923.3, filed Dec. 22, 2015, the disclosures of which are incorporated herein by reference in their entirety.

FIELD OF THE INVENTION

The present invention belongs to the filed of medicine, and relates to a benzopiperidine derivative, a preparation method thereof and a medical use thereof. The present invention discloses a use thereof as an estrogen receptor modulator in the prevention and/or treatment of estrogen receptor mediated or dependent diseases or conditions, particularly preferably breast cancer.

BACKGROUND OF THE INVENTION

After a long period of basic research and clinical monitoring, it is found that diseases such as breast cancer, ovarian cancer, osteoporosis, schizophrenia and Alzheimer's disease are closely related to the abnormality of the estrogen signaling pathway. Estrogen is a steroid hormone secreted by the endocrine system, and plays an important role in the reproductive system, bone tissue, cardiovascular system, immune system and central nervous system. The estrogen signal transduction system plays an important role in the regulation of cell growth, differentiation and apoptosis. The occurrence and development of estrogen-dependent tumors, such as breast cancer, ovarian cancer, and endometrial cancer, are closely related to estrogen. Currently, the main chemotherapy for breast cancer is the use of antiestrogen agents, such as Tamoxifen. However, Tamoxifen exerts estrogen agonist properties in the uterus, thereby stimulating cancer cells in the uterus. Due to these serious side effects, it is imperative to seek a new safe and effective treatment.

One important protein of the estrogen signaling pathway is estrogen receptor (ER). ER is a steroid hormone receptor, and belongs to a ligand-activated transcription factor of the nuclear receptor superfamily that contains two subtypes: ERα (discovered in 1950) and ERβ (discovered in 1996), encoded by different genes, respectively. ERα and ERβ show a high degree of similarity at the amino acid level, and their similarity in the DNA binding domain is up to 97%, and the similarity in the ligand binding domain is up to 56%, but only 24% low homology in the N terminus. ER contains 6 domains from A to F, which comprise four main functional areas. The functional area of the N terminal AB domain has a ligand independent transcriptional activation function AF-1, and AF-1 has a constitutive activity. The transcription of target genes is activated by interaction with basic transcription factors, reactivation factors and other transcription factors. There are multiple phosphorylation sites in this function, and it is reported that the role of AF-1 depends on protein phosphorylation. The DNA binding domain (DBD) composed of the C domain is highly conservative and contains 2 zinc finger domains that can specifically bind to the target DNA, simultaneously, and this domain plays an important role in the dimerization of receptors. The D domain is a hinge region that connects the DBD and the ligand binding domain (LBD), with low conservatism (only 30% homology between two subtypes). The ligand binding domain (LBD) composed of the C terminal E domain determines the specific binding of ER to ligands such as estrogen, selective estrogen receptor modulator (SERM), and selective estrogen receptor downregulator (SERD). LBD has a ligand dependent transcriptional activation function AF-2, which has a synergistic reaction with AF-1 to exert ER receptor's role in activating the transcription of target genes. At the same time, LBD has a strong dimerization interface and still can function without ligands. Therefore, LBD is the key site for receptor dimerization.

ERα is mainly distributed in the uterus, ovary, testis, pituitary, kidney, epididymis and adrenal gland, while ERβ is mainly distributed in the prostate, ovary, lung, bladder, brain and blood vessels. Due to the serious side effects of full agonists or full antagonists, the study of SERM emerges as the times require. The "selectivity" means that SERM acts as an agonist in some tissues such as bone, liver and the cardiovascular system that are rich in ERβ, whereas it acts as an antagonist in some other tissues such as mammary glands. In the uterus, the significant region of ERα, it can be either an agonist or antagonist. So far, commercially available SERMs include Tamoxifen, Raloxifene, Bazedoxifene, Toremifene and the like. However, studies have found that commercially available SERMs still have serious side effects. For example, the long-term use of Tamoxifen and Toremifene can cause endometrial hyperplasia, polyps and endometrial cancer, and the common side effects of Raloxifene include hot flashes, leg pain, breast tenderness and venous thrombosis and the like. Therefore, the research and development of new compounds are still urgent problems to be solved.

Tamoxifen belongs to a class of compounds known as selective estrogen receptor modulators (SERMs), and has the ability to stabilize ERα and slightly up regulate the level of ERα receptors. In contrast, fulvestrant induces rapid degradation of ERα and intensifies the blockage of the ER receptor signaling pathway, and such compounds are called selective estrogen receptor downregulators (SERDs). The differences between the mechanisms of actions of these SERMs and SERDs seem to be the mechanisms responsible for the resistance of these compounds. A large number of tumors that are tamoxifen resistant and ER positive are still sensitive to fulvestrant. It is found clinically that SERDs such as fulvestrant can effectively treat some breast cancers that are ERα positive and tamoxifen resistant. Therefore, the compounds responsible for degradation of ERα can be used to prolong the duration of efficacy in breast cancer patients successfully treated with anti-estrogen therapy, whereas different SERMs, aromatase inhibitiors and SERDs can be used successively.

The patent applications disclosing selective estrogen receptor mediated modulators include WO2014165723, WO2014151899, WO2014141292, WO2014191726, WO2015092634, WO2014135834, and WO2014106848, and EP1113007A discloses structurally similar estrogen agonists/antagonists.

In order to achieve better therapeutic effects and to better meet the needs of the market, the inventors hope to develop a new generation of highly effective and low toxicity SERDs targeting the estrogen signaling pathway. Therefore, in view of the current research in this field, especially the compound AZD-9496 of AstraZeneca Company in the clinical Phase I, the present invention provides a novel structure of SERD, which shows good activities in the inhibition of the binding of estrogen to ER, the degradation of ER, and the proliferation of MCF7 cells, etc, especially more prominent advantage in the Emax value of ER degradation, in comparison to AZD-9496.

SUMMARY OF THE INVENTION

The present invention is directed to a compound of formula (I) or a tautomer, mesomer, racemate, enantiomer, diastereomer, or mixture thereof, or a pharmaceutically acceptable salt thereof, wherein the structure of the compound of formula (I) is as follows:

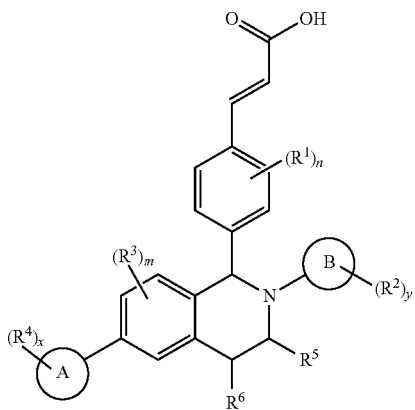

wherein:

ring A is selected from the group consisting of cycloalkyl, heterocyclyl, aryl and heteroaryl;

ring B is aryl or heteroaryl;

each $R^1$ is identical or different and each is independently selected from the group consisting of hydrogen, alkyl, haloalkyl, hydroxyalkyl, alkoxy, amino, cycloalkyl, halogen, cyano, carboxy, aldehyde, hydroxy, nitro, aryl and heteroaryl, wherein the alkyl, cycloalkyl, aryl and heteroaryl are each optionally substituted by one or more groups selected from the group consisting of alkyl, halogen, amino, nitro, cyano, hydroxy, hydroxyalkyl, alkoxy, cycloalkyl, heterocyclyl, aryl and heteroaryl;

each $R^2$ is identical or different and each is independently selected from the group consisting of hydrogen, alkyl, haloalkyl, hydroxyalkyl, alkoxy, amino, cycloalkyl, halogen, cyano, carboxy, aldehyde, hydroxy, nitro, aryl and heteroaryl, wherein the alkyl, cycloalkyl, aryl and heteroaryl are each optionally substituted by one or more groups selected from the group consisting of alkyl, halogen, amino, nitro, cyano, hydroxy, hydroxyalkyl, alkoxy, cycloalkyl, heterocyclyl, aryl and heteroaryl;

each $R^3$ is identical or different and each is independently selected from the group consisting of hydrogen, alkyl, haloalkyl, hydroxyalkyl, alkoxy, amino, cycloalkyl, halogen, cyano, carboxy, aldehyde, hydroxy, nitro, aryl and heteroaryl, wherein the alkyl, cycloalkyl, aryl and heteroaryl are each optionally substituted by one or more groups selected from the group consisting of alkyl, halogen, amino, nitro, cyano, hydroxy, hydroxyalkyl, alkoxy, cycloalkyl, heterocyclyl, aryl and heteroaryl;

each $R^4$ is identical or different and each is independently selected from the group consisting of hydrogen, alkyl, deuteroalkyl, haloalkyl, hydroxyalkyl, alkoxy, amino, cycloalkyl, halogen, cyano, carboxy, aldehyde, hydroxy, nitro, aryl and heteroaryl, wherein the alkyl, cycloalkyl, aryl and heteroaryl are each optionally substituted by one or more groups selected from the group consisting of alkyl, halogen, amino, nitro, cyano, hydroxy, hydroxyalkyl, alkoxy, cycloalkyl, heterocyclyl, aryl and heteroaryl;

$R^5$ is selected from the group consisting of hydrogen, alkyl, cycloalkyl, heterocyclyl, aryl and heteroaryl, wherein the alkyl, cycloalkyl, heterocyclyl, aryl and heteroaryl are each optionally substituted by one or more groups selected from the group consisting of alkyl, halogen, hydroxy, amino, nitro, cyano, alkoxy, hydroxyalkyl, cycloalkyl, heterocyclyl, aryl and heteroaryl;

$R^6$ is selected from the group consisting of hydrogen, alkyl, hydroxy, halogen, cyano, amino, nitro, alkoxy, cycloalkyl, heterocyclyl, aryl and heteroaryl, wherein the alkyl, alkoxy, cycloalkyl, heterocyclyl, aryl and heteroaryl are each optionally substituted by one or more groups selected from the group consisting of alkyl, halogen, hydroxy, amino, nitro, cyano, alkoxy, hydroxyalkyl, cycloalkyl, heterocyclyl, aryl and heteroaryl;

m is 0, 1, 2 or 3;

n is 0, 1, 2, 3 or 4;

x is 0, 1, 2 or 3; and y is 0, 1, 2, 3, 4 or 5.

In a preferred embodiment of the present invention, in a compound of formula (I) or a tautomer, mesomer, racemate, enantiomer, diastereomer, or mixture thereof, or a pharmaceutically acceptable salt thereof, ring A is heteroaryl, preferably pyrazolyl or thiazolyl.

In a preferred embodiment of the present invention, a compound of formula (I) or a tautomer, mesomer, racemate, enantiomer, diastereomer, or mixture thereof, or a pharmaceutically acceptable salt thereof is optionally a compound of formula (II):

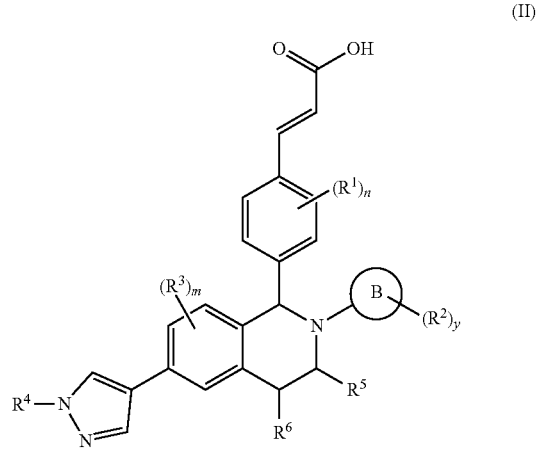

or a tautomer, mesomer, racemate, enantiomer, diastereomer, or mixture thereof, or a pharmaceutically acceptable salt thereof,
wherein:
ring B, R¹ to R⁶, m, n and y are as defined in formula (I).

In a preferred embodiment of the present invention, in a compound of formula (I) or a tautomer, mesomer, racemate, enantiomer, diastereomer, or mixture thereof, or a pharmaceutically acceptable salt thereof, ring B is aryl.

In a preferred embodiment of the present invention, a compound of formula (II) or a tautomer, mesomer, racemate, enantiomer, diastereomer, or mixture thereof, or a pharmaceutically acceptable salt thereof is optionally a compound of formula (III):

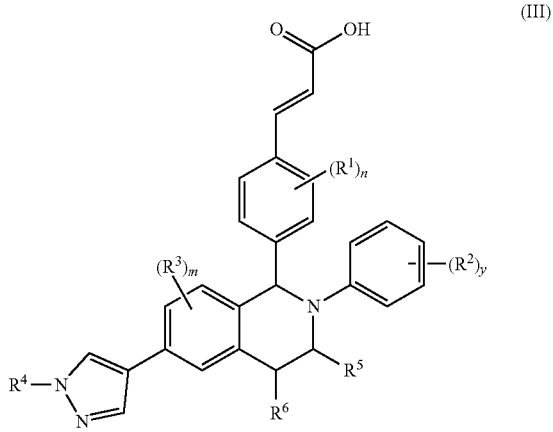

or a tautomer, mesomer, racemate, enantiomer, diastereomer, or mixture thereof, or a pharmaceutically acceptable salt thereof,
wherein:
R¹ to R⁶, m, n and y are as defined in formula (I).

In a preferred embodiment of the present invention, a compound of formula (III) or a tautomer, mesomer, racemate, enantiomer, diastereomer, or mixture thereof, or a pharmaceutically acceptable salt thereof is optionally a compound of formula (III-1):

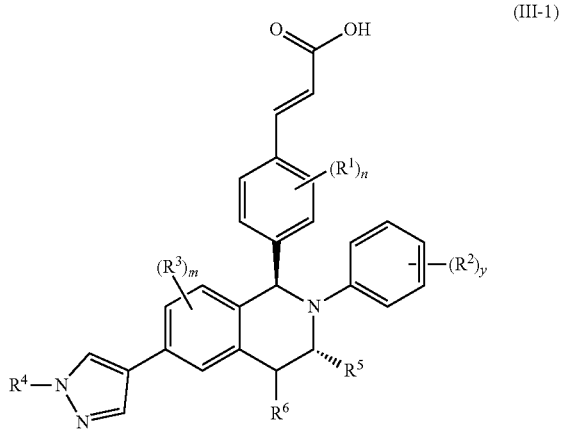

or a tautomer, mesomer, racemate, enantiomer, diastereomer, or mixture thereof, or a pharmaceutically acceptable salt thereof, wherein:
R¹ to R⁶, m, n and y are as defined in formula (I).

In a preferred embodiment of the present invention, in a compound of formula (I) or a tautomer, mesomer, racemate, enantiomer, diastereomer, or mixture thereof, or a pharmaceutically acceptable salt thereof, R¹ is hydrogen or halogen.

In a preferred embodiment of the present invention, in a compound of formula (I) or a tautomer, mesomer, racemate, enantiomer, diastereomer, or mixture thereof, or a pharmaceutically acceptable salt thereof, R² is selected from the group consisting of hydrogen, halogen, alkyl, haloalkyl, alkoxy and cycloalkyl, wherein the alkyl is optionally substituted by one or more groups selected from the group consisting of halogen, alkoxy and cycloalkyl.

In a preferred embodiment of the present invention, in a compound of formula (I) or a tautomer, mesomer, racemate, enantiomer, diastereomer, or mixture thereof, or a pharmaceutically acceptable salt thereof, R³ is hydrogen.

In a preferred embodiment of the present invention, in a compound of formula (I) or a tautomer, mesomer, racemate, enantiomer, diastereomer, or mixture thereof, or a pharmaceutically acceptable salt thereof, R⁴ is selected from the group consisting of hydrogen, deuteroalkyl, haloalkyl and alkyl.

In a preferred embodiment of the present invention, in a compound of formula (I) or a tautomer, mesomer, racemate, enantiomer, diastereomer, or mixture thereof, or a pharmaceutically acceptable salt thereof, R⁵ is hydrogen or alkyl.

In a preferred embodiment of the present invention, in a compound of formula (I) or a tautomer, mesomer, racemate, enantiomer, diastereomer, or mixture thereof, or a pharmaceutically acceptable salt thereof, R⁶ is hydrogen.

In a preferred embodiment of the present invention, in a compound of formula (I) or a tautomer, mesomer, racemate, enantiomer, diastereomer, or mixture thereof, or a pharmaceutically acceptable salt thereof, n is 0 or 2.

In a preferred embodiment of the present invention, in a compound of formula (I) or a tautomer, mesomer, racemate, enantiomer, diastereomer, or mixture thereof, or a pharmaceutically acceptable salt thereof, y is 0, 1 or 2.

In a preferred embodiment of the present invention, in a compound of formula (I) or a tautomer, mesomer, racemate, enantiomer, diastereomer, or mixture thereof, or a pharmaceutically acceptable salt thereof, m is 0.

Typical compounds of formula (I), include, but are not limited to:
| Example No. | Structure and Name |
| --- | --- |
| 1 | 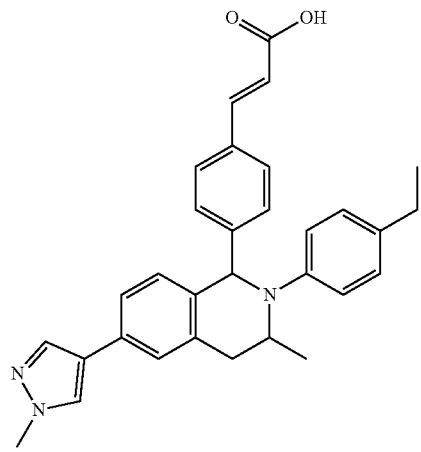<br>1<br><br>(E)-3-(4-((1R,3R/1S,3S)-2-(4-ethylphenyl)-3-methyl-6-(1-methyl-1H-pyrazol-4-yl)-1,2,3,4-tetrahydroisoquinolin-1-yl)phenyl)acrylic acid |
| 2 | 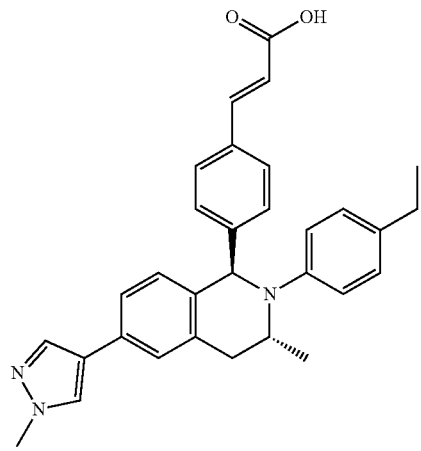<br>2<br><br>(E)-3-(4-((1R,3R)-2-(4-ethylphenyl)-3-methyl-6-(1-methyl-1H-pyrazol-4-yl)-1,2,3,4-tetrahydroisoquinolin-1-yl)phenyl)acrylic acid |

| Example No. | Structure and Name |
|---|---|
| 3 | 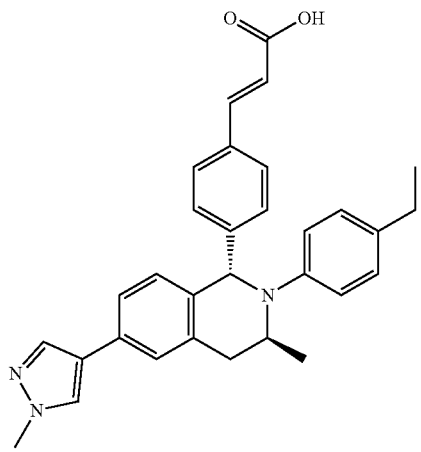<br>3<br>(E)-3-(4-((1S,3S)-2-(4-ethylphenyl)-3-methyl-6-(1-methyl-1H-pyrazol-4-yl)-1,2,3,4-tetrahydroisoquinolin-1-yl)phenyl)acrylic acid |
| 4 | 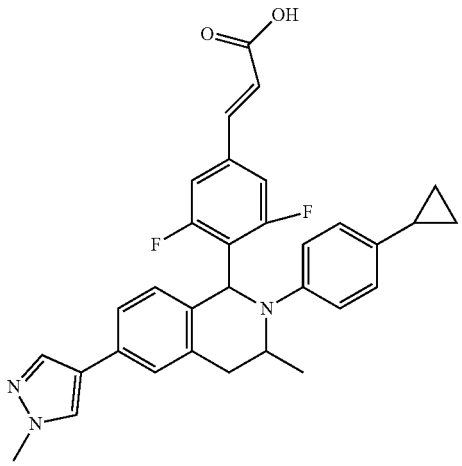<br>4<br>(E)-3-(4-((1S,3R/1R,3S)-2-(4-cyclopropylphenyl)-3-methyl-6-(1-methyl-1H-pyrazol-4-yl)-1,2,3,4-tetrahydroisoquinolin-1-yl)-3,5-difluorophenyl)acrylic acid |

| Example No. | Structure and Name |
|---|---|
| 5 | 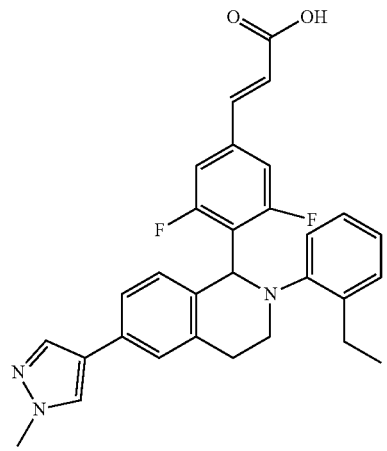<br>(E)-3-(4-(2-(2-ethylphenyl)-6-(1-methyl-1H-pyrazol-4-yl)-1,2,3,4-tetrahydroisoquinolin-1-yl)-3,5-difluorophenyl)acrylic acid |
| 6 | 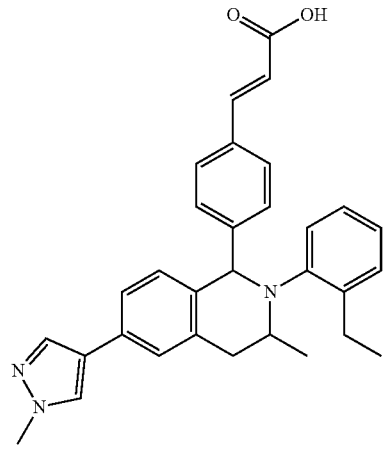<br>(E)-3-(4-((1R,3R/1S,3S)-2-(2-ethylphenyl)-3-methyl-6-(1-methyl-1H-pyrazol-4-yl)-1,2,3,4-tetrahydroisoquinolin-1-yl)phenyl)acrylic acid |

-continued
| Example No. | Structure and Name |
|---|---|
| 7 | 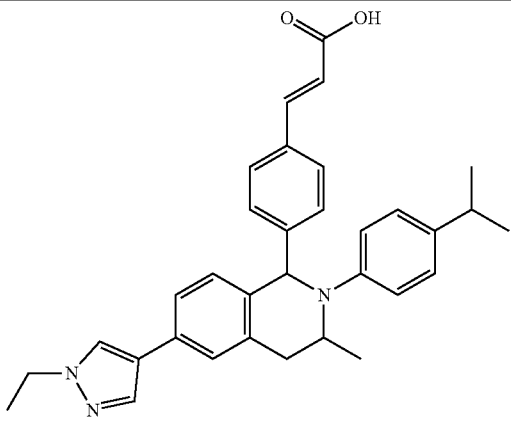
7
(E)-3-(4-((1R,3R/1S,3S)-6-(1-ethyl-1H-pyrazol-4-yl)-2-(4-isopropylphenyl)-3-methyl-1,2,3,4-tetrahydroisoquinolin-1-yl)phenyl)acrylic acid |
| 8 | 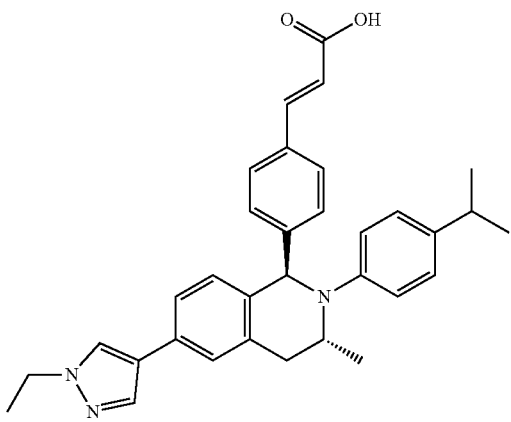
8
(E)-3-(4-((1R,3R)-6-(1-ethyl-1H-pyrazol-4-yl)-2-(4-isopropylphenyl)-3-methyl-1,2,3,4-tetrahydroisoquinolin-1-yl)phenyl)acrylic acid |
| 9 | 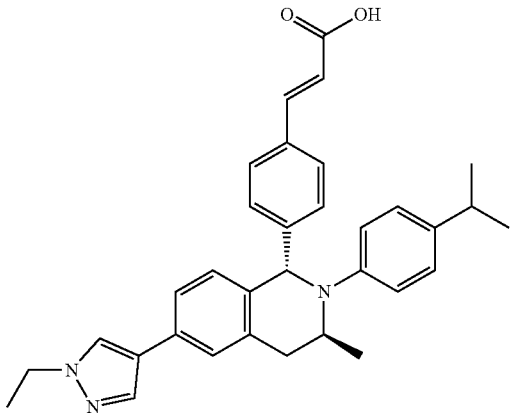
9
(E)-3-(4-((1S,3S)-6-(1-ethyl-1H-pyrazol-4-yl)-2-(4-isopropylphenyl)-3-methyl-1,2,3,4-tetrahydroisoquinolin-1-yl)phenyl)acrylic acid |

-continued

| Example No. | Structure and Name |
|---|---|
| 10 | 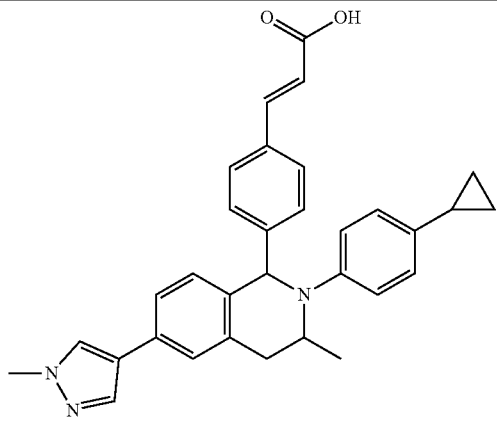<br>10<br><br>(E)-3-(4-((1R,3R/1S,3S)-2-(4-cyclopropylphenyl)-3-methyl-6-(1-methyl-1H-pyrazol-4-yl)-1,2,3,4-tetrahydroisoquinolin-1-yl)phenyl)acrylic acid |
| 11 | 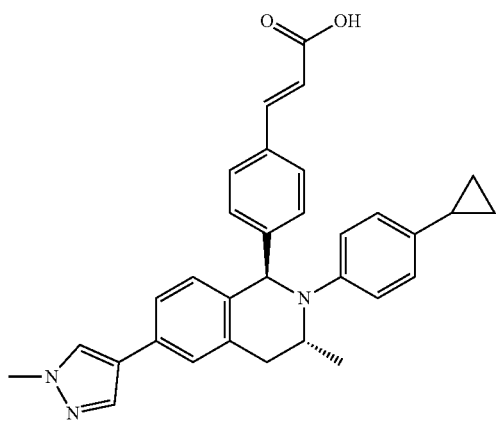<br>11<br><br>(E)-3-(4-((1R,3R)-2-(4-cyclopropylphenyl)-3-methyl-6-(1-methyl-1H-pyrazol-4-yl)-1,2,3,4-tetrahydroisoquinolin-1-yl)phenyl)acrylic acid |
| 12 | 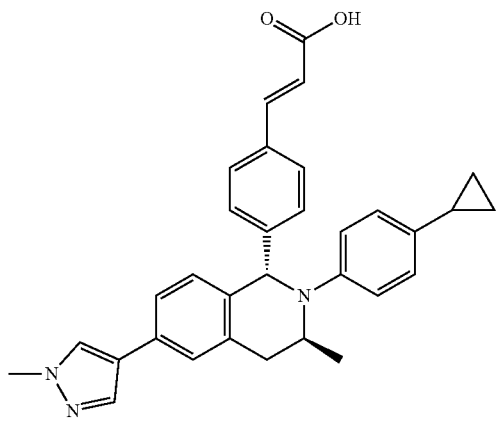<br>12<br><br>(E)-3-(4-((1S,3S)-2-(4-cyclopropylphenyl)-3-methyl-6-(1-methyl-1H-pyrazol-4-yl)-1,2,3,4-tetrahydroisoquinolin-1-yl)phenyl)acrylic acid |

-continued
| Example No. | Structure and Name |
|---|---|
| 13 | 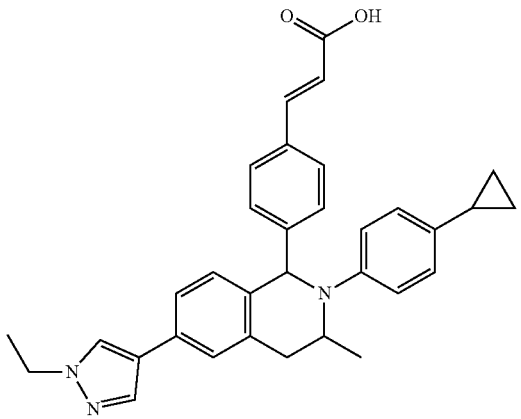
13
(E)-3-(4-((1R,3R/1S,3S)-(2-(4-cyclopropylphenyl)-6-(1-ethyl-1H-pyrazol-4-yl)-3-methyl-1,2,3,4-tetrahydroisoquinolin-1-yl)phenyl)acrylic acid |
| 14 | 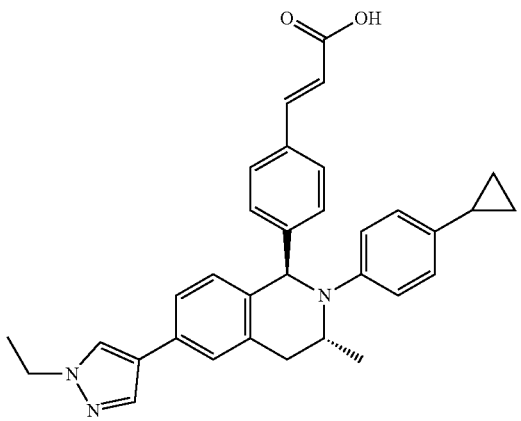
14
(E)-3-(4-((1R,3R)-2-(4-cyclopropylphenyl)-6-(1-ethyl-1H-pyrazol-4-yl)-3-methyl-1,2,3,4-tetrahydroisoquinolin-1-yl)phenyl)acrylic acid |
| 15 | 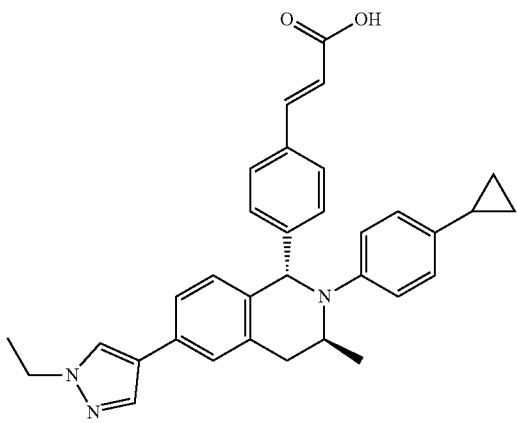
15
(E)-3-(4-((1S,3S)-2-(4-cyclopropylphenyl)-6-(1-ethyl-1H-pyrazol-4-yl)-3-methyl-1,2,3,4-tetrahydroisoquinolin-1-yl)phenyl)acrylic acid |

-continued
| Example No. | Structure and Name |
|---|---|
| 16 | 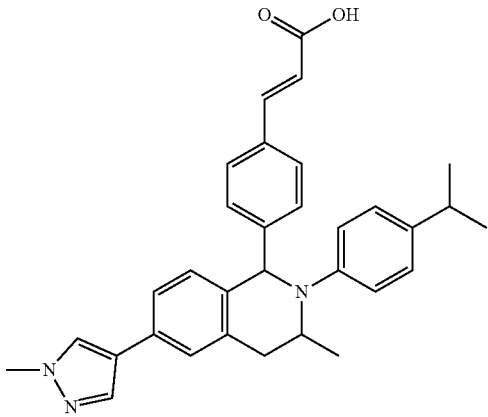<br>16<br><br>(E)-3-(4-((1R,3R/1S,3S)-2-(4-isopropylphenyl)-3-methyl-6-(1-methyl-1H-pyrazol-4-yl)-1,2,3,4-tetrahydroisoquinolin-1-yl)phenyl)acrylic acid |
| 17 | 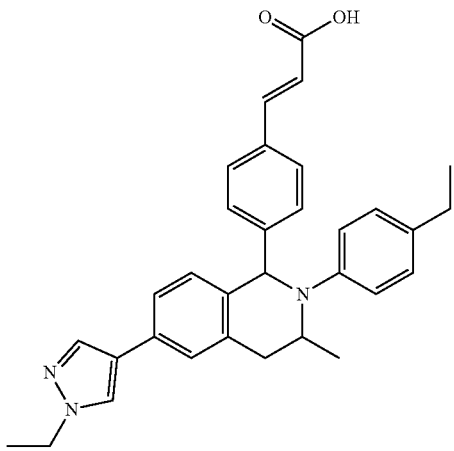<br>17<br><br>(E)-3-(4-((1R,3R/1S,3S)-6-(1-ethyl-1H-pyrazol-4-yl)-2-(4-ethylphenyl)-3-methyl-1,2,3,4-tetrahydroisoquinolin-1-yl)phenyl)acrylic acid |
| 18 | 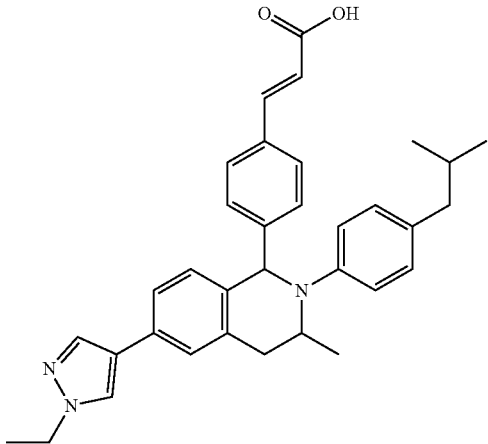<br>18<br><br>(E)-3-(4-((1R,3R/1S,3S)-6-(1-ethyl-1H-pyrazol-4-yl)-2-(4-isobutylphenyl)- |

| Example No. | Structure and Name |
|---|---|
| | 3-methyl-1,2,3,4-tetrahydroisoquinolin-1-yl)phenyl)acrylic acid |
| 19 | 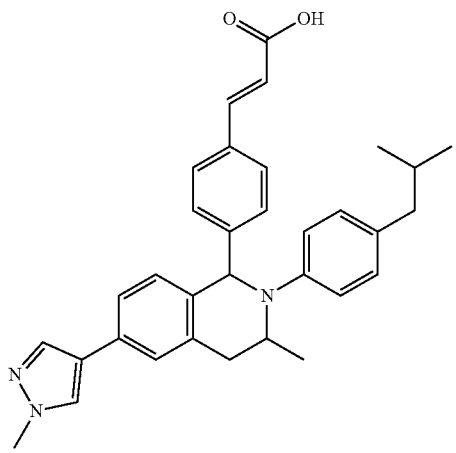
(E)-3-(4-((1R,3R/1S,3S)-2-(4-isobutylphenyl)-3-methyl-6-(1-methyl-1H-pyrazol-4-yl)-1,2,3,4-tetrahydroisoquinolin-1-yl)phenyl)acrylic acid |
| 20 | 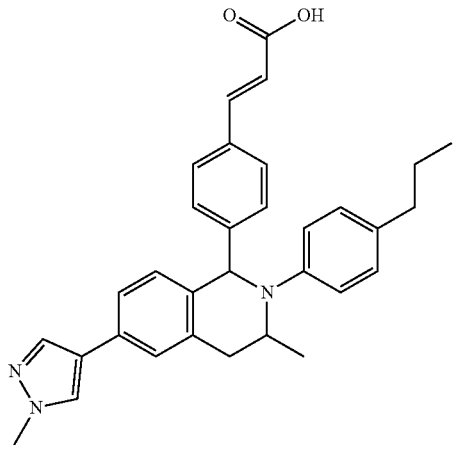
(E)-3-(4-((1R,3R/1S,3S)-3-methyl-6-(1-methyl-1H-pyrazol-4-yl)-2-(4-propylphenyl)-1,2,3,4-tetrahydroisoquinolin-1-yl)phenyl)acrylic acid |

| Example No. | Structure and Name |
|---|---|
| 21 | 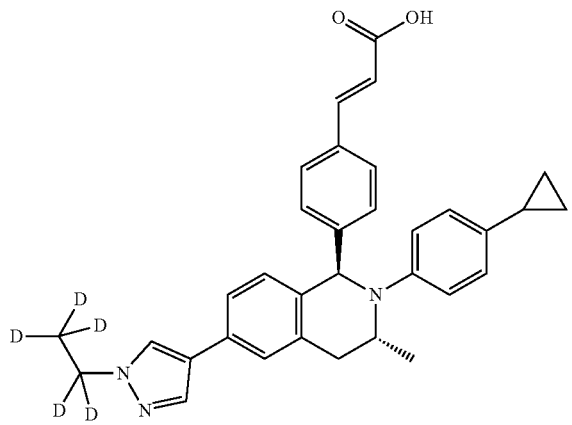
21
(E)-3-(4-((1R,3R)-2-(4-cyclopropylphenyl)-6-(1-ethyl-$d_5$-1H-pyrazol-4-yl)-3-methyl-1,2,3,4-tetrahydroisoquinolin-1-yl)phenyl)acrylic acid 21 |
| 22 | 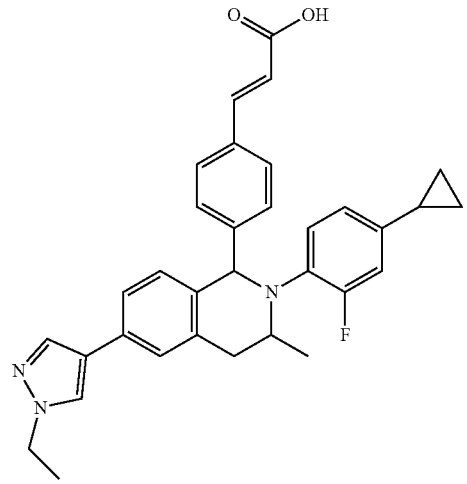
22
(E)-3-(4-((1R,3R/1S,3S)-2-(4-cyclopropyl-2-fluorophenyl)-6-(1-ethyl-1H-pyrazol-4-yl)-3-methyl-1,2,3,4-tetrahydroisoquinolin-1-yl)phenyl)acrylic acid 22 |

| Example No. | Structure and Name |
|---|---|
| 23 | 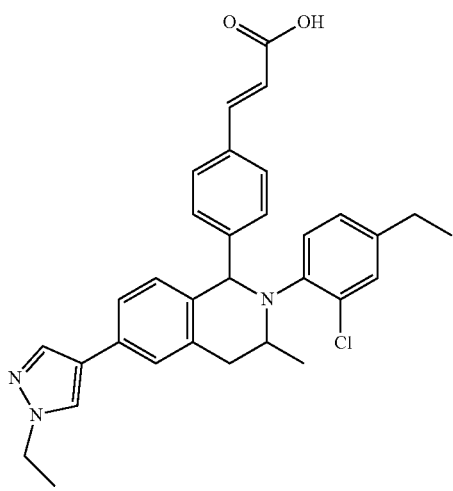 [SMILES: CCc1ccc(N2C(C)Cc3cc(-c4cnn(C)c4)ccc3C2c2ccc(/C=C/C(=O)O)cc2)c(CC)c1]
23
(E)-3-(4-((1R,3R/1S,3S)-2-(2-chloro-4-ethylphenyl)-6-(1-ethyl-1H-pyrazol-4-yl)-3-methyl-1,2,3,4-tetrahydroisoquinolin-1-yl)phenyl)acrylic acid 23 |
| 24 | 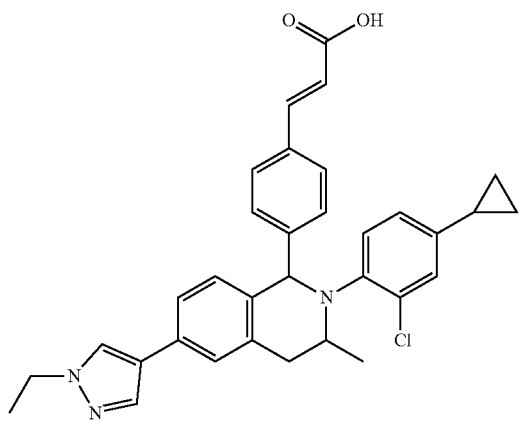
24
(E)-3-(4-((1R,3R/1S,3S)-2-(2-chloro-4-cyclopropylphenyl)-6-(1-ethyl-1H-pyrazol-4-yl)-3-methyl-1,2,3,4-tetrahydroisoquinolin-1-yl)phenyl)acrylic acid 24 |

-continued
| Example No. | Structure and Name |
|---|---|
| 25 | 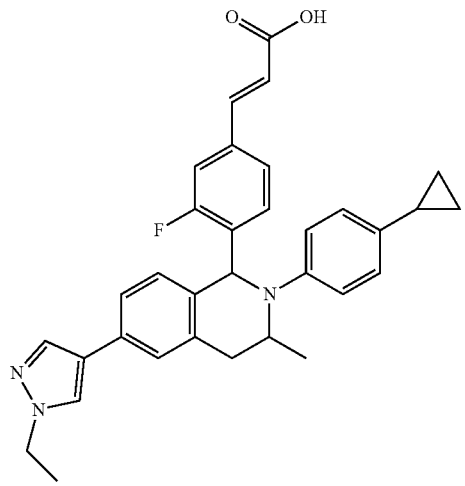
25
(E)-3-(4-((1S,3R/1R,3S)-2-(4-cyclopropylphenyl)-6-(1-ethyl-1H-pyrazol-4-yl)-3-methyl-1,2,3,4-tetrahydroisoquinolin-1-yl)-3-fluorophenyl)acrylic acid 25 |
| 26 | 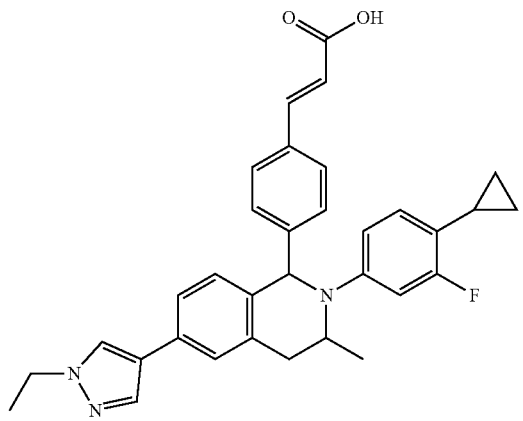
26
(E)-3-(4-((1R,3R/1S,3S)-2-(4-cyclopropyl-3-fluorophenyl)-6-(1-ethyl-1H-pyrazol-4-yl)-3-methyl-1,2,3,4-tetrahydroisoquinolin-1-yl)phenyl)acrylic acid 26 |

| Example No. | Structure and Name |
|---|---|
| 27 | 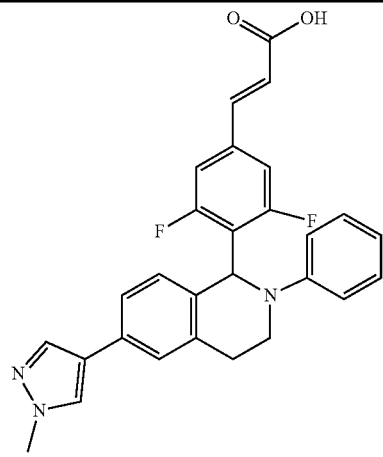<br>27<br><br>(E)-3-(3,5-difluoro-4-(6-(1-methyl-1H-pyrazol-4-yl)-2-phenyl-1,2,3,4-tetrahydroisoquinolin-1-yl)phenyl)acrylic acid 27 |
| 28 | 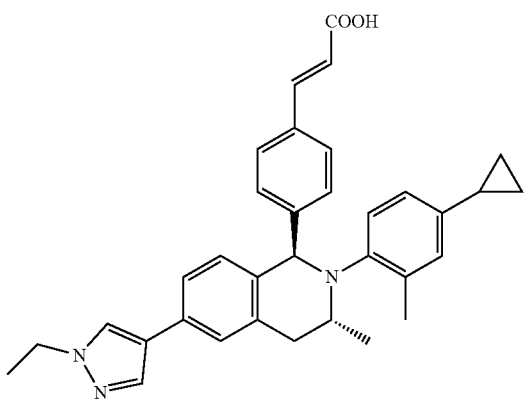<br>28<br><br>(E)-3-(4-((1R,3R)-2-(4-cyclopropyl-2-methylphenyl)-6-(1-ethyl-1H-pyrazol-4-yl)-3-methyl-1,2,3,4-tetrahydroisoquinolin-1-yl)phenyl)acrylic acid 28 |
| 29 | 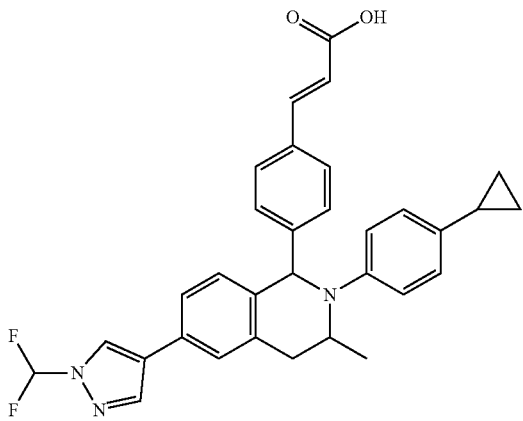<br>29<br><br>(E)-3-(4-((1R,3R/1S,3S)-2-(4-cyclopropylphenyl)-6-(1-(difluoromethyl)-1H-pyrazol-4-yl)-3-methyl-1,2,3,4-tetrahydroisoquinolin-1-yl)phenyl)acrylic acid 29 |

| Example No. | Structure and Name |
|---|---|
| 30 | 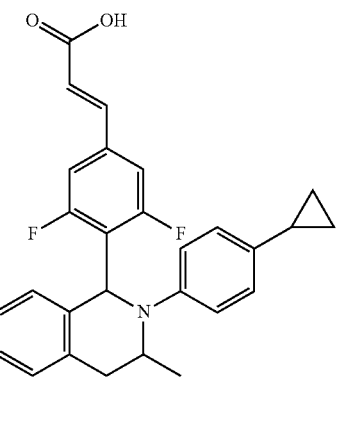<br>(E)-3-(4-((1S,3R/1R,3S)-2-(4-cyclopropylphenyl)-3-methyl-6-(1-ethyl-1H-pyrazol-4-yl)-1,2,3,4-tetrahydroisoquinolin-1-yl)-3,5-difluorophenyl)acrylic acid 30 |
| 31 | 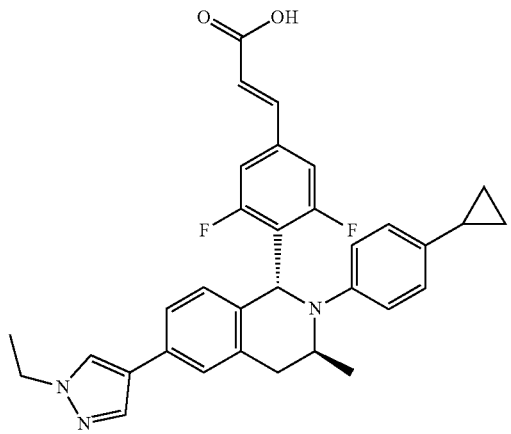<br>(E)-3-(4-((1R,3S)-2-(4-cyclopropylphenyl)-3-methyl-6-(1-ethyl-1H-pyrazol-4-yl)-1,2,3,4-tetrahydroisoquinolin-1-yl)-3,5-difluorophenyl)acrylic acid 31 |

| Example No. | Structure and Name |
|---|---|
| 32 | 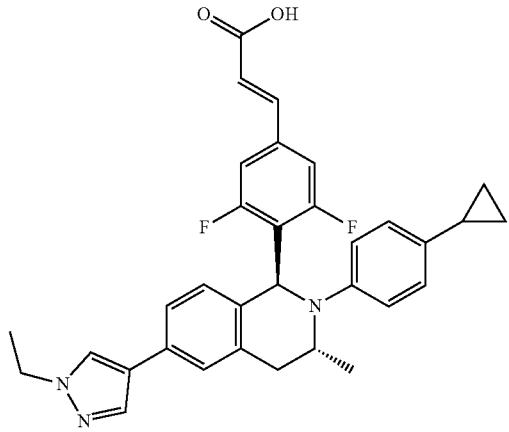<br>32<br>(E)-3-(4-((1S,3R)-2-(4-cyclopropylphenyl))-3-methyl-6-(1-ethyl-1H-pyrazol-4-yl-1,2,3,4-tetrahydroisoquinolin-1-yl)-3,5-difluorophenyl)acrylic acid 32 |
| 33 | 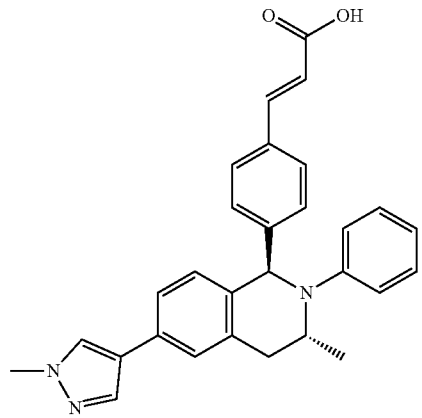<br>33<br>(E)-3-(4-((1R,3R)-3-methyl-6-(1-methyl-1H-pyrazol-4-yl)-2-phenyl-1,2,3,4-tetrahydroisoquinolin-1-yl)phenyl)acrylic acid 33 |
| 34 | 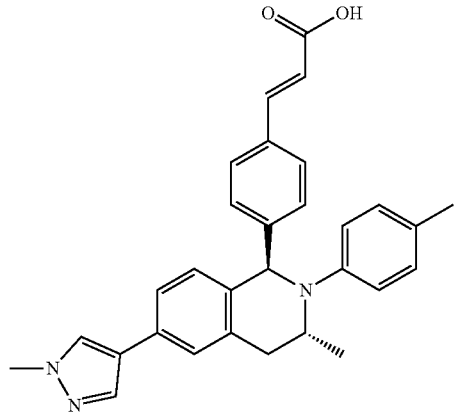<br>34<br>(E)-3-(4-((1R,3R)-3-methyl-6-(1-methyl-1H-pyrazol-4-yl)-2-(p-tolyl)-1,2,3,4-tetrahydroisoquinolin-1-yl)phenyl)acrylic acid 34 |

| Example No. | Structure and Name |
|---|---|
| 35 | 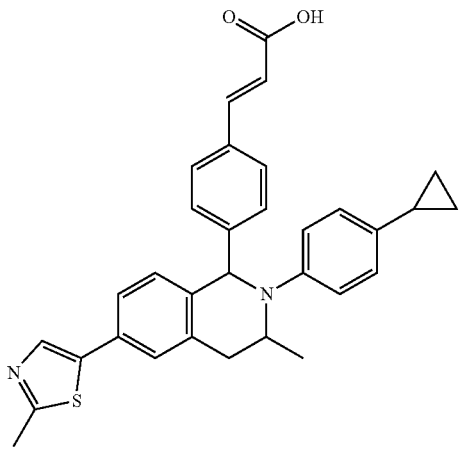<br>35<br><br>(E)-3-(4-((1R,3R/1S,3S)-2-(4-cyclopropylphenyl)-3-methyl-6-(2-methylthiazol-5-yl)-1,2,3,4-tetrahydroisoquinolin-1-yl)phenyl)acrylic acid 35 |
| 36 | 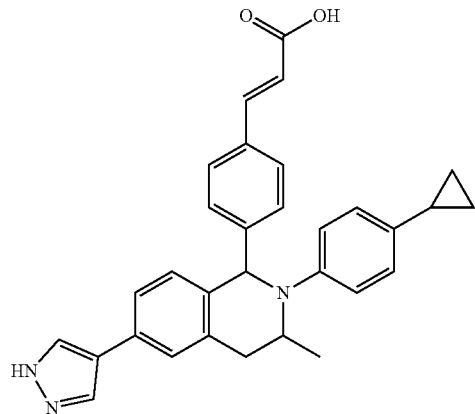<br>36<br><br>(E)-3-(4-((1R,3R/1S,3S)-2-(4-cyclopropylphenyl)-3-methyl-6-(1H-pyrazol-4-yl)-1,2,3,4-tetrahydroisoquinolin-1-yl)phenyl)acrylic acid 36 |

| Example No. | Structure and Name |
|---|---|
| 37 | 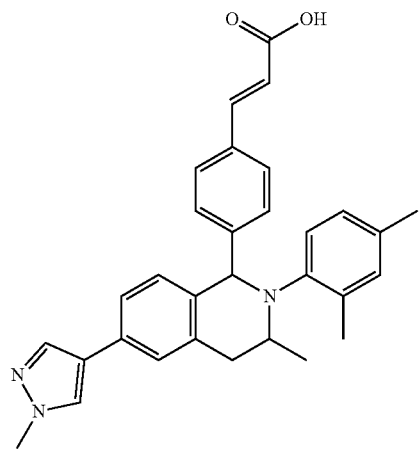<br>37<br>(E)-3-(4-((1R,3R/1S,3S)-2-(2,4-dimethylphenyl)-3-methyl-6-(1-methyl-1H-pyrazol-4-yl)-1,2,3,4-tetrahydroisoquinolin-1-yl)phenyl)acrylic acid |
| 38 | 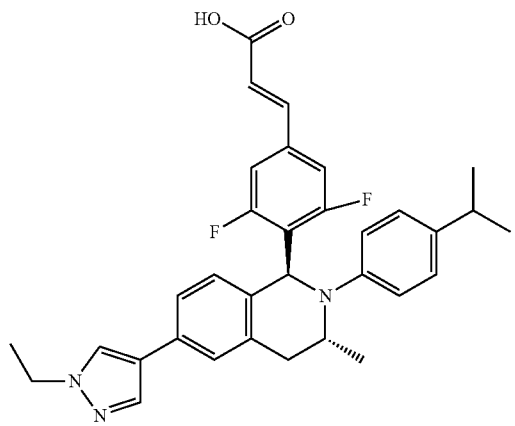<br>38<br>(E)-3-(4-((1S,3R)-6-(1-ethyl-1H-pyrazol-4-yl)-2-(4-isopropylphenyl)-3-methyl-1,2,3,4-tetrahydroisoquinolin-1-yl)-3,5-difluorophenyl)acrylic acid |

| Example No. | Structure and Name |
|---|---|
| 39 | 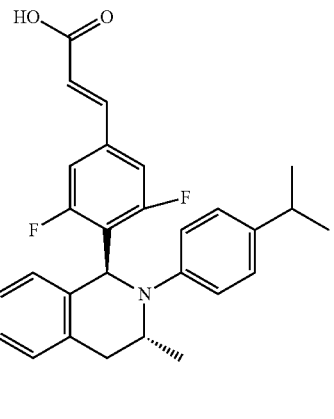<br>39<br><br>(E)-3-(3,5-difluoro-4-((1S,3R)-2-(4-isopropylphenyl)-3-methyl-6-(1-methyl-1H-pyrazol-4-yl)-1,2,3,4-tetrahydroisoquinolin-1-yl)phenyl)acrylic acid |
| 40 | 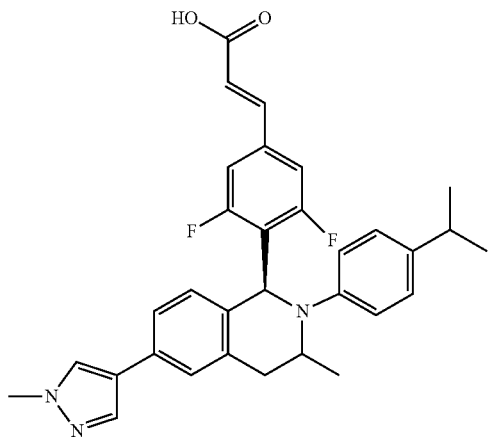<br>40<br><br>(E)-3-(3,5-difluoro-4-((1S,3R/1R,3S)-2-(4-isopropylphenyl)-3-methyl-6-(1-methyl-1H-pyrazol-4-yl)-1,2,3,4-tetrahydroisoquinolin-1-yl)phenyl)acrylic acid 40 |

| Example No. | Structure and Name |
|---|---|
| 41 | 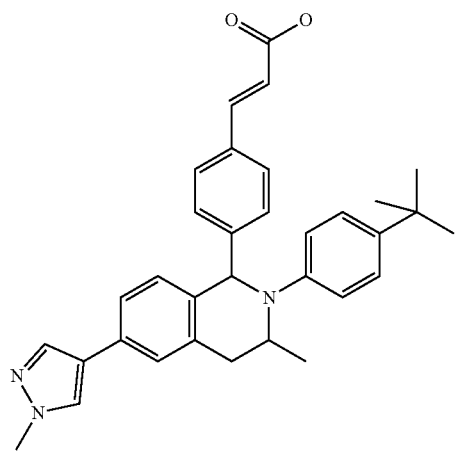<br>41<br><br>(E)-3-(4-((1R,3R/1S,3S)-2-(4-(tert-butyl)phenyl)-3-methyl-6-(1-methyl-1H-pyrazol-4-yl)-1,2,3,4-tetrahydroisoquinolin-1-yl)phenyl)acrylic acid 41 |
| 42 | 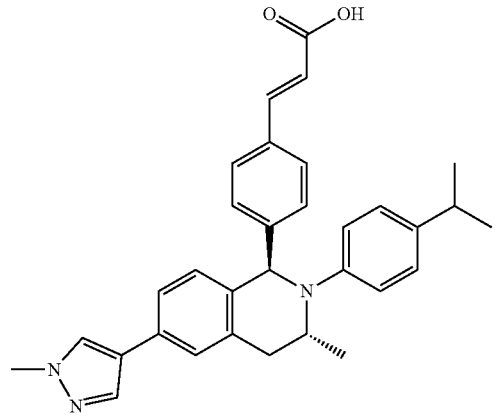<br>42<br><br>(E)-3-(4-((1R,3R)-2-(4-isopropylphenyl)-3-methyl-6-(1-methyl-1H-pyrazol-4-yl)-1,2,3,4-tetrahydroisoquinolin-1-yl)phenyl)acrylic acid 42 |

| Example No. | Structure and Name |
|---|---|
| 43 | 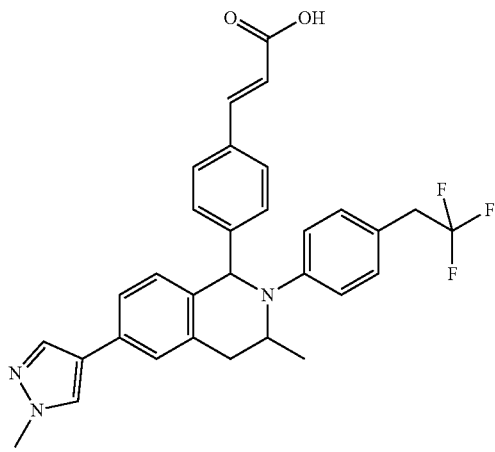<br>(E)-3-(4-((1R,3R/1S,3S)-3-methyl-6-(1-methyl-1H-pyrazol-4-yl)-2-(4-(2,2,2-trifluoroethyl)phenyl)-1,2,3,4-tetrahydroisoquinolin-1-yl)phenyl)acrylic acid 43 |
| 44 | 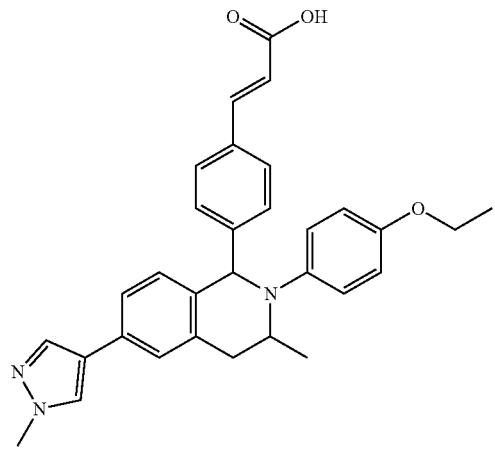<br>(E)-3-(4-((1R,3R/1S,3S)-2-(4-ethoxyphenyl)-3-methyl-6-(1-methyl-1H-pyrazol-4-yl)-1,2,3,4-tetrahydroisoquinolin-1-yl)phenyl)acrylic acid 44 |

| Example No. | Structure and Name |
|---|---|
| 45 | 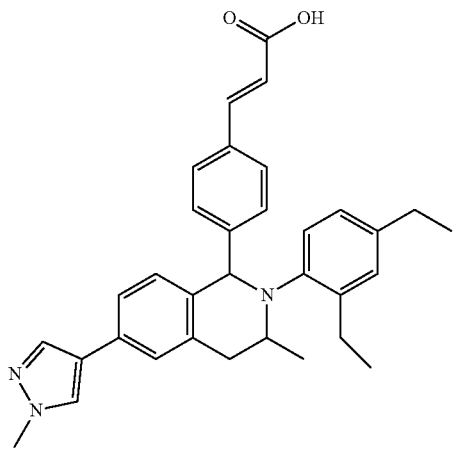<br>45<br><br>(E)-3-(4-((1R,3R/1S,3S)-2-(2,4-diethylphenyl)-3-methyl-6-(1-methyl-1H-pyrazol-4-yl)-1,2,3,4-tetrahydroisoquinolin-1-yl)phenyl)acrylic acid 45 |
| 46 | 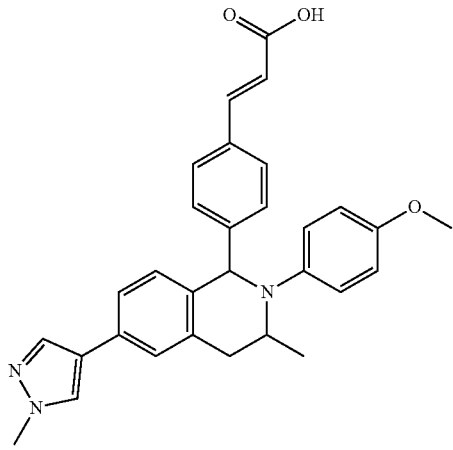<br>46<br><br>(E)-3-(4-((1R,3R/1S,3S)-2-(4-methoxyphenyl)-3-methyl-6-(1-methyl-1H-pyrazol-4-yl)-1,2,3,4-tetrahydroisoquinolin-1-yl)phenyl)acrylic acid 46 |

| Example No. | Structure and Name |
|---|---|
| 47 | 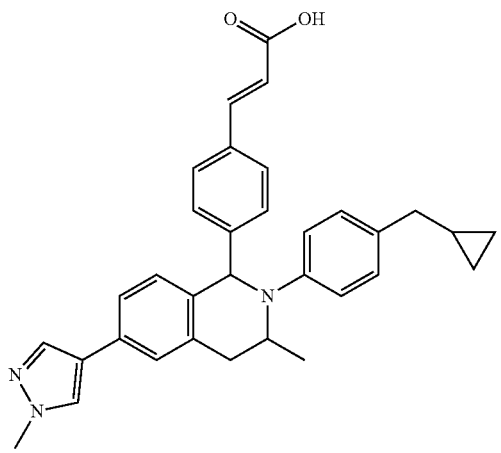<br>47<br><br>(E)-3-(4-((1R,3R/1S,3S)-2-(4-(cyclopropylmethyl)phenyl)-3-methyl-6-(1-methyl-1H-pyrazol-4-yl)-1,2,3,4-tetrahydroisoquinolin-1-yl)phenyl) acrylic acid 47 |
| 48 | 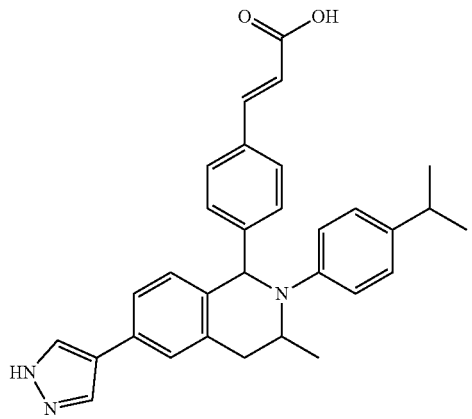<br>48<br><br>(E)-3-(4-((1R,3R/1S,3S)-2-(4-isopropylphenyl)-3-methyl-6-(1H-pyrazol-4-yl)-1,2,3,4-tetrahydroisoquinolin-1-yl)phenyl)acrylic acid 48 |

| Example No. | Structure and Name |
|---|---|
| 49 | 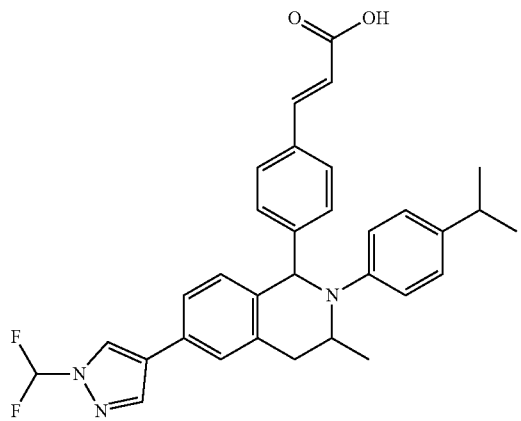<br>49<br>(E)-3-(4-((1R,3R/1S,3S)-6-(1-(difluoromethyl)-1H-pyrazol-4-yl)-2-(4-isopropylphenyl)-3-methyl-1,2,3,4-tetrahydroisoquinolin-1-yl)phenyl) acrylic acid 49 |
| 50 | 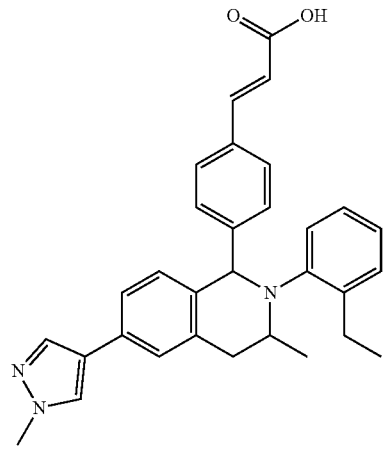<br>50<br>(E)-3-(4-((1R,3S/1S,3R)-2-(2-ethylphenyl)-3-methyl-6-(1-methyl-1H-pyrazol-4-yl)-1,2,3,4-tetrahydroisoquinolin-1-yl)phenyl)acrylic acid 50 |

-continued
| Example No. | Structure and Name |
|---|---|
| 51 | 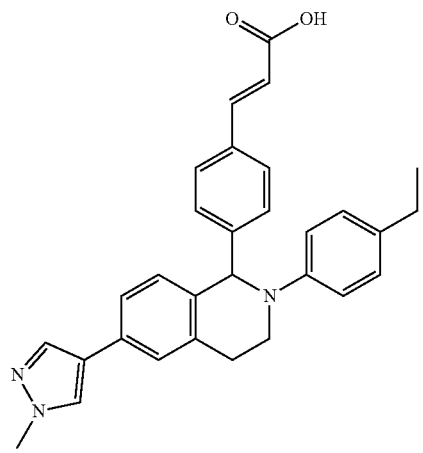<br>(E)-3-(4-(2-(4-ethylphenyl)-6-(1-methyl-1H-pyrazol-4-yl)-1,2,3,4-tetrahydroisoquinolin-1-yl)phenyl)acrylic acid 51 |
| 52 | 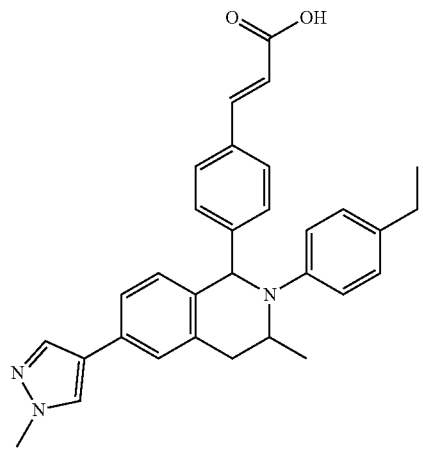<br>(E)-3-(4-(((1R,3S/1S,3R)-2-(4-ethylphenyl)-3-methyl-6-(1-methyl-1H-pyrazol-4-yl)-1,2,3,4-tetrahydroisoquinolin-1-yl)phenyl)acrylic acid 52 |

| Example No. | Structure and Name |
|---|---|
| 53 | 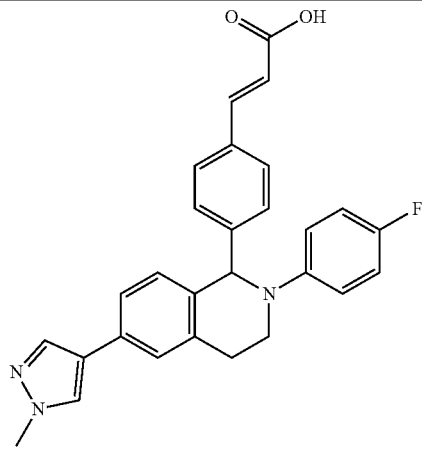<br>(E)-3-(4-(-2-(4-fluorophenyl)-6-(1-methyl-1H-pyrazol-4-yl)-1,2,3,4-tetrahydroisoquinolin-1-yl)phenyl)acrylic acid 53 | or a tautomer, mesomer, racemate, enantiomer, diastereomer thereof, or mixture thereof, or a pharmaceutically acceptable salt thereof.

The present invention further provides a compound of formula (IV):

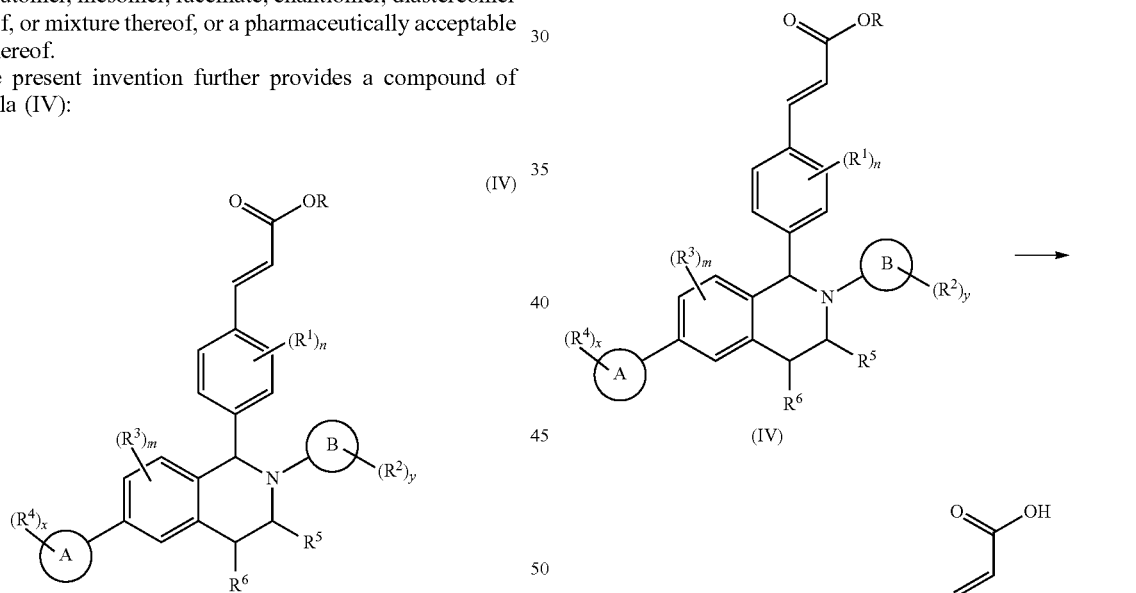

or a tautomer, mesomer, racemate, enantiomer, diastereomer, or mixture thereof, or a pharmaceutically acceptable salt thereof,
wherein:

R is alkyl or cycloalkyl, wherein the alkyl and cycloalkyl are each optionally substituted by one or more groups selected from the group consisting of alkyl, halogen, amino, cyano, hydroxy, alkoxy, carboxy and cycloalkyl; and ring A, ring B, $R^1$ to $R^6$, m, n, x and y are as defined in formula (I).

Another aspect of this invention is directed to a process for preparing the compound of formula (I) or a tautomer, mesomer, racemate, enantiomer, diastereomer, or mixture thereof, or a pharmaceutically acceptable salt thereof, comprising:

hydrolyzing a compound of formula (IV) under an alkaline condition to obtain the compound of formula (I);

wherein:

R is alkyl or cycloalkyl, wherein the alkyl and cycloalkyl are each optionally substituted by one or more groups selected from the group consisting of alkyl, halogen, amino, cyano, hydroxy, alkoxy, carboxy and cycloalkyl; and ring A, ring B, $R^1$ to $R^6$, m, n, x and y are as defined in formula (I).

Another aspect of this invention is directed to a pharmaceutical composition comprising a therapeutically effective amount of the compound of each aforementioned formula or a tautomer, mesomer, racemate, enantiomer, diastereomer, or mixture thereof, or a pharmaceutically acceptable salt thereof, and one or more pharmaceutically acceptable carriers, diluents or excipients. The present invention is further directed to a process for preparing the aforementioned pharmaceutical composition, comprising mixing the compound of each aforementioned formula or a tautomer, mesomer, racemate, enantiomer, diastereomer, or mixture thereof, or a pharmaceutically acceptable salt thereof, with one or more pharmaceutically acceptable carriers, diluents or excipients.

The present invention is further directed to a use of the compound of formula (I) or a tautomer, mesomer, racemate, enantiomer, diastereomer, or mixture thereof, or a pharmaceutically acceptable salt thereof, or the pharmaceutical composition comprising the same, in the preparation of an estrogen receptor modulator.

The present invention is further directed to a use of the compound of formula (I) or a tautomer, mesomer, racemate, enantiomer, diastereomer, or mixture thereof, or a pharmaceutically acceptable salt thereof, or the pharmaceutical composition comprising the same, in the preparation of a medicament for preventing and/or treating an estrogen receptor mediated or dependent disease or condition, wherein the estrogen receptor mediated or dependent disease or condition is selected from the group consisting of cancer, central nervous system (CNS) defects, cardiovascular system defects, hematological system defects, immune and inflammation diseases, susceptibility to infection, metabolic defects, neurological defects, psychiatric defects and reproductive defects; wherein the cancer can be breast cancer, endometrial cancer, cervical cancer, skin cancer, prostate cancer, ovarian cancer, fallopian tube tumor, ovarioncus, hemophilia, leukemia or leiomyomata (e.g. uterine lei omy omas); preferably breast cancer, ovarian cancer, endometrial cancer, prostate cancer or uterine cancer; more preferably breast cancer; wherein the central nervous system (CNS) defects can be alcoholism or migraine; wherein the cardiovascular system defects can be aortic aneurysm, susceptibility to myocardial infarction, aortic valve sclerosis, cardiovascular diseases, coronary artery disease or hypertension; wherein the immune and inflammation diseases can be Grave's disease, arthritis, multiple sclerosis or cirrhosis; wherein the susceptibility to infection can be hepatitis B or chronic liver disease; wherein the metabolic defects can be cholestasis, hypospadias, obesity, osteoarthritis, osteopenia or osteoporosis; wherein the neurological defects can be Alzheimer's disease, Parkinson's disease, migraine, or dizziness; wherein the psychiatric defects can be anorexia nervosa, attention deficit hyperactivity disorder (ADHD), dementia, severe depressive disorder or psychosis; and wherein the reproductive defects can be menarche age, endometriosis and infertility, and the like.

The present invention is further directed to the compound of formula (I) or a tautomer, mesomer, racemate, enantiomer, diastereomer, or mixture thereof, or a pharmaceutically acceptable salt thereof, for use as a medicament.

The present invention is further directed to the compound of formula (I) or a tautomer, mesomer, racemate, enantiomer, diastereomer, or mixture thereof, or a pharmaceutically acceptable salt thereof, for use as a medicament for treating an estrogen receptor mediated or dependent disease or condition, wherein the estrogen receptor mediated or dependent disease or condition is as defined above.

The present invention is further directed to a method for treating an estrogen receptor mediated or dependent disease or condition, comprising a step of administering to a patient in need thereof a therapeutically effective amount of the compound of formula (I), or a tautomer, mesomer, racemate, enantiomer, diastereomer, or mixture thereof, or a pharmaceutically acceptable salt thereof. This method shows outstanding efficacy and fewer side effects. The estrogen receptor mediated or dependent disease or condition is as defined above.

In another aspect, the present invention is directed to a use of the compound of formula (I) or a tautomer, mesomer, racemate, enantiomer, diastereomer, or mixture thereof, or a pharmaceutically acceptable salt thereof, in the preparation of a medicament for preventing and/or treating cancer. The cancer is as defined above.

In another aspect, the present invention is directed to the compound of formula (I) or a tautomer, mesomer, racemate, enantiomer, diastereomer, or mixture thereof, or a pharmaceutically acceptable salt thereof, for use as a medicament for treating cancer. It shows outstanding efficacy and fewer side effects in treating cancer. The cancer is as defined above.

In another aspect, the present invention is directed to a method for treating cancer, comprising administering to a patient in need thereof a therapeutically effective amount of the compound of formula (I) or a tautomer, mesomer, racemate, enantiomer, diastereomer, or mixture thereof, or a pharmaceutically acceptable salt thereof. This method shows outstanding efficacy and fewer side effects. The cancer is as defined above.

In another aspect, the present invention is directed to the compound of formula (I) or a tautomer, mesomer, racemate, enantiomer, diastereomer, or mixture thereof, or a pharmaceutically acceptable salt thereof, for use as a medicament for treating bone cancer, breast cancer, colorectal cancer, endometrial cancer, prostate cancer, ovarian cancer, uterine cancer, cervical cancer, lung cancer, leiomyomata, uterine leiomyomas, alcoholism, migraine, aortic aneurysm, susceptibility to myocardial infarction, aortic valve sclerosis, cardiovascular disease, coronary artery disease, hypertension, deep vein thrombosis, Grave's disease, arthritis, multiple sclerosis, cirrhosis, hepatitis B, chronic liver disease, cholestasis, hypospadias, obesity, osteoarthritis, osteoporosis, osteoporosis, Alzheimer's disease, Parkinson's disease, migraine, dizziness, anorexia nervosa, attention deficit hyperactivity disorder (ADHD), dementia, severe depressive disorder, psychosis, menarche age, endometriosis or infertility in mammals.

In another aspect, the present invention is directed to a method for treating bone cancer, breast cancer, colorectal cancer, endometrial cancer, prostate cancer, ovarian cancer, uterine cancer, cervical cancer, lung cancer, leiomyomata, uterine leiomyomas, alcoholism, migraine, aortic aneurysm, susceptibility to myocardial infarction, aortic valve sclerosis, cardiovascular disease, coronary artery disease, hypertension, deep vein thrombosis, Grave's disease, arthritis, multiple sclerosis, cirrhosis, hepatitis B, chronic liver disease, cholestasis, hypospadias, obesity, osteoarthritis, osteoporosis, osteoporosis, Alzheimer's disease, Parkinson's disease, migraine, dizziness, anorexia nervosa, attention deficit hyperactivity disorder (ADHD), dementia, severe depressive disorder, psychosis, menarche age, endometriosis or infertility in mammals, comprising administering to a patient in need thereof a therapeutically effective amount of the compound of formula (I) or a tautomer, mesomer, racemate, enantiomer, diastereomer, or mixture thereof, or a pharmaceutically acceptable salt thereof.

Pharmaceutical compositions containing the active ingredient can be in a form suitable for oral administration, for example, a tablet, troche, lozenge, aqueous or oily suspension, dispersible powder or granule, emulsion, hard or soft capsule, or syrup or elixir. Oral compositions can be prepared according to any known method in the art for the preparation of pharmaceutical compositions. Such compositions can contain one or more additives selected from the group consisting of sweeteners, flavoring agents, colorants and preservatives, in order to provide a pleasing and palatable pharmaceutical preparation. Tablets contain the active ingredient and nontoxic pharmaceutically acceptable excipients suitable for the manufacture of tablets. These excipients can be inert excipients, granulating agents, disintegrating agents, and lubricants. The tablet can be uncoated or coated by means of a known technique to mask the taste of the drug or delay the disintegration and absorption of the drug in the gastrointestinal tract, thereby providing sustained release over an extended period. For example, water soluble taste masking materials can be used.

Oral formulations can also be provided as soft gelatin capsules in which the active ingredient is mixed with an inert solid diluent, or the active ingredient is mixed with a water soluble carrier.

An aqueous suspension contains the active ingredient in admixture with excipients suitable for the manufacture of an aqueous suspension. Such excipients are suspending agents, dispersants or humectants, and can be naturally occurring phospholipids. The aqueous suspension can also contain one or more preservatives, one or more colorants, one or more flavoring agents, and one or more sweeteners.

An oil suspension can be formulated by suspending the active ingredient in a vegetable oil, or in a mineral oil. The oil suspension can contain a thickener. The aforementioned sweeteners and flavoring agents can be added to provide a palatable preparation. These compositions can be preserved by adding an antioxidant.

The active ingredient and the dispersants or wetting agents, suspending agent or one or more preservatives can be prepared as a dispersible powder or granule suitable for the preparation of an aqueous suspension by adding water. Suitable dispersants or wetting agents and suspending agents are exemplified by those already mentioned above. Additional excipients, such as sweeteners, flavoring agents and colorants, can also be added. These compositions can be preserved by adding an antioxidant such as ascorbic acid.

The present pharmaceutical composition can also be in the form of an oil-in-water emulsion. The oil phase can be a vegetable oil, or a mineral oil, or mixture thereof. Suitable emulsifying agents can be naturally occurring phospholipids. Sweeteners can be used. Such formulations can also contain moderators, preservatives, colorants and antioxidants.

The pharmaceutical composition can be in the form of a sterile injectable aqueous solution. The acceptable vehicles and solvents that can be employed are water, Ringer's solution and isotonic sodium chloride solution. The sterile injectable preparation can also be a sterile injectable oil-in-water microemulsion in which the active ingredient is dissolved in the oil phase. The injectable solution or microemulsion can be introduced into an individual's bloodstream by local bolus injection. Alternatively, it can be advantageous to administer the solution or microemulsion in such a way as to maintain a constant circulating concentration of the present compound. In order to maintain such a constant concentration, a continuous intravenous delivery device can be utilized. An example of such a device is Deltec CADD-PLUS™ 5400 intravenous injection pump.

The pharmaceutical composition can be in the form of a sterile injectable aqueous or oily suspension for intramuscular and subcutaneous administration. Such a suspension can be formulated with suitable dispersants or wetting agents and suspending agents as described above according to known techniques. The sterile injectable preparation can also be a sterile injectable solution or suspension prepared in a nontoxic parenterally acceptable diluent or solvent. Moreover, sterile fixed oils can easily be used as a solvent or suspending medium, and fatty acids can also be used to prepare injections.

The present compound can be administered in the form of a suppository for rectal administration. These pharmaceutical compositions can be prepared by mixing the drug with a suitable non-irritating excipient that is solid at ordinary temperatures, but liquid in the rectum, thereby melting in the rectum to release the drug.

It is well known to those skilled in the art that the dosage of a drug depends on a variety of factors, including, but not limited to, the following factors: activity of the specific compound, age, weight, general health, behavior, diet of the patient, administration time, administration route, excretion rate, drug combination and the like. In addition, the best treatment, such as treatment mode, daily dose of the compound of formula (I) or the type of pharmaceutically acceptable salt thereof can be verified by traditional therapeutic regimens.

DETAILED DESCRIPTION OF THE INVENTION

Unless otherwise stated, the terms used in the specification and claims have the meanings described below.

"Alkyl" refers to a saturated aliphatic hydrocarbon group including $C_1$ to $C_{20}$ straight chain and branched chain groups, preferably an alkyl having 1 to 12 carbon atoms. Non-limiting examples include methyl, ethyl, n-propyl, isopropyl, n-butyl, isobutyl, tert-butyl, sec-butyl, n-pentyl, 1,1-dimethylpropyl, 1,2-dimethylpropyl, 2,2-dimethylpropyl, 1-ethylpropyl, 2-methylbutyl, 3-methylbutyl, n-hexyl, 1-ethyl-2-methylpropyl, 1,1,2-trimethylpropyl, 1,1-dimethylbutyl, 1,2-dimethylbutyl, 2,2-dimethylbutyl, 1,3-dimethylbutyl, 2-ethylbutyl, 2-methylpentyl, 3-methylpentyl, 4-methylpentyl, 2,3-dimethylbutyl, n-heptyl, 2-methylhexyl, 3-methylhexyl, 4-methylhexyl, 5-methylhexyl, 2,3-dimethylpentyl, 2,4-dimethylpentyl, 2,2-dimethylpentyl, 3,3-dimethylpentyl, 2-ethylpentyl, 3-ethylpentyl, n-octyl, 2,3-dimethylhexyl, 2,4-dimethylhexyl, 2,5-dimethylhexyl, 2,2-dimethylhexyl, 3,3-dimethylhexyl, 4,4-dimethylhexyl, 2-ethylhexyl, 3-ethylhexyl, 4-ethylhexyl, 2-methyl-2-ethylpentyl, 2-methyl-3-ethylpentyl, n-nonyl, 2-methyl-2-ethylhexyl, 2-methyl-3-ethylhexyl, 2,2-dimethylpentyl, n-decyl, 3,3-diethylhexyl, 2,2-diethylhexyl, and branched isomers thereof. More preferably, an alkyl group is a lower alkyl having 1 to 6 carbon atoms, and non-limiting examples include methyl, ethyl, n-propyl, isopropyl, n-butyl, isobutyl, tert-butyl, sec-butyl, n-pentyl, 1,1-dimethylpropyl, 1,2-dimethylpropyl, 2,2-dimethylpropyl, 1-ethylpropyl, 2-methylbutyl, 3-methylbutyl, n-hexyl, 1-ethyl-2-methylpropyl, 1,1,2-trimethylpropyl, 1,1-dimethylbutyl, 1,2-dimethylbutyl, 2,2-dimethylbutyl, 1,3-dimethylbutyl, 2-ethylbutyl, 2-methylpentyl, 3-methylpentyl, 4-methylpentyl, 2,3-dimethylbutyl, and the like. The alkyl group can be substituted or unsubstituted. When substituted, the substituent group(s) can be substituted at any available connection point. The substituent group(s) is preferably one or more groups independently selected from the group consisting of alkyl, alkenyl, alkynyl, alkoxy, alkylthio, alkylamino, halogen, thiol, hydroxy, nitro, cyano, cycloalkyl, heterocyclyl, aryl, heteroaryl, cycloalkoxy, heterocylic alkoxy, cycloalkylthio, heterocyclic alkylthio, oxo, carboxy, and alkoxycarbonyl.

"Cycloalkyl" refers to a saturated and/or partially unsaturated monocyclic or polycyclic hydrocarbon group having 3 to 20 carbon atoms, preferably 3 to 12 carbon atoms, and more preferably 3 to 6 carbon atoms. Non-limiting examples of monocyclic cycloalkyl include cyclopropyl, cyclobutyl, cyclopentyl, cyclopentenyl, cyclohexyl, cyclohexenyl, cyclohexadienyl, cycloheptyl, cycloheptatrienyl, cyclooctyl, and the like. Polycyclic cycloalkyl includes a cycloalkyl having a spiro ring, fused ring or bridged ring.

"Spiro cycloalkyl" refers to a 5 to 20 membered polycyclic group with rings connected through one common carbon atom (called a spiro atom), wherein one or more rings can contain one or more double bonds, but none of the rings has a completely conjugated pi-electron system, preferably 6 to 14 membered spiro cycloalkyl, and more preferably 7 to 10 membered spiro cycloalkyl. According to the number of the spiro atoms shared between the rings, spiro cycloalkyl can be divided into mono-spiro cycloalkyl, di-spiro cycloalkyl, or poly-spiro cycloalkyl, preferably a mono-spiro cycloalkyl or di-spiro cycloalkyl, and more preferably 4-membered/4-membered, 4-membered/5-membered, 4-membered/6-membered, 5-membered/5-membered, or 5-membered/6-membered mono-spiro cycloalkyl. Non-limiting examples of spiro cycloalkyls include:

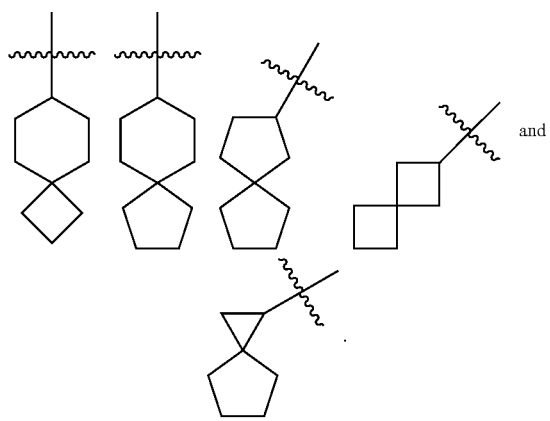

"Fused cycloalkyl" refers to a 5 to 20 membered full-carbon polycyclic group, wherein each ring in the system shares an adjacent pair of carbon atoms with another ring, wherein one or more rings can contain one or more double bonds, but none of the rings has a completely conjugated pi-electron system, preferably 6 to 14 membered fused cycloalkyl, more preferably 7 to 10 membered fused cycloalkyl. According to the number of membered rings, fused cycloalkyl can be divided into bicyclic, tricyclic, tetracyclic or polycyclic fused cycloalkyl, preferably bicyclic or tricyclic fused cycloalkyl, and more preferably 5-membered/5-membered, or 5-membered/6-membered bicyclic fused cycloalkyl. Non-limiting examples of fused cycloalkyl include:

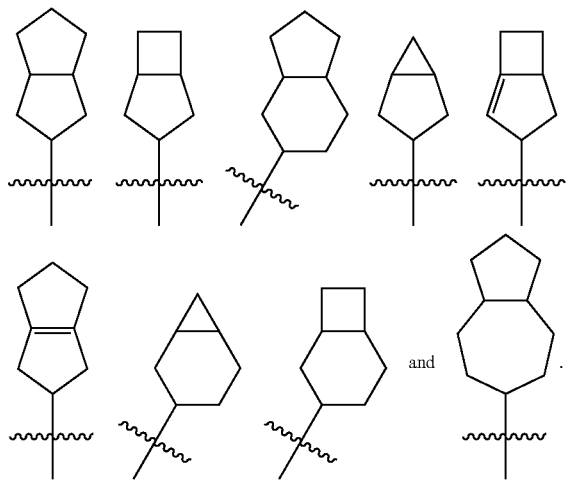

"Bridged cycloalkyl" refers to a 5 to 20 membered full-carbon polycyclic group, wherein every two rings in the system share two disconnected atoms, wherein the rings can have one or more double bonds, but none of the rings has a completely conjugated pi-electron system, preferably 6 to 14 membered bridged cycloalkyl, and more preferably 7 to 10 membered bridged cycloalkyl. According to the number of membered rings, bridged cycloalkyl can be divided into bicyclic, tricyclic, tetracyclic or polycyclic bridged cycloalkyl, preferably bicyclic, tricyclic or tetracyclic bridged cycloalkyl, and more preferably bicyclic or tricyclic bridged cycloalkyl. Non-limiting examples of bridged cycloalkyls include:

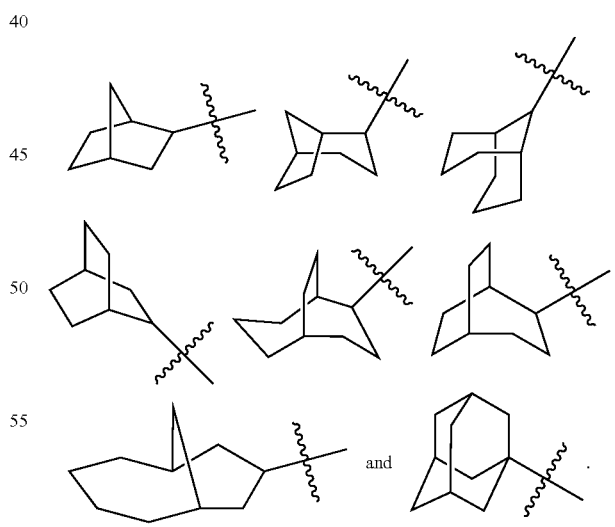

The cycloalkyl ring can be fused to the ring of aryl, heteroaryl or heterocyclyl, wherein the ring bound to the parent structure is cycloalkyl. Non-limiting examples include indanyl, tetrahydronaphthyl, benzocycloheptyl and the like. The cycloalkyl can be optionally substituted or unsubstituted. When substituted, the substituent group(s) is preferably one or more groups independently selected from the group consisting of alkyl, alkenyl, alkynyl, alkoxy, alkylthio, alkylamino, halogen, thiol, hydroxy, nitro, cyano, cycloalkyl, heterocyclyl, aryl, heteroaryl, cycloalkoxy, heterocylic alkoxy, cycloalkylthio, heterocyclic alkylthio, oxo, carboxy and alkoxycarbonyl.

"Heterocyclyl" refers to a 3 to 20 membered saturated and/or partially unsaturated monocyclic or polycyclic hydrocarbon group having one or more heteroatoms selected from the group consisting of N, O, and S(O)m (wherein m is an integer of 0 to 2) as ring atoms, but excluding —O—O—, —O—S— or —S—S— in the ring, with the remaining ring atoms being carbon atoms. Preferably, heterocyclyl has 3 to 12 atoms wherein 1 to 4 atoms are heteroatoms, and more preferably 3 to 6 atoms. Non-limiting examples of monocyclic heterocyclyl include pyrrolidinyl, imidazolidinyl, tetrahydrofuranyl, tetrahydrothienyl, dihydroimidazolyl, dihydrofuryl, dihydropyrazolyl, dihydropyrrolyl, piperidinyl, piperazinyl, morpholinyl, thiomorpholinyl, homopiperazinyl and the like, and preferably piperidinyl or pyrrolidinyl. Polycyclic heterocyclyl includes a heterocyclyl having a spiro ring, fused ring or bridged ring.

"Spiro heterocyclyl" refers to a 5 to 20 membered polycyclic heterocyclyl with rings connected through one common atom (called a spiro atom), wherein the rings have one or more heteroatoms selected from the group consisting of N, O, and S(O)m (wherein m is an integer of 0 to 2) as ring atoms, with the remaining ring atoms being carbon atoms, wherein one or more rings can contain one or more double bonds, but none of the rings has a completely conjugated pi-electron system, preferably 6 to 14 membered spiro heterocyclyl, and more preferably 7 to 10 membered spiro heterocyclyl. According to the number of the spiro atoms shared between the rings, spiro heterocyclyl can be divided into mono-spiro heterocyclyl, di-spiro heterocyclyl, or polyspiro heterocyclyl, preferably mono-spiro heterocyclyl or di-spiro heterocyclyl, and more preferably 4-membered/4-membered, 4-membered/5-membered, 4-membered/6-membered, 5-membered/5-membered, or 5-membered/6-membered mono-spiro heterocyclyl. Non-limiting examples of spiro heterocyclyls include:

"Fused heterocyclyl" refers to a 5 to 20 membered polycyclic heterocyclyl group, wherein each ring in the system shares an adjacent pair of atoms with another ring, wherein one or more rings can contain one or more double bonds, but none of the rings has a completely conjugated pi-electron system, and wherein the rings have one or more heteroatoms selected from the group consisting of N, O, and S(O)m (wherein m is an integer of 0 to 2) as ring atoms, with the remaining ring atoms being carbon atoms, preferably 6 to 14 membered fused heterocyclyl, and more preferably 7 to 10 membered fused heterocyclyl. According to the number of membered rings, fused heterocyclyl can be divided into bicyclic, tricyclic, tetracyclic or polycyclic fused heterocyclyl, preferably bicyclic or tricyclic fused heterocyclyl, and more preferably 5-membered/5-membered, or 5-membered/6-membered bicyclic fused heterocyclyl. Non-limiting examples of fused heterocyclyl include:

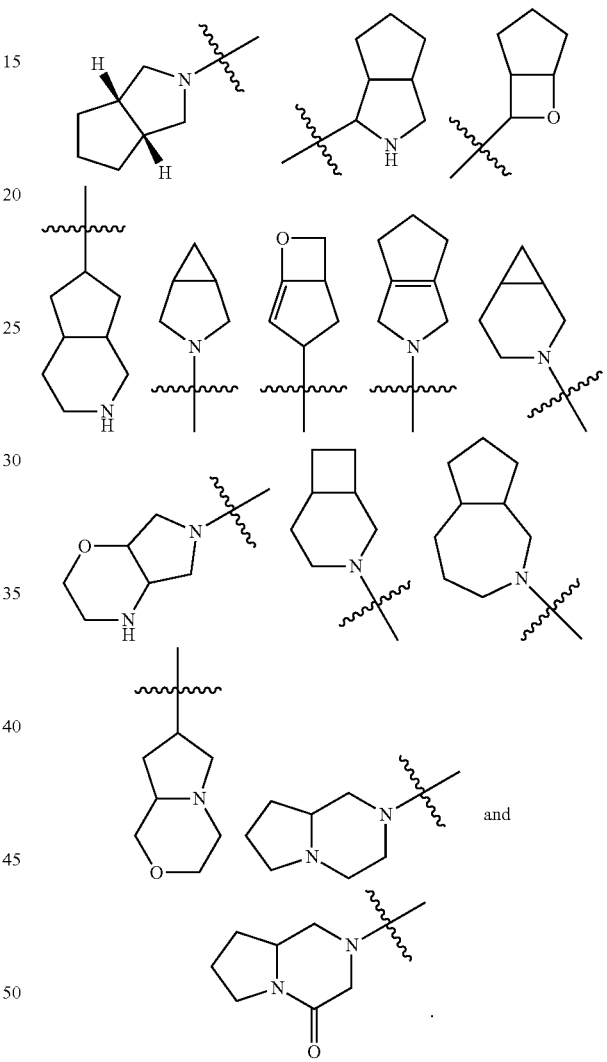

"Bridged heterocyclyl" refers to a 5 to 14 membered polycyclic heterocyclyl group, wherein every two rings in the system share two disconnected atoms, wherein the rings can have one or more double bonds, but none of the rings has a completely conjugated pi-electron system, and the rings have one or more heteroatoms selected from the group consisting of N, O, and S(O)m (wherein m is an integer of 0 to 2) as ring atoms, with the remaining ring atoms being carbon atoms, preferably 6 to 14 membered bridged heterocyclyl, and more preferably 7 to 10 membered bridged heterocyclyl. According to the number of membered rings, bridged heterocyclyl can be divided into bicyclic, tricyclic, tetracyclic or polycyclic bridged heterocyclyl, preferably bicyclic, tricyclic or tetracyclic bridged heterocyclyl, and more preferably bicyclic or tricyclic bridged heterocyclyl. Non-limiting examples of bridged heterocyclyls include:

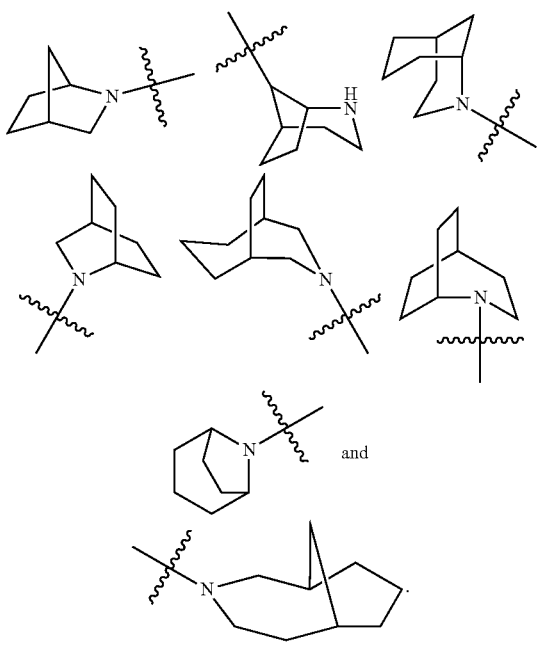

The heterocyclyl ring can be fused to the ring of aryl, heteroaryl or cycloalkyl, wherein the ring bound to the parent structure is heterocyclyl. Non-limiting examples include:

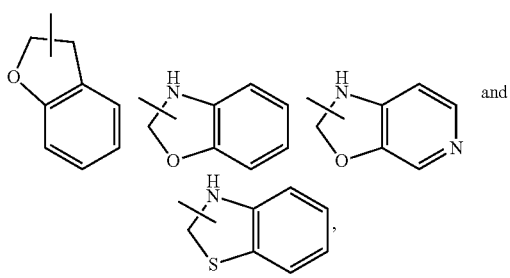

and the like.

The heterocyclyl can be optionally substituted or unsubstituted. When substituted, the substituent group(s) is preferably one or more group(s) independently selected from the group consisting of alkyl, alkenyl, alkynyl, alkoxy, alkylthio, alkylamino, halogen, thiol, hydroxy, nitro, cyano, cycloalkyl, heterocyclyl, aryl, heteroaryl, cycloalkoxy, heterocylic alkoxy, cycloalkylthio, heterocyclic alkylthio, oxo, carboxy and alkoxycarbonyl.

"Aryl" refers to a 6 to 14 membered full-carbon monocyclic ring or polycyclic fused ring (i.e. each ring in the system shares an adjacent pair of carbon atoms with another ring in the system) having a completely conjugated pi-electron system, preferably 6 to 10 membered aryl, for example, phenyl and naphthyl. The aryl ring can be fused to the ring of heteroaryl, heterocyclyl or cycloalkyl, wherein the ring bound to the parent structure is aryl ring. Non-limiting examples include:

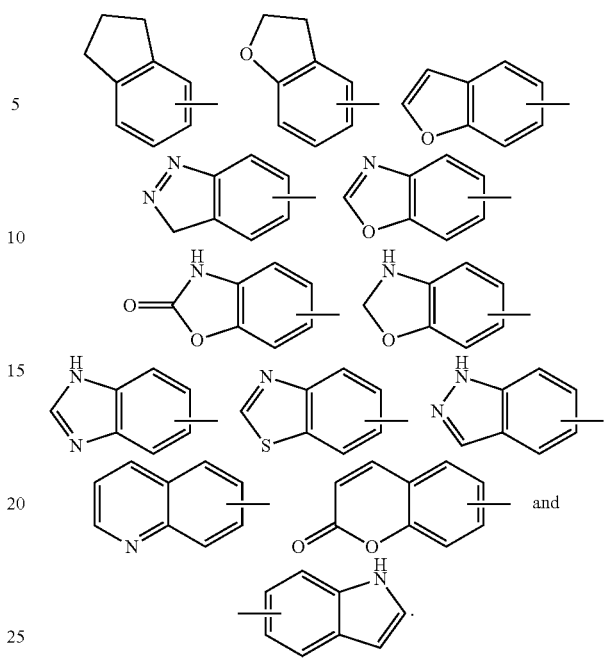

The aryl can be optionally substituted or unsubstituted. When substituted, the substituent group(s) is preferably one or more groups independently selected from the group consisting of alkyl, alkenyl, alkynyl, alkoxy, alkylthio, alkylamino, halogen, thiol, hydroxy, nitro, cyano, cycloalkyl, heterocyclyl, aryl, heteroaryl, cycloalkoxy, heterocylic alkoxy, cycloalkylthio, heterocyclic alkylthio, carboxy and alkoxycarbonyl, and preferably phenyl.

"Heteroaryl" refers to a 5 to 14 membered heteroaromatic system having 1 to 4 heteroatoms selected from the group consisting of O, S and N as ring atoms, preferably 5 to 10 membered heteroaryl, and more preferably 5 or 6 membered heteroaryl, for example, imidazolyl, furyl, thienyl, thiazolyl, pyrazolyl, oxazolyl, pyrrolyl, tetrazolyl, pyridinyl, pyrimidinyl, thiadiazole, pyrazinyl and the like, preferably imidazolyl, pyrazolyl, pyrimidinyl or thiazolyl, and more preferably pyrazolyl or thiazolyl. The heteroaryl ring can be fused to the ring of aryl, heterocyclyl or cycloalkyl, wherein the ring bound to the parent structure is heteroaryl ring. Non-limiting examples include:

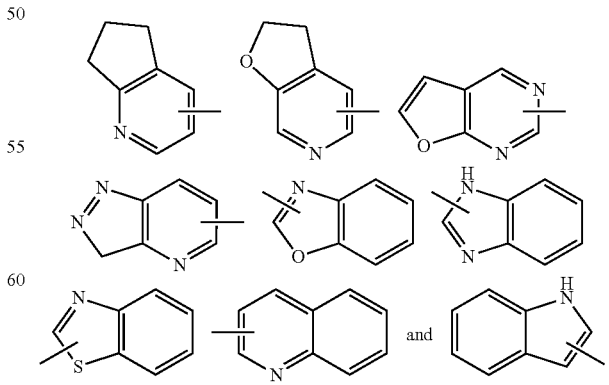

The heteroaryl can be optionally substituted or unsubstituted. When substituted, the substituent group(s) is preferably one or more groups independently selected from the group consisting of alkyl, alkenyl, alkynyl, alkoxy, alkylthio, alkylamino, halogen, thiol, hydroxy, nitro, cyano, cycloalkyl, heterocyclyl, aryl, heteroaryl, cycloalkoxy, heterocylic alkoxy, cycloalkylthio, heterocyclic alkylthio, carboxy and alkoxycarbonyl.

"Alkoxy" refers to an —O-(alkyl) or an —O-(unsubstituted cycloalkyl) group, wherein the alkyl is as defined above. Non-limiting examples include methoxy, ethoxy, prop oxy, butoxy, cyclopropyloxy, cyclobutyloxy, cyclopentyloxy, cyclohexyloxy. The alkoxy can be optionally substituted or unsubstituted. When substituted, the substituent(s) is preferably one or more groups independently selected from the group consisting of alkyl, alkenyl, alkynyl, alkoxy, alkylthio, alkylamino, halogen, thiol, hydroxy, nitro, cyano, cycloalkyl, heterocyclyl, aryl, heteroaryl, cycloalkoxy, heterocylic alkoxy, cycloalkylthio, heterocyclic alkylthio, carboxy and alkoxycarbonyl.

"Hydroxyalkyl" refers to an alkyl substituted by hydroxy, wherein the alkyl is as defined above.

"Haloalkyl" refers to an alkyl substituted by halogen, wherein the alkyl is as defined above.

"Deuteroalkyl" refers to an alkyl substituted by deuterium atom, wherein the alkyl is as defined above.

"Hydroxy" refers to an —OH group.

"Halogen" refers to fluorine, chlorine, bromine or iodine.

"Amino" refers to a —$NH_2$ group.

"Cyano" refers to a —CN group.

"Nitro" refers to a —$NO_2$ group.

"Carboxy" refers to a —C(O)OH group.

"Aldehyde" refers to a —CHO group.

"Alkoxycarbonyl" refers to a —C(O)O(alkyl) or —C(O)O(cycloalkyl) group, wherein the alkyl and cycloalkyl are as defined above.

"Acyl halide" refers to a compound comprising a —C(O)-halogen group.

"Optional" or "optionally" means that the event or circumstance described subsequently can, but need not, occur, and such a description includes the situation in which the event or circumstance does or does not occur. For example, "the heterocyclyl group optionally substituted by an alkyl" means that an alkyl group can be, but need not be, present, and such a description includes the situation of the heterocyclyl group being substituted by an alkyl and the heterocyclyl group being not substituted by an alkyl.

"Substituted" refers to one or more hydrogen atoms in a group, preferably up to 5, and more preferably 1 to 3 hydrogen atoms, independently substituted by a corresponding number of substituents. It goes without saying that the substituents only exist in their possible chemical position. The person skilled in the art is able to determine whether the substitution is possible or impossible by experiments or theory without paying excessive efforts. For example, the combination of amino or hydroxy having free hydrogen and carbon atoms having unsaturated bonds (such as olefinic) can be unstable.

A "pharmaceutical composition" refers to a mixture of one or more of the compounds according to the present invention or physiologically/pharmaceutically acceptable salts or prodrugs thereof and other chemical components, and other components such as physiologically/pharmaceutically acceptable carriers and excipients. The purpose of a pharmaceutical composition is to facilitate administration of a compound to an organism, which is conducive to the absorption of the active ingredient, thus displaying biological activity.

"Pharmaceutically acceptable salt" refers to a salt of the compound of the present invention, which is safe and effective in mammals and has the desired biological activity.

In the present invention, different terms, such as "X is selected from the group consisting of A, B or C", "X is selected from the group consisting of A, B and C", "X is A, B or C" and "X is A, B and C", are the same meaning. It means that X can be any one or more of A, B, and C.

Synthesis Method of the Compound of the Present Invention

In order to achieve the object of the present invention, the present invention applies the following synthesis technical solutions.

A process for preparing a compound of formula (I) of the present invention or a tautomer, mesomer, racemate, enantiomer, diastereomer, or mixture thereof, or a pharmaceutically acceptable salt thereof, comprises the following steps:

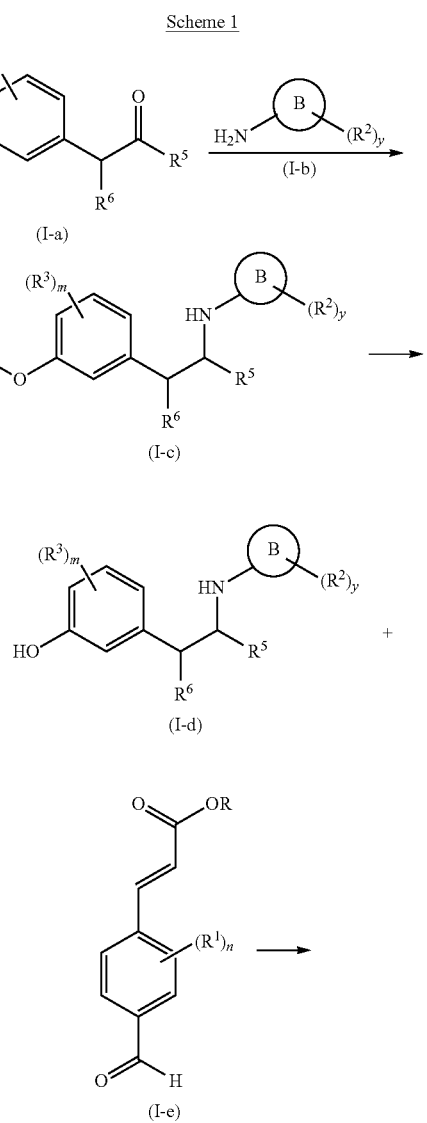

Scheme 1

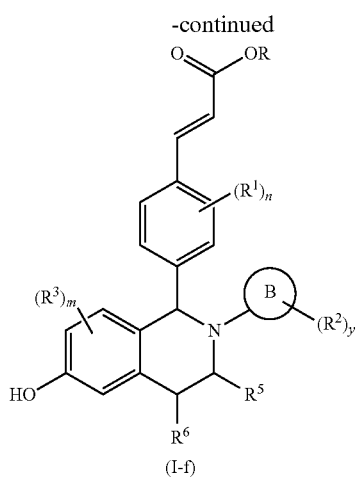

(I-f)

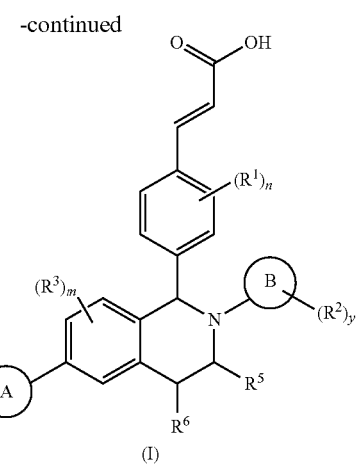

(I)

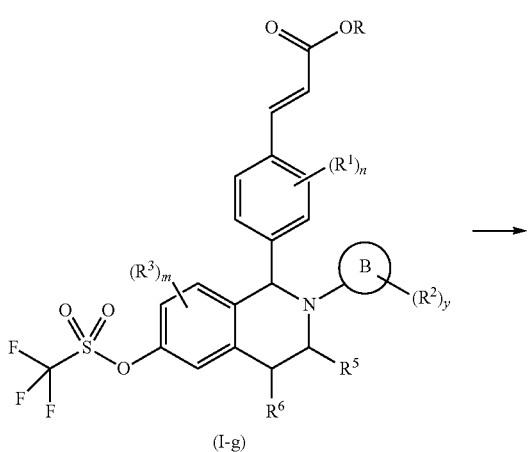

(I-g)

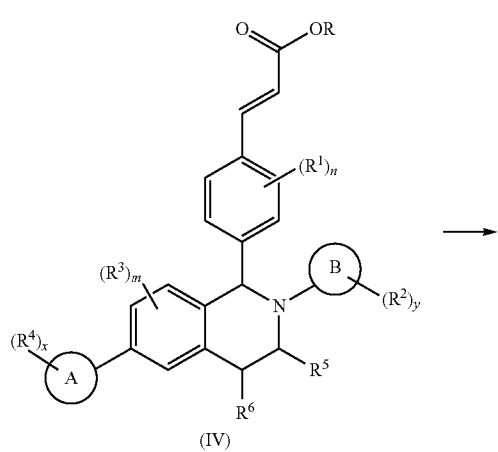

(IV)

A compound of formula (I-a) reacts with a compound of formula (I-b) under an alkaline condition to obtain a compound of formula (I-c), wherein the alkaline reagent for this reaction is preferably sodium triacetoxyborohydride. The resulting compound of formula (I-c) reacts with boron tribomide at room temperature to obtain a compound of formula (I-d). The resulting compound of formula (I-d) reacts with a compound of formula (I-e) and triisopropylsilyl chloride under heating to obtain a compound of formula (I-f). The resulting compound of formula (I-f) further reacts with trifluoromethanesulfonic anhydride at low temperature to obtain a compound of formula (I-g). The resulting compound of formula (I-g) reacts with a borane compound in the presence of a catalyst to obtain a compound of formula (IV), wherein the catalyst for the reaction is preferably [1,1'-bis(diphenylphosphino)ferrocene]dichloropalladium. The resulting compound of formula (IV) is hydrolyzed under an alkaline condition to obtain a compound of formula (I), wherein the alkline reagent for this reaction is preferably lithium hydroxide or sodium hydroxide.

The reagent that provides an alkaline condition includes organic bases and inorganic bases, wherein the organic bases include, but are not limited to, triethylamine, N,N-diisopropylethylamine, n-butyllithium, lithium diisopropylamide, potassium acetate, sodium tert-butoxide and potassium tert-butoxide, and wherein the inorganic bases include, but are not limited to, sodium hydride, potassium phosphate, sodium carbonate, potassium carbonate or cesium carbonate, sodium hydroxide and lithium hydroxide.

The catalyst involved includes, but is not limited to, 2-dicyclohexylphosphino-2,4,6-triisopropylbiphenyl, (±)-2,2'-bis(diphenylphosphino)-1,1'-binaphthalene, tris(dibenzylideneacetone)dipalladium, palladium acetate, [1,1'-bis(diphenylphosphino)ferrocene]dichloropalladium, triphenylphosphine, tetrakistriphenylphosphine palladium.

The solvent used herein includes, but is not limited to, acetic acid, methanol, ethanol, toluene, tetrahydrofuran, dichloromethane, dimethylsulfoxide, 1,4-dioxane, water and N,N-dimethylformamide.

Wherein:

R is alkyl or cycloalkyl, wherein the alkyl and cycloalkyl are each optionally substituted by one or more groups selected from the group consisting of alkyl, halogen, amino, cyano, hydroxy, alkoxy, carboxy and cycloalkyl; and ring A, ring B, $R^1$ to $R^6$, m, n, x and y are as defined in formula (I).

The compounds of formula (I) of the present invention can also be prepared as follows:

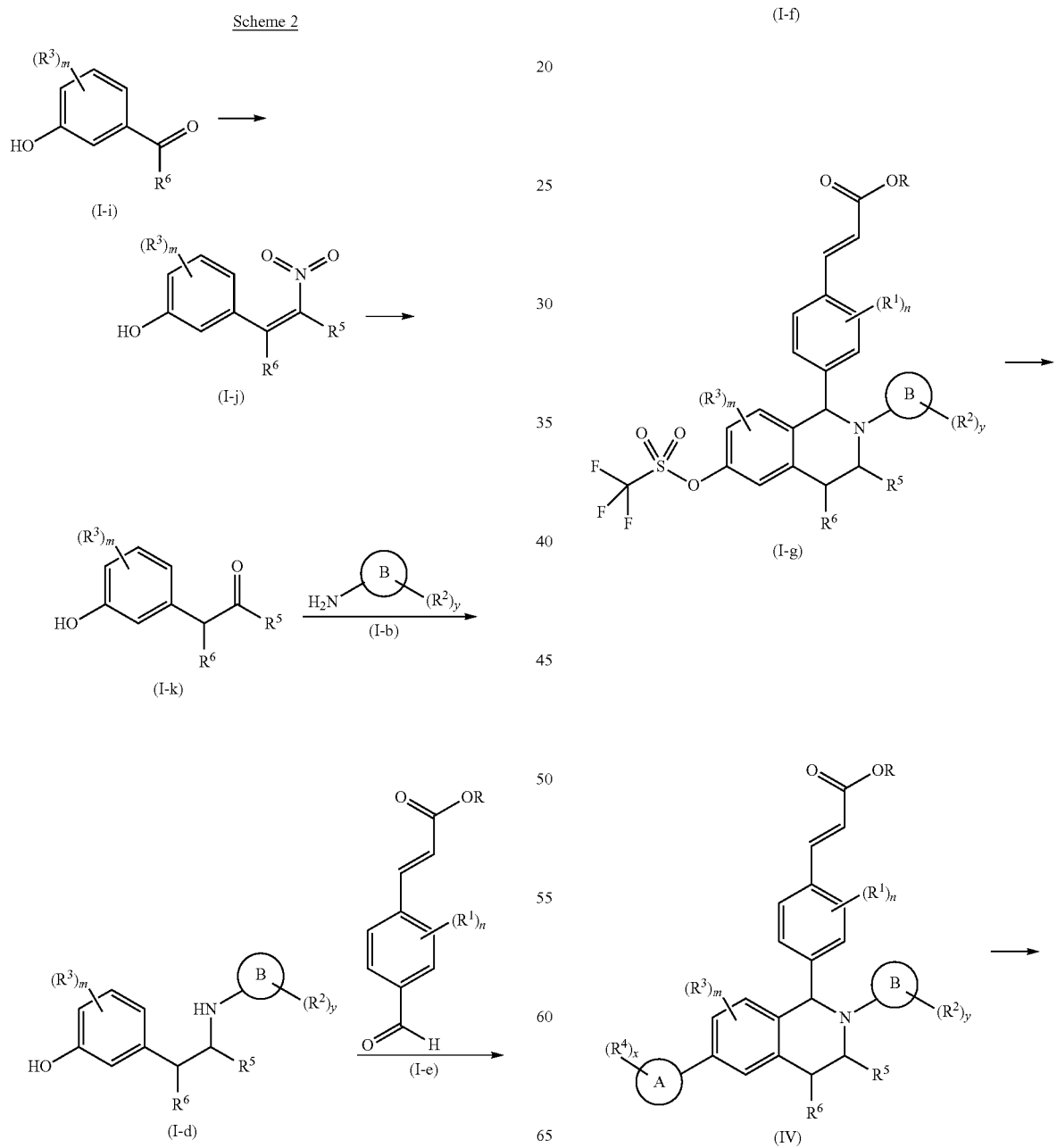

-continued

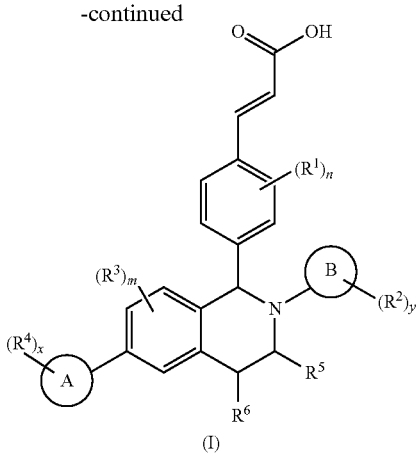

(I)

A compound of formula (I-i) reacts with a nitroalkane compound, methylamine and ammonium acetate under heating to obtain a compound of formula (I-j). The resulting compound of formula (I-j) reacts with Raney nickel under an acidic condition to obtain a compound of formula (I-k), wherein the acidic reagent for this reaction is preferably acetic acid. The resulting compound of formula (I-k) reacts with a compound of formula (I-b) under an alkaline condition to obtain a compound of formula (I-d), wherein the alkaline reagent for this reaction is preferably sodium triacetoxyborohydride and triethylamine. The resulting compound of formula (I-d) reacts with a compound of formula (I-e) and triisopropylsilyl chloride under heating to obtain a compound of formula (I-f). The resulting compound of formula (I-f) further reacts with trifluoromethanesulfonic anhydride at low temperature to obtain a compound of formula (I-g). The resulting compound of formula (I-g) reacts with a borane compound in the presence of a catalyst to obtain a compound of formula (IV), wherein the catalyst for the reaction is preferably [1,1'-bis(diphenylphosphino)ferrocene]dichloropalladium. The resulting compound of formula (IV) is hydrolyzed under an alkaline condition to obtain a compound of formula (I), wherein the alkline reagent for this reaction is preferably lithium hydroxide or sodium hydroxide.

The reagent that provides an alkaline condition includes organic bases and inorganic bases, wherein the organic bases include, but are not limited to, triethylamine, N,N-diisopropylethylamine, n-butyllithium, lithium diisopropylamide, potassium acetate, sodium tert-butoxide and potassium tert-butoxide, and wherein the inorganic bases include, but are not limited to, sodium hydride, potassium phosphate, sodium carbonate, potassium carbonate or cesium carbonate, sodium hydroxide and lithium hydroxide.

The solvent used herein includes, but is not limited to, acetic acid, methanol, ethanol, toluene, tetrahydrofuran, dichloromethane, dimethylsulfoxide, 1,4-dioxane, water and N,N-dimethylformamide.

Wherein:

R is alkyl or cycloalkyl, wherein the alkyl and cycloalkyl are each optionally substituted by one or more groups selected from the group consisting of alkyl, halogen, amino, cyano, hydroxy, alkoxy, carboxy and cycloalkyl; and ring A, ring B, $R^1$ to $R^6$, m, n, x and y are as defined in formula (I).

PREFERRED EMBODIMENTS

The present invention will be further described with reference to the following examples, but the examples should not be considered as limiting the scope of the invention.

EXAMPLES

The structures of the compounds were identified by nuclear magnetic resonance (NMR) and/or mass spectrometry (MS). NMR chemical shifts ($\delta$) are given in $10^{-6}$ (ppm). NMR was determined by a Bruker AVANCE-400 machine. The solvents for determination were deuterated-dimethyl sulfoxide (DMSO-$d_6$), deuterated-chloroform (CDCl$_3$) and deuterated-methanol (CD$_3$OD), and the internal standard was tetramethylsilane (TMS).

MS was determined by a FINNIGAN LCQAd (ESI) mass spectrometer (manufacturer: Thermo, type: Finnigan LCQ advantage MAX).

High performance liquid chromatography (HPLC) was determined on an Agilent 1200DAD high pressure liquid chromatography spectrometer (Sunfire C18 150×4.6 mm chromatographic column) and a Waters 2695-2996 high pressure liquid chromatography spectrometer (Gimini C18 150×4.6 mm chromatographic column).

Chiral HPLC was determined on a LC-10A vp (Shimadzu) or SFC-analytical (Berger Instruments Inc.).

The average kinase inhibition rates and IC$_{50}$ values was determined by a NovoStar ELISA (BMG Co., Germany).

Yantai Huanghai HSGF254 or Qingdao GF254 silica gel plate was used for thin-layer silica gel chromatography (TLC). The dimension of the silica gel plate used in TLC was 0.15 mm to 0.2 mm, and the dimension of the silica gel plate used in product purification was 0.4 mm to 0.5 mm.

Yantai Huanghai 200 to 300 mesh silica gel was used as a carrier for column chromatography.

Prep Star SD-1 (Varian Instruments Inc.) or SFC-multigram (Berger Instruments Inc.) was used for chiral preparation column chromatography.

The known starting materials of the present invention can be prepared by the conventional synthesis methods in the art, or can be purchased from ABCR GmbH & Co. KG, Acros Organnics, Aldrich Chemical Company, Accela ChemBio Inc., or Dari chemical Company, etc.

Unless otherwise stated, the reactions were carried out under a nitrogen atmosphere or argon atmosphere.

The term "nitrogen atmosphere" or "argon atmosphere" means that a reaction flask is equipped with a 1 L argon or nitrogen balloon.

The term "hydrogen atmosphere" means that a reaction flask is equipped with a 1 L hydrogen balloon.

Pressurized hydrogenation reactions were performed with a Parr 3916EKX hydrogenation instrument and a QL-500 hydrogen generator or HC2-SS hydrogenation instrument.

In hydrogenation reactions, the reaction system is generally vacuumed and filled with hydrogen, with the above operation repeated three times.

CEM Discover-S 908860 type microwave reactor was used in microwave reactions.

Unless otherwise stated, the solution used in the reactions refers to an aqueous solution.

Unless otherwise stated, the reaction temperature in the reactions refers to room temperature from 20° C. to 30° C.

The reaction process was monitored by thin layer chromatography (TLC), and the developing solvent system included: A: dichloromethane and methanol, B: n-hexane and ethyl acetate, C: petroleum ether and ethyl acetate, D: acetone. The ratio of the volume of the solvent was adjusted according to the polarity of the compounds. The elution system for purification of the compounds by column chromatography and thin layer chromatography included: A: dichloromethane and methanol, B: n-hexane and ethyl acetate, C: dichloromethane and acetone. The ratio of the volume of the solvent was adjusted according to the polarity of the compounds, and sometimes a little alkaline reagent such as triethylamine or acidic reagent such as acetic acid was added.

Example 1

(E)-3-(4-((1R,3R/1S, 3 S)-2-(4-Ethylphenyl)-3-methyl-6-(1-methyl-1H-pyrazol-4-yl)-1,2,3,4-tetrahydroisoquinolin-1-yl)phenyl)acrylic acid

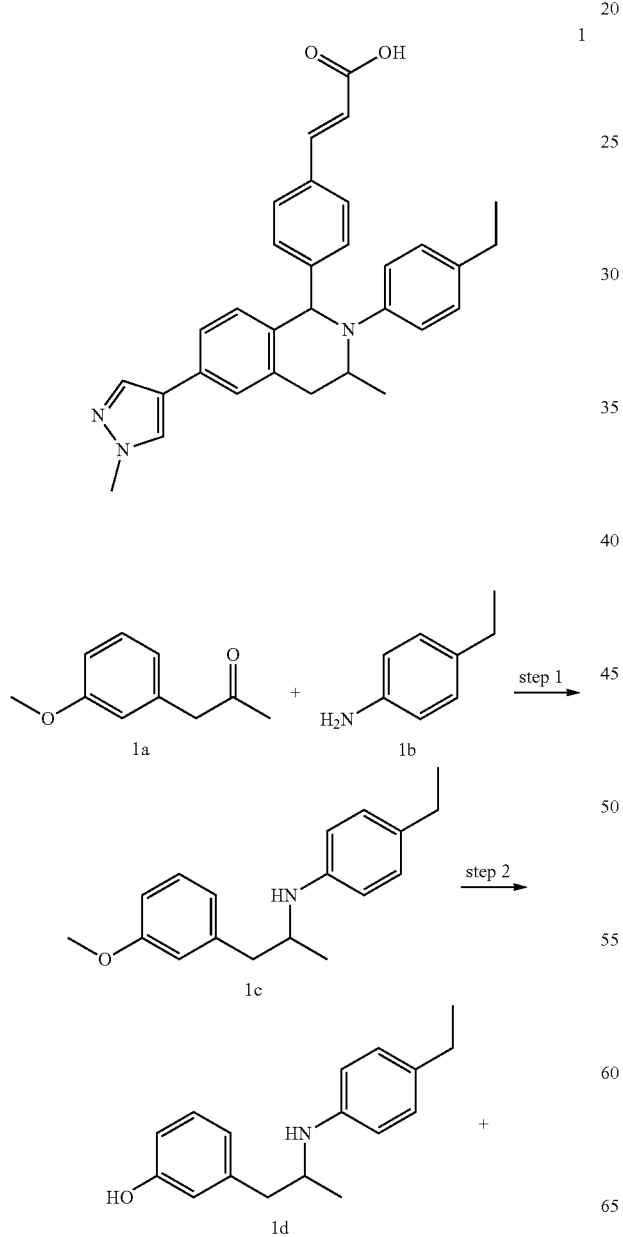

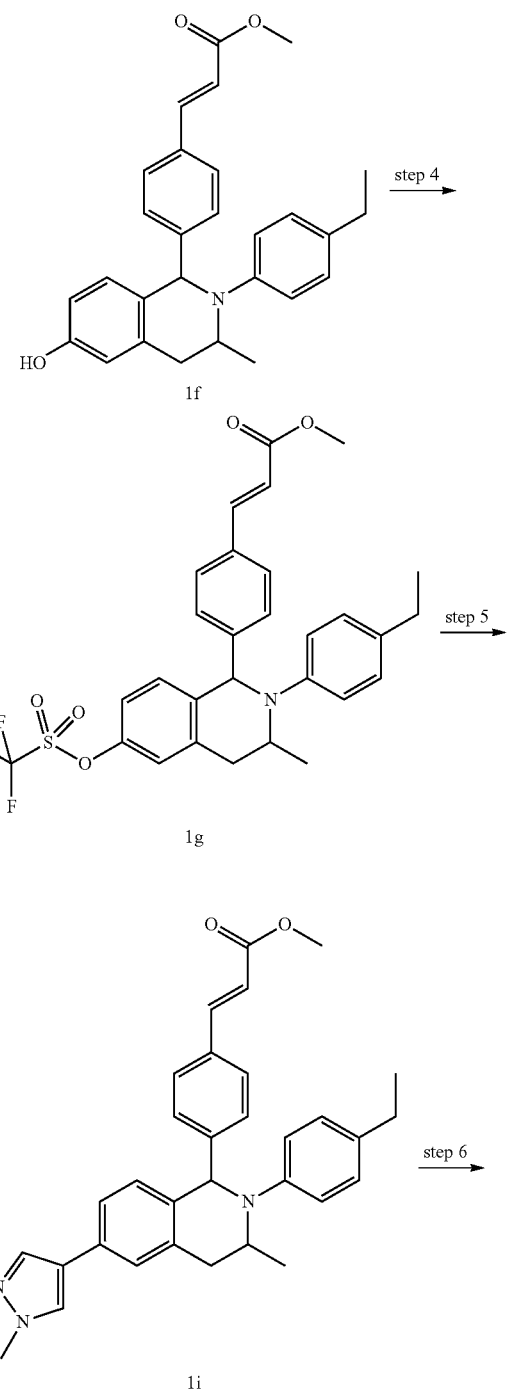

-continued

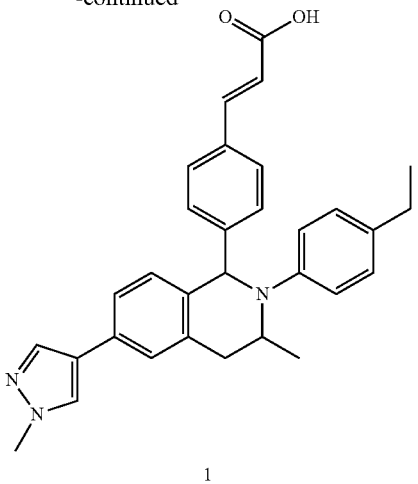

1

Step 1

4-Ethyl-N-(1-(3-methoxyphenyl)propan-2-yl)aniline 1c 1-(3-methoxyphenyl)propan-2-one 1a (820 mg, 5 mmol), 4-ethylaniline 1b (0.75 mL, 6 mmol) and sodium triacetoxyborohydride (1.58 g, 7.5 mmol) were dissolved in 30 mL of 1,2-dichloroethane. The mixture was stirred for 16 hours. Then, 30 mL of water were added to quench the reaction. The reaction solution was extracted with dichloromethane (30 mL×2). The organic phases were combined, dried over anhydrous sodium sulfate, and filtrated to remove the desiccant. The filtrate was concentrated under reduced pressure. The resulting residue was purified by silica gel column chromatography with elution system B to obtain the title compound 1c (700 mg, yield 51.9%) as a yellow oil.

MS m/z (ESI): 270.2 [M+1]

Step 2

3-(2-((4-Ethylphenyl)amino)propyl)phenol 1d

Compound 1c (640 mg, 2.37 mmol) was dissolved in 18 mL of dichloromethane, then a solution of 1 M boron tribromide in dichloromethane (4.7 mL, 4.7 mmol) was added dropwise in an ice bath. After completion of the addition, the reaction was stirred for 16 hours at room temperature. Then, 30 mL of water were added to quench the reaction. The reaction solution was concentrated under reduced pressure to remove dichloromethane. Another 30 mL of water were added. The mixture was stirred uniformly, and extracted with ethyl acetate (25 mL×3). The organic phases were combined, dried over anhydrous sodium sulfate, and filtrated to remove the desiccant. The filtrate was concentrated under reduced pressure. The resulting residue was purified by silica gel column chromatography with elution system A to obtain the title compound 1d (540 mg, yield 89.4%) as a yellow oil.

Step 3

(E)-Methyl 3-(4-(2-(4-ethylphenyl)-6-hydroxy-3-methyl-1,2,3,4-tetrahydroisoquinolin-1-yl)phenyl)acrylate 1f Compound 1d (270 mg, 1.06 mmol), (E)-methyl 3-(4-formylphenyl)acrylate 1e (402 mg, 2.11 mmol) and triisopropylsilyl chloride (1.02 g, 5.29 mmol) were added to 10 mL of N,N-dimethylformaminde. After completion of the addition, the mixture was heated to 120° C. and stirred for 3 hours. After stopping heating, the reaction solution was cooled to room temperature, and 30 mL of water were added. The mixture was extracted with ethyl acetate (30 mL×3). The organic phases were combined, washed with saturated sodium chloride solution (30 mL), dried over anhydrous sodium sulfate, and filtrated to remove the desiccant. The filtrate was concentrated under reduced pressure. The resulting residue was purified by silica gel column chromatography with elution system B to obtain the title compound 1f (292 mg, yield 64.6%) as a yellow solid.

Step 4

(E)-Methyl 3-(4-((1R,3R/1S,3S)-2-(4-ethylphenyl)-3-methyl-6-(((trifluoromethyl) sulfonyl)oxy)-1,2,3,4-tetrahydroisoquinolin-1-yl)phenyl)acrylate 1g Compound 1f (292 mg, 0.68 mmol) was dissolved in 30 mL of dichloromethane, then 2,6-lutidine (110 mg, 1.02 mmol) was added. After completion of the addition, the reaction was cooled to 0° C. in an ice bath, and trifluoromethanesulfonic anhydride (289 mg, 1.02 mmol) was added dropwise. After completion of the addition, the ice bath was removed, and the reaction was stirred for 16 hours at room temperature. Then, 30 mL of water were added to quench the reaction, and two phases were separated. The organic phase was dried over anhydrous sodium sulfate, and filtrated to remove the desiccant. The filtrate was concentrated under reduced pressure. The resulting residue was purified by silica gel column chromatography with elution system B to obtain the title compound 1g (163 mg, yield 42.7%) as a light yellow solid.

Step 5

(E)-Methyl 3-(4-((1R,3R/1S,3S)-2-(4-ethylphenyl)-3-methyl-6-(1-methyl-1H-pyrazol-4-yl)-1,2,3,4-tetrahydroisoquinolin-1-yl)phenyl)acrylate 1i Compound 1g (163 mg, 0.29 mmol), 1-methyl-4-(4,4,5,5-tetramethyl-1,3,2-dioxaborolan-2-yl)-1H-pyrazole (91 mg, 0.44 mmol), and [1,1'-bis(diphenylphosphino)ferrocene]dichloropalladium (21 mg, 0.03 mmol) were dissolved in 12 mL of a mixture of 1,4-dioxane and water (V:V=7:1). 2M sodium carbonate solution (0.29 mL, 0.58 mmol) was added. After completion of the addition, the mixture was stirred in a microwave at 120° C. for 40 minutes. After cooling to room temperature, 30 mL of water were added, and the mixture was extracted with ethyl acetate (30 mL×3). The organic phases were combined, washed with saturated sodium chloride solution (20 mL×2), dried over anhydrous sodium sulfate, and filtrated to remove the desiccant. The filtrate was concentrated under reduced pressure to obtain the crude title compound 1i (143 mg) as a yellow solid, which was used directly in next step.

Step 6

(E)-3-(4-((1R,3R/1S,3S)-2-(4-Ethylphenyl)-3-methyl-6-(1-methyl-1H-pyrazol-4-yl)-1,2,3,4-tetrahydroisoquinolin-1-yl)phenyl)acrylic acid 1

The crude compound 1i (143 mg, 0.29 mmol) was dissolved in 5 mL of methanol, then 2M sodium hydroxide solution (0.73 mL, 1.45 mmol) was added. After completion of the addition, the reaction was stirred for 16 hours. Then, 1N hydrochloric acid was added dropwise to adjust the pH of the reaction solution to 2. The mixture was extracted with ethyl acetate (20 mL×2). The organic phases were combined, washed with saturated sodium chloride solution (10 mL), dried over anhydrous sodium sulfate, and filtrated to remove the desiccant. The filtrate was concentrated under reduced pressure. The resulting residue was purified by silica gel column chromatography with elution system A to obtain the title compound 1 (85 mg, yield 61.2%) as an off-white solid.

MS m/z (ESI): 478.5 [M+1]

$^1$H NMR (400 MHz, CDCl$_3$) δ7.74 (s, 1H), 7.66 (d, 1H), 7.59 (s, 1H), 7.39 (s, 3H), 7.31 (s, 2H), 7.26 (s, 2H), 7.04 (d, 2H), 6.73-6.77 (m, 2H), 6.36 (d, 1H), 5.70 (s, 1H), 4.47-4.53 (m, 1H), 3.95 (s, 3H), 3.32-3.43 (m, 1H), 2.70-2.78 (m, 1H), 2.51-2.59 (m, 2H), 1.26 (d, 3H), 1.19 (t, 3H).

Examples 2, 3

(E)-3-(4-((1R,3R)-2-(4-Ethylphenyl)-3-methyl-6-(1-methyl-1H-pyrazol-4-yl)-1,2,3,4-tetrahydroisoquinolin-1-yl)phenyl)acrylic acid 2

(E)-3-(4-((1S,3S)-2-(4-Ethylphenyl)-3-methyl-6-(1-methyl-1H-pyrazol-4-yl)-1,2,3,4-tetrahydroisoquinolin-1-yl)phenyl)acrylic acid 3

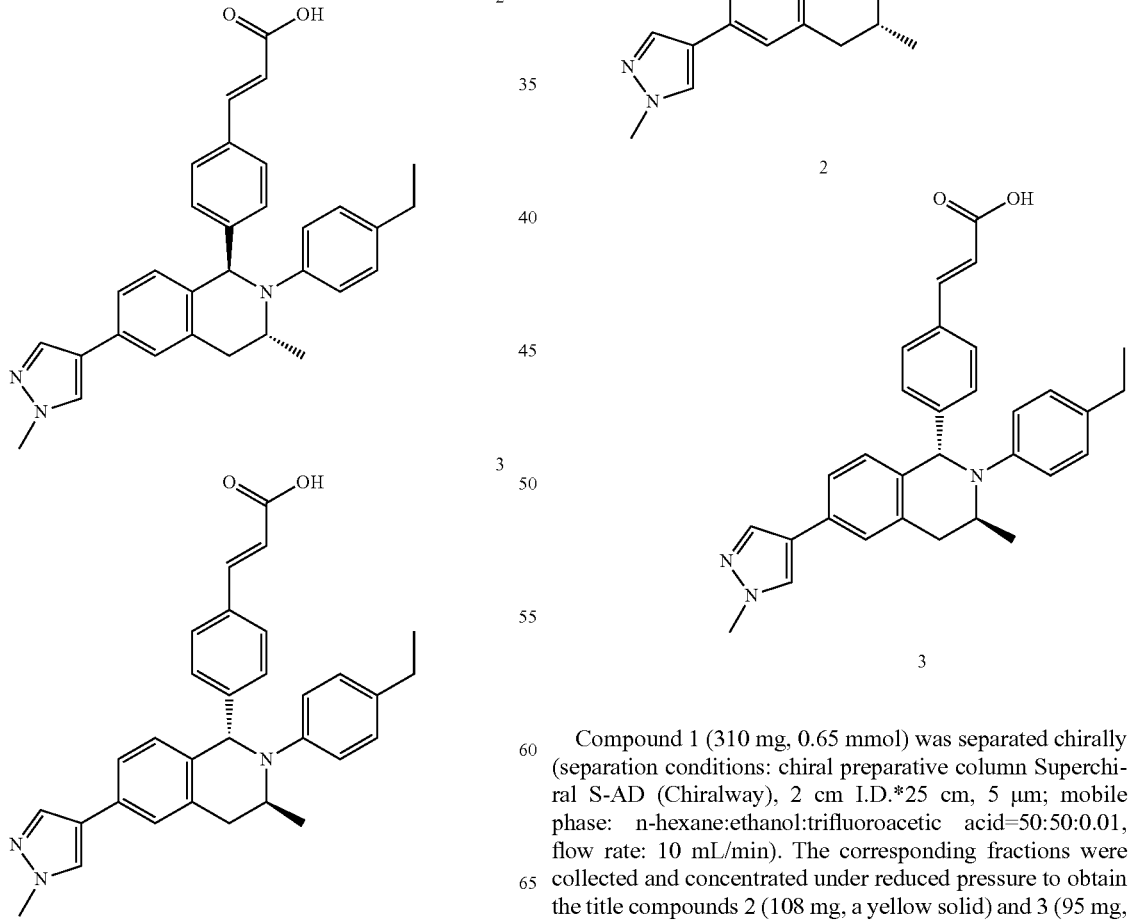

Compound 1 (310 mg, 0.65 mmol) was separated chirally (separation conditions: chiral preparative column Superchiral S-AD (Chiralway), 2 cm I.D.*25 cm, 5 μm; mobile phase: n-hexane:ethanol:trifluoroacetic acid=50:50:0.01, flow rate: 10 mL/min). The corresponding fractions were collected and concentrated under reduced pressure to obtain the title compounds 2 (108 mg, a yellow solid) and 3 (95 mg, a yellow solid).

Compound 2:

MS m/z (ESI): 478.5 [M+1];

Chiral HPLC analysis: retention time 17.940 minutes, chiral purity: 99.1% (chromatographic column: Superchiral S-AD (Chiralway), 0.46 cm I.D.*25 cm, 5 μm; mobile phase: n-hexane:ethanol:trifluoroacetic acid=50:50:0.01 (v/v/v)).

¹H NMR (400 MHz, CDCl₃) δ7.74 (s, 1H), 7.66 (d, 1H), 7.59 (s, 1H), 7.39 (s, 3H), 7.31 (s, 2H), 7.26 (s, 2H), 7.04 (d, 2H), 6.73-6.77 (m, 2H), 6.36 (d, 1H), 5.70 (s, 1H), 4.47-4.53 (m, 1H), 3.95 (s, 3H), 3.32-3.43 (m, 1H), 2.70-2.78 (m, 1H), 2.51-2.59 (m, 2H), 1.16-1.20 (m, 3H), 0.95 (d, 3H).

Compound 3:

MS m/z (ESI): 478.5 [M+1];

Chiral HPLC analysis: retention time 23.198 minutes, chiral purity: 99.3% (chromatographic column: Superchiral S-AD (Chiralway), 0.46 cm I.D.*25 cm, 5 μm; mobile phase: n-hexane:ethanol:trifluoroacetic acid=50:50:0.01 (v/v/v)).

¹H NMR (400 MHz, CDCl₃) δ 7.74 (s, 1H), 7.66 (d, 1H), 7.59 (s, 1H), 7.39 (s, 3H), 7.31 (s, 2H), 7.26 (s, 2H), 7.04 (d, 2H), 6.73-6.77 (m, 2H), 6.36 (d, 1H), 5.70 (s, 1H), 4.47-4.53 (m, 1H), 3.95 (s, 3H), 3.32-3.43 (m, 1H), 2.70-2.78 (m, 1H), 2.51-2.59 (m, 2H), 1.16-1.20 (m, 3H), 1.06 (d, 3H).

Example 4

(E)-3-(4-((1S,3R/1R, 3 S)-2-(4-Cyclopropylphenyl)-3-methyl-6-(1-methyl-1H-pyrazol-4-yl)-1,2,3,4-tetrahydroisoquinolin-1-yl)-3,5-difluorophenyl)acrylic acid

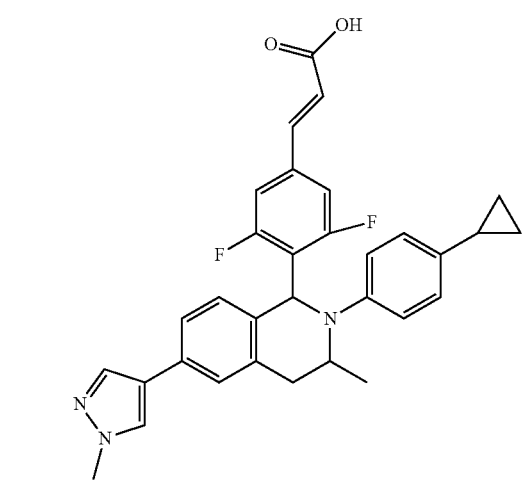

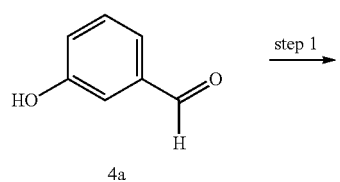

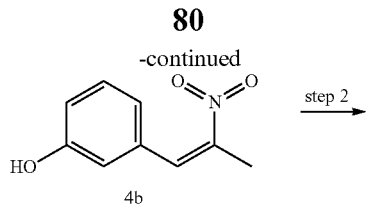

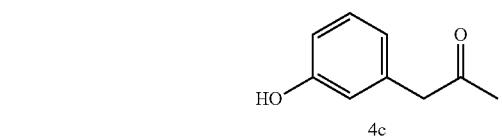

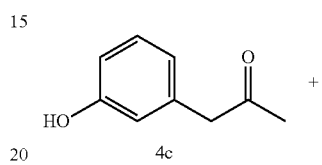

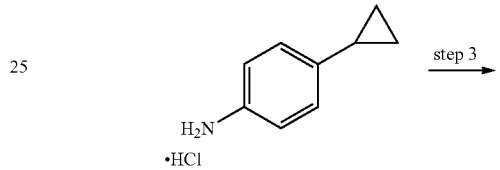

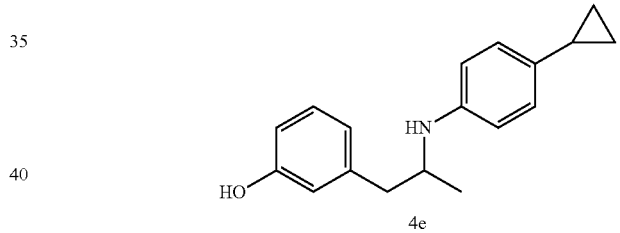

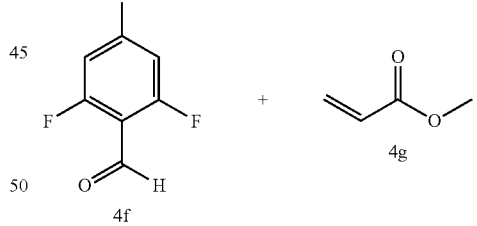

-continued

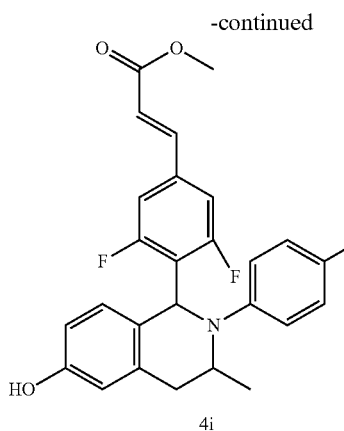

4i

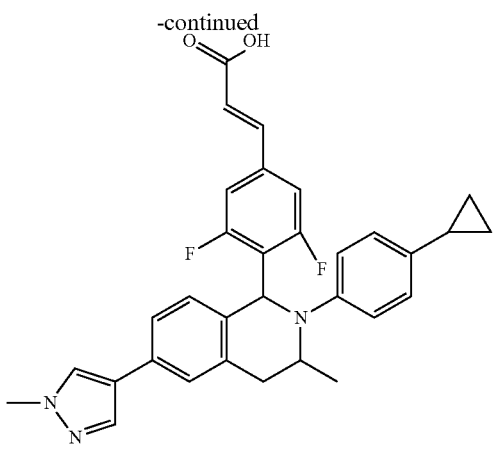

4

Step 1

3-(2-Nitroprop-1-en-1-yl)phenol 4b 3-hydroxybenzaldehyde 4a (10 g, 81.9 mmol), nitroethane (60 g, 819 mmol) and ammonium acetate (1.54 g, 20 mmol) were added to a reaction flask. The mixture was heated to 80° C., and methylamine was added (1 g, 32.2 mmol). After completion of the addition, the reaction was stirred for 2 hours. Then, 50 mL of water were added, and the mixture was extracted with ethyl acetate (30 mL×3). The organic phases were combined, dried over anhydrous sodium sulfate, and filtrated to remove the desiccant. The filtrate was concentrated under reduced pressure. The resulting residue was purified by silica gel column chromatography with elution system B to obtain the title compound 4b (9.5 g, yield 64.6%) as a yellow solid.

Step 2

1-(3-Hydroxyphenyl)propan-2-one 4c

Compound 4b (9.5 g, 53 mmol) was added to 110 mL of a mixture of methanol and water (V:V=10:1), then raney nickel (10%, 9.5 g) and acetic acid (3.2 g, 53 mmol) were added. After completion of the addition, the reaction system was purged with hydrogen three times, and the reaction was stirred for 16 hours. After filtration, the filtrate was evaporated to remove most of the solvent, and the mixture was extracted with ethyl acetate (50 mL×3). The organic phases were combined, dried over anhydrous sodium sulfate, and filtrated to remove the desiccant. The filtrate was concentrated under reduced pressure. The resulting residue was purified by silica gel column chromatography with elution system B to obtain the title compound 4c (3.7 g, yield 46.8%) as a yellow oil.

Step 3

3-(2-((4-Cyclopropylphenyl)amino)propyl)phenol 4e 4-cyclopropylaniline hydrochloride (390 mg, 2.30 mmol, Bidepharmatech) was dissolved in 10 mL of dichloromethane, then triethylamine (233 mg, 2.30 mmol) was added. After the mixture was stirred for 5 minutes, 4c (345 mg, 2.30 mmol) and sodium triacetoxyborohydride (730 mg, 3.45 mmol) were added, and the reaction was stirred for 12 hours. 10 mL of water was added, and the mixture was extracted with dichloromethane (10 mL×3). The organic phases were combined, dried over anhydrous sodium sulfate, and filtrated to remove the desiccant. The filtrate was concentrated under reduced pressure. The resulting residue was purified by silica gel column chromatography with elution system B to obtain the title compound 4e (540 mg, yield 87.8%) as a brown viscous material.

Step 4

(E)-Methyl 3-(3,5-difluoro-4-formylphenyl)acrylate

Under an argon atmosphere, 4-bromo-2,6-difluorobenzaldehyde 4f (10 g, 45.2 mmol), methyl acrylate 4 g (6.1 mL, 67.9 mmol), tri(o-methylphenyl)phosphine (1.4 g, 4.52 mmol), palladium acetate (507 mg, 2.26 mmol) and triethylamine (12.5 mL, 90.4 mmol) were added to 100 mL of N',N'-dimethylaniline. After completion of the addition, the mixture was heated to 80° C. and stirred for 16 hours. After stopping heating, the reaction solution was naturally cooled to room temperature, and 300 mL of water were added. The reaction solution was filtered, and the filter cake was successively washed with water (50 mL×3) and n-hexane (50 mL×3) and dried to obtain the title compound 4h (10 g, yield 98.0%) as a yellow solid.

Step 5

(E)-Methyl 3-(4-(2-(4-cyclopropylphenyl)-6-hydroxy-3-methyl-1,2,3,4-tetrahydroisoquinolin-1-yl)-3,5-difluorophenyl)acrylate 4i Compound 4e (4.8 g, 18.7 mmol), compound 4h (8.5 g, 37.4 mmol) and triisopropylsilyl chloride (7.2 g, 37.4 mmol) were added to 120 mL of N,N-dimethylformamide. After completion of the addition, the mixture was heated to 120° C. and stirred for 3 hours. After stopping heating, the reaction solution was cooled to room temperature, and 50 mL of water were added. The mixture was extracted with ethyl acetate (100 mL×4). The organic phases were combined and, dried over anhydrous magnesium sulfate, and filtrated to remove the desiccant. The filtrate was concentrated under reduced pressure. The resulting residue was purified by silica gel column chromatography with elution system B to obtain the title compound 4l (7.0 g, yield 85.4%) as a yellow oil.

Step 6

(E)-Methyl 3-(4-(1S,3R/1R,3S)-2-(4-cyclopropylphenyl)-3-methyl-6-(((trifluoromethyl) sulfonyl)oxy)-1,2,3,4-tetrahydroisoquinolin-1-yl)-3,5-difluorophenyl)acrylate 4j Compound 4i (3 g, 6.8 mmol) was dissolved in 50 mL of dichloromethane, then 2,6-lutidine (1.1 g, 10.2 mmol) was added. After completion of the addition, the mixture was cooled to 0° C. in an ice bath, and trifluoromethanesulfonic anhydride (2.5 g, 8.87 mmol) was added dropwise. After completion of the addition, the ice bath was removed, and the reaction was stirred for 16 hours at room temperature. Then, 30 mL of water were added, and the reaction solution was extracted with dichloromethane (15 mL×3). The organic phases were combined, washed with saturated sodium chloride solution, dried over anhydrous sodium sulfate, and filtrated to remove the desiccant. The filtrate was concentrated under reduced pressure. The resulting residue was purified by silica gel column chromatography with elution system B to obtain the title compound 4j (1.6 g, yield 39.0%) as a yellow oil.

Step 7

(E)-Methyl 3-(4-((1S,3R/1R,3S)-2-(4-cyclopropylphenyl)-3-methyl-6-(1-methyl-1H-pyrazol-4-yl)-1,2,3,4-tetrahydroisoquinolin-1-yl)-3,5-difluorophenyl)acrylate 4k Compound 4j (1.0 g, 1.65 mmol), 1-methyl-4-(4,4,5,5-tetramethyl-1,3,2-dioxaborolan-2-yl)-1H-pyrazole (514 mg, 2.47 mmol), and [1,1'-bis(diphenylphosphino)ferrocene]dichloropalladium (120 mg, 0.165 mmol) were dissolved in 14 mL of a mixture of 1,4-dioxane and water (V:V=5:2). Then, 2M sodium carbonate solution (1.65 mL, 3.3 mmol) was added. After completion of the addition, the mixture was stirred in a microwave at 120° C. for 1 hour. After cooling to room temperature, 50 mL of water were added, and the mixture was extracted with ethyl acetate (50 mL×3). The organic phases were combined, dried over anhydrous magnesium sulfate, and filtrated to remove the desiccant. The filtrate was concentrated under reduced pressure. The resulting residue was purified by silica gel column chromatography with elution system B to obtain the title compound 4k (420 mg, yield 47.3%) as a yellow oil.

Step 8

(E)-3-(4-((1S,3R/1R,3S)-2-(4-Cyclopropylphenyl)-3-methyl-6-(1-methyl-1H-pyrazol-4-yl)-1,2,3,4-tetrahydroisoquinolin-1-yl)-3,5-difluorophenyl)acrylic acid 4

Compound 4k (420 mg, 0.78 mmol) was dissolved in 20 mL of a mixture of methanol and tetrahydrofuran (V:V=1:1), then 2 M sodium hydroxide solution (2 mL, 4.0 mmol) was added. After completion of the addition, the reaction was stirred for 16 hours. Then, 1N hydrochloric acid was added dropwise to adjust the pH of the reaction solution to 3. The mixture was extracted with ethyl acetate (30 mL×3). The organic phases were combined, dried over anhydrous magnesium sulfate, and filtrated to remove the desiccant. The filtrate was concentrated under reduced pressure. The resulting residue was purified by silica gel column chromatography with elution system A to obtain the title compound 4 (180 mg, yield 61.5%) as a yellow solid.

MS m/z (ESI): 525.6 [M+1]

$^1$H NMR (400 MHz, CDCl$_3$): δ 12.05 (s, 1H), 7.75 (s, 1H), 7.60 (s, 1H), 7.52 (d, 1H), 7.29 (s, 1H), 7.21 (d, 1H), 7.01-6.90 (m, 6H), 6.32 (d, 1H), 6.12 (s, 1H), 4.35-4.28 (m, 1H), 3.94 (s, 3H), 3.69-3.60 (m, 1H), 2.81-2.68 (m, 2H), 1.83-1.74 (m, 1H), 1.07-0.96 (m, 2H), 0.91-0.84 (m, 2H), 0.60 (d, 3H).

Example 5
(E)-3-(4-(2-(2-Ethylphenyl)-6-(1-methyl-1H-pyrazol-4-yl)-1,2,3,4-tetrahydroisoquinolin-1-yl)-3,5-difluorophenyl)acrylic acid
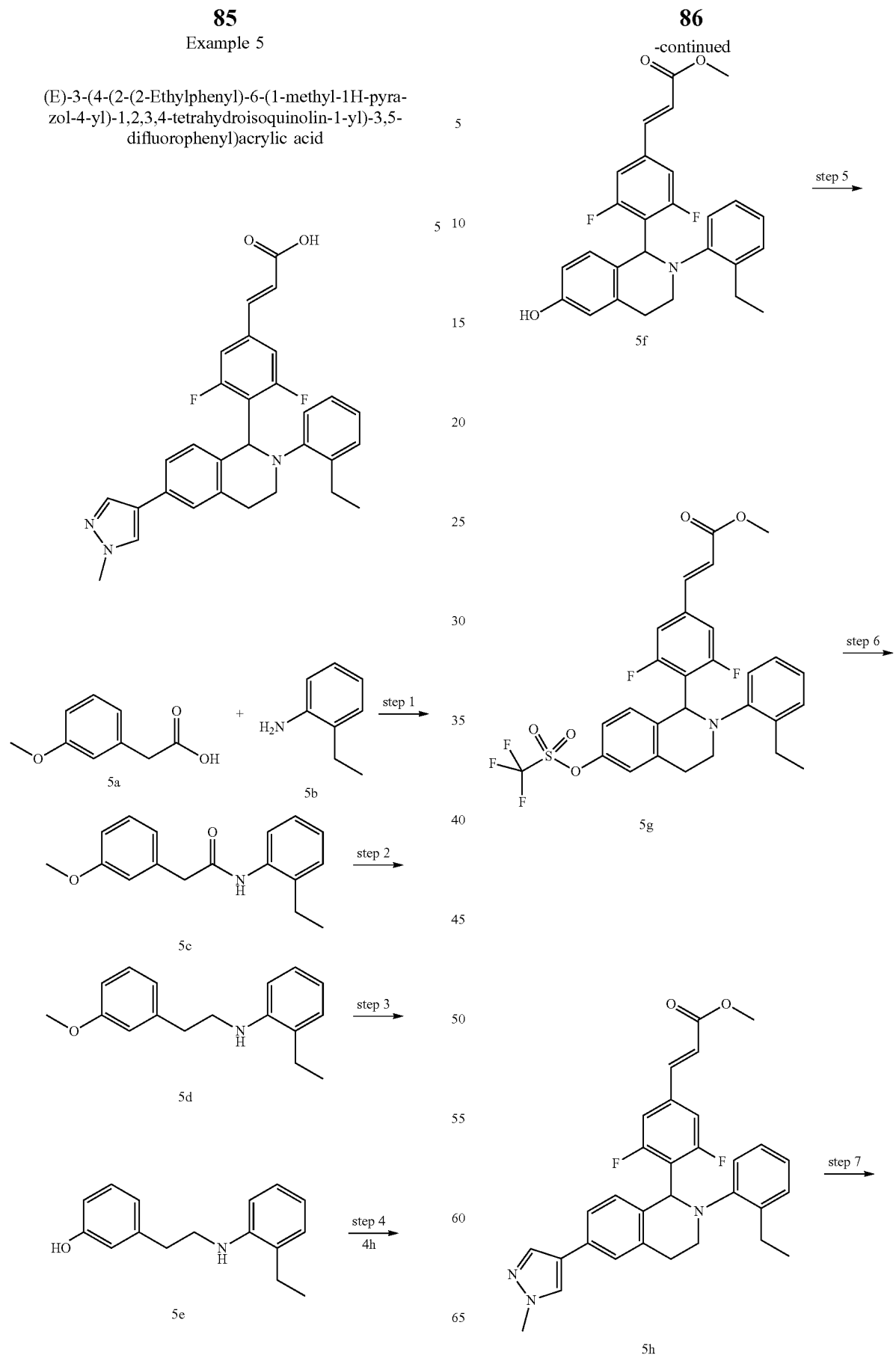

-continued

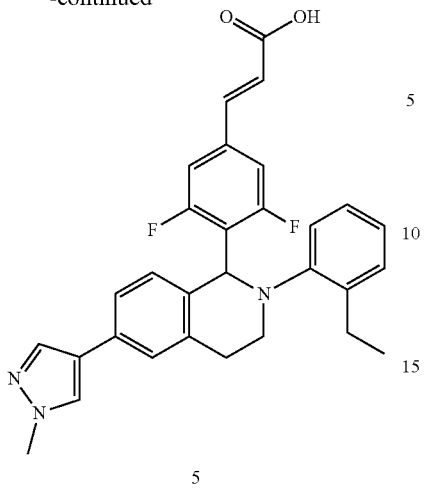

5

Step 1

N-(2-Ethylphenyl)-2-(3-methoxyphenyl)acetamide 5c 3-methoxyphenylacetic acid 5a (1.66 g, 10 mmol), 2-ethylaniline 5b (1.21 g, 10 mmol), 1-(3-dimethylaminopropyl)-3-ethylcarbodiimide hydrochloride (2.3 g, 12 mmmol) and 4-dimethylaminopyridine (122 mg, 1 mmol) were added to 30 mL of N,N-dimethylformamide. After completion of the addition, the reaction was stirred for 16 hours. The reaction solution was concentrated under reduced pressure. The resulting residue was purified by silica gel column chromatography with elution system B to obtain the title compound 5c (2.45 g, yield 91.1%) as a white solid.

Step 2

2-Ethyl-N-(3-methoxyphenethyl)aniline 5d

Compound 5c (2.45 g, 9.1 mmol) was added to 60 mL of tetrahydrofuran, then lithium aluminum tetrahydride (1.73 g, 45.5 mmol) was added in batches. After completion of the addition, the reaction was stirred for 16 hours. Then, 2 mL of water were added to quench the reaction, and sodium hydroxide solution (5%, 5.2 mL) was added dropwise. The mixture was stirred uniformly, filtered through celite, and the filtrate was concentrated under reduced pressure. The resulting residue was purified by silica gel column chromatography with elution system B to obtain the title compound 5d (1.05 g, yield 45.0%) as a brown oil.

Step 3

3-(2-((2-Ethylphenyl)amino)ethyl)phenol 5e

Compound 5d (1.05 g, 4.11 mmol) was dissolved in 30 mL of dichloromethane. After the reaction was cooled to −78° C. in a dry ice-acetone bath, a solution of boron bromide in dichloromethane (1M, 8.2 mL) was added dropwise. After completion of the addition, the dry ice-acetone bath was removed. The reaction solution was warmed up to room temperature and stirred for 16 hours. Then, 30 mL of water were added to quench the reaction. The reaction solution was evaporated under reduced pressure to remove dichloromethane. Another 30 mL of water were added. The mixture was mixed uniformly, and extracted with ethyl acetate (25 mL×3). The organic phases were combined, dried over anhydrous sodium sulfate, and filtered to remove the desiccant. The filtrate was concentrated under reduced pressure. The resulting residue was purified by silica gel column chromatography with elution system A to obtain the title compound 5e (620 mg, yield 62.6%) as a yellow solid.

Step 4

(E)-Methyl 3-(4-(2-(2-ethylphenyl)-6-hydroxy-1,2,3,4-tetrahydroisoquinolin-1-yl)-3,5-difluorophenyl) acrylate 5f Compound 5e (520 mg, 2.15 mmol), 4h (975 mg, 4.31 mmol) and triisopropylsilyl chloride (2.07 g, 10.75 mmol) were added to 15 mL of N,N-dimethylformamide. After completion of the addition, the mixture was heated to 120° C. and stirred for 2 hours. After stopping heating, the reaction solution was cooled to room temperature, and 50 mL of water was added. The mixture was extracted with ethyl acetate (80 mL×2). The organic phases were combined, dried over anhydrous sodium sulfate, and filtrated to remove the desiccant. The filtrate was concentrated under reduced pressure. The resulting residue was purified by silica gel column chromatography with elution system B to obtain the title compound 5f (720 mg, yield 74.6%) as a colorless oil.

Step 5

(E)-Methyl 3-(4-(2-(2-ethylphenyl)-6-(((trifluoromethyl)sulfonyl)oxy)-1,2,3,4-tetrahydroisoquinolin-1-yl)-3,5-difluorophenyl)acrylate 5 g Compound 5f (720 mg, 1.6 mmol) was dissolved in 50 mL of dichloromethane, then 2,6-lutidine (0.28 mL, 2.4 mmol) and trifluoromethanesulfonic anhydride (0.4 mL, 2.4 mmol) were added. After completion of the addition, the reaction was stirred for 3 hours. Then, 0.5 mL of water was added, and the reaction solution was extracted with dichloromethane (15 mL×3). The organic phases were combined, washed with saturated sodium chloride solution, dried over anhydrous sodium sulfate, and filtrated to remove the desiccant. The filtrate was concentrated under reduced pressure. The resulting residue was purified by silica gel column chromatography with elution system B to obtain the title compound 5 g (660 mg, yield 71.0%) as a white solid.

Step 6

(E)-Methyl 3-(4-(2-(2-ethylphenyl)-6-(1-methyl-1H-pyrazol-4-yl)-1,2,3,4-tetrahydroisoquinolin-1-yl)-3,5-difluorophenyl)acrylate 5h Compound 5 g (104.6 mg, 0.18 mmol), 1-methyl-4-(4,4,5,5-tetramethyl-1,3,2-dioxaborolan-2-yl)-1H-pyrazole (56.1 mg, 0.27 mmol), and [1,1'-bis(diphenylphosphino)ferrocene]dichloropalladium (13 mg, 0.018 mmol) were dissolved in 2.4 mL of a mixture of 1,4-dioxane and water (V:V=7:1), then 2M sodium carbonate solution (0.18 mL, 0.36 mmol) was added. After completion of the addition, the mixture was stirred in a microwave at 120° C. for 1 hour. After cooling to room temperature, 20 mL of water were added, and the mixture was extracted with ethyl acetate (15 mL×3). The organic phases were combined, dried over anhydrous magnesium sulfate, and filtrated to remove the desiccant. The filtrate was concentrated under reduced pressure. The resulting residue was purified by silica gel column chromatography with elution system B to obtain the title compound 5h (60 mg, yield 65.0%) as a colorless oil.

Step 7

(E)-3-(4-(2-(2-Ethylphenyl)-6-(1-methyl-1H-pyrazol-4-yl)-1,2,3,4-tetrahydroisoquinolin-1-yl)-3,5-difluorophenyl)acrylic acid 5

Compound 5h (60 mg, 0.12 mmol) was dissolved in 6 mL of a mixture of methanol and tetrahydrofuran (V:V=1:1), then 2 M sodium hydroxide solution (1 mL, 2.0 mmol) was added. After completion of the addition, the reaction was stirred for 16 hours. Then, 1N hydrochloric acid was added dropwise to adjust the pH of the reaction solution to 3. The mixture was filtered, and the filter cake was dried to obtain the title compound 5 (40 mg, yield 68.5%) as a yellow solid.

MS m/z (ESI): 500.5 [M+1]

1H NMR (400 MHz, DMSO-$d_6$) δ 8.08 (s, 1H), 7.81 (s, 1H), 7.42 (s, 1H), 7.20-7.29 (m, 4H), 7.10-7.13 (m, 2H), 7.00-7.02 (d, 1H), 6.69-6.71 (d, 1H), 6.51-6.55 (d, 1H), 5.90 (s, 1H), 3.85 (s, 3H), 3.12-3.21 (m, 2H), 2.84-2.89 (m, 1H), 2.60-2.64 (m, 2H), 1.22-1.25 (m, 2H), 1.01-1.06 (t, 3H).

Example 6

(E)-3-(4-((1R,3R/1S,3S)-2-(2-Ethylphenyl)-3-methyl-6-(1-methyl-1H-pyrazol-4-yl)-1,2,3,4-tetrahydroisoquinolin-1-yl)phenyl)acrylic acid

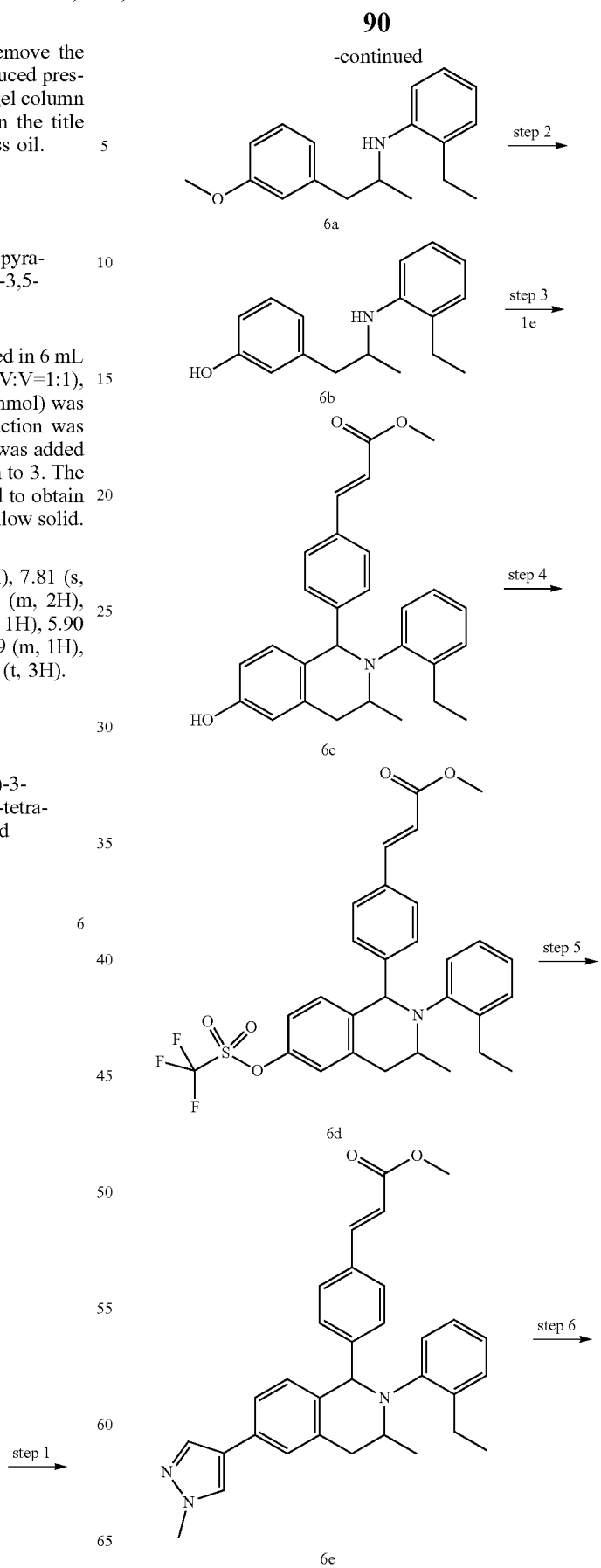

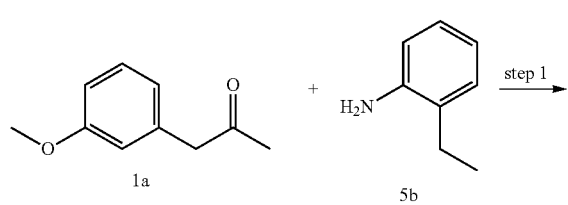

-continued

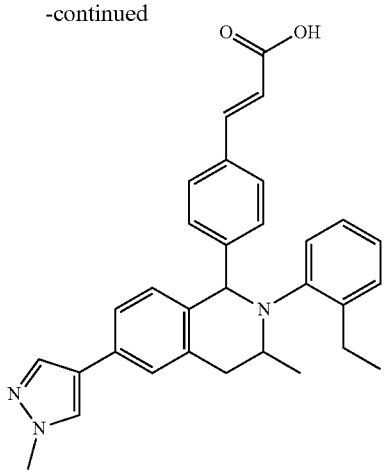

6

Step 1

2-Ethyl-N-(1-(3-methoxyphenyl)propan-2-yl)aniline
6a

Compound 1a (820 mg, 5 mmol), compound 5b (0.75 mL, 6 mmol) and sodium triacetoxyborohydride (1.58 g, 7.5 mmol) were dissolved in 30 mL of trichloroethane. The mixture was stirred for 16 hours. Then, 30 mL of water were added to quench the reaction. The reaction solution was extracted with dichloromethane (25 mL×3). The organic phases were combined, dried over anhydrous sodium sulfate, and filtered to remove the desiccant. The filtrate was concentrated under reduced pressure. The resulting residue was purified by silica gel column chromatography with elution system B to obtain the title compound 6a (800 mg, yield 59.3%) as a yellow oil.

Step 2

3-(2-((2-Ethylphenyl)amino)propyl)phenol 6b

Compound 6a (800 mg, 2.97 mmol) was dissolved in 20 mL of dichloromethane, then a solution of 1 M boron tribromide in dichloromethane (6 mL, 6.0 mmol) was added dropwise in an ice bath. After completion of the addition, the reaction was stirred for 16 hours at room temperature. Then, 15 mL of water were added to quench the reaction. The reaction solution was evaporated under reduced pressure to remove dichloromethane, and then extracted with ethyl acetate (30 mL×3). The organic phases were combined, washed with saturated sodium chloride solution, dried over anhydrous sodium sulfate, and filtered to remove the desiccant. The filtrate was concentrated under reduced pressure to obtain the title compound 6b (540 mg, yield 71.2%) as a yellow oil.

Step 3

(E)-Methyl 3-(4-(2-(2-ethylphenyl)-6-hydroxy-3-methyl-1,2,3,4-tetrahydroisoquinolin-1-yl)phenyl)acrylate 6c Compound 6b (400 mg, 1.56 mmol), 1e (596 mg, 3.13 mmol) and triisopropylsilyl chloride (1.5 g, 7.8 mmol) were added to 10 mL of N,N-dimethylformaminde. After completion of the addition, the mixture was heated to 120° C. and stirred for 3 hours. After stopping heating, the reaction solution was cooled to room temperature, and 30 mL of water were added. The mixture was extracted with ethyl acetate (30 mL×3). The organic phases were combined, dried over anhydrous sodium sulfate, and filtrated to remove the desiccant. The filtrate was concentrated under reduced pressure. The resulting residue was purified by silica gel column chromatography with elution system B to obtain the title compound 6c (440 mg, yield 65.7%) as a yellow solid.

Step 4

(E)-Methyl 3-(4-((1R,3R/1S,3S)-2-(2-ethylphenyl)-3-methyl-6-(((trifluoromethyl) sulfonyl)oxy)-1,2,3,4-tetrahydroisoquinolin-1-yl)phenyl)acrylate 6d Compound 6c (440 mg, 1.03 mmol) was dissolved in 50 mL of dichloromethane in an ice bath, then 2,6-lutidine (165 mg, 1.54 mmol) was added, followed by trifluoromethanesulfonic anhydride (436 mg, 1.54 mmol). After completion of the addition, the ice bath was removed, and the reaction was stirred for 16 hours at room temperature. Then, 50 mL of water were added to the reaction solution, and two phases were separated. The organic phase was dried over anhydrous sodium sulfate, and filtrated to remove the desiccant. The filtrate was concentrated under reduced pressure. The resulting residue was purified by silica gel column chromatography with elution system B to obtain the title compound 6d (61 mg, yield 10.6%) as a light yellow solid.

Step 5

(E)-Methyl 3-(4-((1R,3R/1S,3S)-2-(2-ethylphenyl)-3-methyl-6-(1-methyl-1H-pyrazol-4-yl)-1,2,3,4-tetrahydroisoquinolin-1-yl)phenyl)acrylate 6e Compound 6d (47 mg, 0.084 mmol), 1-methyl-4-(4,4,5,5-tetramethyl-1,3,2-dioxaborolan-2-yl)-1H-pyrazole (26 mg, 0.13 mmol), and [1,1'-bis(diphenylphosphino)ferrocene]dichloropalladium (6 mg, 0.0084 mmol) were dissolved in 2.4 mL of a mixture of 1,4-dioxane and water (V:V=7:1), then 2M sodium carbonate solution (0.08 mL, 0.16 mmol) was added. After completion of the addition, the mixture was stirred in a microwave at 120° C. for 40 minutes. After cooling to room temperature, 20 mL of water were added, and the mixture was extracted with ethyl acetate (20 mL×3). The organic phases were combined, washed with saturated sodium chloride solution (10 mL×2), dried over anhydrous sodium sulfate, and filtrated to remove the desiccant. The filtrate was concentrated under reduced pressure to obtain the crude title compound 6e (40 mg, yield 97.6%) as a yellow solid.

Step 6

(E)-3-(4-((1R,3R/1S,3S)-2-(2-Ethylphenyl)-3-methyl-6-(1-methyl-1H-pyrazol-4-yl)-1,2,3,4-tetrahydroisoquinolin-1-yl)phenyl)acrylic acid 6

The crude compound 6e (40 mg, 0.08 mmol) was dissolved in 5 mL of methanol, then 2 M sodium hydroxide solution (0.2 mL, 0.4 mmol) was added. After completion of the addition, the reaction was stirred for 16 hours. Then, 1N hydrochloric acid was added dropwise to adjust the pH of the reaction solution to 2. The mixture was extracted with ethyl acetate (10 mL×3). The organic phases were combined, washed with saturated sodium chloride solution (10 mL), dried over anhydrous sodium sulfate, and filtrated to remove the desiccant. The filtrate was concentrated under reduced pressure. The resulting residue was purified by silica gel column chromatography with elution system A to obtain the title compound 6 (4 mg, yield 10.3%) as an off-white solid.

MS m/z (ESI): 478.5 [M+1]

$^1$H NMR (400 MHz, CDCl$_3$) δ7.92 (s, 1H), 7.78 (s, 1H), 7.66-7.62 (m, 1H), 7.50-7.44 (m, 2H), 7.37 (s, 1H), 7.30 (d, 2H), 7.20-7.17 (m, 2H), 7.04-7.00 (m, 2H), 6.58 (d, 1H), 6.36 (d, 1H), 5.33 (s, 1H), 3.91 (s, 3H), 3.05 (d, 1H), 2.95 (d, 1H), 2.62-2.56 (m, 2H), 2.38-2.35 (m, 1H), 0.84 (d, 3H), 0.81 (t, 3H).

Example 7

(E)-3-(4-((1R,3R/1S,3S)-6-(1-Ethyl-1H-pyrazol-4-yl)-2-(4-isopropylphenyl)-3-methyl-1,2,3,4-tetrahydroisoquinolin-1-yl)phenyl)acrylic acid

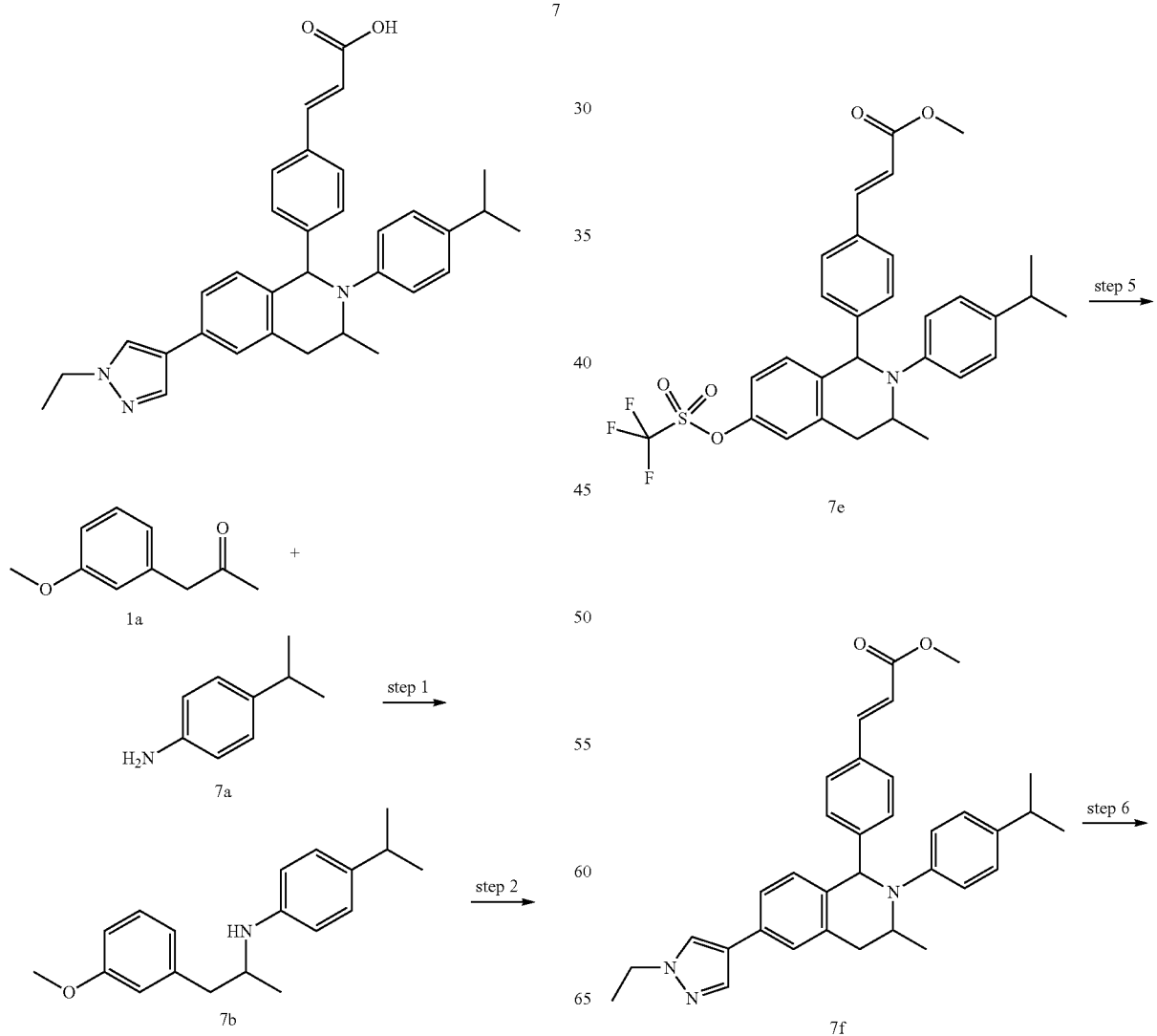

-continued

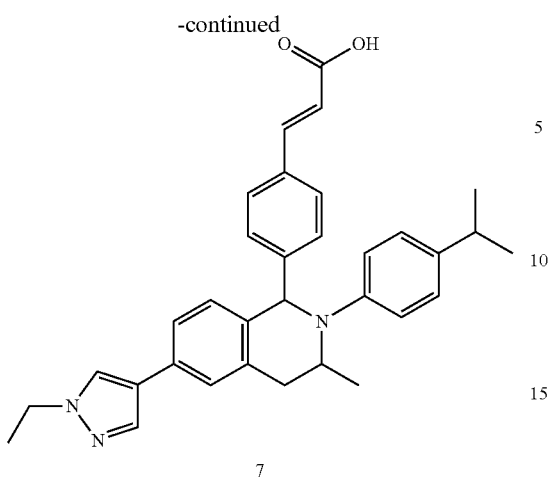

7

Step 1

4-Isopropyl-N-(1-(3-methoxyphenyl)propan-2-yl) aniline 7b

Compound 1a (2.0 g, 12 mmol), 4-isopropylaniline 7a (1.95 g, 14.4 mmol) and sodium triacetoxyborohydride (3.81 g, 18 mmol) were dissolved in 50 mL of dichloromethane. The mixture was stirred for 5 hours. Then, 20 mL of water were added to quench the reaction. The reaction solution was extracted with dichloromethane (20 mL×2). The organic phases were combined, and concentrated under reduced pressure. The resulting residue was purified by silica gel column chromatography with elution system B to obtain the title compound 7b (2.5 g, yield 75.3%) as a brown oil.

Step 2

3-(2-((4-Isopropylphenyl)amino)propyl)phenol 7c

Compound 7b (2.5 g, 8.82 mmol) was dissolved in 70 mL of dichloromethane, then a solution of 1 M boron tribromide in dichloromethane (17.6 mL, 17.6 mmol) was added dropwise in an ice bath. After completion of the addition, the reaction was stirred for 16 hours at room temperature. Then, 50 mL of water were added to quench the reaction. The reaction solution was extracted with dichloromethane (20 mL×2). The organic phases were combined, washed with saturated sodium bicarbonate solution (20 mL), and concentrated under reduced pressure. The resulting residue was purified by silica gel column chromatography with elution system B to to obtain the title compound 7c (2.3 g, yield 96.6%) as a brown oil.

Step 3

(E)-Methyl 3-(4-(6-hydroxy-2-(4-isopropylphenyl)-3-methyl-1,2,3,4-tetrahydroisoquinolin-1-yl)phenyl) acrylate 7d Compound 1e (2.44 g, 12.8 mmol), 7c (2.3 g, 8.6 mmol) and triisopropylsilyl chloride (8.23 g, 42.69 mmol) were added to 50 mL of N,N-dimethylformamide. After completion of the addition, the mixture was heated to 120° C. and stirred for 3 hours. After stopping heating, the reaction solution was concentrated under reduced pressure. Then, 20 mL of water were added to the resulting residue, then the mixture was stirred uniformly and extracted with ethyl acetate (20 mL×3). The organic phases were combined and concentrated under reduced pressure. The resulting residue was purified by silica gel column chromatography with elution system B to obtain the title compound 7d (2.3 g, yield 61.0%) as a yellow solid.

Step 4

(E)-Methyl 3-(4-((1R,3R/1S,3S)-2-(4-isopropylphenyl)-3-methyl-6-(((trifluoromethyl) sulfonyl)oxy)-1,2,3,4-tetrahydroisoquinolin-1-yl)phenyl)acrylate 7e Compound 7d (2.3 g, 5.21 mmol) was dissolved in 50 mL of dichloromethane, then 2,6-lutidine (840 mg, 7.82 mmol) was added. After completion of the addition, the reaction was cooled to 0° C. in an ice bath. Then, trifluoromethanesulfonic anhydride (1.91 g, 6.77 mmol) was added dropwise. After completion of the addition, the ice bath was removed, and the reaction was stirred for 16 hours at room temperature. Then, 20 mL of water were added to quench the reaction, and the reaction solution was extracted with dichloromethane (20 mL×2). The organic phases were combined and concentrated under reduced pressure. The resulting residue was purified by silica gel column chromatography with elution system B to obtain the title compound 7e (1.36 g, yield 45.5%) as a yellow solid.

Step 5

(E)-Methyl 3-(4-((1R,3R/1S,3S)-6-(1-ethyl-1H-pyrazol-4-yl)-2-(4-isopropylphenyl)-3-methyl-1,2,3,4-tetrahydroisoquinolin-1-yl)phenyl)acrylic acid 7f Compound 7e (300 mg, 0.52 mmol), 1-ethyl-4-(4,4,5,5-tetramethyl-1,3,2-dioxaborolan-2-yl)-1H-pyrazole (173 mg, 0.78 mmol), and [1,1'-bis(diphenylphosphino)ferrocene]dichloropalladium (38 mg, 0.052 mmol) were dissolved in 4.8 mL of a mixture of 1,4-dioxane and water (V:V=7:1), then 2M sodium carbonate solution (0.52 mL, 1.04 mmol) was added. After completion of the addition, the mixture was stirred in a microwave at 120° C. for 40 minutes. After cooling to room temperature, 10 mL of water were added, and the mixture was extracted with ethyl acetate (10 mL×3). The organic phases were combined and concentrated under reduced pressure. The resulting residue was purified by silica gel column chromatography with elution system B to obtain the crude title compound 7f (200 mg, yield 74.1%) as a light yellow solid.

Step 6

(E)-3-(4-((1R,3R/1S,3S)-6-(1-Ethyl-1H-pyrazol-4-yl)-2-(4-isopropylphenyl)-3-methyl-1,2,3,4-tetrahydroisoquinolin-1-yl)phenyl)acrylic acid 7

Compound 7f (200 mg, 0.38 mmol) was dissolved in 12.8 mL of a mixture of methanol and tetrahydrofuran (V:V=1:1), then 2 M sodium hydroxide solution (1 mL, 2 mmol) was added. After completion of the addition, the reaction was stirred for 16 hours. The reaction solution was concentrated under reduced pressure. Then, 10 mL of water were added to the resulting residue, then the mixture was stirred uniformly. Then, 2N hydrochloric acid was added dropwise to adjust the pH of the reaction solution to 3. The mixture was extracted with ethyl acetate (10 mL×3). The organic phases were combined, washed with saturated sodium chloride solution (10 mL×1), dried over anhydrous sodium sulfate, and filtrated to remove the desiccant. The filtrate was concentrated under reduced pressure. The resulting residue was purified by silica gel column chromatography with elution system A to obtain the title compound 7 (180 mg, yield 92.3%) as a yellow solid.

MS m/z (ESI): 504.5 [M+1]

$^1$H NMR (400 MHz, CDCl$_3$) δ 7.76 (s, 1H), 7.65 (d, 1H), 7.62 (s, 1H), 7.39 (s, 3H), 7.31 (s, 2H), 7.26 (s, 2H), 7.06 (d, 2H), 6.73-6.77 (m, 2H), 6.34 (d, 1H), 5.68 (s, 1H), 4.47-4.53 (m, 1H), 4.20 (q, 2H), 3.32-3.43 (m, 1H), 2.70-2.81 (m, 2H), 1.51 (t, 3H), 1.19 (d, 6H), 1.06 (s, 3H).

Examples 8, 9

(E)-3-(4-((1R,3R)-6-(1-Ethyl-1H-pyrazol-4-yl)-2-(4-isopropylphenyl)-3-methyl-1,2,3,4-tetrahydroisoquinolin-1-yl)phenyl)acrylic acid 8

(E)-3-(4-((1S,3S)-6-(1-Ethyl-1H-pyrazol-4-yl)-2-(4-isopropylphenyl)-3-methyl-1,2,3,4-tetrahydroisoquinolin-1-yl)phenyl)acrylic acid 9

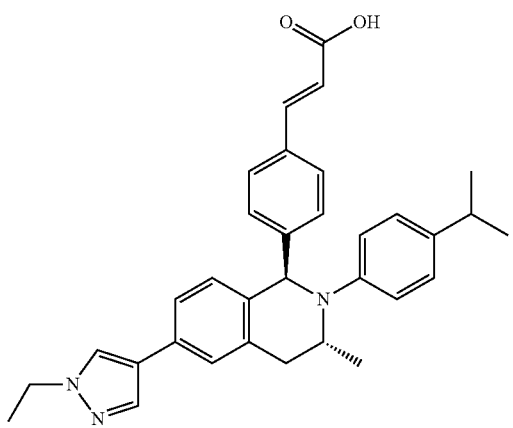

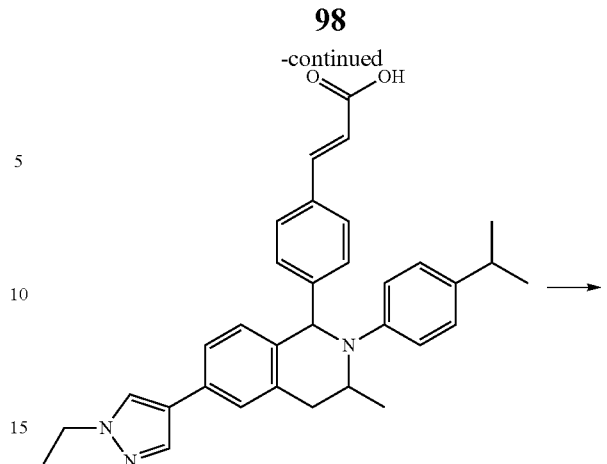

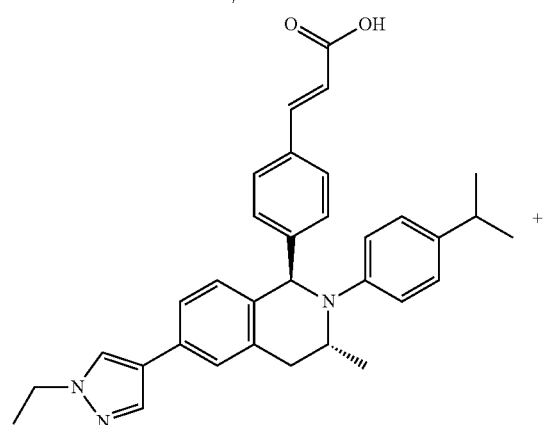

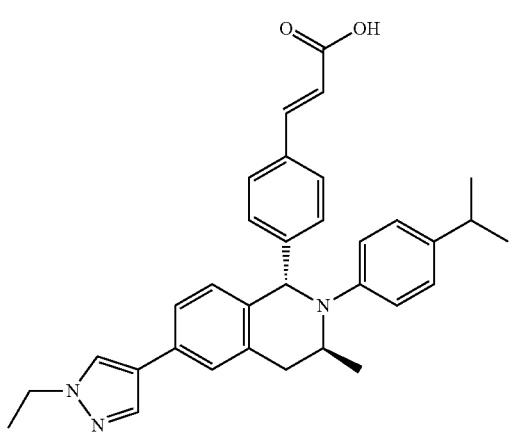

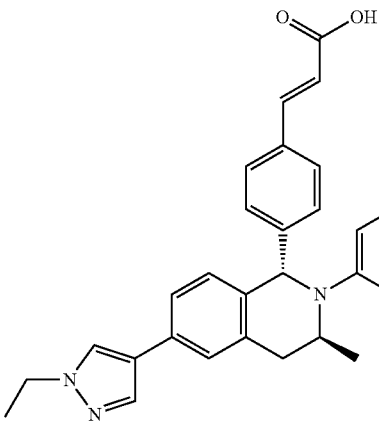

Compound 7 (500 mg, 0.96 mmol) was separated chirally (separation conditions: Superchiral S-AD (Chiralway), 2 cm I.D.*25 cm, 5 μm; mobile phase: carbon dioxide:ethanol:diethylamine=60:40:0.05, flow rate: 50 mL/min). The corresponding fractions were collected and concentrated under reduced pressure to obtain the title compounds 8 (160 mg, a yellow solid) and 9 (160 mg, a yellow solid).

Compound 8:

MS m/z (ESI): 504.5 [M+1]

Chiral HPLC analysis: retention time 9.84 minutes, chiral purity: 100% (chromatographic column: Superchiral S-AD (Chiralway), 2 cm I.D.*25 cm, 5 μm; mobile phase: carbon dioxide:ethanol:diethylamine=60:40:0.05).

¹H NMR (400 MHz, CDCl₃) δ7.76 (s, 1H), 7.65 (d, 1H), 7.62 (s, 1H), 7.39 (s, 3H), 7.31 (s, 2H), 7.26 (s, 2H), 7.06 (d, 2H), 6.73-6.77 (m, 2H), 6.34 (d, 1H), 5.68 (s, 1H), 4.47-4.53 (m, 1H), 4.20 (q, 2H), 3.32-3.43 (m, 1H), 2.70-2.81 (m, 2H), 1.51 (t, 3H), 1.19 (d, 6H), 1.06 (s, 3H).

Compound 9:

MS m/z (ESI): 508.1 [M+1]

Chiral HPLC analysis: retention time 14.26 minutes, chiral purity: 99.0% (chromatographic column: Superchiral S-AD (Chiralway), 0.46 cm I.D.*25 cm, 5 µm; mobile phase: carbon dioxide:ethanol:diethylamine=60:40:0.05).

¹H NMR (400 MHz, CDCl₃) δ 7.76 (s, 1H), 7.65 (d, 1H), 7.62 (s, 1H), 7.39 (s, 3H), 7.31 (s, 2H), 7.26 (s, 2H), 7.06 (d, 2H), 6.73-6.77 (m, 2H), 6.34 (d, 1H), 5.68 (s, 1H), 4.47-4.53 (m, 1H), 4.20 (q, 2H), 3.32-3.43 (m, 1H), 2.70-2.81 (m, 2H), 1.51 (t, 3H), 1.19 (d, 6H), 1.06 (s, 3H).

Example 10

(E)-3-(4-((1R,3R/1S,3S)-2-(4-Cyclopropylphenyl)-3-methyl-6-(1-methyl-1H-pyrazol-4-yl)-1,2,3,4-tetrahydroisoquinolin-1-yl)phenyl)acrylic acid

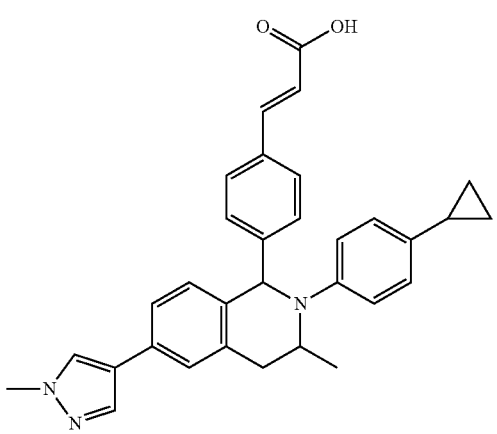

10

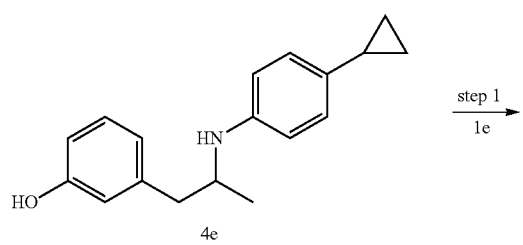

4e step 1
1e
→

-continued

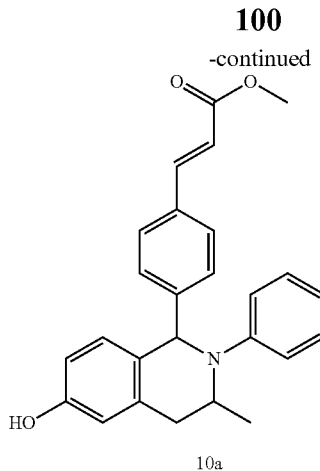

10a step 2 →

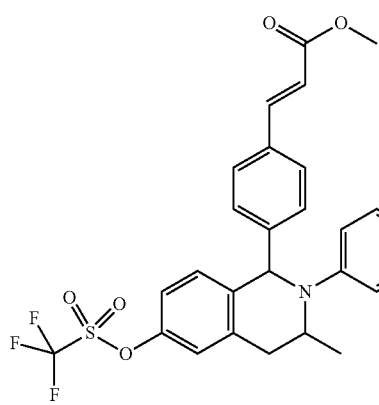

10b step 3 →

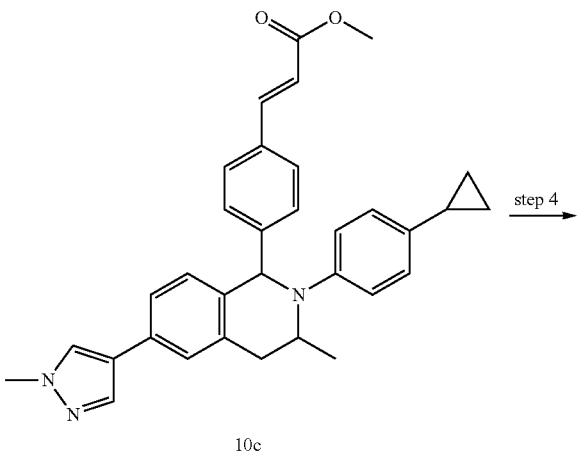

10c step 4 →

-continued

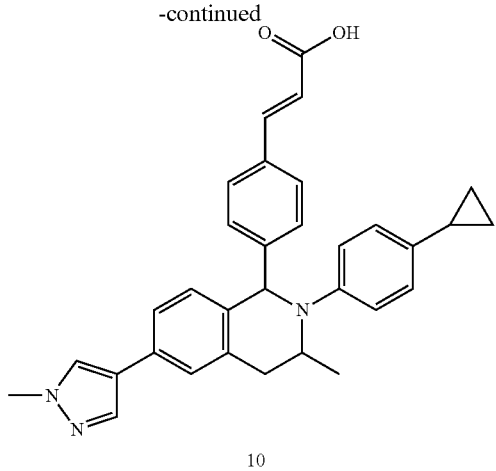

10

Step 1

(E)-Methyl 3-(4-(2-(4-cyclopropylphenyl)-6-hydroxy-3-methyl-1,2,3,4-tetrahydroisoquinolin-1-yl)phenyl)acrylate 10a Compound 4e (540 mg, 2.02 mmol), compound 1e (576 mg, 3.03 mmol) and triisopropylsilyl chloride (1.95 g, 10.10 mmol) were added to 10 mL of N,N-dimethylformamide. After completion of the addition, the mixture was heated to 120° C. and stirred for 3 hours. The reaction solution was cooled to room temperature and concentrated under reduced pressure. Then, 20 mL of water were added to the resulting residue, then the mixture was stirred uniformly and extracted with ethyl acetate (10 mL×3). The organic phases were combined and concentrated under reduced pressure. The resulting residue was purified by silica gel column chromatography with elution system B to obtain the title compound 10a (490 mg, yield 55.2%) as a brown solid.

Step 2

(E)-Methyl 3-(4-((1R,3R/1S,3S)-2-(4-cyclopropylphenyl)-3-methyl-6-(((trifluoromethyl)sulfonyl)oxy)-1,2,3,4-tetrahydroisoquinolin-1-yl)phenyl)acrylate 10b Compound 10a (490 mg, 1.11 mmol) was dissolved in 10 mL of dichloromethane, then 2,6-lutidine (180 mg, 1.67 mmol) and trifluoromethanesulfonic anhydride (409 mg, 1.45 mmol) were added successively in an ice bath. After completion of the addition, the ice bath was removed, and the reaction was stirred for 16 hours. Then, 10 mL of water were added to quench the reaction, and the reaction solution was extracted with dichloromethane (10 mL×2). The organic phases were combined and concentrated under reduced pressure. The resulting residue was purified by silica gel column chromatography with elution system B to obtain the title compound 10b (230 mg, yield 36.3%) as a yellow solid.

Step 3

(E)-Methyl 3-(4-((1R,3R/1S,3S)-2-(4-cyclopropylphenyl)-3-methyl-6-(1-methyl-1H-pyrazol-4-yl)-1,2,3,4-tetrahydroisoquinolin-1-yl)phenyl)acrylate 10c Compound 10b (100 mg, 0.17 mmol), 1-methyl-4-(4,4,5,5-tetramethyl-1,3,2-dioxaborolan-2-yl)-1H-pyrazole (55 mg, 0.26 mmol), and [1,1'-bis(diphenylphosphino)ferrocene]dichloropalladium (12 mg, 0.017 mmol) were dissolved in 1.6 mL of a mixture of 1,4-dioxane and water (V:V=7:1), then 2M sodium carbonate solution (0.17 mL, 0.34 mmol) was added. After completion of the addition, the mixture was stirred in a microwave at 120° C. for 30 minutes. After cooling to room temperature, 10 mL of water were added, and the mixture was extract with ethyl acetate (10 mL×3). The organic phases were combined and concentrated under reduced pressure. The resulting residue was purified by silica gel column chromatography with elution system B to obtain the title compound 10c (55 mg, yield 64%) as a yellow solid.

Step 4

(E)-3-(4-((1R,3R/1S,3S)-2-(4-Cyclopropylphenyl)-3-methyl-6-(1-methyl-1H-pyrazol-4-yl)-1,2,3,4-tetrahydroisoquinolin-1-yl)phenyl)acrylic acid 10

Compound 10c (55 mg, 0.1 mmol) was dissolved in 4 mL of a mixture of methanol and tetrahydrofuran (V:V=1:1), then 2 M sodium hydroxide solution (0.25 mL, 0.5 mmol) was added. After completion of the addition, the reaction was stirred for 60 hours. The reaction solution was concentrated under reduced pressure. Then, 10 mL of water were added to the resulting residue, then the mixture was stirred uniformly. Then, 2N hydrochloric acid was added dropwise to adjust the pH of the reaction solution to 2 to 3. The mixture was extracted with ethyl acetate (10 mL×3). The organic phases were combined and concentrated under reduced pressure. The resulting residue was purified by silica gel column chromatography with elution system A to obtain the title compound 10 (50 mg, yield 100%) as a yellow solid.

MS m/z (ESI): 490.5 [M+1]

$^1$H NMR (400 MHz, CDCl$_3$) δ 7.74 (s, 1H), 7.65 (d, 1H), 7.58 (s, 1H), 7.38 (s, 3H), 7.30 (s, 2H), 7.24 (s, 2H), 6.92 (d, 2H), 6.71-6.73 (m, 2H), 6.33 (d, 1H), 5.68 (s, 1H), 4.46 (m, 1H), 3.93 (s, 3H), 3.32-3.43 (m, 1H), 2.72 (d, 1H), 1.76-1.79 (m, 1H), 1.05 (d, 3H), 0.83 (m, 2H), 0.57 (m, 2H).

Examples 11, 12

(E)-3-(4-((1R,3R)-2-(4-Cyclopropylphenyl)-3-methyl-6-(1-methyl-1H-pyrazol-4-yl)-1,2,3,4-tetrahydroisoquinolin-1-yl)phenyl)acrylic acid 11

(E)-3-(4-((1S,3S)-2-(4-Cyclopropylphenyl)-3-methyl-6-(1-methyl-1H-pyrazol-4-yl)-1,2,3,4-tetrahydroisoquinolin-1-yl)phenyl)acrylic acid 12

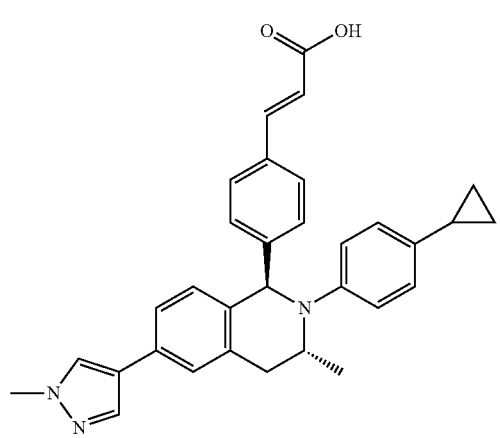

11

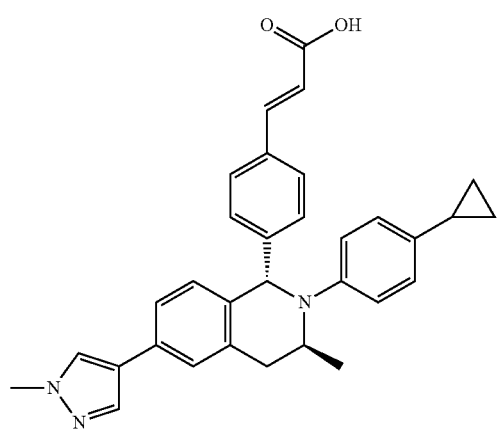

12

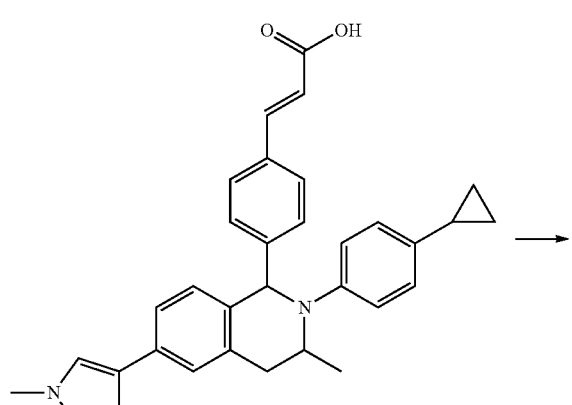

10

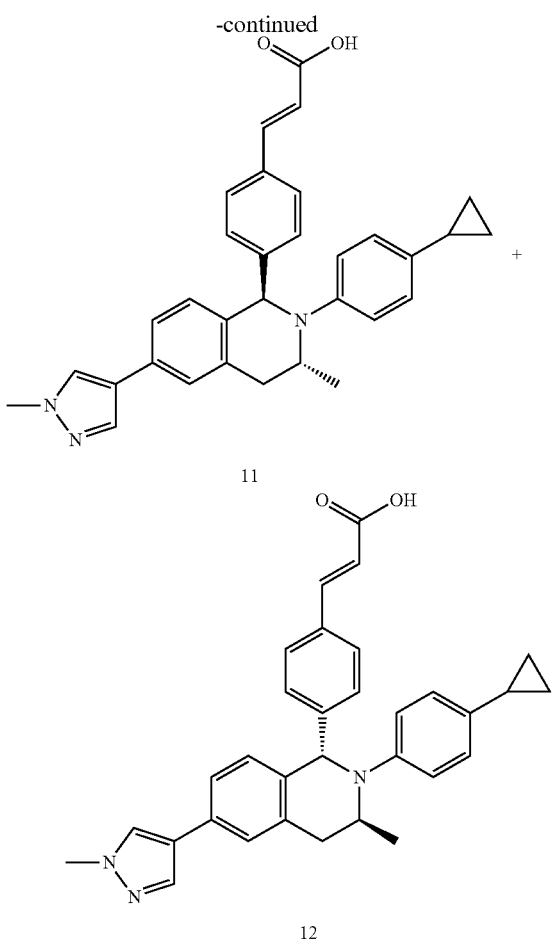

Compound 10 (390 mg, 0.797 mmol) was separated chirally (separation conditions: chiral column: Superchiral S-AD (Chiralway), 2 cm I.D.*25 cm, 5 μm; mobile phase: carbon dioxide: ethanol=60:40, flow rate: 50 mL/min). The corresponding fractions were collected and concentrated under reduced pressure to obtain the title compounds 11 (165 mg, a yellow solid) and 12 (165 mg, a yellow solid).

Example 11

MS m/z (ESI): 490.5 [M+1]

Chiral HPLC analysis: retention time 8.822 minutes, chiral purity: 100% (chromatographic column: Superchiral S-AD (Chiralway), 0.46 cm I.D.*15 cm, 5 μm; mobile phase: carbon dioxide: ethanol=60:40).

$^1$H NMR (400 MHz, CD$_3$OD) δ 7.92 (s, 1H), 7.80 (d, 1H), 7.58 (d, 1H), 7.36-7.42 (m, 7H), 6.90 (d, 2H), 6.77 (d, 2H), 6.36 (d, 1H), 5.74 (s, 1H), 4.48-4.52 (m, 1H), 3.92 (s, 3H), 3.38-3.43 (m, 1H), 2.82-2.77 (d, 1H), 1.73-1.80 (m, 1H), 1.04 (d, 3H), 0.81-0.84 (m, 2H), 0.55-0.53 (m, 2H).

Example 12

MS m/z (ESI): 490.5 [M+1]

Chiral HPLC analysis: retention time 12.539 minutes, chiral purity: 99.4% (chromatographic column: Superchiral S-AD (Chiralway), 0.46 cm I.D.*15 cm, 5 μm; mobile phase: carbon dioxide: ethanol=60:40).

$^1$H NMR (400 MHz, CD$_3$OD) δ7.92 (s, 1H), 7.80 (d, 1H), 7.58 (d, 1H), 7.36-7.42 (m, 7H), 6.90 (d, 2H), 6.77 (d, 2H), 6.36 (d, 1H), 5.74 (s, 1H), 4.48-4.52 (m, 1H), 3.92 (s, 3H), 3.38-3.43 (m, 1H), 2.82-2.77 (d, 1H), 1.73-1.80 (m, 1H), 1.04 (d, 3H), 0.81-0.84 (m, 2H), 0.55-0.53 (m, 2H).

Example 13

(E)-3-(4-((1R,3R/1S,3S)-2-(4-Cyclopropylphenyl)-6-(1-ethyl-1H-pyrazol-4-yl)-3-methyl-1,2,3,4-tetrahydroisoquinolin-1-yl)phenyl)acrylic acid

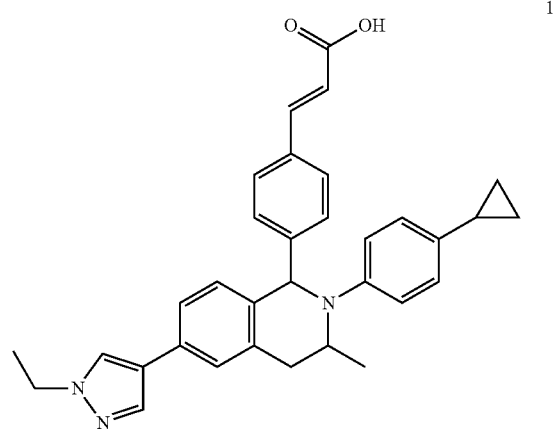

13

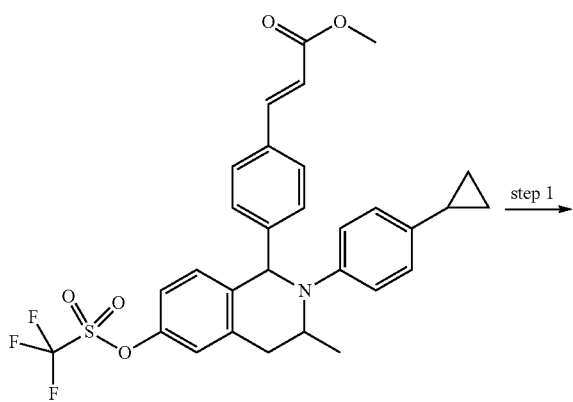

10b

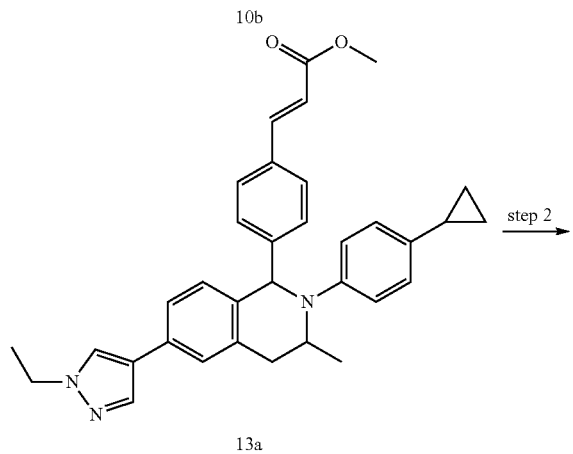

13a

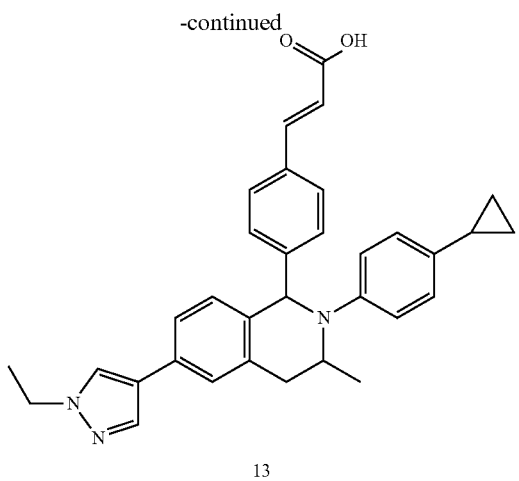

13

Step 1

(E)-Methyl 3-(4-((1R,3R/1S,3S)-2-(4-cyclopropylphenyl)-6-(1-ethyl-1H-pyrazol-4-yl)-3-methyl-1,2,3,4-tetrahydroisoquinolin-1-yl)phenyl)acrylate 13a Compound 10b (485 mg, 0.85 mmol), 1-ethyl-4-(4,4,5,5-tetramethyl-1,3,2-dioxaborolan-2-yl)-1H-pyrazole (283 mg, 1.275 mmol), and [1,1'-bis(diphenylphosphino)ferrocene]dichloropalladium (63 mg, 0.085 mmol) were dissolved in 8 mL of a mixture of 1,4-dioxane and water (V:V=7:1), then 2M sodium carbonate solution (0.85 mL, 1.7 mmol) was added. After completion of the addition, the mixture was stirred in a microwave at 120° C. for 1 hour. After cooling to room temperature, 20 mL of water were added, and the mixture was extracted with ethyl acetate (50 mL×3). The organic phases were combined, dried over anhydrous sodium sulfate and filtered. The filtrate was concentrated under reduced pressure. The resulting residue was purified by silica gel column chromatography with elution system B to obtain the crude title compound 13a (352 mg, yield 80%) as a yellow solid.

MS m/z (ESI): 518.5 [M+1]

Step 2

(E)-3-(4-((1R,3R/1S,3S)-2-(4-Cyclopropylphenyl)-6-(1-ethyl-1H-pyrazol-4-yl)-3-methyl-1,2,3,4-tetrahydroisoquinolin-1-yl)phenyl)acrylic acid 13

Compound 13a (350 mg, 0.676 mmol) was dissolved in 28 mL of a mixture of methanol and tetrahydrofuran (V/V=1:1), then 2 M sodium hydroxide solution (1.7 mL, 3.38 mmol) was added. After completion of the addition, the reaction was stirred for 16 hours. The reaction solution was concentrated under reduced pressure. Then, 10 mL of water were added to the resulting residue, then the mixture was stirred uniformly. Then, 2N hydrochloric acid was added dropwise to adjust the pH of the reaction solution to 2 to 3. The mixture was extracted with ethyl acetate (50 mL×3). The organic phases were combined, dried over anhydrous sodium sulfate and filtered. The filtrate was concentrated under reduced pressure. The resulting residue was purified by silica gel column chromatography with elution system A to obtain the title compound 13 (260 mg, yield 76%) as a yellow solid.

MS m/z (ESI): 504.5 [M+1]

¹H NMR (400 MHz, DMSO-d₆) δ7.95 (s, 1H), 7.79 (s, 1H), 7.54-7.58 (d, 1H), 7.32-7.42 (m, 7H), 6.86-6.88 (d, 2H), 6.75-6.77 (d, 2H), 6.34-6.38 (d, 1H), 5.72 (s, 1H), 4.72 (m, 1H), 4.16-4.22 (m, 2H), 3.36-3.41 (m, 1H), 2.75-2.79 (d, 1H), 1.73-1.77 (m, 1H), 1.45-1.49 (m, 3H), 1.00-1.02 (d, 3H), 0.78-0.80 (m, 2H), 0.50-0.51 (m, 2H).

Examples 14, 15

(E)-3-(4-((1R,3R)-2-(4-Cyclopropylphenyl)-6-(1-ethyl-1H-pyrazol-4-yl)-3-methyl-1,2,3,4-tetrahydroisoquinolin-1-yl)phenyl)acrylic acid 14

(E)-3-(4-((1S,3S)-2-(4-Cyclopropylphenyl)-6-(1-ethyl-1H-pyrazol-4-yl)-3-methyl-1,2,3,4-tetrahydroisoquinolin-1-yl)phenyl)acrylic acid 15

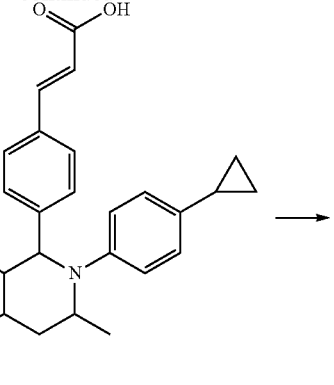

13

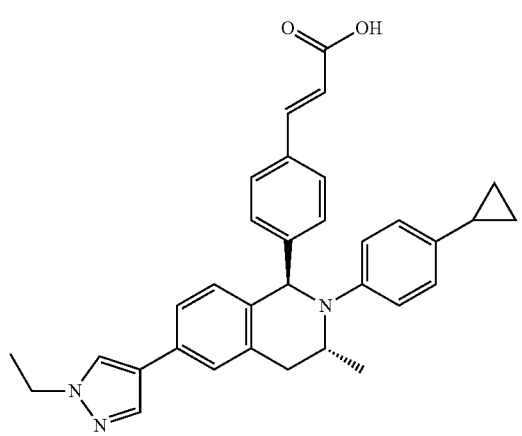

14

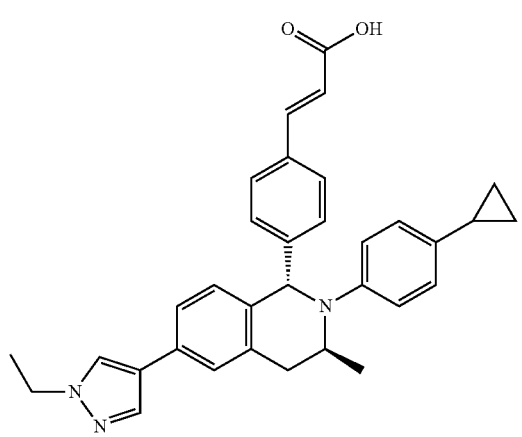

15

Compound 13 (250 mg, 0.497 mmol) was separated chirally (separation conditions: chiral column: Superchiral S-AD (Chiralway), 2 cm I.D.*25 cm, 5 μm; mobile phase: carbon dioxide: ethanol=60:40, flow rate: 50 g/min). The corresponding fractions were collected and concentrated under reduced pressure to obtain the title compounds 14 (105 mg, a yellow solid) and 15 (110 mg, a yellow solid).

Compound 14:

MS m/z (ESI): 504.5 [M+1];

Chiral HPLC analysis: retention time 9.317 minutes, chiral purity: 100% (chromatographic column: Superchiral S-AD (Chiralway), 0.46 cm I.D.*15 cm, 5 μm; mobile phase: carbon dioxide: ethanol=60:40).

¹H NMR (400 MHz, DMSO-d₆) δ7.95 (s, 1H), 7.79 (s, 1H), 7.54-7.58 (d, 1H), 7.32-7.42 (m, 7H), 6.86-6.88 (d, 2H), 6.75-6.77 (d, 2H), 6.34-6.38 (d, 1H), 5.72 (s, 1H), 4.72 (m, 1H), 4.16-4.22 (m, 2H), 3.36-3.41 (m, 1H), 2.75-2.79 (d, 1H), 1.73-1.77 (m, 1H), 1.45-1.49 (m, 3H), 1.00-1.02 (d, 3H), 0.78-0.80 (m, 2H), 0.50-0.51 (m, 2H).

Compound:

MS m/z (ESI): 504.5 [M+1];

Chiral HPLC analysis: retention time 14.061 minutes, chiral purity: 100% (chromatographic column: Superchiral S-AD (Chiralway), 0.46 cm I.D.*15 cm, 5 μm; mobile phase: carbon dioxide: ethanol=60:40).

¹H NMR (400 MHz, DMSO-d₆) δ7.95 (s, 1H), 7.79 (s, 1H), 7.54-7.58 (d, 1H), 7.32-7.42 (m, 7H), 6.86-6.88 (d, 2H), 6.75-6.77 (d, 2H), 6.34-6.38 (d, 1H), 5.72 (s, 1H), 4.72 (m, 1H), 4.16-4.22 (m, 2H), 3.36-3.41 (m, 1H), 2.75-2.79 (d, 1H), 1.73-1.77 (m, 1H), 1.45-1.49 (m, 3H), 1.00-1.02 (d, 3H), 0.78-0.80 (m, 2H), 0.50-0.51 (m, 2H).

Example 16

(E)-3-(4-((1R,3R/1S,3S)-2-(4-Isopropylphenyl)-3-methyl-6-(1-methyl-1H-pyrazol-4-yl)-1,2,3,4-tetrahydroisoquinolin-1-yl)phenyl)acrylic acid 16

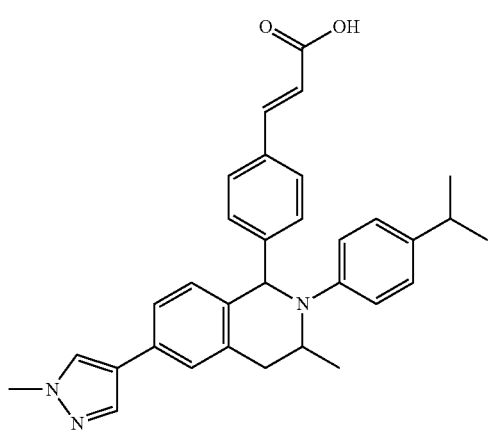

In accordance with the synthetic route of Example 7, the starting materials used in step 5 were replaced with compound 7e and 1-methyl-4-(4,4,5,5-tetramethyl-1,3,2-dioxaborolan-2-yl)-1H-pyrazole, accordingly, the title compound 16 was prepared.

MS m/z (ESI): 492.5[M+1]

¹H NMR (400 MHz, CDCl₃) δ 7.74 (s, 1H), 7.67 (d, 1H), 7.58 (s, 1H), 7.39 (s, 3H), 7.31 (s, 2H), 7.25 (s, 2H), 7.06 (d, 2H), 6.73-6.77 (m, 2H), 6.33 (d, 1H), 5.68 (s, 1H), 4.47-4.53 (m, 1H), 3.93 (s, 3H), 3.32-3.43 (m, 1H), 2.71-2.83 (m, 2H), 1.19 (d, 6H), 1.06 (s, 3H).

Example 17

(E)-3-(4-((1R,3R/1S,3S)-6-(1-Ethyl-1H-pyrazol-4-yl)-2-(4-ethylphenyl)-3-methyl-1,2,3,4-tetrahydroisoquinolin-1-yl)phenyl)acrylic acid 17

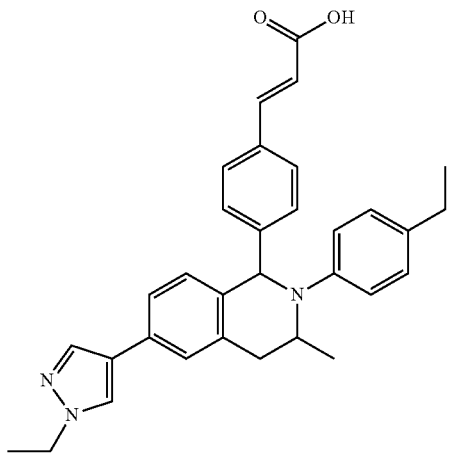

In accordance with the synthetic route of Example 1, the starting materials used in step 5 were replaced with compound 1g and 1-ethyl-4-(4,4,5,5-tetramethyl-1,3,2-dioxaborolan-2-yl)-1H-pyrazole, accordingly, the title compound 17 was prepared.

MS m/z (ESI): 492.5[M+1]

¹H NMR (400 MHz, DMSO-d₆) δ 8.17 (d, 1H), 7.83 (d, 1H), 7.33-7.55 (m, 8H), 6.98 (d, 2H), 6.73 (d, 2H), 6.43 (d, 1H), 5.81 (s, 1H), 4.54-4.63 (m, 1H), 4.10-4.21 (m, 2H), 3.32-3.35 (m, 1H), 2.78 (d, 1H), 2.39-2.51 (m, 2H), 1.37-1.41 (m, 3H), 1.08-1.12 (m, 3H), 0.95 (d, 3H).

Example 18

(E)-3-(4-((1R,3R/1S,3S)-6-(1-Ethyl-1H-pyrazol-4-yl)-2-(4-isobutylphenyl)-3-methyl-1,2,3,4-tetrahydroisoquinolin-1-yl)phenyl)acrylic acid 18

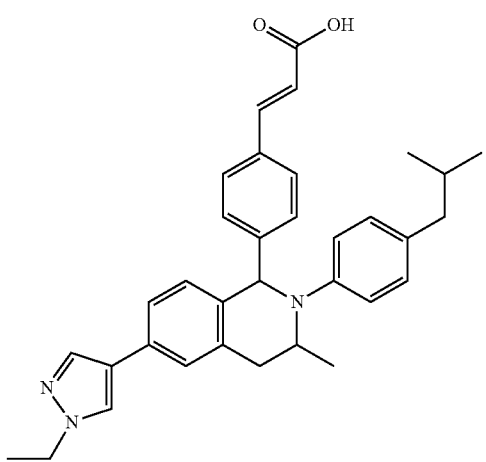

In accordance with the synthetic route of Example 7, the starting materials used in step 1 were replaced with compound 1a and 4-isopropylaniline, accordingly, the title compound 18 was prepared.

MS m/z (ESI): 520.5[M+1]

$^1$H NMR (400 MHz, CD$_3$OD) δ7.96 (s, 1H), 7.79 (s, 1H), 7.57 (d, 1H), 7.37-7.44 (m, 6H), 6.92 (d, 2H), 6.77 (d, 2H), 6.37 (d, 1H), 5.74 (s, 1H), 4.51 (m, 1H), 4.19 (q, 2H), 3.38 (dd, 1H), 2.78 (dd, 1H), 2.31 (d, 2H), 1.75 (m, 1H), 1.47 (t, 3H), 1.03 (d, 3H), 0.90 (m, 1H), 0.85 (d, 6H).

Example 19

(E)-3-(4-((1R,3R/1S,3S)-2-(4-Isobutylphenyl)-3-methyl-6-(1-methyl-1H-pyrazol-4-yl)-1,2,3,4-tetrahydroisoquinolin-1-yl)phenyl)acrylic acid 19

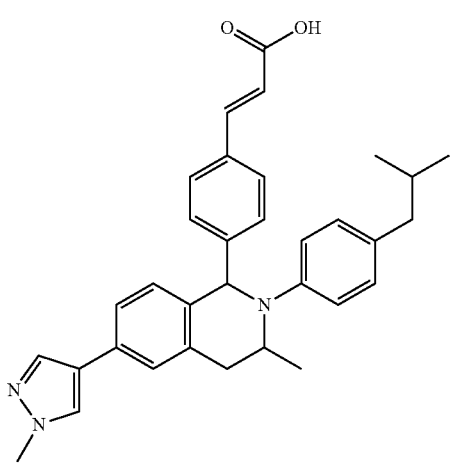

In accordance with the synthetic route of Example 1, the starting materials used in step 1 were replaced with compound 1a and 4-isopropylaniline, accordingly, the title compound 19 was prepared.

MS m/z (ESI): 506.5[M+1]

$^1$H NMR (400 MHz, CD$_3$OD) δ7.90 (s, 1H), 7.78 (s, 1H), 7.55 (d, 1H), 7.389-7.34 (m, 6H), 6.92 (d, 2H), 6.76 (d, 2H), 6.36 (d, 1H), 5.73 (s, 1H), 4.50 (m, 1H), 3.90 (s, 3H), 3.38 (dd, 1H), 2.77 (dd, 1H), 2.31 (d, 2H), 1.74 (m, 1H), 1.02 (d, 3H), 0.90 (m, 1H), 0.85 (d, 6H).

Example 20

(E)-3-(4-((1R,3R/1S,3S)-3-Methyl-6-(1-methyl-1H-pyrazol-4-yl)-2-(4-propylphenyl)-1,2,3,4-tetrahydroisoquinolin-1-yl)phenyl)acrylic acid 20

In accordance with the synthetic route of Example 1, the starting materials used in step 1 were replaced with compound 1a and 4-isopropylaniline, accordingly, the title compound 20 was prepared.

MS m/z (ESI): 492.5 [M+1]

$^1$H NMR (400 MHz, DMSO-d$_6$) g 8.08 (s, 1H), 7.81 (s, 1H), 7.43-7.53 (m, 6H), 7.37-7.39 (m, 2H), 6.93-6.95 (d, 2H), 6.70-6.72 (d, 2H), 6.36-6.42 (d, 1H), 5.80 (s, 1H), 4.51-4.52 (m, 1H), 3.81 (s, 3H), 3.32-3.34 (m, 2H), 2.74-2.78 (d, 1H), 2.35-2.39 (m, 2H), 1.45-1.51 (m, 2H), 0.92-0.94 (d, 2H), 0.82-0.86 (m, 3H).

Example 21

(E)-3-(4-((1R,3R)-2-(4-Cyclopropylphenyl)-6-(1-ethyl-d$_5$-1H-pyrazol-4-yl)-3-methyl-1,2,3,4-tetrahydroisoquinolin-1-yl)phenyl)acrylic acid 21

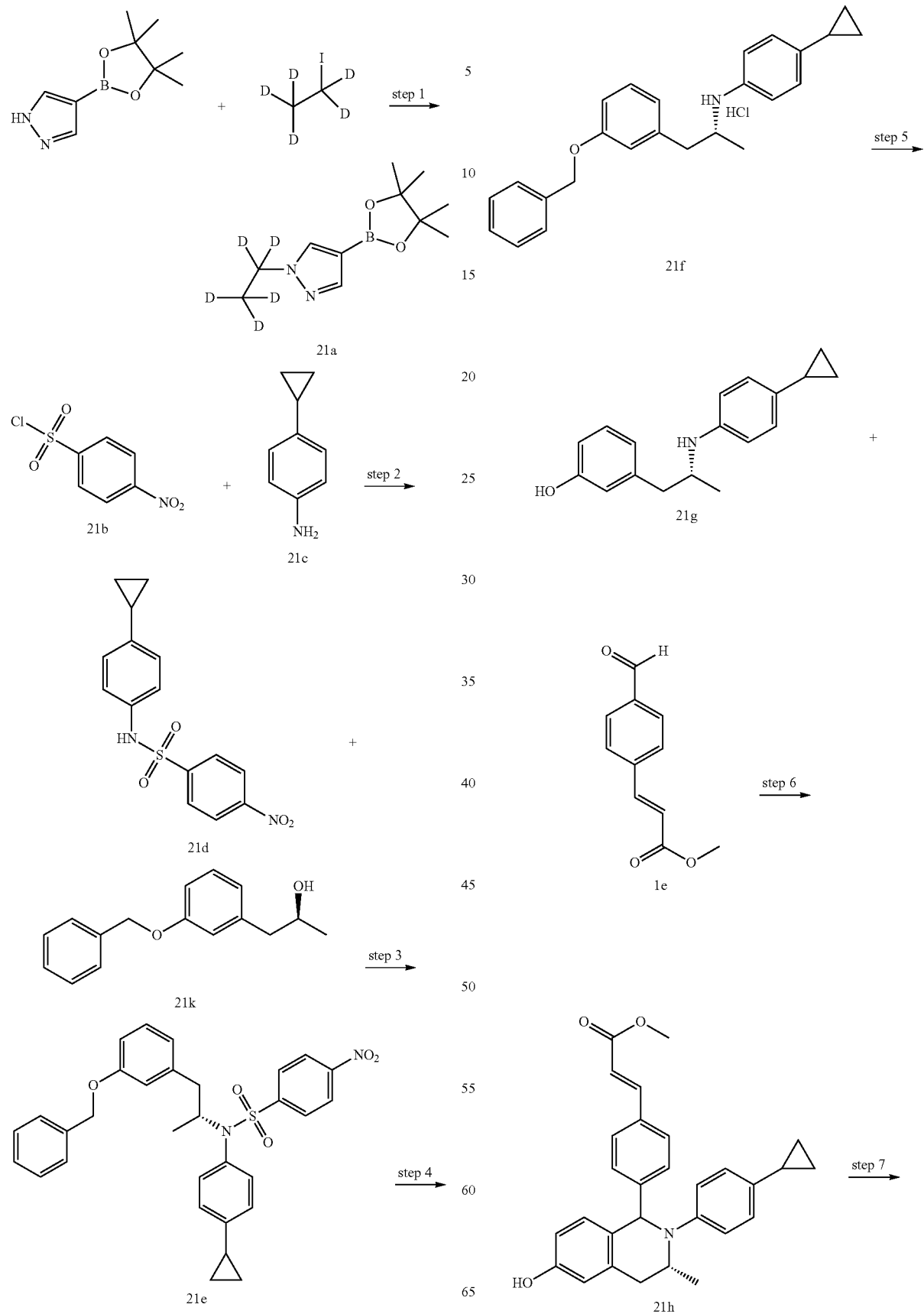

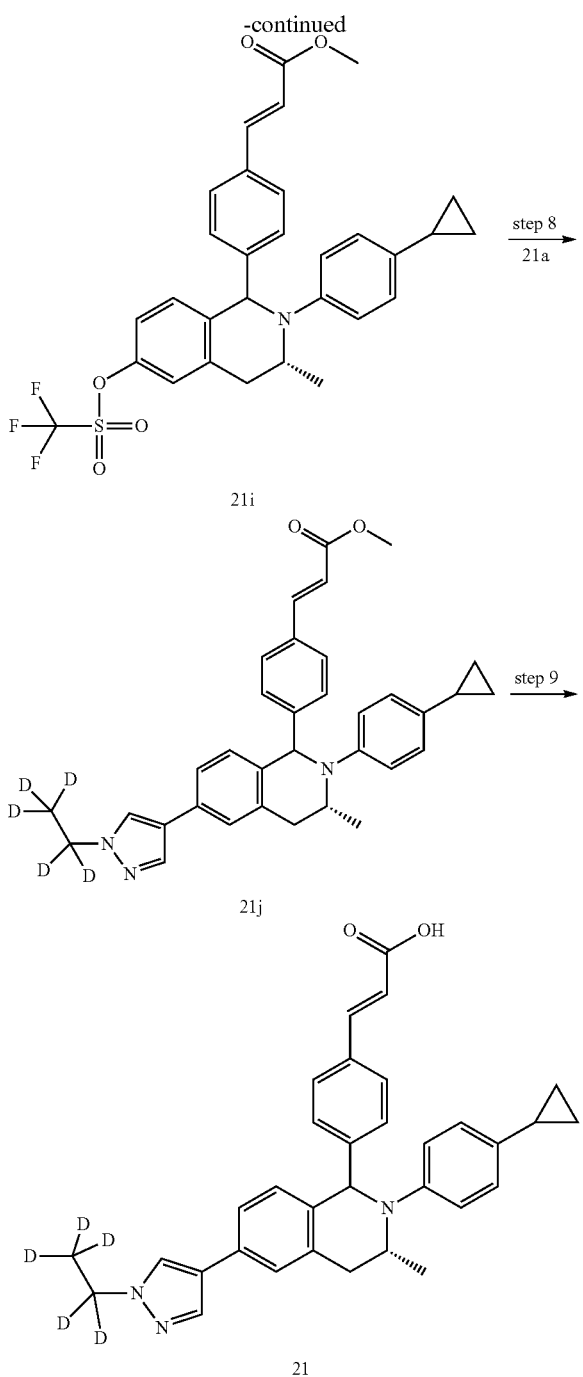

pressure. The residue was washed with 50 mL of ethyl acetate, and filtered. The filtrate was concentrated under reduced pressure to obtain the crude title product 21a (2.13 g, a solid-liquid mixture), which was used directly in the next step without further purification.

MS m/z (ESI): 228.5 [M+1]

Step 2

N-(4-Cyclopropylphenyl)-4-nitrobenzenesulfonamide 21d 4-cyclopropylaniline 21c (80.8 g, 0.61 mol, prepared by a well known method disclosed in "*Journal of the American Chemical Society,* 2016, 138(27), 8533-8537) and 2,6-lutidine (97.5 g, 0.91 mol) was dissolved in 400 mL of dichloromethane. The reaction solution was cooled to 0-5° C. under an argon atmosphere. Then, a solution of 4-nitrobenzene-1-sulfonyl chloride 21b (134.5 g, 0.61 mol) in 40 mL of dichloromethane was added dropwise to the above reaction solution. After completion of the addition, the reaction was stirred for 20 minutes. The reaction solution was warmed up to room temperature, and 500 mL of water was added. The mixture was stirred until a solid was precipitated. After filtration, the filter cake and the filtrate were collected to obtain the crude title compound 21d (340.3 g, a black viscous liquid), which was used directly in the next step without further purification.

Step 3

(R)—N-(1-(3-(Benzyloxy)phenyl)propan-2-yl)-N-(4-cyclopropylphenyl)-4-nitrobenzenesulfonamide 21e The crude compound 21d (305.5 g, 0.78 mol), (S)-1-(3-(benzyloxy)phenyl)propan-2-ol 21k (188.8 g, 0.78 mol, prepared by a method disclosed in the patent application publication "WO2014133361A1") and triphenylphosphine (306.5 g, 1.17 mol) were dissolved in 2 L of tetrahydrofuran. The reaction solution was cooled to 0° C. under an argon atmosphere, then diethyl azodicarboxylate (203.5 g, 1.17 mol) was added dropwise to the above reaction solution. The reaction temperature was kept at 0 to 10° C. After completion of the addition, the reaction was stirred for 12 hours at room temperature. The reaction solution was concentrated under reduced pressure, and triturated with 2 L of tert-butyl methyl ether and 2 L of petroleum ether successively to obtain the crude title compound 21e (701.7 g) as a light yellow solid, which was used directly in the next step without further purification.

Step 4

(R)—N-(1-(3-(Benzyloxy)phenyl)propan-2-yl)-4-cyclopropylaniline hydrochloride 21f The crude compound 21e (550 g, 0.66 mol), lithium hydroxide hydrate (273.1 g, 6.65 mol) and 2-amino-3-mercaptopropionic acid (96.6 g, 0.80 mol) were dissolved in 3.5 L of N,N-dimethylformamide. After stirring for 18 hours, 6 L of water were added, and the reaction solution was extracted with ethyl acetate (1.5 L×3). The organic phases were combined, washed with water (500 mL), and concentrated under reduced pressure. Then, 170 mL of 6 N hydrochloric acid and 2 L of a mixture of ethyl acetate and petroleum ether (V:V=1:1) were added to the resulting Step 1

1-Ethyl-$d_5$-4-(4,4,5,5-tetramethyl-1,3,2-dioxaborolan-2-yl)-1H-pyrazole 21a 4-(4,4,5,5-tetramethyl-1,3,2-dioxaborolan-2-yl)-1H-pyrazole (2 g, 10.3 mmol) and potassium carbonate (2.14 g, 15.5 mmol) were added to 20 mL of N,N-dimethylformamide, then iodoethane-d5 (2 g, 12.4 mmol) was added. The reaction was stirred for 16 hours. Since the starting materials were not reacted completely, the reaction was warmed up to 50° C. and stirred for 3 hours. The reaction solution was filtered, and the filtrate was concentrated under reduced residue. The mixture was filtered, and the filter cake was collected to obtain the crude title compound 21f (120.1 g) as a light yellow solid, which was used directly in next step without further purification.

Step 5

(R)-3-(2-((4-Cyclopropylphenyl)amino)propyl)phenol 21 g

The crude compound 21f (120.1 g, 0.30 mol) and sodium iodide (182.8 g, 1.22 mol) were dissolved in 840 mL of acetonitrile, then trimethylsilyl chloride (132.5 g, 1.22 mol) was added dropwise under an argon atmosphere. The mixture was stirred for 12 hours, and 360 mL of 1N hydrochloric acid were added. The reaction was stirred for 5 minutes. Saturated sodium dithionite solution was added until the red of iodine disappeared. The mixture was extracted with ethyl acetate (300 mL×3). The organic phases were combined, washed with saturated sodium chloride solution (200 mL), dried over anhydrous sodium sulfate and filtered. The filtrate was concentrated under reduced pressure to obtain the crude title compound 21g (140.6 g) as a colorless viscous solid, which was used directly in the next step without further purification.

Step 6

(E)-Methyl 3-(4-((1R,3R)/(1S,3R)-2-(4-cyclopropylphenyl)-6-hydroxy-3-methyl-1,2,3,4-tetrahydroisoquinolin-1-yl)phenyl)acrylate 21h The crude compound 21 g (127.2 g, 0.48 mmol), compound 1e (144.8 g, 0.76 mol) and triisopropylsilyl chloride (183.4 g, 0.95 mol) were added to 1200 mL of N,N-dimethylformaminde. After completion of the addition, the mixture was heated to 140° C. under an argon atmosphere and stirred for 2 hours. After stopping heating, the reaction solution was concentrated under reduced pressure. Then, 500 mL of water and 500 mL of ethyl acetate were added successively and filtered. Two phases were separated, and aqueous phase was washed with ethyl acetate (300 mL×2). The organic phases were combined, washed with saturated sodium chloride solution (300 mL), dried over anhydrous sodium sulfate, and filtered. The filtrate was concentrated under reduced pressure. The resulting residue was purified by silica gel column chromatography with elution system C to obtain the title compound 21h (78.7 g, yield 37.6%) as an orange solid.

Step 7

(E)-Methyl 3-(4-((1R,3R)-2-(4-cyclopropylphenyl)-3-methyl-6-(((trifluoromethyl) sulfonyl)oxy)-1,2,3,4-tetrahydroisoquinolin-1-yl)phenyl)acrylate 21i Compound 21h (20 g, 45.5 mmol) and 2,6-lutidine (7.3 g, 68.3 mmol) were dissolved in 400 mL of dichloromethane. After completion of the addition, the reaction was cooled to 0° C. in an ice bath under an argon atmosphere. Then, trifluoromethanesulfonic anhydride (16.7 g, 59.2 mmol) was added dropwise. After completion of the addition, the ice bath was removed, and the reaction was stirred for 12 hours at room temperature. Then, 100 mL of water were added to quench the reaction. Two phases were separated, and the aqueous phase was extracted with dichloromethane (100 mL). The organic phases were combined, washed with saturated sodium chloride solution (100 mL), dried over anhydrous sodium sulfate, and filtrated to remove the desiccant. The filtrate was concentrated under reduced pressure. The resulting residue was purified by silica gel column chromatography with elution system C to obtain the title compound 21l (4.5 g, yield 17.3%) as an orange viscous solid.

MS m/z (ESI): 572.2 [M+1]

Step 8

(E)-Methyl 3-(4-((1R,3R)-2-(4-cyclopropylphenyl)-6-(1-ethyl-d$_5$-1H-pyrazol-4-yl)-3-methyl-1,2,3,4-tetrahydroisoquinolin-1-yl)phenyl)acrylate 21j The crude compound 21a (2.04 g, 9 mmol), compound 21l (4.1 g, 7.2 mmol) and [1,1'-bis(diphenylphosphino) ferrocene]dichloropalladium (1.31 g, 1.8 mmol) were dissolved in 44 mL of a mixture of 1,4-dioxane and water (V:V=10:1), then potassium carbonate (3.72 mL, 26.9 mmol) was added. The mixture was stirred for 12 hours at 80° C. After cooling to room temperature, 100 mL of water were added, and the mixture was extracted with ethyl acetate (100 mL×3). The organic phases were combined, dried over anhydrous sodium sulfate and filtered. The filtrate was concentrated under reduced pressure. The resulting residue was purified by silica gel column chromatography with elution system C to obtain the crude title compound 21j (1.8 g, yield 38.3%) as a yellow solid.

MS m/z (ESI): 523.6 [M+1]

Step 9

(E)-3-(4-((1R,3R)-2-(4-Cyclopropylphenyl)-6-(1-ethyl-d$_5$-1H-pyrazol-4-yl)-3-methyl-1,2,3,4-tetrahydroisoquinolin-1-yl)phenyl)acrylic acid 21

Compound 21j (1.71 g, 3.3 mmol) was dissolved in 24 mL of a mixture of methanol and tetrahydrofuran (V:V=1:5), then sodium hydroxide (982 mg, 24.5 mmol) and 20 mL of water were added. The reaction was stirred for 16 hours under an argon atmosphere in the dark. The reaction solution was concentrated under reduced pressure. Then, 20 mL of saturated citric acid solution were added to the residue, then the mixture was extracted with ethyl acetate (50 mL×3). The organic phases were combined, washed with saturated sodium chloride solution, dried over anhydrous sodium sulfate, and filtered. The filtrate was concentrated under reduced pressure. The resulting residue was purified by High Performance Liquid Chromatography to obtain the title compound 21 (1.05 g, yield 63.2%) as a yellow solid.

MS m/z (ESI): 509.6 [M+1]

$^1$H NMR (400 MHz, DMSO-d$_6$) δ7.98 (s, 1H), 7.82 (s, 1H), 7.59 (d, 1H), 7.41-7.33 (m, 7H), 6.90 (d, 2H), 6.79 (d, 2H), 6.39 (d, 1H), 5.76 (s, 1H), 4.48-4.51 (m, 1H), 3.42 (dd, 1H), 2.82 (d, 1H), 1.74-1.81 (m, 1H), 1.04 (d, 3H), 0.82-0.84 (d, 2H), 0.53-0.54 (m, 2H).

Example 22

(E)-3-(4-((1R,3R/1S,3S)-2-(4-Cyclopropyl-2-fluorophenyl)-6-(1-ethyl-1H-pyrazol-4-yl)-3-methyl-1,2,3,4-tetrahydroisoquinolin-1-yl)phenyl)acrylic acid 22

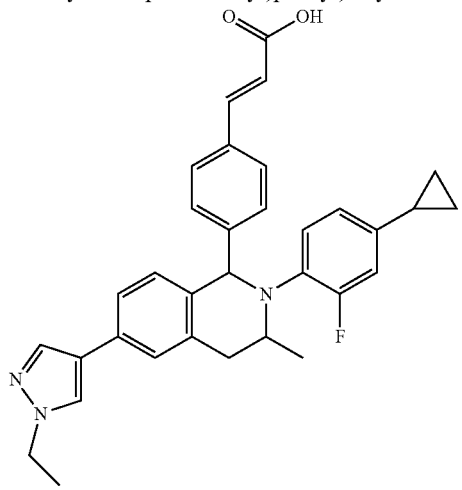

In accordance with the synthetic route of Example 7, the starting material 7a used in step 1 was replaced with 4-cyclopropyl-2-fluoroaniline (prepared by a well known method disclosed in "*Tetrahedron Lett*, 2002, 43, 6987"), accordingly, the title compound 22 (270 mg, a yellow solid) was prepared.

MS m/z (ESI): 522.6 [M+1]

$^1$H NMR (400 MHz, CD$_3$OD) δ 7.96 (s, 1H), 7.80 (s, 1H), 7.57 (d, 1H), 7.41-7.35 (m, 5H), 7.24 (dd, 1H), 7.07 (t, 1H), 6.87 (d, 1H), 6.69 (s, 1H), 6.69-6.62 (m, 1H), 6.38 (d, 1H), 5.69 (s, 1H), 4.21 (q, 2H), 3.91 (dd, 1H), 3.59 (dd, 1H), 2.78 (dd, 1H), 1.78 (ddd, 1H), 1.49 (t, 3H), 1.07 (d, 3H), 0.93-0.84 (m, 2H), 0.61-0.51 (m, 2H).

Example 23

(E)-3-(4-((1R,3R/1S,3S)-2-(2-Chloro-4-ethylphenyl)-6-(1-ethyl-1H-pyrazol-4-yl)-3-methyl-1,2,3,4-tetrahydroisoquinolin-1-yl)phenyl)acrylic acid 23

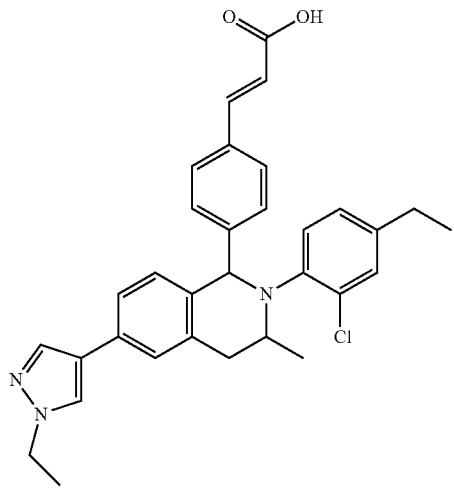

In accordance with the synthetic route of Example 7, the starting material 7a used in step 1 was replaced with 2-chloro-4-ethylaniline (prepared by a well known method disclosed in "*Journal of Chemical and Engineering Data*, 1963, 8, 122-130"), accordingly, the title compound 23 (390 mg, a yellow solid) was prepared.

MS m/z (ESI): 527.1 [M+1]

$^1$H NMR (400 MHz, CD$_3$OD) δ 7.96 (s, 1H), 7.80 (s, 1H), 7.54 (d, 1H), 7.47-7.42 (m, 2H), 7.41-7.35 (m, 3H), 7.33-7.26 (m, 1H), 7.21 (d, 1H), 7.15 (s, 1H), 6.95 (d, 1H), 6.83 (d, 1H), 6.36 (dd, 1H), 5.75 (s, 1H), 4.20 (q, 2H), 3.90-3.85 (m, 1H), 3.80-3.72 (m, 1H), 2.77 (d, 1H), 2.50 (q, 2H), 1.48 (t, 3H), 1.14 (t, 3H), 1.08 (d, 3H).

Example 24

(E)-3-(4-((1R,3R/1S,3S)-2-(2-Chloro-4-cyclopropylphenyl)-6-(1-ethyl-1H-pyrazol-4-yl)-3-methyl-1,2,3,4-tetrahydroisoquinolin-1-yl)phenyl)acrylic acid 24

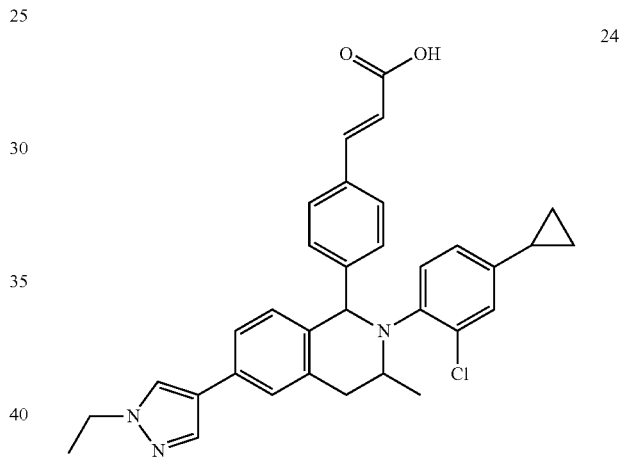

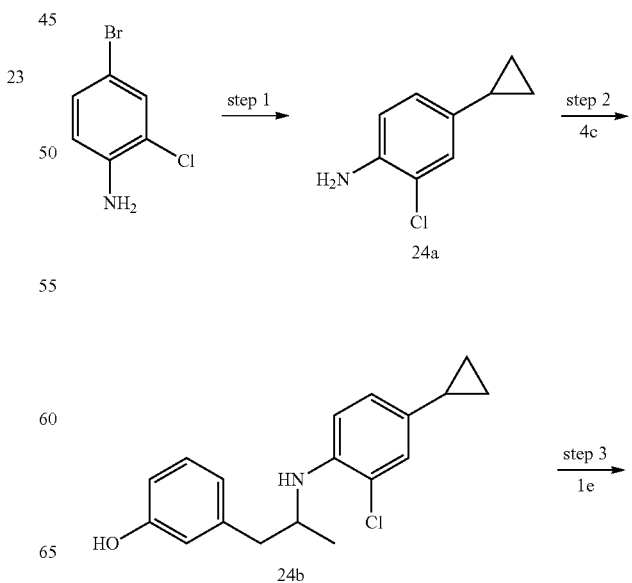

-continued

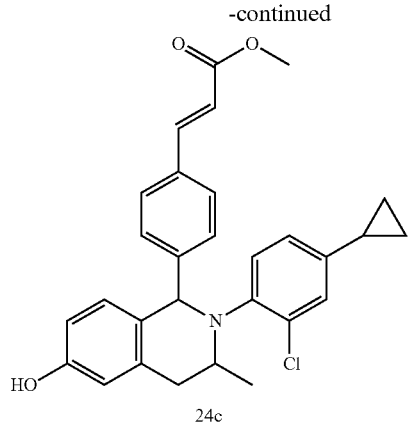

24c

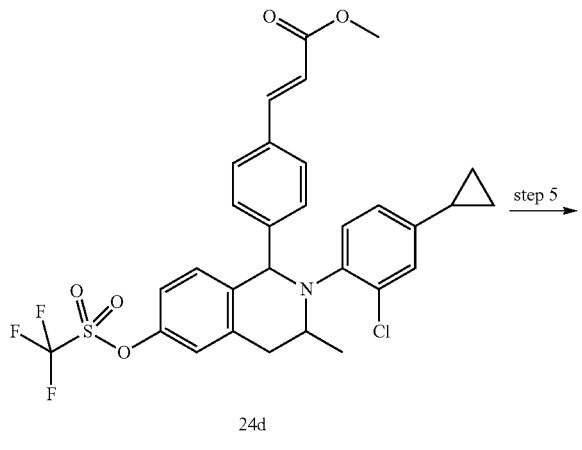

24d

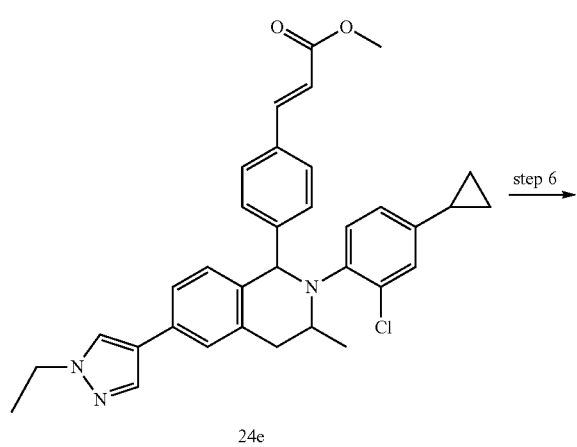

24e

-continued

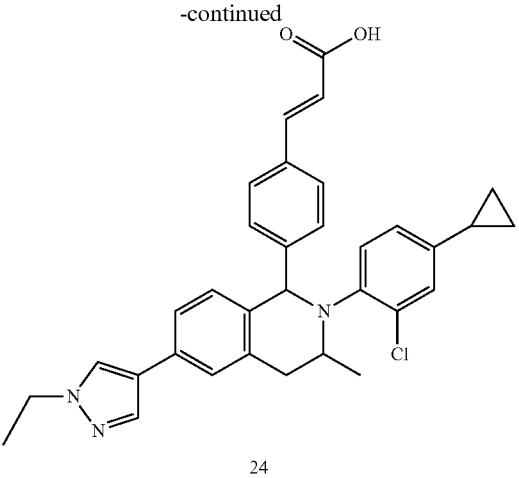

24

Step 1

2-Chloro-4-cyclopropylaniline 24a 4-bromo-2-chloroaniline (5 g, 24.2 mmol), cyclopropylboronic acid (4 g, 48.4 mmol), tricyclohexylphosphine (680 mg, 2.42 mmol), palladium acetate (271 mg, 1.21 mmol) and potassium carbonate (15.4 g, 72.6 mmol) were added to 130 mL of a mixture of toluene and water (V:V=25:1). The mixture was heated to 100° C. and stirred for 12 hours. The reaction solution was filtered, and the filtrate was concentrated under reduced pressure. The resulting residue was purified by silica gel column chromatography with elution system B to obtain the title compound 24a (2.5 g, yield 61.7%) as a yellow liquid.
MS m/z (ESI): 168.1 [M+1]

Step 2

3-(2-(2-Chloro-4-cyclopropylphenylamino)propyl) phenol 24b

Compound 4c (2.46 g, 16.4 mmol), compound 24a (2.5 g, 14.9 mmol) and sodium triacetoxyborohydride (5.2 g, 24.6 mmol) were dissolved in 60 mL of dichloroethane. The mixture was stirred for 12 hours. Then, 20 mL of water were added to quench the reaction. The reaction solution was extracted with dichloromethane (20 mL×2). The organic phases were combined and concentrated under reduced pressure. The resulting residue was purified by silica gel column chromatography with elution system B to obtain the title compound 24b (1.5 g, yield 33.5%) as a yellow oil.
MS m/z (ESI): 302.1 [M+1]

Step 3

(E)-Methyl 3-(4-((1R,3R/1S,3S)-2-(2-chloro-4-cyclopropylphenyl)-6-hydroxy-3-methyl-1,2,3,4-tetrahydroisoquinolin-1-yl)phenyl)acrylate 24c Compound 24b (1.5 g, 5 mmol), compound 1e (1.9 g, 10 mmol) and triisopropylsilyl chloride (1.9 g, 10 mmol) were added to 30 mL of N,N-dimethylformaminde. After completion of the addition, the mixture was heated to 140° C. and stirred for 3 hours. After stopping heating, the reaction solution was concentrated under reduced pressure. Then, 20 mL of water were added to the resulting residue, then the mixture was stirred uniformly and extracted with ethyl acetate (20 mL×3). The organic phases were combined and dried over anhydrous sodium sulfate. The filtrate was concentrated under reduced pressure. The resulting residue was purified by silica gel column chromatography with elution system B to obtain the title compound 24c (1.5 g, yield 65.2%) as a yellow solid.

MS m/z (ESI): 474.2 [M+1]

Step 4

(E)-Methyl 3-(4-((1R,3R/1S,3S)-2-(2-chloro-4-cyclopropylphenyl)-3-methyl-6-(((trifluoromethyl)sulfonyl)oxy)-1,2,3,4-tetrahydroisoquinolin-1-yl)phenyl)acrylate 24d Compound 24c (1.5 g, 3.16 mmol) and 2,6-lutidine (508 mg, 4.74 mmol) were dissolved in 30 mL of dichloromethane. After the reaction was cooled to 0° C., trifluoromethanesulfonic anhydride (1.16 g, 4.11 mmol) was added dropwise. The reaction was stirred for 12 hours at room temperature. Then, 20 mL of water were added to quench the reaction, and the reaction solution was extracted with dichloromethane (50 mL×2). The organic phases were combined and concentrated under reduced pressure. The resulting residue was purified by silica gel column chromatography with elution system B to obtain the title compound 24d (0.95 g, yield 49.7%) as a yellow solid.

MS m/z (ESI): 606.2 [M+1]

Step 5

(E)-Methyl 3-(4-((1R,3R/1S,3S)-2-(2-chloro-4-cyclopropylphenyl)-6-(1-ethyl-1H-pyrazol-4-yl)-3-methyl-1,2,3,4-tetrahydroisoquinolin-1-yl)phenyl)acrylate 24e Compound 24d (750 mg, 1.24 mmol), 1-ethyl-4-(4,4,5,5-tetramethyl-1,3,2-dioxaborolan-2-yl)-1H-pyrazole (412 mg, 1.86 mmol), and [1,1'-bis(diphenylphosphino)ferrocene]dichloropalladium (91 mg, 0.124 mmol) were dissolved in 13.5 mL of a mixture of 1,4-dioxane and water (V:V=8:1), then 2N sodium carbonate solution (1.24 mL) was added. After completion of the addition, the mixture was stirred in a microwave at 120° C. for 45 minutes. After cooling to room temperature, 20 mL of water were added, and the mixture was extracted with ethyl acetate (30 mL×3). The organic phases were combined and dried over anhydrous sodium sulfate. The filtrate was concentrated under reduced pressure. The residue was purified by silica gel column chromatography with elution system B to obtain the title compound 24e (480 mg, yield 70.2%) as a yellow solid.

MS m/z (ESI): 552.3 [M+1]

Step 6

(E)-3-(4-((1R,3R/1S,3S)-2-(2-Chloro-4-cyclopropylphenyl)-6-(1-ethyl-1H-pyrazol-4-yl)-3-methyl-1,2,3,4-tetrahydroisoquinolin-1-yl)phenyl)acrylic acid 24

Compound 24e (480 mg, 0.87 mmol) was dissolved in 10 mL of a mixture of methanol and tetrahydrofuran (V:V=1:1), then 2 N sodium hydroxide solution (2.17 mL) was added. After completion of the addition, the reaction was stirred for 12 hours. The reaction solution was concentrated under reduced pressure. Then, 10 mL of water were added to the resulting residue, then the mixture was stirred uniformly. Then, 1N hydrochloric acid was added dropwise to adjust the pH of the reaction solution to 5. The mixture was extracted with ethyl acetate (30 mL×2). The organic phases were combined, dried over anhydrous sodium sulfate, and filtrated to remove the desiccant. The filtrate was concentrated under reduced pressure. The resulting residue was purified by silica gel column chromatography with elution system A to obtain the title compound 24 (200 mg, yield 64.1%) as a yellow solid.

MS m/z (ESI): 538.4 [M+1]

$^1$H NMR (400 MHz, CD$_3$OD) δ7.95 (s, 1H), 7.79 (s, 1H), 7.56 (d, 1H), 7.47-7.40 (m, 2H), 7.38-7.35 (m, 3H), 7.27-7.20 (m, 2H), 7.00 (s, 1H), 6.83 (d, 2H), 6.63 (d, 1H), 5.73 (s, 1H), 4.19 (q, 2H), 3.87-3.83 (m, 1H), 3.80-3.72 (m, 1H), 2.81-2.71 (m, 1H), 1.79-1.72 (m, 1H), 1.48 (t, 3H), 1.08 (d, 3H), 0.88-0.86 (m, 2H), 0.59-0.54 (m, 2H).

Example 25

(E)-3-(4-((1S,3R/1R,3S)-2-(4-Cyclopropylphenyl)-6-(1-ethyl-1H-pyrazol-4-yl)-3-methyl-1,2,3,4-tetrahydroisoquinolin-1-yl)-3-fluorophenyl)acrylic acid 25

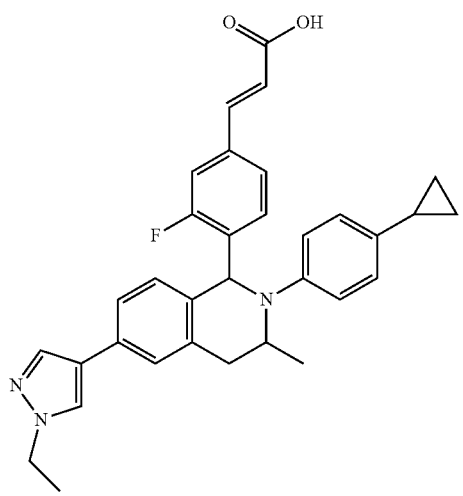

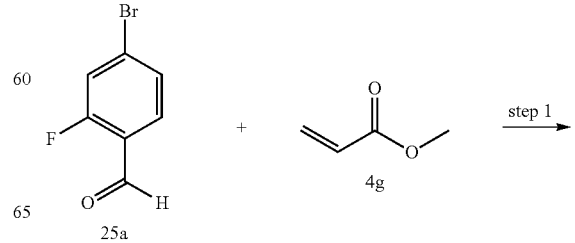

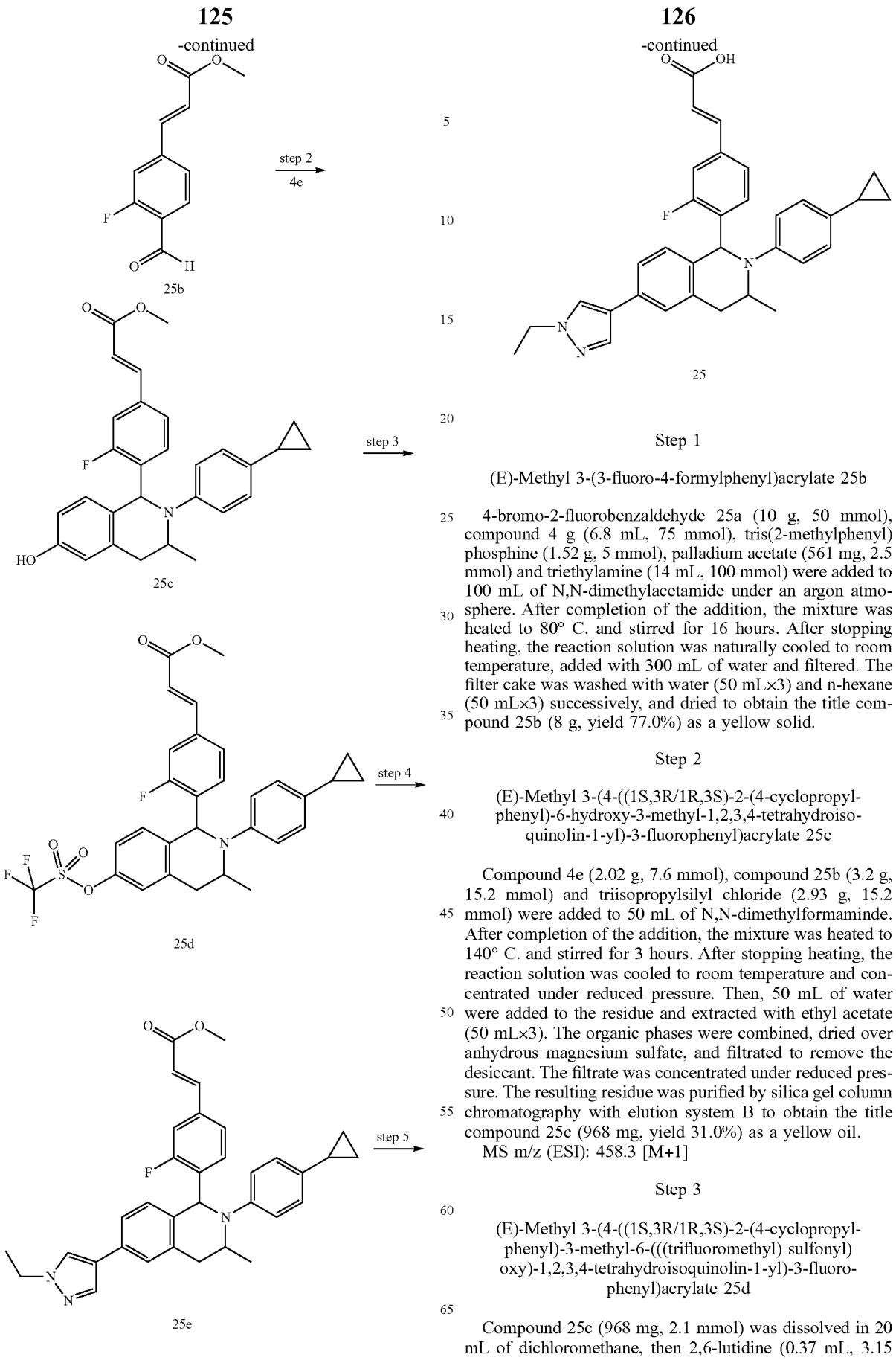

Step 1

(E)-Methyl 3-(3-fluoro-4-formylphenyl)acrylate 25b 4-bromo-2-fluorobenzaldehyde 25a (10 g, 50 mmol), compound 4 g (6.8 mL, 75 mmol), tris(2-methylphenyl) phosphine (1.52 g, 5 mmol), palladium acetate (561 mg, 2.5 mmol) and triethylamine (14 mL, 100 mmol) were added to 100 mL of N,N-dimethylacetamide under an argon atmosphere. After completion of the addition, the mixture was heated to 80° C. and stirred for 16 hours. After stopping heating, the reaction solution was naturally cooled to room temperature, added with 300 mL of water and filtered. The filter cake was washed with water (50 mL×3) and n-hexane (50 mL×3) successively, and dried to obtain the title compound 25b (8 g, yield 77.0%) as a yellow solid.

Step 2

(E)-Methyl 3-(4-((1S,3R/1R,3S)-2-(4-cyclopropyl-phenyl)-6-hydroxy-3-methyl-1,2,3,4-tetrahydroiso-quinolin-1-yl)-3-fluorophenyl)acrylate 25c Compound 4e (2.02 g, 7.6 mmol), compound 25b (3.2 g, 15.2 mmol) and triisopropylsilyl chloride (2.93 g, 15.2 mmol) were added to 50 mL of N,N-dimethylformaminde. After completion of the addition, the mixture was heated to 140° C. and stirred for 3 hours. After stopping heating, the reaction solution was cooled to room temperature and concentrated under reduced pressure. Then, 50 mL of water were added to the residue and extracted with ethyl acetate (50 mL×3). The organic phases were combined, dried over anhydrous magnesium sulfate, and filtrated to remove the desiccant. The filtrate was concentrated under reduced pressure. The resulting residue was purified by silica gel column chromatography with elution system B to obtain the title compound 25c (968 mg, yield 31.0%) as a yellow oil.

MS m/z (ESI): 458.3 [M+1]

Step 3

(E)-Methyl 3-(4-((1S,3R/1R,3S)-2-(4-cyclopropyl-phenyl)-3-methyl-6-(((trifluoromethyl) sulfonyl) oxy)-1,2,3,4-tetrahydroisoquinolin-1-yl)-3-fluoro-phenyl)acrylate 25d Compound 25c (968 mg, 2.1 mmol) was dissolved in 20 mL of dichloromethane, then 2,6-lutidine (0.37 mL, 3.15 mmol) was added. After completion of the addition, the reaction was cooled to 0° C. in an ice bath, and trifluoromethanesulfonic anhydride (0.45 mL, 2.73 mmol) was added dropwise. After completion of the addition, the ice bath was removed, and the reaction was stirred for 3 hours at room temperature. Then, 30 mL of water were added, and the reaction solution was extracted with dichloromethane (15 mL×3). The organic phases were combined, washed with saturated sodium chloride solution, dried over anhydrous sodium sulfate, and filtrated to remove the desiccant. The filtrate was concentrated under reduced pressure. The resulting residue was purified by silica gel column chromatography with elution system B to obtain the title compound 25d (530 mg, yield 42.4%) as a yellow oil.

MS m/z (ESI): 590.2 [M+1]

Step 4

(E)-Methyl 3-(4-((1S,3R/1R,3S)-2-(4-cyclopropylphenyl)-6-(1-ethyl-1H-pyrazol-4-yl)-3-methyl-1,2,3,4-tetrahydroisoquinolin-1-yl)-3-fluorophenyl)acrylate 25e Compound 25d (530 mg, 0.9 mmol), 1-ethyl-4-(4,4,5,5-tetramethyl-1,3,2-dioxaborolan-2-yl)-1H-pyrazole (300 mg, 1.35 mmol), and [1,1'-bis(diphenylphosphino)ferrocene] dichloropalladium (66 mg, 0.09 mmol) were dissolved in 8 mL of a mixture of 1,4-dioxane and water (V:V=7:1), then 2M sodium carbonate solution (0.9 mL, 1.8 mmol) was added. After completion of the addition, the mixture was stirred in a microwave at 120° C. for 45 minutes. After cooling to room temperature, 50 mL of water were added, and the mixture was extracted with ethyl acetate (50 mL×3). The organic phases were combined, dried over anhydrous magnesium sulfate, and filtrated to remove the desiccant. The filtrate was concentrated under reduced pressure. The resulting residue was purified by silica gel column chromatography with elution system B to obtain the title compound 25e (306 mg, yield 64.0%) as a yellow oil.

MS m/z (ESI): 536.2 [M+1]

Step 5

(E)-3-(4-((1S,3R/1R,3S)-2-(4-Cyclopropylphenyl)-6-(1-ethyl-1H-pyrazol-4-yl)-3-methyl-1,2,3,4-tetrahydroisoquinolin-1-yl)-3-fluorophenyl)acrylic acid 25

Compound 25e (306 mg, 0.57 mmol) was dissolved in 10 mL of a mixture of methanol and tetrahydrofuran (V:V=1:1), then 2 M sodium hydroxide solution (1.4 mL, 2.8 mmol) was added. After completion of the addition, the reaction was stirred for 16 hours. 1M hydrochloric acid was added dropwise to adjust the pH of the reaction solution to 3. The mixture was extracted with ethyl acetate (30 mL×3). The organic phases were combined, dried over anhydrous magnesium sulfate, and filtrated to remove the desiccant. The filtrate was concentrated under reduced pressure. The resulting residue was purified by silica gel column chromatography with elution system A to obtain the title compound 25 (135 mg, yield 47.0%) as a yellow solid.

MS m/z (ESI): 522.6 [M+1]

$^1$H NMR (400 MHz, CDCl$_3$): δ 7.78 (s, 1H), 7.65 (s, 1H), 7.63 (d, 1H), 7.30 (s, 1H), 7.23 (d, 1H), 7.13 (d, 1H), 6.96 (d, 2H), 6.90-6.74 (m, 4H), 6.36 (d, 1H), 6.06 (s, 1H), 4.56-4.48 (m, 1H), 4.24 (q, 2H), 3.64-3.52 (m, 1H), 2.82 (d, 2H), 1.85-1.75 (m, 1H), 1.56 (t, 3H), 1.09 (d, 3H), 0.88 (q, 2H), 0.61 (q, 2H).

Example 26

(E)-3-(4-((1R,3R/1S,3S)-2-(4-Cyclopropyl-3-fluorophenyl)-6-(1-ethyl-1H-pyrazol-4-yl)-3-methyl-1,2,3,4-tetrahydroisoquinolin-1-yl)phenyl)acrylic acid 26

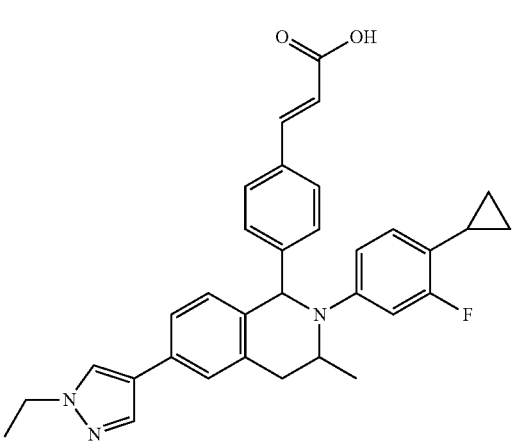

26

In accordance with the synthetic route of Example 24, the starting material 4-bromo-2-chloroaniline used in step 1 was replaced with 4-bromo-3-fluoroaniline, accordingly, the title compound 26 (140 mg, a yellow solid) was prepared.

MS m/z (ESI): 522.6 [M+1]

$^1$H NMR (400 MHz, CDCl$_3$) δ 7.75 (s, 1H), 7.66 (d, 1H), 7.62 (s, 1H), 7.41-7.34 (m, 6H), 6.73 (t, 1H), 6.52-6.38 (m, 2H), 6.34 (d, 1H), 5.66 (s, 1H), 4.52-4.43 (m, 1H), 4.20 (q, 2H), 3.34 (dd, 1H), 2.73 (d, 1H), 2.07-1.90 (m, 1H), 1.51 (t, 3H), 1.06 (d, 3H), 0.88-0.82 (m, 3H), 0.58 (q, 2H).

Example 27

(E)-3-(3,5-Difluoro-4-(6-(1-methyl-1H-pyrazol-4-yl)-2-phenyl-1,2,3,4-tetrahydroisoquinolin-1-yl)phenyl)acrylic acid 27

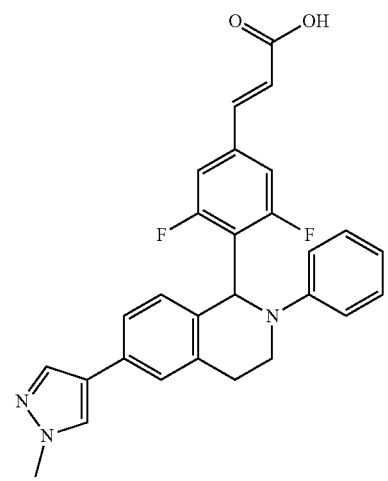

27

In accordance with the synthetic route of Example 5, the starting material 5b used in step 1 was replaced with aniline, accordingly, the title compound 27 (36 mg, a yellow solid) was prepared.

MS m/z (ESI): 472.5 [M+1]

$^1$H NMR (400 MHz, CDCl$_3$) δ 7.91 (s, 1H), 7.78 (s, 1H), 7.49 (d, 1H), 7.40 (s, 1H), 7.28 (d, 1H), 7.17-7.11 (m, 4H), 7.02 (d, 2H), 6.90 (d, 1H), 6.78 (t, 1H), 6.46 (d, 1H), 6.23 (s, 1H), 3.91 (s, 3H), 3.67-3.61 (m, 2H), 3.18-3.05 (m, 2H).

Example 28

(E)-3-(4-((1R,3R)-2-(4-Cyclopropyl-2-methylphenyl)-6-(1-ethyl-1H-pyrazol-4-yl)-3-methyl-1,2,3,4-tetrahydroisoquinolin-1-yl)phenyl)acrylic acid 28

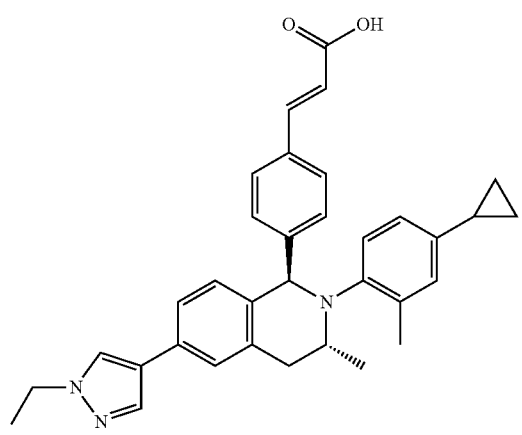

28

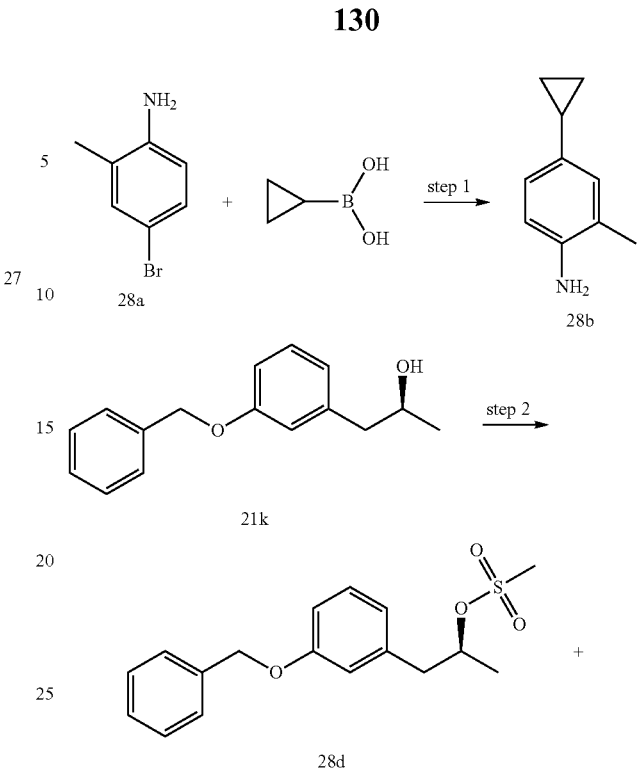

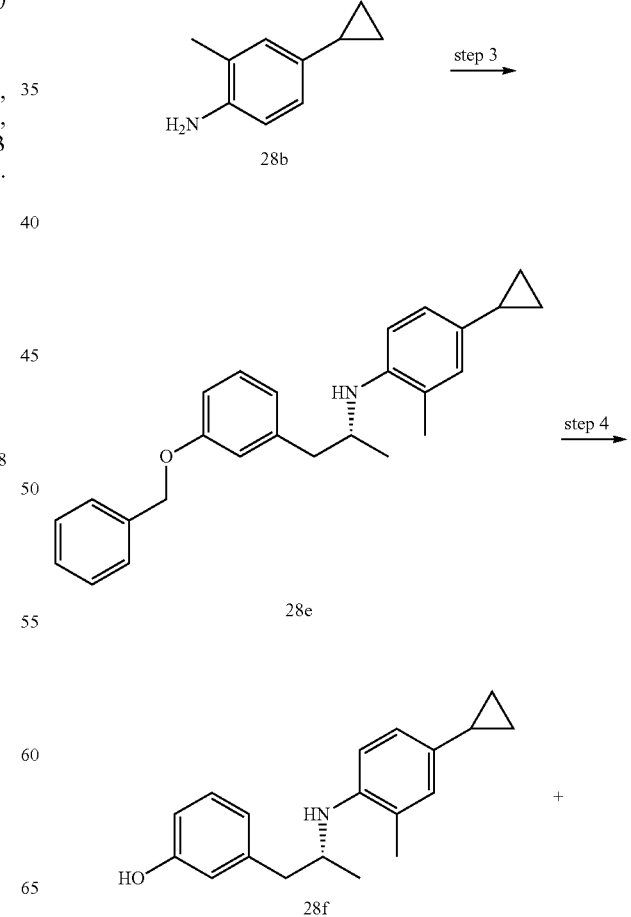

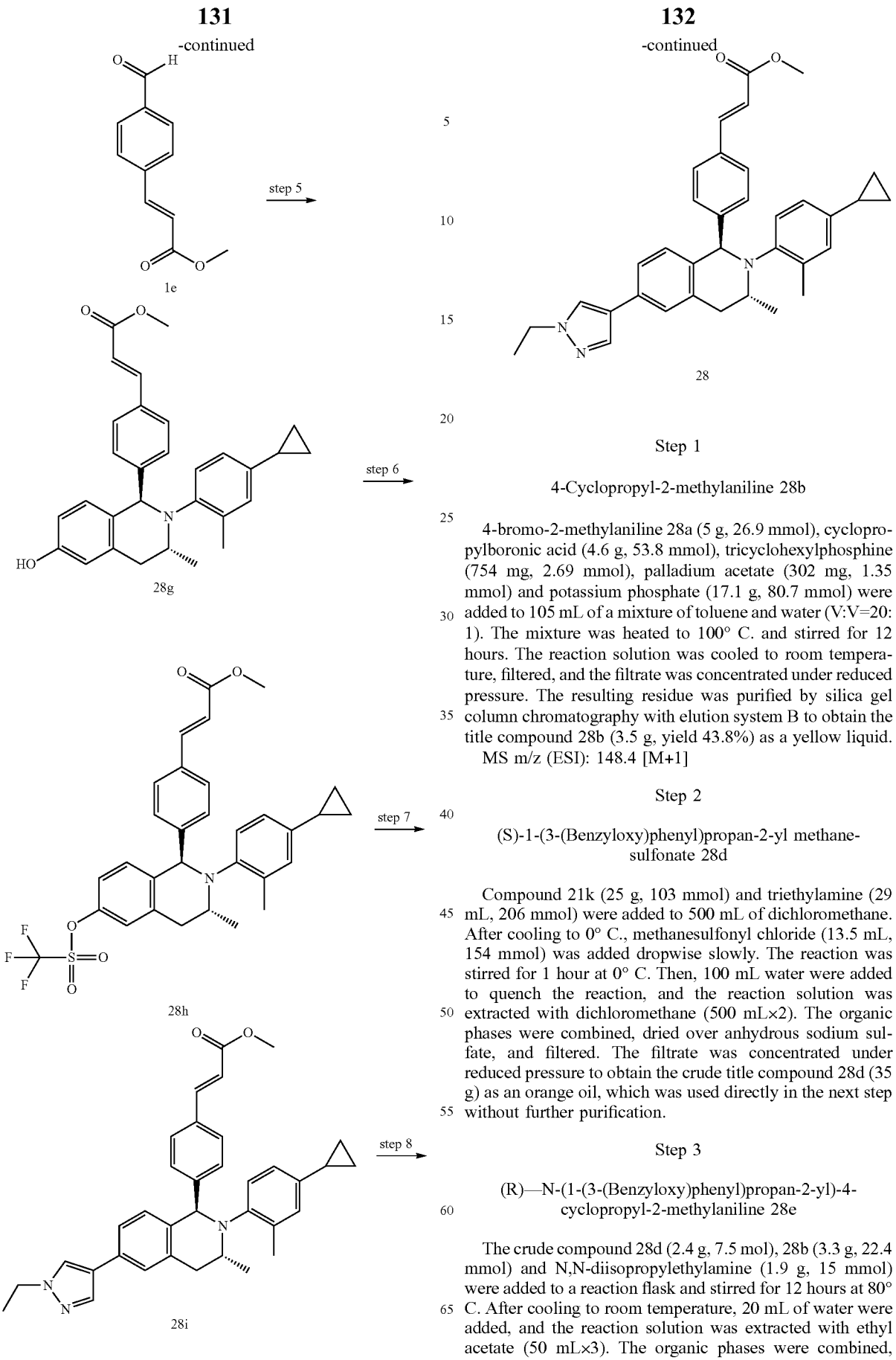

Step 1

4-Cyclopropyl-2-methylaniline 28b 4-bromo-2-methylaniline 28a (5 g, 26.9 mmol), cyclopropylboronic acid (4.6 g, 53.8 mmol), tricyclohexylphosphine (754 mg, 2.69 mmol), palladium acetate (302 mg, 1.35 mmol) and potassium phosphate (17.1 g, 80.7 mmol) were added to 105 mL of a mixture of toluene and water (V:V=20:1). The mixture was heated to 100° C. and stirred for 12 hours. The reaction solution was cooled to room temperature, filtered, and the filtrate was concentrated under reduced pressure. The resulting residue was purified by silica gel column chromatography with elution system B to obtain the title compound 28b (3.5 g, yield 43.8%) as a yellow liquid.

MS m/z (ESI): 148.4 [M+1]

Step 2

(S)-1-(3-(Benzyloxy)phenyl)propan-2-yl methanesulfonate 28d

Compound 21k (25 g, 103 mmol) and triethylamine (29 mL, 206 mmol) were added to 500 mL of dichloromethane. After cooling to 0° C., methanesulfonyl chloride (13.5 mL, 154 mmol) was added dropwise slowly. The reaction was stirred for 1 hour at 0° C. Then, 100 mL water were added to quench the reaction, and the reaction solution was extracted with dichloromethane (500 mL×2). The organic phases were combined, dried over anhydrous sodium sulfate, and filtered. The filtrate was concentrated under reduced pressure to obtain the crude title compound 28d (35 g) as an orange oil, which was used directly in the next step without further purification.

Step 3

(R)—N-(1-(3-(Benzyloxy)phenyl)propan-2-yl)-4-cyclopropyl-2-methylaniline 28e

The crude compound 28d (2.4 g, 7.5 mol), 28b (3.3 g, 22.4 mmol) and N,N-diisopropylethylamine (1.9 g, 15 mmol) were added to a reaction flask and stirred for 12 hours at 80° C. After cooling to room temperature, 20 mL of water were added, and the reaction solution was extracted with ethyl acetate (50 mL×3). The organic phases were combined, dried over anhydrous sodium sulfate and filtered. The filtrate was concentrated under reduced pressure. The resulting residue was purified by silica gel column chromatography with elution system B to obtain the title compound 28e (1.3 g, yield 46.4%) as a yellow oil.

MS m/z (ESI): 372.4 [M+1]

Step 4

(R)-3-(2-((4-Cyclopropyl-2-methylphenyl)amino)propyl)phenol 28f

Compound 28e (2 g, 5.4 mmol) was added to 20 mL of a mixture of toluene and trifluoroacetic acid (V:V=1:1). The mixture was heated to 130° C. and stirred for 5 hours. Then, 20 mL of water were added to the reaction solution, and a 2 M sodium hydroxide solution was added to adjust the pH to 7-8. The mixture was extracted with ethyl acetate (50 mL×3). The organic phases were combined and concentrated under reduced pressure. The resulting residue was purified by silica gel column chromatography with elution system B to obtain the title compound 28f (1 g, yield 44.4%) as a yellow oil.

MS m/z (ESI): 282.2 [M+1]

Step 5

(E)-Methyl 3-(4-((1R,3R)-2-(4-cyclopropyl-2-methylphenyl)-6-hydroxy-3-methyl-1,2,3,4-tetrahydroisoquinolin-1-yl)phenyl)acrylate 28 g Compound 28f (1 g, 3.6 mol), compound 1e (1.37 g, 7.2 mol) and triisopropylsilyl chloride (1.4 g, 7.2 mmol) were added to 20 mL of N,N-dimethylformamide. After completion of the addition, the mixture was heated to 130° C. and stirred for 4 hours. After stopping heating, the reaction solution was concentrated under reduced pressure. Then, 20 mL of water were added to the resulting residue, then the mixture was stirred uniformly and extracted with ethyl acetate (20 mL×3). The organic phases were combined and concentrated under reduced pressure. The resulting residue was purified by silica gel column chromatography with elution system B to obtain the title compound 28 g (800 mg, yield 50.0%) as a yellow solid.

MS m/z (ESI): 454.4 [M+1]

Step 6

(E)-Methyl 3-(4-((1R,3R)-2-(4-cyclopropyl-2-methylphenyl)-3-methyl-6-(((trifluoromethyl)sulfonyl)oxy)-1,2,3,4-tetrahydroisoquinolin-1-yl)phenyl)acrylate 28h Compound 28 g (700 mg, 1.54 mmol) was dissolved in 30 mL of dichloromethane, then 2,6-lutidine (7.3 g, 68.3 mmol) was added. After completion of the addition, the reaction was cooled to 0° C. in an ice bath. Then, trifluoromethanesulfonic anhydride (654 mg, 2.31 mmol) was added dropwise. After completion of the addition, the ice bath was removed, and the reaction was stirred for 16 hours at room temperature. Then, 20 mL of water were added to quench the reaction, and two phases were separated. The organic phase was dried over anhydrous sodium sulfate, and filtrated to remove the desiccant. The filtrate was concentrated under reduced pressure. The resulting residue was purified by silica gel column chromatography with elution system B to obtain the title compound 28h (420 mg, yield 40.8%) as a light yellow solid.

MS m/z (ESI): 586.3 [M+1]

Step 7

(E)-Methyl 3-(4-((1R,3R)-2-(4-cyclopropyl-2-methylphenyl)-6-(1-ethyl-1H-pyrazol-4-yl)-3-methyl-1,2,3,4-tetrahydroisoquinolin-1-yl)phenyl)acrylate 28i Compound 28h (420 mg, 0.72 mmol) 1-ethyl-4-(4,4,5,5-tetramethyl-1,3,2-dioxaborolan-2-yl)-1H-pyrazole (240 mg, 1.08 mmol), and [1,1'-bis(diphenylphosphino)ferrocene]dichloropalladium (53 mg, 0.072 mmol) were dissolved in 13 mL of a mixture of 1,4-dioxane and water (V:V=10:3), then sodium carbonate (152 mg, 1.44 mmol) was added. After completion of the addition, the mixture was stirred in a microwave at 120° C. for 45 minutes. After cooling to room temperature, 10 mL of water were added, and the mixture was extracted with ethyl acetate (30 mL×3). The organic phases were combined and concentrated under reduced pressure. The resulting residue was purified by silica gel column chromatography with elution system B to obtain the title compound 28i (200 mg, yield 52.5%) as a yellow oil.

MS m/z (ESI): 532.4 [M+1]

Step 8

(E)-3-(4-((1R,3R)-2-(4-Cyclopropyl-2-methylphenyl)-6-(1-ethyl-1H-pyrazol-4-yl)-3-methyl-1,2,3,4-tetrahydroisoquinolin-1-yl)phenyl)acrylic acid 28

Compound 28i (200 mg, 0.38 mmol) was dissolved in 7 mL of a mixture of methanol and tetrahydrofuran (V:V=1:1), then 2M sodium hydroxide solution (0.9 mL, 1.9 mmol) was added. After completion of the addition, the reaction was stirred for 16 hours. The reaction solution was concentrated under reduced pressure. Then, 10 mL of water were added to the resulting residue, then the mixture was stirred uniformly. 1M hydrochloric acid was added dropwise to adjust the pH of the reaction solution to 5. The mixture was extracted with ethyl acetate (10 mL×3). The organic phases were combined, washed with saturated sodium chloride solution (10 mL×1), dried over anhydrous sodium sulfate, and filtrated to remove the desiccant. The filtrate was concentrated under reduced pressure. The resulting residue was purified by silica gel column chromatography with elution system A to obtain the title compound 28 (130 mg, yield 66.3%) as a yellow solid.

MS m/z (ESI): 518.3 [M+1]

$^1$H NMR (400 MHz, DMSO-$d_6$) δ 8.11 (s, 1H), 7.79 (s, 1H), 7.43-7.34 (m, 5H), 7.24-7.20 (m, 2H), 6.76-6.65 (m, 3H), 6.37 (d, 1H), 5.74 (d, 1H), 4.12 (q, 2H), 3.65-3.56 (m, 1H), 3.50-3.41 (m, 1H), 3.37-3.28 (m, 1H), 2.73-2.67 (m, 1H), 2.25 (s, 3H), 1.73-1.67 (m, 1H), 1.38 (t, 3H), 0.94 (d, 3H), 0.82-0.79 (m, 2H), 0.57-0.49 (m, 2H).

Example 29

(E)-3-(4-((1R,3R/1S,3S)-2-(4-Cyclopropylphenyl)-6-(1-(difluoromethyl)-1H-pyrazol-4-yl)-3-methyl-1,2,3,4-tetrahydroisoquinolin-1-yl)phenylacrylic acid 29

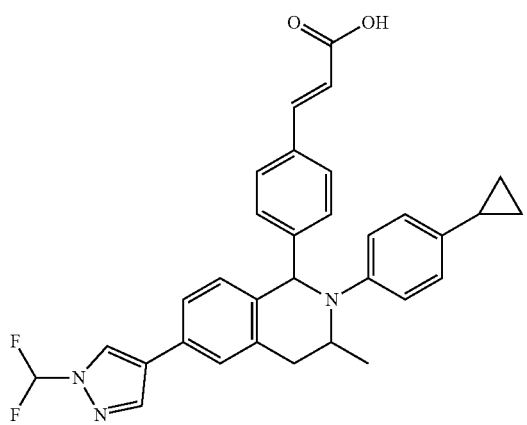

In accordance with the synthetic route of Example 10, the starting material 1-methyl-4-(4,4,5,5-tetramethyl-1,3,2-dioxaborolan-2-yl)-1H-pyrazole used in step 3 was replaced with 1-(difluoromethyl)-4-4-(4,4,5,5-tetramethyl-1,3,2-dioxaborolan-2-yl)-1H-pyrazole (prepared by a method disclosed in the patent application publication "US20100197651A1"), accordingly, the title compound 29 (60 mg, a yellow solid) was prepared.

MS m/z (ESI):526.6 [M+1]

$^1$H NMR (400 MHz, CDCl$_3$) δ 7.74 (s, 1H), 7.66 (d, 1H), 7.59 (s, 1H), 7.39 (s, 3H), 7.36 (s, 1H), 7.31 (s, 2H), 7.26 (s, 2H), 7.04 (d, 2H), 6.73-6.77 (m, 2H), 6.36 (d, 1H), 5.70 (s, 1H), 3.32-3.43 (m, 1H), 2.67-2.57 (m, 1H), 2.42-2.32 (m, 1H), 1.63-1.52 (m, 1H), 1.26 (d, 3H), 1.28-1.21 (m, 2H), 0.13-0.94 (m, 2H).

Example 30

(E)-3-(4-((1S,3R/1R,3S)-2-(4-Cyclopropylphenyl)-6-(1-ethyl-1H-pyrazol-4-yl)-3-methyl-1,2,3,4-tetrahydroisoquinolin-1-yl)-3,5-difluorophenyl)acrylic acid 30

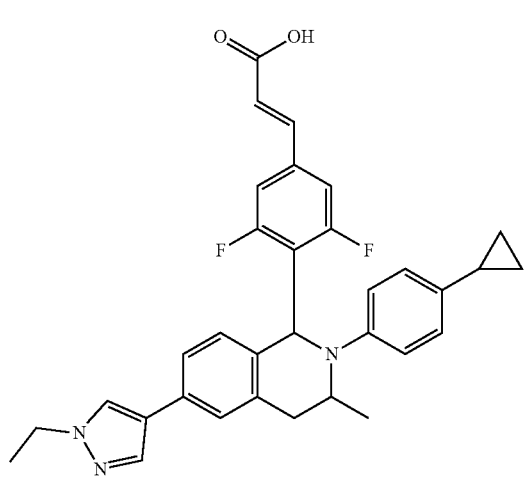

In accordance with the synthetic route of Example 4, the starting material 1-methyl-4-(4,4,5,5-tetramethyl-1,3,2-dioxaborolan-2-yl)-1H-pyrazole used in step 7 was replaced with 1-ethyl-4-(4,4,5,5-tetramethyl-1,3,2-dioxaborolan-2-yl)-1H-pyrazole, accordingly, the title compound 30 (200 mg, a yellow solid) was prepared.

MS m/z (ESI): 540.6 [M+1]

$^1$H NMR (400 MHz, CDCl$_3$): δ 7.75 (s, 1H), 7.60 (s, 1H), 7.52 (d, 1H), 7.29 (s, 1H), 7.21 (d, 1H), 7.01-6.90 (m, 6H), 6.32 (d, 1H), 6.12 (s, 1H), 4.35-4.28 (m, 1H), 3.97 (q, 2H), 3.69-3.60 (m, 1H), 2.81-2.68 (m, 2H), 1.83-1.74 (m, 1H), 1.29 (t, 3H), 1.07-0.96 (m, 2H), 0.91-0.84 (m, 2H), 0.60 (d, 3H).

Examples 31, 32

(E)-3-(4-((1R,3S)-2-(4-Cyclopropylphenyl)-6-(1-ethyl-1H-pyrazol-4-yl)-3-methyl-1,2,3,4-tetrahydroisoquinolin-1-yl)-3,5-difluorophenyl)acrylic acid 31

(E)-3-(4-((1S,3R)-2-(4-Cyclopropylphenyl)-6-(1-ethyl-1H-pyrazol-4-yl)-3-methyl-1,2,3,4-tetrahydroisoquinolin-1-yl)-3,5-difluorophenylacrylic acid 32

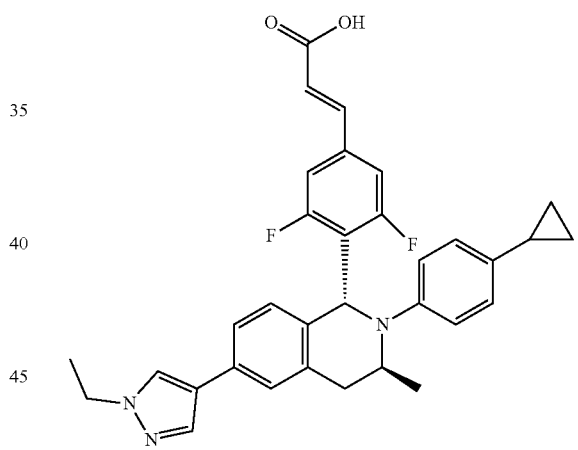

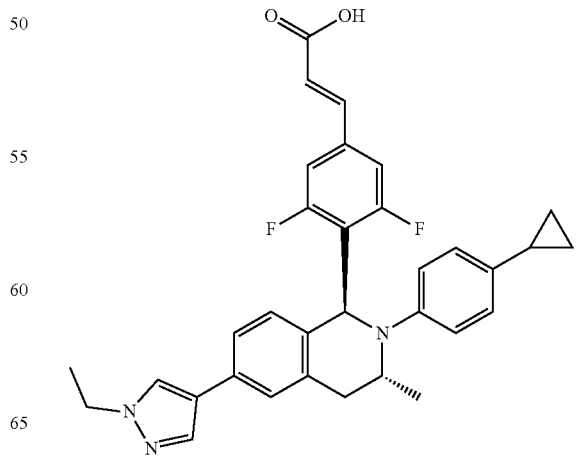

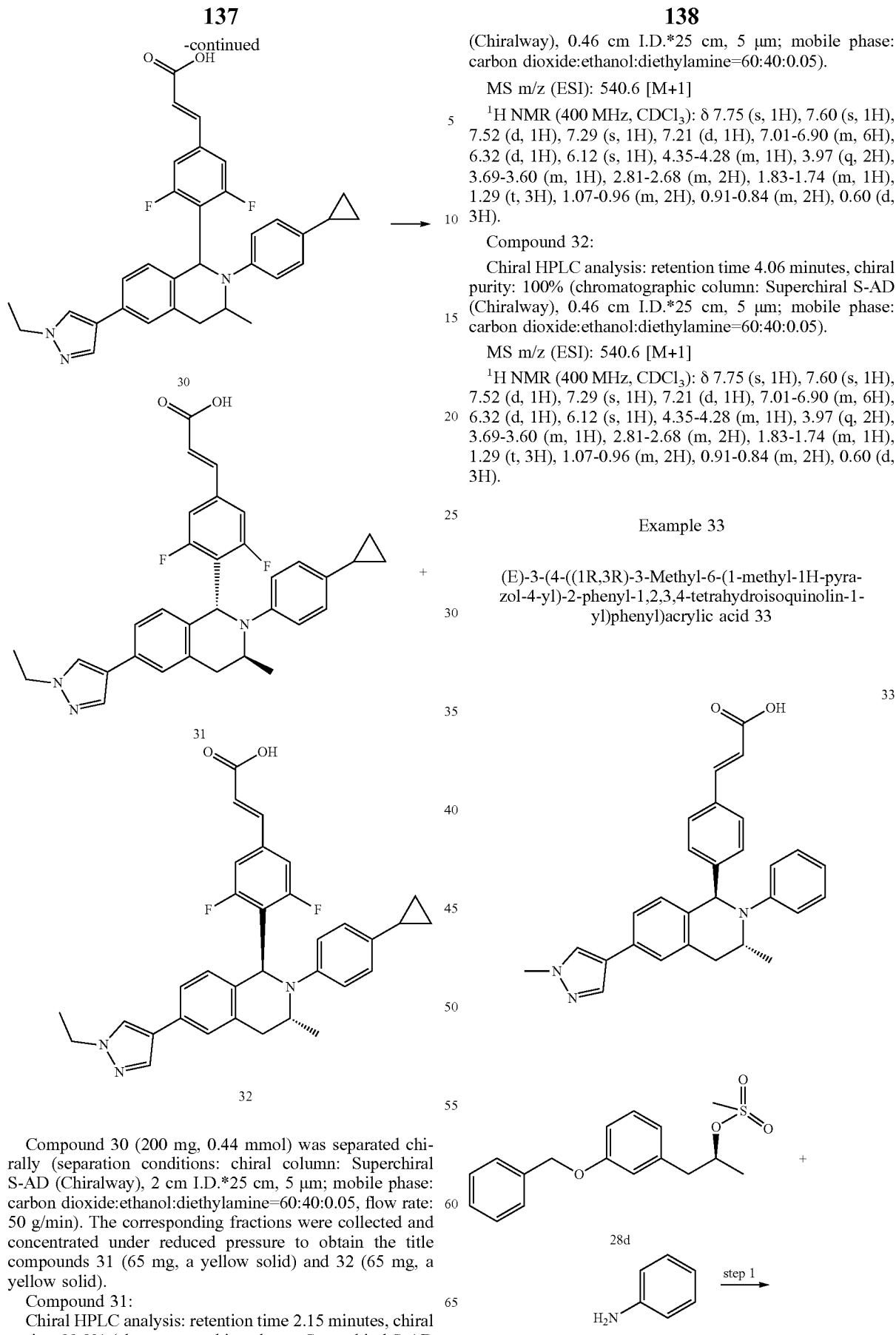

(Chiralway), 0.46 cm I.D.*25 cm, 5 μm; mobile phase: carbon dioxide:ethanol:diethylamine=60:40:0.05).

MS m/z (ESI): 540.6 [M+1]

$^1$H NMR (400 MHz, CDCl$_3$): δ 7.75 (s, 1H), 7.60 (s, 1H), 7.52 (d, 1H), 7.29 (s, 1H), 7.21 (d, 1H), 7.01-6.90 (m, 6H), 6.32 (d, 1H), 6.12 (s, 1H), 4.35-4.28 (m, 1H), 3.97 (q, 2H), 3.69-3.60 (m, 1H), 2.81-2.68 (m, 2H), 1.83-1.74 (m, 1H), 1.29 (t, 3H), 1.07-0.96 (m, 2H), 0.91-0.84 (m, 2H), 0.60 (d, 3H).

Compound 32:

Chiral HPLC analysis: retention time 4.06 minutes, chiral purity: 100% (chromatographic column: Superchiral S-AD (Chiralway), 0.46 cm I.D.*25 cm, 5 μm; mobile phase: carbon dioxide:ethanol:diethylamine=60:40:0.05).

MS m/z (ESI): 540.6 [M+1]

$^1$H NMR (400 MHz, CDCl$_3$): δ 7.75 (s, 1H), 7.60 (s, 1H), 7.52 (d, 1H), 7.29 (s, 1H), 7.21 (d, 1H), 7.01-6.90 (m, 6H), 6.32 (d, 1H), 6.12 (s, 1H), 4.35-4.28 (m, 1H), 3.97 (q, 2H), 3.69-3.60 (m, 1H), 2.81-2.68 (m, 2H), 1.83-1.74 (m, 1H), 1.29 (t, 3H), 1.07-0.96 (m, 2H), 0.91-0.84 (m, 2H), 0.60 (d, 3H).

Example 33

(E)-3-(4-((1R,3R)-3-Methyl-6-(1-methyl-1H-pyrazol-4-yl)-2-phenyl-1,2,3,4-tetrahydroisoquinolin-1-yl)phenyl)acrylic acid 33

Compound 30 (200 mg, 0.44 mmol) was separated chirally (separation conditions: chiral column: Superchiral S-AD (Chiralway), 2 cm I.D.*25 cm, 5 μm; mobile phase: carbon dioxide:ethanol:diethylamine=60:40:0.05, flow rate: 50 g/min). The corresponding fractions were collected and concentrated under reduced pressure to obtain the title compounds 31 (65 mg, a yellow solid) and 32 (65 mg, a yellow solid).

Compound 31:

Chiral HPLC analysis: retention time 2.15 minutes, chiral purity: 99.0% (chromatographic column: Superchiral S-AD

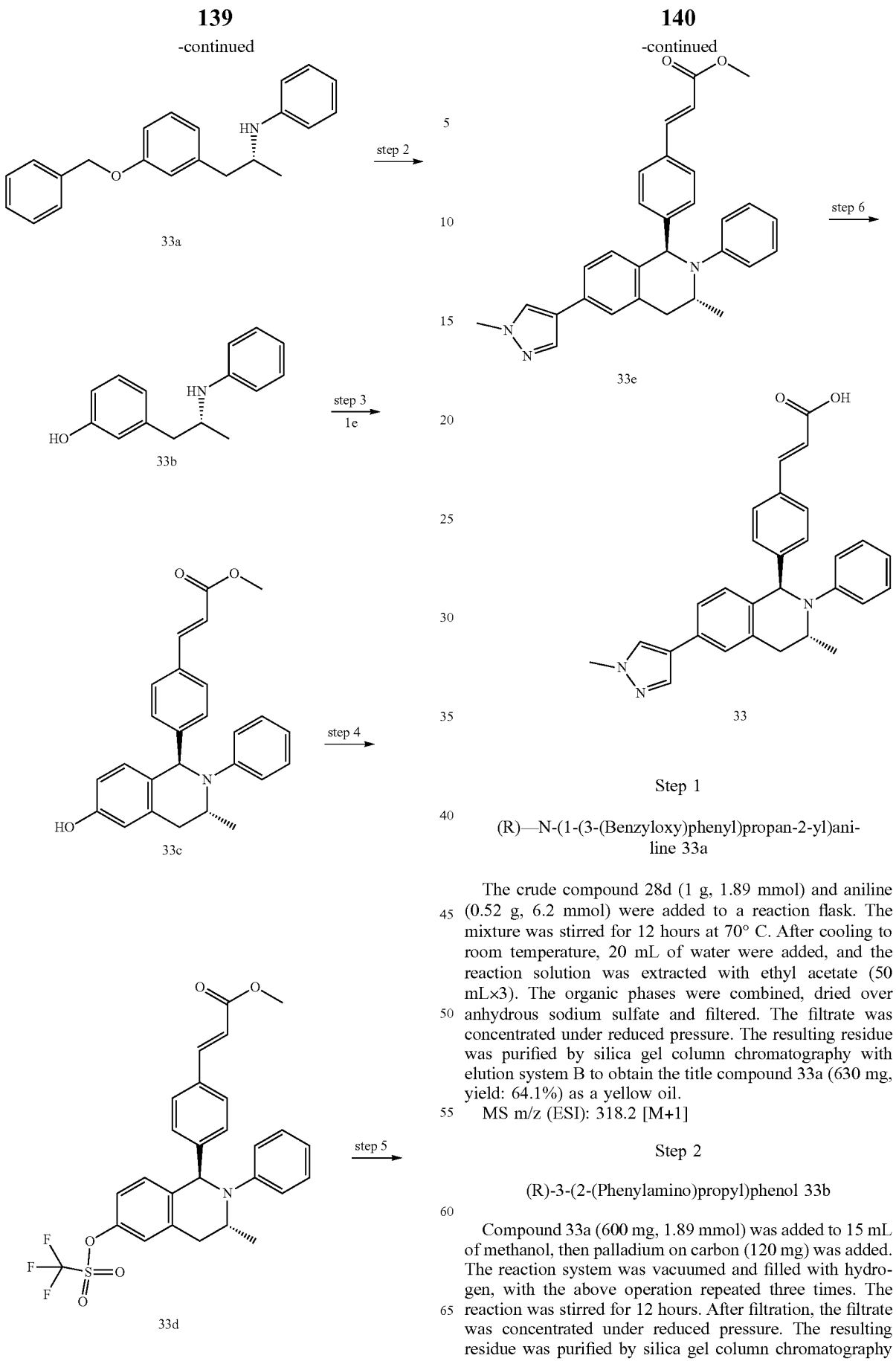

Step 1

(R)—N-(1-(3-(Benzyloxy)phenyl)propan-2-yl)aniline 33a

The crude compound 28d (1 g, 1.89 mmol) and aniline (0.52 g, 6.2 mmol) were added to a reaction flask. The mixture was stirred for 12 hours at 70° C. After cooling to room temperature, 20 mL of water were added, and the reaction solution was extracted with ethyl acetate (50 mL×3). The organic phases were combined, dried over anhydrous sodium sulfate and filtered. The filtrate was concentrated under reduced pressure. The resulting residue was purified by silica gel column chromatography with elution system B to obtain the title compound 33a (630 mg, yield: 64.1%) as a yellow oil.

MS m/z (ESI): 318.2 [M+1]

Step 2

(R)-3-(2-(Phenylamino)propyl)phenol 33b

Compound 33a (600 mg, 1.89 mmol) was added to 15 mL of methanol, then palladium on carbon (120 mg) was added. The reaction system was vacuumed and filled with hydrogen, with the above operation repeated three times. The reaction was stirred for 12 hours. After filtration, the filtrate was concentrated under reduced pressure. The resulting residue was purified by silica gel column chromatography with elution system B to obtain the title compound 33b (300 mg, yield 70.0%) as a yellow oil.

Step 3

(E)-Methyl 3-(4-((1R,3R)-6-hydroxy-3-methyl-2-phenyl-1,2,3,4-tetrahydroisoquinolin-1-yl)phenyl)acrylate 33c Compound 33b (300 mg, 1.32 mmol), compound 1e (501 mg, 2.64 mmol) and triisopropylsilyl chloride (509 mg, 2.64 mmol) were added to 10 mL of N,N-dimethylformaminde. After completion of the addition, the mixture was heated to 140° C. and stirred for 2 hours. After stopping heating, the reaction solution was concentrated under reduced pressure. Then, 20 mL of water were added to the resulting residue, and the mixture was stirred uniformly and extracted with ethyl acetate (20 mL×3). The organic phases were combined and concentrated under reduced pressure. The resulting residue was purified by silica gel column chromatography with elution system B to obtain the title compound 33c (300 mg, yield 56.9%) as a yellow solid.
MS m/z (ESI): 400.2 [M+1]

Step 4

(E)-Methyl 3-(4-((1R,3R)-3-methyl-2-phenyl-6-(((trifluoromethyl)sulfonyl)oxy)-1,2,3,4-tetrahydroisoquinolin-1-yl)phenyl)acrylate 33d Compound 33c (100 mg, 0.25 mmol) was dissolved in 5 mL of dichloromethane, then 2,6-lutidine (54 mg, 0.5 mmol) was added. After completion of the addition, the reaction was cooled to 0° C. in an ice bath, and trifluoromethanesulfonic anhydride (106 mg, 0.38 mmol) was added dropwise. After completion of the addition, the ice bath was removed, and the reaction was stirred for 16 hours at room temperature. Then, 20 mL of water was added to quench the reaction, and two phases were separated. The organic phase was dried over anhydrous sodium sulfate, and filtrated to remove the desiccant. The filtrate was concentrated under reduced pressure. The resulting residue was purified by silica gel column chromatography with elution system B to obtain the title compound 33d (80 mg, yield 60.6%) as a yellow solid.

Step 5

(E)-Methyl 3-(4-((1R,3R)-3-methyl-6-(1-methyl-1H-pyrazol-4-yl)-2-phenyl-1,2,3,4-tetrahydroisoquinolin-1-yl)phenyl)acrylate 33e Compound 33d (50 mg, 0.056 mmol), 1-methyl-4-(4,4,5,5-tetramethyl-1,3,2-dioxaborolan-2-yl)-1H-pyrazole (18 mg, 0.085 mmol), and [1,1'-bis(diphenylphosphino)ferrocene]dichloropalladium (4 mg, 0.0056 mmol) were dissolved in 3 mL of a mixture of 1,4-dioxane and water (V:V=2:1), then sodium carbonate (12 mg, 0.112 mmol) was added. After completion of the addition, the mixture was stirred in a microwave at 120° C. for 45 minutes. After cooling to room temperature, 10 mL of water were added, and the mixture was extracted with ethyl acetate (30 mL×3). The organic phases were combined and concentrated under reduced pressure. The resulting residue was purified by silica gel column chromatography with elution system B to obtain the title compound 33e (40 mg, yield 93.0%) as a yellow solid.

Step 6

(E)-3-(4-((1R,3R)-3-Methyl-6-(1-methyl-1H-pyrazol-4-yl)-2-phenyl-1,2,3,4-tetrahydroisoquinolin-1-yl)phenyl)acrylic acid 33

Compound 33e (40 mg, 0.086 mmol) was dissolved in 5 mL of a mixture of methanol and tetrahydrofuran (V:V=1:1), then 2 M sodium hydroxide solution (0.2 mL, 0.4 mmol) was added. After completion of the addition, the reaction was stirred for 16 hours. The reaction solution was concentrated under reduced pressure. Then, 10 mL of water were added to the resulting residue, and the mixture was stirred uniformly. Then, 1M hydrochloric acid was added to adjust the pH of the reaction solution to 5. The mixture was extracted with ethyl acetate (10 mL×3). The organic phases were combined, washed with saturated sodium chloride solution, dried over anhydrous sodium sulfate, and filtrated to remove the desiccant. The filtrate was concentrated under reduced pressure. The resulting residue was purified by silica gel column chromatography with elution system A to obtain the title compound 33 (30 mg, yield 77.0%) as a yellow solid.
MS m/z (ESI): 450.5 [M+1]
$^1$H NMR (400 MHz, CDCl$_3$) δ 7.74 (s, 1H), 7.66 (d, 1H), 7.59 (s, 1H), 7.39 (s, 3H), 7.31 (s, 2H), 7.26 (s, 2H), 7.04 (d, 2H), 6.73-6.77 (m, 2H), 6.69 (t, 1H), 6.36 (d, 1H), 5.70 (s, 1H), 3.95 (s, 3H), 3.32-3.43 (m, 1H), 2.67-2.57 (m, 1H), 2.42-2.32 (m, 1H), 1.26 (d, 3H).

Example 34

(E)-3-(4-(1R,3R)-3-Methyl-6-(1-methyl-1H-pyrazol-4-yl)-2-p-tolyl-1,2,3,4-tetrahydroisoquinolin-1-yl)phenyl)acrylic acid 34

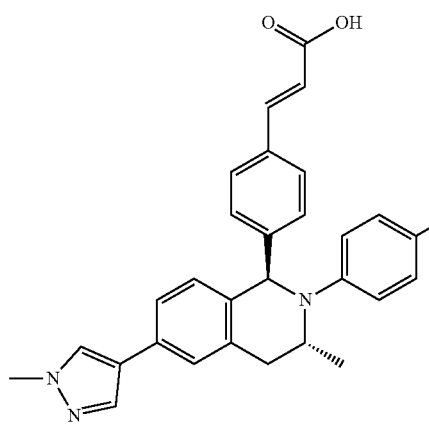

34

In accordance with the synthetic route of Example 33, the starting material aniline used in step 1 was replaced with methylaniline, accordingly, the title compound 34 (9 mg, a yellow solid) was prepared.
MS m/z (ESI): 464.6 [M+1]
$^1$H NMR (400 MHz, CDCl$_3$) δ 7.74 (s, 1H), 7.66 (d, 1H), 7.59 (s, 1H), 7.39 (s, 3H), 7.31 (s, 2H), 7.26 (s, 2H), 7.04 (d, 2H), 6.73-6.77 (m, 2H), 6.36 (d, 1H), 5.70 (s, 1H), 3.95 (s, 3H), 3.32-3.43 (m, 1H), 2.67-2.57 (m, 1H), 2.42-2.32 (m, 1H), 2.34 (s, 3H), 1.26 (d, 3H).

Example 35

(E)-3-(4-((1R,3R/1S,3S)-2-(4-Cyclopropylphenyl)-3-methyl-6-(2-methylthiazol-5-yl)-1,2,3,4-tetrahydroisoquinolin-1-yl)phenyl)acrylic acid 35

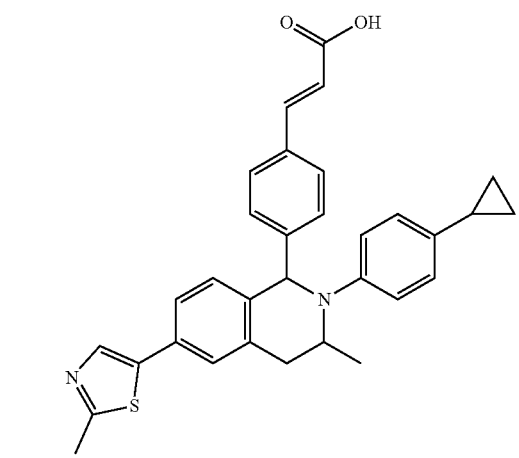

35

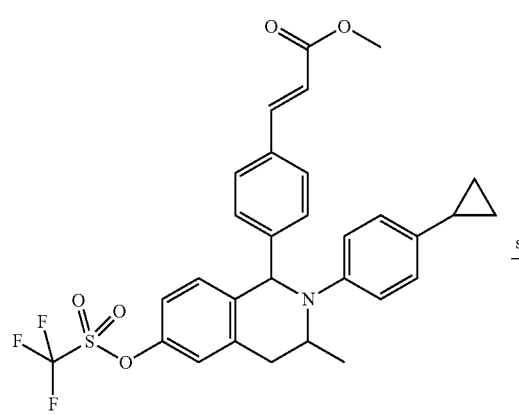

10b

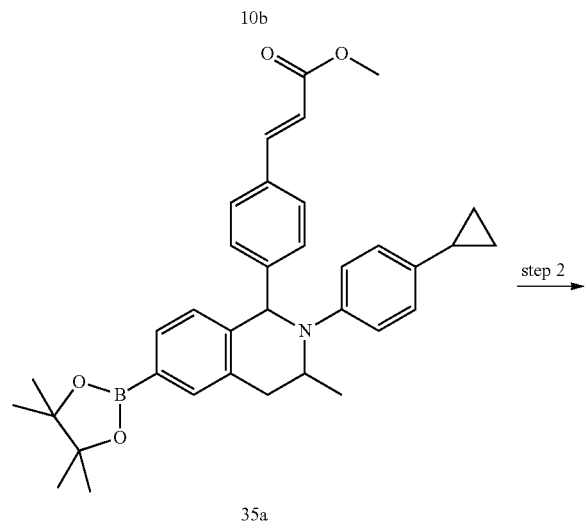

35a

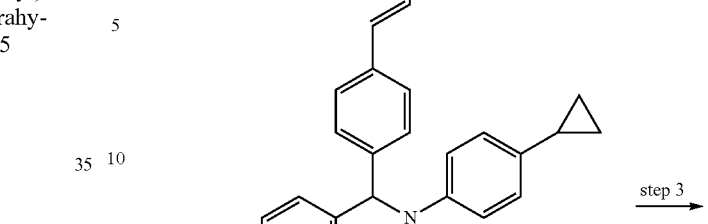

35b

Step 1

(E)-Methyl 3-(4-((1R,3R/1S,3S)-2-(4-cyclopropylphenyl)-3-methyl-6-(4,4,5,5-tetramethyl-1,3,2-dioxaborolan-2-yl)-1,2,3,4-tetrahydroisoquinolin-1-yl)phenyl)acrylate 35a Compound 10b (300 mg, 0.52 mmol), bis(pinacolato)diboron (160 mg, 0.63 mmol), potassium acetate (102 mg, 1.05 mmol) and [1,1'-bis(diphenylphosphino)ferrocene]dichloropalladium (4 mg, 0.0056 mmol) were added to 15 mL of N,N-dimethylformamide. The mixture was heated to 90° C. and stirred for 2 hours. The reaction solution was concentrated under reduced pressure. Then, 10 mL of water were added to the resulting residue, and the mixture was extracted with ethyl acetate (30 mL×3). The organic phases were combined, washed with saturated sodium chloride solution (10 mL×1), dried over anhydrous sodium sulfate, and filtrated to remove the desiccant. The filtrate was concentrated under reduced pressure. The resulting residue was purified by silica gel column chromatography with elution system B to obtain the title compound 35a (55 mg, yield: 77.0%) as a yellow oil.

MS m/z (ESI): 550.3 [M+1]

Step 2

(E)-Methyl 3-(4-((1R,3R/1S,3S)-2-(4-cyclopropyl-phenyl)-3-methyl-6-(2-methylthiazol-5-yl)-1,2,3,4-tetrahydroisoquinolin-1-yl)phenyl)acrylate Compound 35a (30 mg, 0.054 mmol), 5-bromo-2-methylthiazole (15 mg, 0.082 mmol), 2-dicyclohexylphosphino-2,4,6-triisopropylbiphenyl (3 mg, 0.007 mmol) and tris (dibenzylideneacetone)dipalladium (2 mg, 0.002 mmol) were dissolved in 2 mL of a mixture of 1,4-dioxane and water (V:V=4:1), then potassium phosphate (23 mg, 0.11 mmol) was added. After completion of the addition, the mixture was stirred in a microwave at 100° C. for 45 minutes. After cooling to room temperature, 10 mL of water were added, and the mixture was extracted with ethyl acetate (30 mL×3). The organic phases were combined and concentrated under reduced pressure. The resulting residue was purified by silica gel column chromatography with elution system B to obtain the title compound 35b (10 mg, yield 35.7%) as a yellow oil.

MS m/z (ESI): 521.2 [M+1]

Step 3

(E)-3-(4-((1R,3R/1S,3S)-2-(4-Cyclopropylphenyl)-3-methyl-6-(2-methylthiazol-5-yl)-1,2,3,4-tetrahydroisoquinolin-1-yl)phenyl)acrylic acid 35

Compound 35b (10 mg, 0.02 mmol) was dissolved in 5 mL of a mixture of methanol and tetrahydrofuran (V:V=1:1), then 2 M sodium hydroxide solution (0.05 mL, 0.096 mmol) was added. After completion of the addition, the reaction was stirred for 16 hours. The reaction solution was concentrated under reduced pressure. Then, 10 mL of water were added to the resulting residue, and the mixture was stirred uniformly. Then, 1M hydrochloric acid was added to adjust the pH of the reaction solution to 5. The mixture was extracted with ethyl acetate (10 mL×3). The organic phases were combined, washed with saturated sodium chloride solution (10 mL×1), dried over anhydrous sodium sulfate, and filtrated to remove the desiccant. The filtrate was concentrated under reduced pressure. The resulting residue was purified by silica gel column chromatography with elution system A to obtain the title compound 35 (6 mg, yield 60.0%) as a yellow solid.

MS m/z (ESI): 507.6 [M+1]

$^1$H NMR (400 MHz, CDCl$_3$) δ7.59 (s, 1H), 7.39 (s, 3H), 7.31 (s, 2H), 7.26 (s, 2H), 7.04 (d, 2H), 7.00 (s, 1H), 6.73-6.77 (m, 2H), 6.36 (d, 1H), 5.70 (s, 1H), 3.32-3.43 (m, 1H), 2.67-2.57 (m, 1H), 2.42-2.32 (m, 1H), 2.34 (s, 3H), 1.63-1.52 (m, 1H), 1.26 (d, 3H), 1.28-1.21 (m, 2H), 0.13-0.94 (m, 2H).

Example 36

(E)-3-(4-((1R,3R/1S,3S)-2-(4-cyclopropylphenyl)-3-methyl-6-(1H-pyrazol-4-yl)-1,2,3,4-tetrahydroisoquinolin-1-yl)phenyl)acrylic acid 36

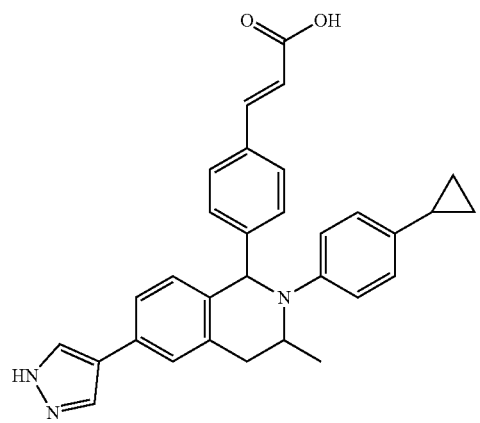

36

In accordance with the synthetic route of Example 10, the starting material 1-methyl-4-(4,4,5,5-tetramethyl-1,3,2-dioxaborolan-2-yl)-1H-pyrazole used in step 3 was replaced with tert-butyl 4-(4,4,5,5-tetramethyl-1,3,2-dioxaborolan-2-yl)-1H-pyrazole-1-carboxylate, accordingly, the title compound 36 (30 mg, a yellow solid) was prepared after removing tert-butyloxycarbonyl.

MS m/z (ESI): 476.58 [M+1]

$^1$H NMR (400 MHz, CDCl$_3$) δ 7.74 (s, 1H), 7.66 (d, 1H), 7.59 (s, 1H), 7.39 (s, 3H), 7.31 (s, 2H), 7.26 (s, 2H), 7.04 (d, 2H), 6.73-6.77 (m, 2H), 6.36 (d, 1H), 5.70 (s, 1H), 3.32-3.43 (m, 1H), 2.67-2.57 (m, 1H), 2.42-2.32 (m, 1H), 1.63-1.52 (m, 1H), 1.26 (d, 3H), 1.28-1.21 (m, 2H), 0.13-0.94 (m, 2H).

Example 37

(E)-3-(4-((1R,3R/1S,3S)-2-(2,4-Dimethylphenyl)-3-methyl-6-(1-methyl-1H-pyrazol-4-yl)-1,2,3,4-tetrahydroisoquinolin-1-yl)phenyl)acrylic acid 37

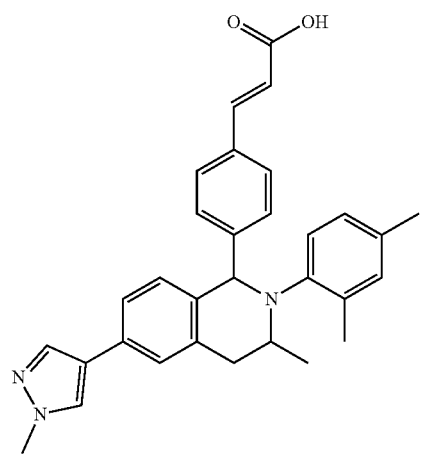

37

In accordance with the synthetic route of Example 6, the starting material 2-ethylaniline used in step 1 was replaced with 2,4-dimethyl aniline, accordingly, the title compound 37 (60 mg, a yellow solid) was prepared.

MS m/z (ESI): 478.4 [M+1]

¹H NMR (400 MHz, CDCl₃) δ 7.73 (s, 1H), 7.66 (d, 1H), 7.58 (s, 1H), 7.38 (s, 3H), 7.30 (s, 2H), 7.24 (s, 1H), 6.92 (d, 2H), 6.71 (s, 1H), 6.32 (d, 1H), 6.66 (d, 1H), 4.46 (d, 1H), 3.93 (s, 3H), 3.35 (d, 1H), 2.28 (s, 3H), 2.72 (d, 1H), 2.17 (s, 3H), 1.25 (s, 1H), 1.04 (d, 3H).

Example 38

(E)-3-(4-((1S,3R)-6-(1-Ethyl-1H-pyrazol-4-yl)-2-(4-isopropylphenyl)-3-methyl-1,2,3,4-tetrahydroisoquinolin-1-yl)-3,5-difluorophenyl)acrylic acid 38

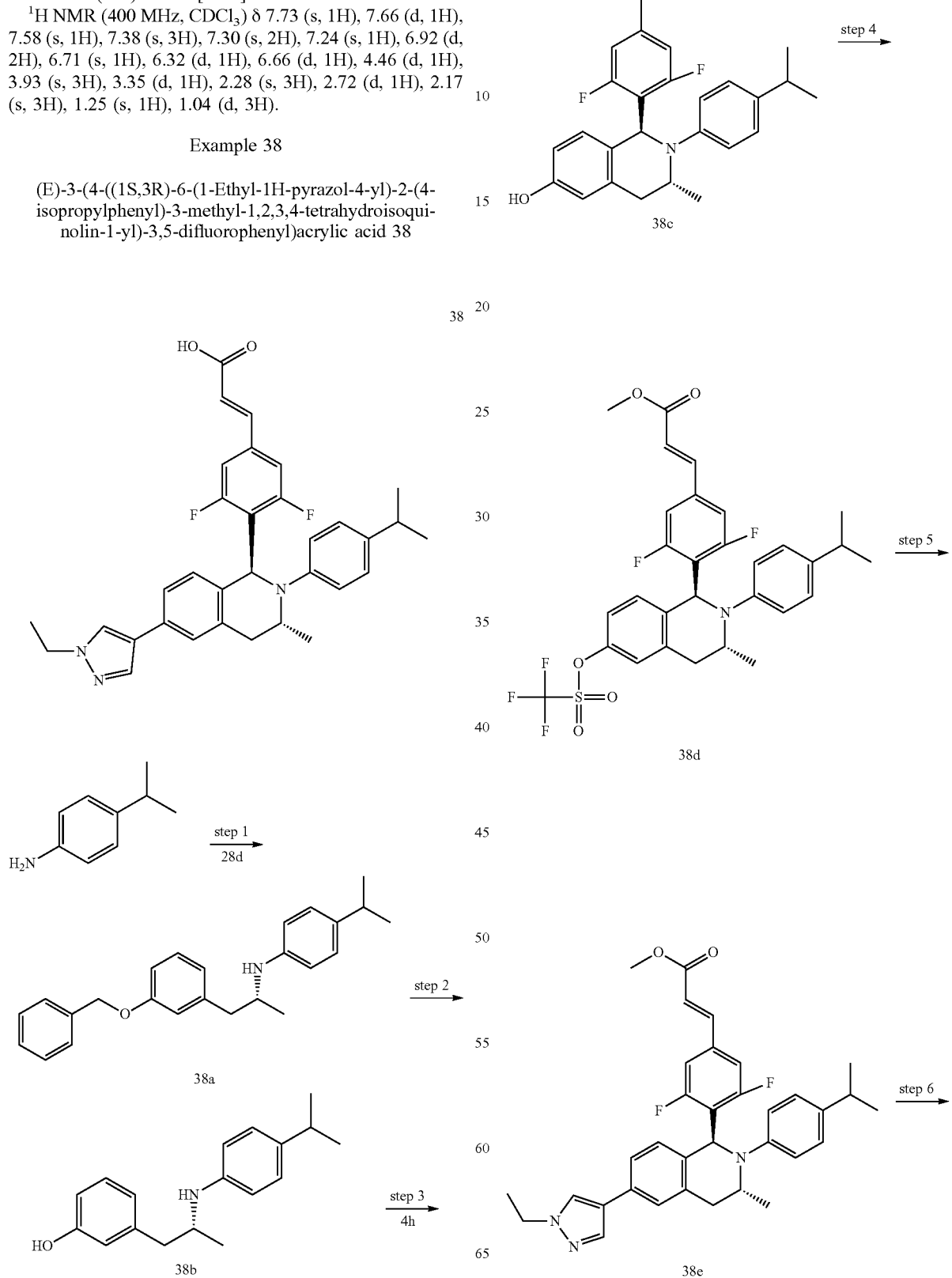

149

-continued

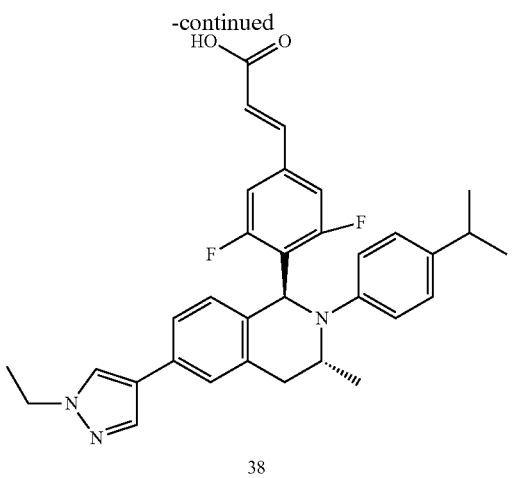

38

Step 1

(R)—N-(1-(3-(Benzyloxy)phenyl)propan-2-yl)-4-isopropylaniline 38a

The crude compound 28d (29 g, 85 mmol) and 4-isopropylaniline (20 g, 153 mmol) were added to a reaction flask. The mixture was stirred for 2 hours at 100° C. After cooling to room temperature, 150 mL of water were added, and the mixture was extracted with ethyl acetate (300 mL×3). The organic phases were combined, dried over anhydrous sodium sulfate and filtered. The filtrate was concentrated under reduced pressure. The resulting residue was purified by silica gel column chromatography with elution system B to obtain the title compound 38a (21 g, yield: 70.0%) as a yellow oil.

Step 2

(R)-3-(2-((4-Isopropylphenyl)amino)propyl)phenol 38b

Compound 38a (10.5 g, 29.2 mmol) was added to 200 mL of methanol, then palladium on carbon (10%, 2 g) was added. The reaction system was vacuumed and filled with hydrogen, with the above operation repeated three times. The reaction was stirred for 12 hours. After filtration, the filtrate was concentrated under reduced pressure. The resulting residue was purified by silica gel column chromatography with elution system B to obtain the title compound 38b (7 g, yield 88.6%) as a red solid.

Step 3

(E)-Methyl 3-(3,5-difluoro-4-((1S,3R)-6-hydroxy-2-(4-isopropylphenyl)-3-methyl-1,2,3,4-tetrahydroisoquinolin-1-yl)phenyl)acrylate 38c Compound 38b (5 g, 18.6 mmol), 4h (8.4 g, 37.2 mmol) and triisopropylsilyl chloride (7.2 g, 37.2 mmol) were added to 100 mL of N,N-dimethylformaminde. After completion of the addition, the mixture was heated to 140° C. and stirred for 2 hours. After stopping heating, the reaction solution was concentrated under reduced pressure. Then, 50 mL of water were added to the resulting residue, and the mixture was stirred uniformly. The mixture was extracted with ethyl acetate (50 mL×4). The organic phases were combined and concentrated under reduced pressure. The resulting residue was purified by silica gel column chromatography with elution system B to obtain the title compound 38c (8.8 g, yield 100%) as a yellow solid.

Step 4

(E)-Methyl 3-(3,5-difluoro-4-((1S,3R)-2-(4-isopropylphenyl)-3-methyl-6-(((trifluoromethyl)sulfonyl)oxy)-1,2,3,4-tetrahydroisoquinolin-1-yl)phenyl)acrylate 38d Compound 38c (8.8 g, 18.6 mmol) was dissolved in 200 mL of dichloromethane, then 2,6-lutidine (3 g, 27.9 mmol) was added. After completion of the addition, the reaction was cooled to 0° C. in an ice bath, and trifluoromethanesulfonic anhydride (6.82 g, 24.2 mmol) was added dropwise. After completion of the addition, the ice bath was removed, and the reaction was stirred for 16 hours at room temperature. Then, 100 mL of water were added to quench the reaction, and two phases were separated. The aqueous phase was extracted with dichloromethane (150 mL×3). The organic phase was dried over anhydrous sodium sulfate, and filtrated to remove the desiccant. The filtrate was concentrated under reduced pressure. The resulting residue was purified by silica gel column chromatography with elution system B to obtain the title compound 38d (3.5 g, yield 30.9%) as a yellow solid.

Step 5

(E)-Methyl 3-(4-((1S,3R)-6-(1-ethyl-1H-pyrazol-4-yl)-2-(4-isopropylphenyl)-3-methyl-1,2,3,4-tetrahydroisoquinolin-1-yl)-3,5-difluorophenyl)acrylate 38e Compound 38d (1.6 g, 2.62 mmol), 1-ethyl-4-(4,4,5,5-tetramethyl-1,3,2-dioxaborolan-2-yl)-1H-pyrazole (0.87 g, 3.94 mmol), and [1,1'-bis(diphenylphosphino)ferrocene]dichloropalladium (190 mg, 0.26 mmol) were dissolved in 25 mL of a mixture of 1,4-dioxane and water (V:V=4:1), then sodium carbonate (555 mg, 5.24 mmol) was added. The mixture was stirred in a microwave at 120° C. for 1 hour. After cooling to room temperature, 50 mL of water were added, and the mixture was extracted with ethyl acetate (100 mL×3). The organic phases were combined and concentrated under reduced pressure. The resulting residue was purified by silica gel column chromatography with elution system B to obtain the title compound 38e (1.0 g, yield 69.0%) as a yellow oil.

MS m/z (ESI): 556.5 [M+1]

Step 6

(E)-3-(4-((1S,3R)-6-(1-Ethyl-1H-pyrazol-4-yl)-2-(4-isopropylphenyl)-3-methyl-1,2,3,4-tetrahydroisoquinolin-1-yl)-3,5-difluorophenyl)acrylic acid 38

Compound 38e (1 g, 1.8 mmol) was dissolved in 30 mL of a mixture of methanol and tetrahydrofuran (V:V=1:2), then 2 M sodium hydroxide solution (5.4 mL, 10.8 mmol) was added. After completion of the addition, the reaction was stirred for 16 hours. The reaction solution was concentrated under reduced pressure. Then, 50 mL of water were added to the resulting residue, and the mixture was stirred uniformly. Then, 2M hydrochloric acid was added dropwise to adjust the pH of the reaction solution to 5. The mixture was extracted with ethyl acetate (50 mL×3). The organic phases were combined, dried over anhydrous sodium sulfate, and filtrated to remove the desiccant. The filtrate was concentrated under reduced pressure. The resulting residue was purified by silica gel column chromatography with elution system A to obtain the title compound 38 (700 mg, yield 71.8%) as a yellow solid.

MS m/z (ESI): 542.5 [M+1]

$^1$H NMR (400 MHz, CD$_3$OD) δ7.93 (s, 1H), 7.78 (s, 1H), 7.36-7.43 (m, 3H), 7.27-7.25 (dd, 1H), 7.05-6.98 (m, 5H), 6.94 (d, 1H), 6.38 (d, 1H), 6.11 (s, 1H), 4.25-4.35 (m, 1H), 4.18 (q, 2H), 3.64 (dd, 1H), 2.68-2.81 (m, 2H), 1.47 (t, 3H), 1.11-1.18 (m, 6H), 0.96 (d, 3H).

Example 39

(E)-3-(3,5-Difluoro-4-((1S,3R)-2-(4-isopropylphenyl)-3-methyl-6-(1-methyl-1H-pyrazol-4-yl)-1,2,3,4-tetrahydroisoquinolin-1-yl)phenyl)acrylic acid 39

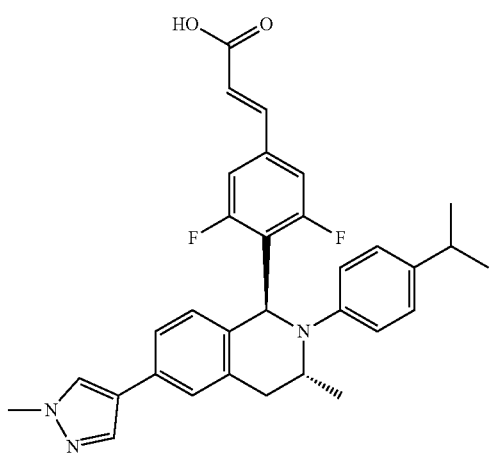

In accordance with the synthetic route of Example 38, the starting material 1-ethyl-4-(4,4,5,5-tetramethyl-1,3,2-dioxaborolan-2-yl)-1H-pyrazole used in step 5 was replaced with 1-methyl-4-(4,4,5,5-tetramethyl-1,3,2-dioxaborolan-2-yl)-1H-pyrazole, accordingly, the title compound 39 (330 mg, a yellow solid) was prepared.

MS m/z (ESI): 528.4 [M+1]

$^1$H NMR (400 MHz, DMSO-d$_6$) δ 12.53 (br, 1H), 8.09 (s, 1H), 7.82 (s, 1H), 7.45-7.31 (m, 5H), 7.06 (d, 2H), 6.98-6.94 (m, 3H), 6.58 (d, 1H), 6.03 (d, 1H), 4.37 (s, 1H), 3.85 (s, 3H), 3.58-3.51 (m, 1H), 2.79-2.73 (m, 2H), 1.13 (d, 6H), 0.87 (d, 3H).

Example 40

(E)-3-(3,5-Difluoro-4-((1S,3R/1R,3S)-2-(4-isopropylphenyl)-3-methyl-6-(1-methyl-1H-pyrazol-4-yl)-1,2,3,4-tetrahydroisoquinolin-1-yl)phenyl)acrylic acid 40

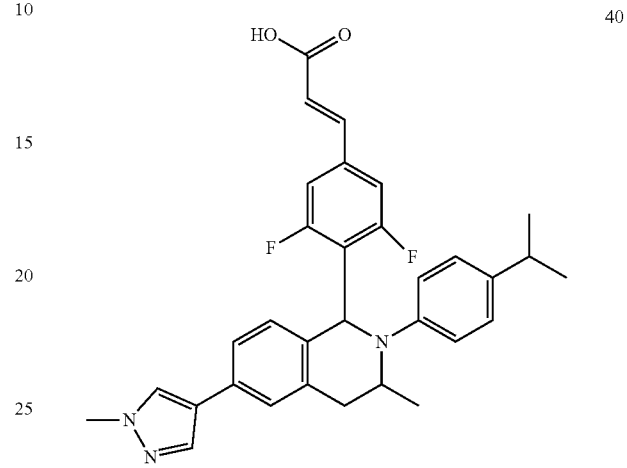

In accordance with the synthetic route of Example 4, the starting material 4d used in step 3 was replaced with 4-isopropylaniline, accordingly, the title compound 40 (60 mg, a light yellow solid) was prepared.

MS m/z (ESI): 528.5 [M+1]

$^1$H NMR (400 MHz, CD$_3$OD) δ 7.94 (s, 1H), 7.78 (s, 1H), 7.38-7.42 (m, 3H), 7.27-7.25 (dd, 1H), 7.05-6.98 (m, 5H), 6.96 (d, 1H), 6.38 (d, 1H), 6.12 (s, 1H), 4.25-4.35 (m, 1H), 4.2 (s, 3H), 3.64 (dd, 1H), 2.68-2.81 (m, 2H), 1.47 (t, 3H), 1.11-1.18 (m, 6H).

Example 41

(E)-3-(4-((1R,3R/1S,3S)-2-(4-(tert-Butyl)phenyl)-3-methyl-6-(1-methyl-1H-pyrazol-4-yl)-1,2,3,4-tetrahydroisoquinolin-1-yl)phenyl)acrylic acid 41

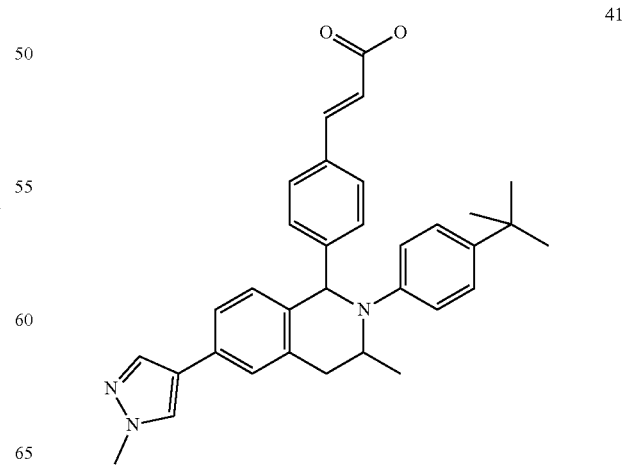

In accordance with the synthetic route of Example 1, the starting material 1b used in step 1 was replaced with 4-tert-butylaniline, accordingly, the title compound 41 (15 mg, a yellow solid) was prepared.

MS m/z (ESI): 506.5 [M+1]

$^1$H NMR (400 MHz, CD$_3$OD) δ 7.92 (s, 1H), 7.79 (s, 1H), 7.57 (d, 1H), 7.43 (s, 4H), 7.35-7.38 (m, 3H), 7.17 (d, 2H), 6.79 (d, 2H), 6.38 (d, 1H), 5.76 (s, 1H), 4.54 (m, 1H), 3.91 (s, 3H), 3.40 (dd, 1H), 2.80 (dd, 1H), 1.24 (s, 9H), 1.02 (d, 3H).

Example 42

(E)-3-(4-((1R,3R)-2-(4-Isopropylphenyl)-3-methyl-6-(1-methyl-1H-pyrazol-4-yl)-1,2,3,4-tetrahydroisoquinolin-1-yl)phenyl)acrylic acid 42

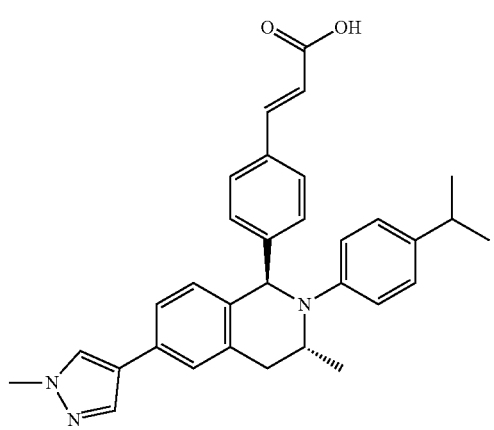

In accordance with the synthetic route of Example 33, the starting material aniline used in step 1 was replaced with 4-isopropylaniline, accordingly, the title compound 42 (457 mg, a yellow solid) was prepared.

MS m/z (ESI): 492.6 [M+1]

$^1$H NMR (400 MHz, CDCl$_3$) δ 7.74 (s, 1H), 7.66 (d, 1H), 7.59 (s, 1H), 7.39 (s, 3H), 7.31 (s, 2H), 7.26 (s, 2H), 7.04 (d, 2H), 6.73-6.77 (m, 2H), 6.36 (d, 1H), 5.70 (s, 1H), 3.95 (s, 3H), 3.32-3.43 (m, 1H), 2.89-2.78 (m, 1H), 2.67-2.57 (m, 1H), 2.42-2.32 (m, 1H), 1.26-1.20 (m, 9H).

Example 43

(E)-3-(4-((1R,3R/1S,3S)-3-Methyl-6-(1-methyl-1H-pyrazol-4-yl)-2-(4-(2,2,2-trifluoroethyl)phenyl)-1,2,3,4-tetrahydroisoquinolin-1-yl)phenyl)acrylic acid 43

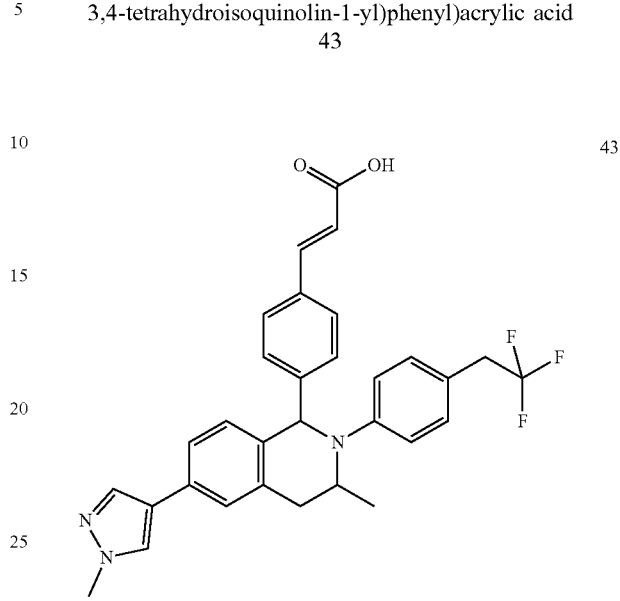

In accordance with the synthetic route of Example 1, the starting material 1b used in step 1 was replaced with 4-(2,2,2-trifluoroethyl)aniline, accordingly, the title compound 43 (40 mg, a yellow solid) was prepared.

MS m/z (ESI): 532.5 [M+1]

$^1$H NMR (400 MHz, CDCl$_3$) δ 7.74 (s, 1H), 7.66 (d, 1H), 7.59 (s, 1H), 7.39 (s, 3H), 7.31 (s, 2H), 7.26 (s, 2H), 7.04 (d, 2H), 6.73-6.77 (m, 2H), 6.36 (d, 1H), 5.70 (s, 1H), 3.95 (s, 3H), 3.32-3.43 (m, 1H), 3.12-3.03 (m, 2H), 2.67-2.57 (m, 1H), 2.42-2.32 (m, 1H), 1.26 (d, 3H).

Example 44

(E)-3-(4-((1R,3R/1S,3S)-2-(4-Ethoxyphenyl)-3-methyl-6-(1-methyl-1H-pyrazol-4-yl)-1,2,3,4-tetrahydroisoquinolin-1-yl)phenyl)acrylic acid 44

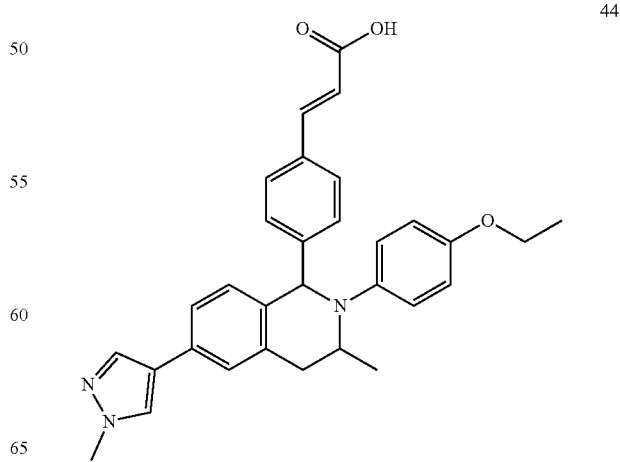

In accordance with the synthetic route of Example 1, the starting material 1b used in step 1 was replaced with 4-ethoxyaniline, accordingly, the title compound 44 (20 mg, a yellow solid) was prepared.

MS m/z (ESI): 494.6 [M+1]

$^1$H NMR (400 MHz, CDCl$_3$) g 7.74 (s, 1H), 7.66 (d, 1H), 7.59 (s, 1H), 7.39 (s, 3H), 7.31 (s, 2H), 7.26 (s, 2H), 7.04 (d, 2H), 6.73-6.77 (m, 2H), 6.36 (d, 1H), 5.70 (s, 1H), 4.09 (q, 2H), 3.95 (s, 3H), 3.32-3.43 (m, 1H), 2.67-2.57 (m, 1H), 2.42-2.32 (m, 1H), 1.32 (t, 3H), 1.26 (d, 3H).

Example 45

(E)-3-(4-((1R,3R/1S,3S)-2-(2,4-Diethylphenyl)-3-methyl-6-(1-methyl-1H-pyrazol-4-yl)-1,2,3,4-tetra-hydroisoquinolin-1-yl)phenyl)acrylic acid 45

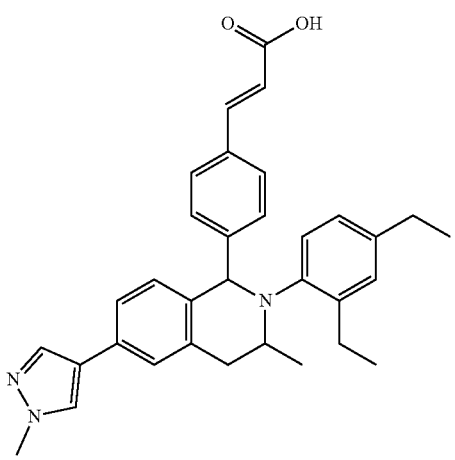

In accordance with the synthetic route of Example 1, the starting material 1b used in step 1 was replaced with 2,4-diethylaniline, accordingly, the title compound 45 (53 mg, a yellow solid) was prepared.

MS m/z (ESI): 506.6 [M+1]

$^1$H NMR (400 MHz, CDCl$_3$) δ 7.74 (s, 1H), 7.66 (d, 1H), 7.59 (s, 1H), 7.39 (s, 3H), 7.31 (s, 2H), 7.26 (s, 2H), 7.04 (d, 2H), 6.73-6.77 (m, 1H), 6.36 (d, 1H), 5.70 (s, 1H), 3.95 (s, 3H), 3.32-3.43 (m, 1H), 2.67-2.56 (m, 5H), 2.42-2.32 (m, 1H), 1.26 (d, 3H), 1.22-1.16 (m, 6H).

Example 46

(E)-3-(4-((1R,3R/1S,3S)-2-(4-Methoxyphenyl)-3-methyl-6-(1-methyl-1H-pyrazol-4-yl)-1,2,3,4-tetra-hydroisoquinolin-1-yl)phenyl)acrylic acid 46

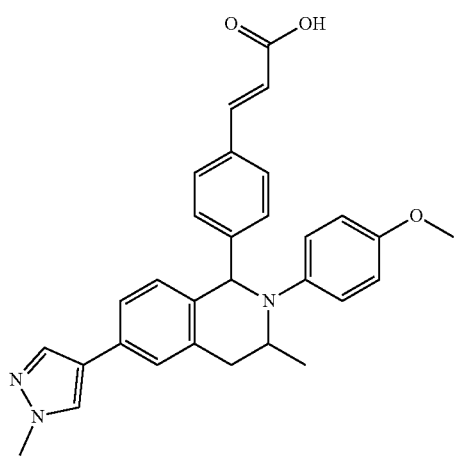

In accordance with the synthetic route of Example 1, the starting material 1b used in step 1 was replaced with 4-methoxyaniline, accordingly, the title compound 46 (50 mg, a yellow solid) was prepared.

MS m/z (ESI): 480.4 [M+1]

$^1$H NMR (400 MHz, CDCl$_3$) δ 7.73 (s, 1H), 7.66 (d, 1H), 7.58 (s, 1H), 7.38 (s, 3H), 7.30 (s, 2H), 7.24 (s, 1H), 6.92 (d, 2H), 6.71 (d, 2H), 6.32 (d, 1H), 6.66 (d, 1H), 4.46 (d, 1H), 4.36 (s, 3H), 3.93 (s, 3H), 3.35 (d, 1H), 2.72 (d, 1H), 1.25 (s, 1H), 1.04 (d, 3H).

Example 47

(E)-3-(4-((1R,3R/1S,3S)-2-(4-(Cyclopropylmethyl)phenyl)-3-methyl-6-(1-methyl-1H-pyrazol-4-yl)-1,2,3,4-tetrahydroisoquinolin-1-yl)phenyl)acrylic acid 47

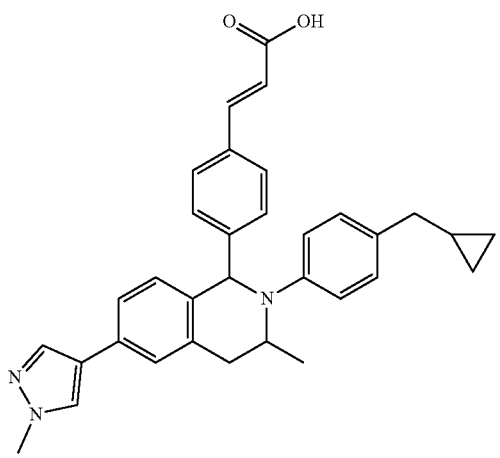

In accordance with the synthetic route of Example 1, the starting material 1b used in step 1 was replaced with 4-(Cyclopropylmethyl)aniline (prepared by a method disclosed in the patent application publication "U.S. Pat. No. 5,455,252A1"), accordingly, the title compound 47 (120 mg, a yellow solid) was prepared.

MS m/z (ESI): 504.6 [M+1]

$^1$H NMR (400 MHz, CDCl$_3$) δ 7.74 (s, 1H), 7.66 (d, 1H), 7.59 (s, 1H), 7.39 (s, 3H), 7.31 (s, 2H), 7.26 (s, 2H), 7.04 (d, 2H), 6.73-6.77 (m, 2H), 6.36 (d, 1H), 5.70 (s, 1H), 3.95 (s, 3H), 3.32-3.43 (m, 1H), 2.67-2.57 (m, 1H), 2.54 (d, 2H), 2.42-2.32 (m, 1H), 1.26 (d, 3H), 0.67-0.62 (m, 1H), 0.33-0.27 (m, 2H), 0.07-0.03 (m, 2H).

Example 48

(E)-3-(4-((1R,3R/1S,3S)-2-(4-Isopropylphenyl)-3-methyl-6-(1H-pyrazol-4-yl)-1,2,3,4-tetrahydroisoquinolin-1-yl)phenyl)acrylic acid 48

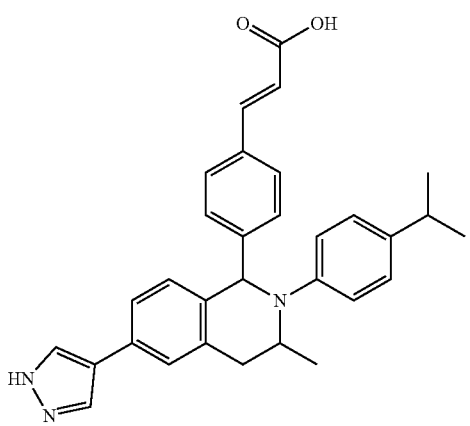

In accordance with the synthetic route of Example 7, the starting material 1-ethyl-4-(4,4,5,5-tetramethyl-1,3,2-dioxaborolan-2-yl)-1H-pyrazole used in step 5 was replaced with tert-butyl 4-(4,4,5,5-tetramethyl-1,3,2-dioxaborolan-2-yl)-1H-pyrazole, accordingly, the title compound 48 (130 mg, a yellow solid) was prepared after removing tert-butyloxycarbonyl.

MS m/z (ESI): 478.4 [M+1]

$^1$H NMR (400 MHz, DMSO-d$_6$) δ 12.58 (br, 1H), 8.02 (s, 2H), 7.55-7.43 (m, 7H), 6.99 (d, 2H), 6.74 (d, 2H), 6.43 (d, 1H), 5.81 (s, 1H), 4.59 (br, 1H), 2.80-2.70 (m, 2H), 1.24 (s, 2H), 1.11 (d, 6H), 0.94 (d, 3H).

Example 49

(E)-3-(4-((1R,3R/1S,3S)-(6-(1-(Difluoromethyl)-1H-pyrazol-4-yl)-2-(4-isopropylphenyl)-3-methyl-1,2,3,4-tetrahydroisoquinolin-1-yl)phenyl)acrylic acid 49

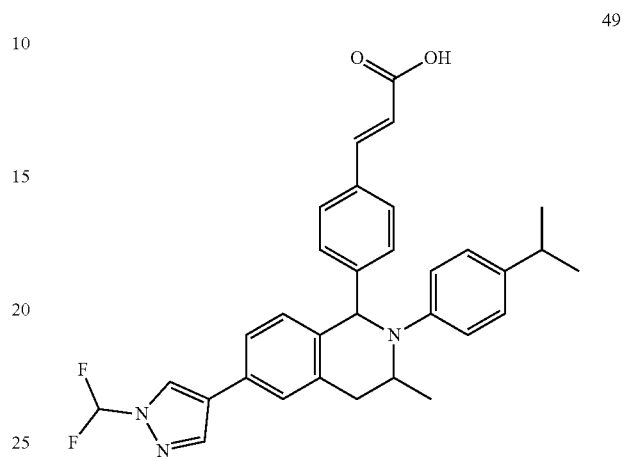

In accordance with the synthetic route of Example 7, the starting material 1-ethyl-4-(4,4,5,5-tetramethyl-1,3,2-dioxaborolan-2-yl)-1H-pyrazole used in step 5 was replaced with 1-(difluoromethyl)-4-(4,4,5,5-tetramethyl-1,3,2-dioxaborolan-2-yl)-1H-pyrazole, accordingly, the title compound 49 (35 mg, a yellow solid) was prepared.

MS m/z (ESI): [M+1] 528.6

$^1$H NMR (400 MHz, DMSO-d$_6$) δ 10.9 (s, 1H), 8.80 (s, 1H), 8.20 (s, 1H), 7.74 (s, 1H), 7.57-7.63 (m, 3H), 7.11-7.25 (m, 7H), 6.67-6.71 (m, 2H), 6.31-6.33 (d, 1H), 5.18-5.22 (m, 1H), 3.15-3.18 (m, 1H), 2.85-2.88 (m, 1H), 2.63-2.65 (m, 1H), 2.35-2.37 (m, 1H), 1.20-1.25 (m, 9H).

Example 50

(E)-3-(4-((1R,3S/1S,3R)-2-(2-Ethylphenyl)-3-methyl-6-(1-methyl-1H-pyrazol-4-yl)-1,2,3,4-tetrahydroisoquinolin-1-yl)phenyl)acrylic acid 50

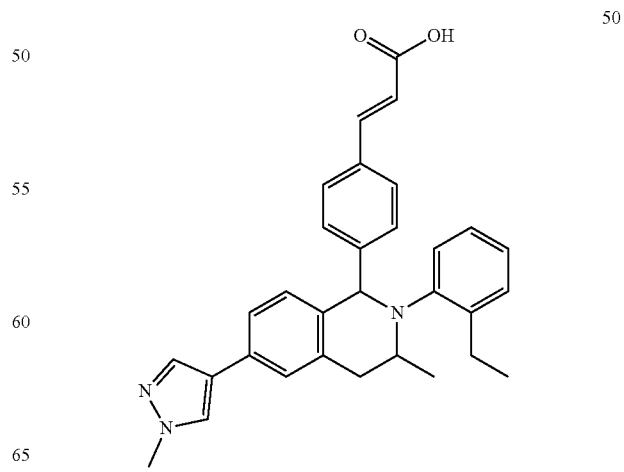

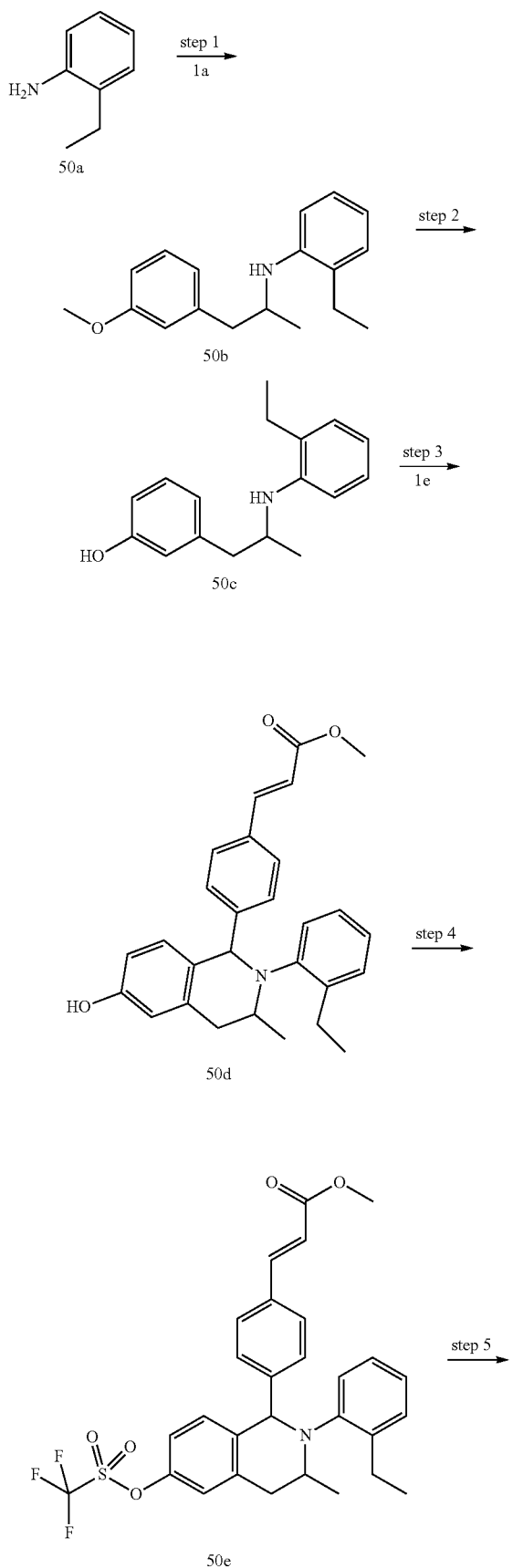

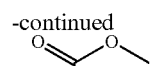

Step 1

2-Ethyl-N-(1-(3-methoxyphenyl)propan-2-yl)aniline 50b

Compound 1a (820 mg, 5 mmol), 2-ethylaniline 50a (0.75 mL, 6 mmol) and sodium triacetoxyborohydride (1.58 g, 7.5 mmol) were dissolved in 30 mL of 1,2-dichloroethane. The mixture was stirred for 16 hours. Then, 30 mL of water were added to quench the reaction. The reaction solution was extracted with dichloromethane (25 mL×3). The organic phases were combined, dried over anhydrous sodium sulfate, and filtrated to remove the desiccant. The filtrate was concentrated under reduced pressure. The resulting residue was purified by silica gel column chromatography with elution system B to obtain the title compound 50b (0.8 g, yield 59.3%) as a yellow oil.

MS m/z (ESI): 270.1 [M+1]

Step 2

3-(2-((2-Ethylphenyl)amino)propyl)phenol 50c

Compound 50b (800 mg, 2.97 mmol) was dissolved in 20 mL of dichloromethane, then 6 mL of a solution of 1 M boron tribromide in dichloromethane were added dropwise in an ice bath. After completion of the addition, the reaction was stirred for 16 hours at room temperature. Then, 15 mL of water were added to quench the reaction. The reaction solution was concentrated under reduced pressure. The residue was extracted with ethyl acetate (30 mL×3), dried over anhydrous magnesium sulfate and filtered. The filtrate was concentrated under reduced pressure to obtain the crude title compound 50c (500 mg) as a yellow solid, which was used directly in next step without further purification.

Step 3

(E)-Methyl 3-(4-((1R,3S/1S,3R)-6-hydroxy-2-(2-ethylphenyl)-3-methyl-1,2,3,4-tetrahydroisoquinolin-1-yl)phenyl)acrylate 50d The crude compound 50c (400 mg, 1.57 mmol), 1e (596 mg, 3.13 mmol) and triisopropylsilyl chloride (1.51 g, 7.83 mmol) were added to 10 mL of N,N-dimethylformamide. After completion of the addition, the mixture was heated to 120° C. and stirred for 3 hours. After stopping heating, 20 mL of water were added, and the reaction solution was extracted with ethyl acetate (20 mL×3). The organic phases were combined, washed with saturated sodium chloride solution, and dried over anhydrous sodium sulfate. The filtrate was concentrated under reduced pressure. The resulting residue was purified by silica gel column chromatography with elution system B to obtain the title compound 50d (440 mg, yield 65.7%) as a yellow solid.

MS m/z (ESI): 428.3 [M+1]

Step 4

(E)-Methyl 3-(4-((1R,3S/1S,3R)-2-(2-ethylphenyl)-3-methyl-6-(((trifluoromethyl) sulfonyl)oxy)-1,2,3,4-tetrahydroisoquinolin-1-yl)phenyl)acrylate 50e Compound 50d (440 mg, 1.03 mmol) and 2,6-lutidine (165 mg, 1.54 mmol) were dissolved in 50 mL of dichloromethane. After the reaction was cooled to 0° C., trifluoromethanesulfonic anhydride (436 mg, 1.54 mmol) was added dropwise. The reaction was stirred for 12 hours at room temperature. Then, 20 mL of water were added to quench the reaction, and the reaction solution was extracted with dichloromethane (50 mL×2). The organic phases were combined and dried over anhydrous sodium sulfate. The filtrate was concentrated under reduced pressure. The resulting residue was purified by silica gel column chromatography with elution system B to obtain the title compound 50e (176 mg, yield 30.6%) as a light yellow solid.

MS m/z (ESI): 560.2 [M+1]

Step 5

(E)-Methyl 3-(4-((1R,3S/1S,3R)-2-(2-ethylphenyl)-3-methyl-6-(1-methyl-1H-pyrazol-4-yl)-1,2,3,4-tetrahydroisoquinolin-1-yl)phenyl)acrylate 50f Compound 50e (101 mg, 0.18 mmol), 1-ethyl-4-(4,4,5,5-tetramethyl-1,3,2-dioxaborolan-2-yl)-1H-pyrazole (56 mg, 0.27 mmol), and [1,1'-bis(diphenylphosphino)ferrocene]dichloropalladium (13 mg, 0.018 mmol) were dissolved in 3.6 mL of a mixture of 1,4-dioxane and water (V:V=5:1), then 0.18 mL of 2N sodium carbonate solution was added. After completion of the addition, the mixture was stirred in a microwave at 120° C. for 40 minutes. After cooling to room temperature, 20 mL of water were added, and the mixture was extracted with ethyl acetate (30 mL×3). The organic phases were combined, washed with saturated sodium chloride solution, and dried over anhydrous sodium sulfate. The filtrate was concentrated under reduced pressure to obtain the crude title compound 50f (80 mg) as a yellow solid, which was used directly in next step without further purification.

MS m/z (ESI): 492.3[M+1]

Step 6

(E)-3-(4-((1R,3S/1S,3R)-2-(2-Ethylphenyl)-3-methyl-6-(1-methyl-1H-pyrazol-4-yl)-1,2,3,4-tetrahydroisoquinolin-1-yl)phenyl)acrylic acid 50

Compound 50f (80 mg, 0.16 mmol) was dissolved in 5 mL of methanol, then 0.4 mL of 2 M sodium hydroxide solution was added. After completion of the addition, the reaction was stirred for 16 hours. 1M hydrochloric acid was added dropwise to adjust the pH of the reaction solution to 3. The mixture was extracted with ethyl acetate (10 mL×2). The organic phases were combined, washed with saturated sodium chloride solution, dried over anhydrous sodium sulfate, and filtrated to remove the desiccant. The filtrate was concentrated under reduced pressure. The resulting residue was purified by silica gel column chromatography with elution system A to obtain the title compound 50 (44 mg, yield 56.4%) as a yellow solid.

MS m/z (ESI): 478.5 [M+1]

$^1$H NMR (400 MHz, CDCl$_3$) δ 7.76 (s, 1H), 7.62 (d, 1H), 7.59 (s, 1H), 7.31-7.27 (m, 5H), 7.26-7.24 (m, 1H), 7.17-7.13 (m, 2H), 7.05-7.03 (m, 1H), 7.01-6.98 (m, 1H), 6.76 (d, 1H), 6.31 (d, 1H), 5.67 (s, 1H), 3.95 (s, 3H), 3.72-3.67 (m, 1H), 3.58-3.56 (m, 1H), 2.93-2.87 (m, 1H), 2.75-2.63 (m, 2H), 1.17 (t, 3H), 1.09 (d, 3H).

Example 51

(E)-3-(4-(2-(4-Ethylphenyl)-6-(1-methyl-1H-pyrazol-4-yl)-1,2,3,4-tetrahydroisoquinolin-1-yl)phenyl) acrylic acid 51

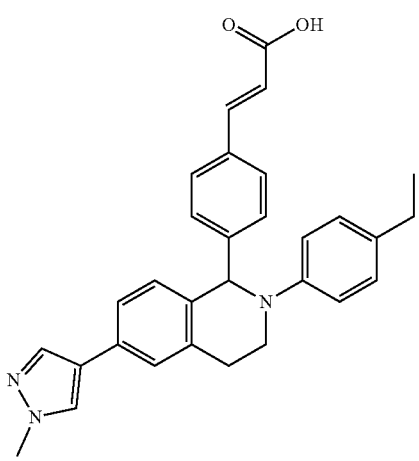

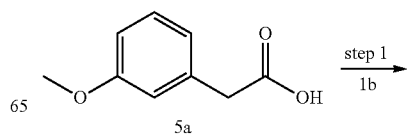

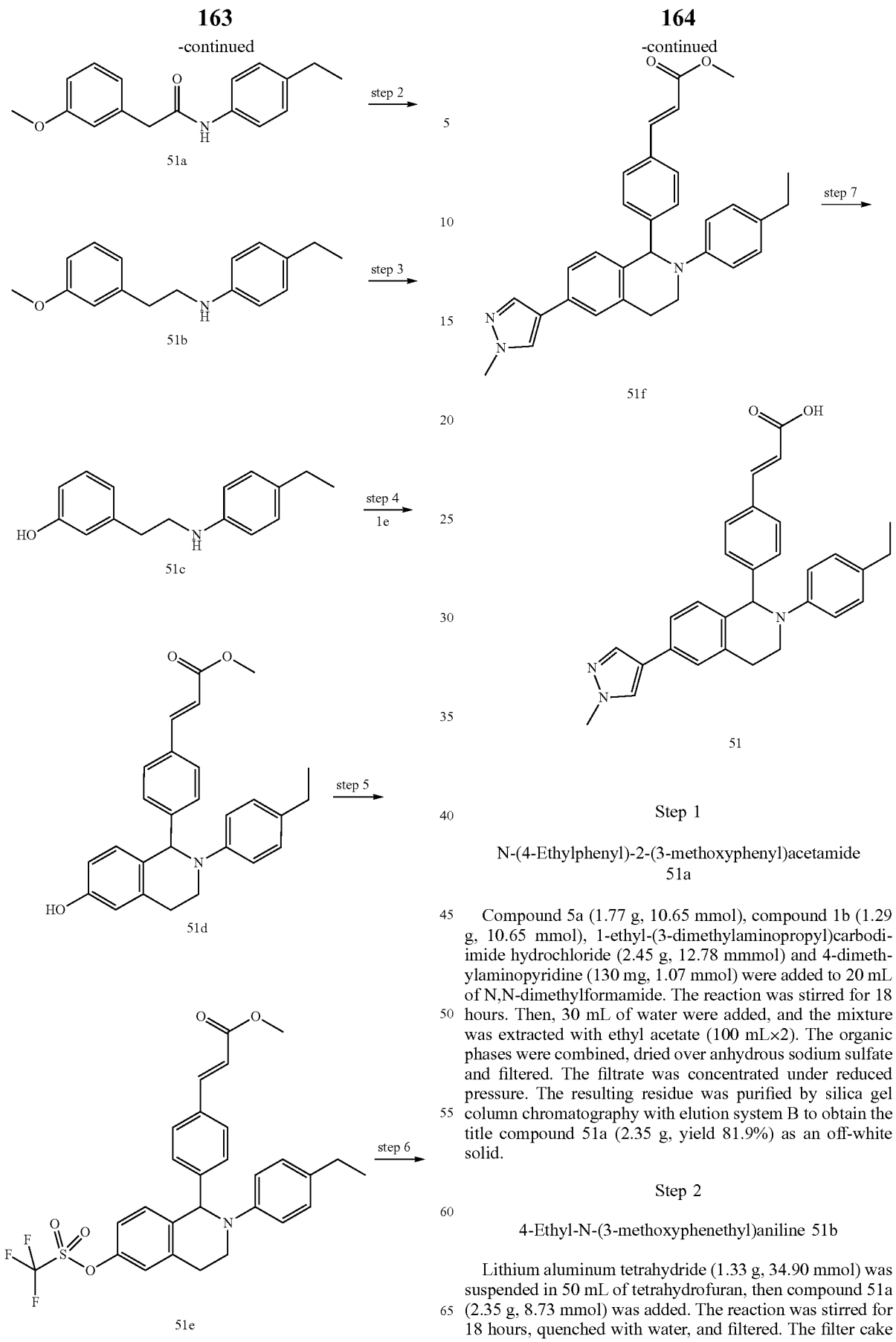

Step 1

N-(4-Ethylphenyl)-2-(3-methoxyphenyl)acetamide 51a

Compound 5a (1.77 g, 10.65 mmol), compound 1b (1.29 g, 10.65 mmol), 1-ethyl-(3-dimethylaminopropyl)carbodiimide hydrochloride (2.45 g, 12.78 mmmol) and 4-dimethylaminopyridine (130 mg, 1.07 mmol) were added to 20 mL of N,N-dimethylformamide. The reaction was stirred for 18 hours. Then, 30 mL of water were added, and the mixture was extracted with ethyl acetate (100 mL×2). The organic phases were combined, dried over anhydrous sodium sulfate and filtered. The filtrate was concentrated under reduced pressure. The resulting residue was purified by silica gel column chromatography with elution system B to obtain the title compound 51a (2.35 g, yield 81.9%) as an off-white solid.

Step 2

4-Ethyl-N-(3-methoxyphenethyl)aniline 51b

Lithium aluminum tetrahydride (1.33 g, 34.90 mmol) was suspended in 50 mL of tetrahydrofuran, then compound 51a (2.35 g, 8.73 mmol) was added. The reaction was stirred for 18 hours, quenched with water, and filtered. The filter cake was washed with dichloromethane. The filtrate was combined, dried over anhydrous sodium sulfate, and filtered. The filtrate was concentrated under reduced pressure. The resulting residue was purified by silica gel column chromatography with elution system B to obtain the title compound 51b (1.68 g, yield: 75.3%) as a yellow oil.

MS m/z (ESI): 256.2 [M+1]

Step 3

3-(2-((4-Ethylphenyl)amino)ethyl)phenol 51c

Compound 51b (1.68 g, 6.58 mmol) was dissolved in 50 mL of dichloromethane. After cooling to −78° C., a solution of 1M boron tribromide in dichloromethane (13.2 mL, 13.20 mmol) was added dropwise. After completion of the addition, the reaction was warmed up to room temperature and stirred for 16 hours. Then, 2 mL of 2M hydrochloric acid solution were added to to quench the reaction, then 5 mL of water were added to precipitate a solid. The mixture was filtered, and the filter cake was washed with dichloromethane. The solid was dried to obtain the title compound 51c (1.19 g, yield 74.8%) as a yellow solid.

MS m/z (ESI): 242.1 [M+1]

Step 4

(E)-Methyl 3-(4-(2-(4-ethylphenyl)-6-hydroxy-1,2,3,4-tetrahydroisoquinolin-1-yl)phenyl)acrylate 51d Compound 51c (367 mg, 1.52 mmol), compound 1e (578 mg, 3.04 mmol) and triisopropylsilyl chloride (1.47 g, 7.60 mmol) were added to 10 mL of N,N-dimethylformamide. After completion of the addition, the mixture was heated to 120° C. and stirred for 3 hours. After stopping heating, the reaction solution was cooled to room temperature, and 30 mL of water were added. The mixture was extracted with ethyl acetate (50 mL×3). The organic phases were combined, washed with saturated sodium chloride solution (30 mL), dried over anhydrous sodium sulfate, and filtrated to remove the desiccant. The filtrate was concentrated under reduced pressure. The resulting residue was purified by silica gel column chromatography with elution system B to obtain the title compound 51d (437 mg, yield 69.5%) as a yellow solid.

MS m/z (ESI): 414.2 [M+1]

Step 5

(E)-Methyl 3-(4-(2-(4-ethylphenyl)-6-(trifluoromethylsulfonyloxy)-1,2,3,4-tetrahydroisoquinolin-1-yl)phenyl)acrylate 51e Compound 51d (437 mg, 1.06 mmol) was dissolved in 50 mL of dichloromethane, then 2,6-lutidine (170 mL, 1.59 mmol) was added. After completion of the addition, the mixture was cooled to 0° C. in an ice bath, and trifluoromethanesulfonic anhydride (447 mg, 1.59 mmol) was added. After completion of the addition, the ice bath was removed, and the reaction was stirred for 16 hours. Then, 30 mL of water were added to quench the reaction, and two phases were separated. The organic phase was dried over anhydrous sodium sulfate, and filtrated to remove the desiccant. The filtrate was concentrated under reduced pressure. The resulting residue was purified by silica gel column chromatography with elution system B to obtain the title compound 51e (359 mg, yield 62.2%) as a light yellow solid.

MS m/z (ESI): 546.2 [M+1]

Step 6

(E)-Methyl 3-(4-(2-(4-ethylphenyl)-6-(1-methyl-1H-pyrazol-4-yl)-1,2,3,4-tetrahydroisoquinolin-1-yl)phenyl)acrylate 51f Compound 51e (359 mg, 0.66 mmol), 1-methyl-4-(4,4,5,5-tetramethyl-1,3,2-dioxaborolan-2-yl)-1H-pyrazole (205 mg, 0.99 mmol), and [1,1'-bis(diphenylphosphino)ferrocene]dichloropalladium (48 mg, 0.07 mmol) were dissolved in 12 mL of a mixture of 1,4-dioxane and water (V:V=5:1), then 2M sodium carbonate solution (0.66 mL, 1.32 mmol) was added. After completion of the addition, the mixture was stirred in a microwave at 120° C. for 40 minutes. After cooling to room temperature, 30 mL of water were added, and the mixture was extracted with ethyl acetate (30 mL×3). The organic phases were combined, washed with saturated sodium chloride solution (20 mL×2), dried over anhydrous sodium sulfate, and filtrated to remove the desiccant. The filtrate was concentrated under reduced pressure to obtain the crude title compound 51f (190 mg) as a yellow solid, which was used directly in the next step without further purification.

MS m/z (ESI): 478.3 [M+1]

Step 6

(E)-3-(4-(2-(4-Ethylphenyl)-6-(1-methyl-1H-pyrazol-4-yl)-1,2,3,4-tetrahydroisoquinolin-1-yl)phenyl)acrylic acid 51

The crude 51f (190 mg, 0.40 mmol) was dissolved in 5 mL of methanol, then 2 M sodium hydroxide solution (1 mL, 2.0 mmol) was added. After completion of the addition, the reaction was stirred for 16 hours. 1M hydrochloric acid was added dropwise to adjust the pH of the reaction solution to 4, and the mixture was extracted with ethyl acetate (30 mL×2). The organic phases were combined, washed with 10 mL of saturated sodium chloride solution, dried over anhydrous sodium sulfate, and filtrated to remove the desiccant. The filtrate was concentrated under reduced pressure, and the resulting residue was purified by silica gel column chromatography with elution system A to obtain the title compound 51 (141 mg, yield 76.6%) as a yellow solid.

MS m/z (ESI): 464.5[M+1]

$^1$H NMR (400 MHz, CD$_3$OD) δ 7.91 (s, 1H), 7.79 (s, 1H), 7.59 (d, 1H), 7.43 (d, 2H), 7.36 (d, 2H), 7.25-7.20 (m, 3H), 7.02 (d, 2H), 6.81 (d, 2H), 6.40 (d, 1H), 5.79 (s, 1H), 3.91 (s, 3H), 3.65-3.61 (m, 1H), 3.46-3.40 (m, 1H), 2.99-2.93 (m, 2H), 2.55-2.49 (dd, 2H), 1.16 (t, 3H).

Example 52

(E)-3-(4-((1R,3S/1S,3R)-2-(4-Ethylphenyl)-3-methyl-6-(1-methyl-1H-pyrazol-4-yl)-1,2,3,4-tetrahydroisoquinolin-1-yl)phenyl)acrylic acid 52

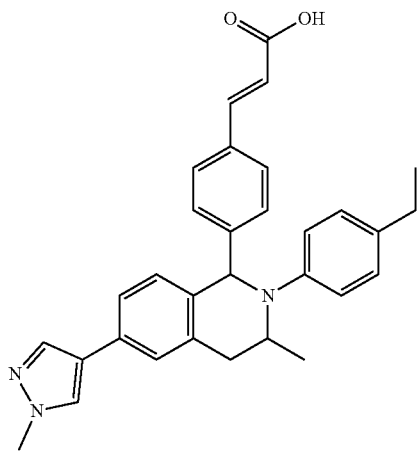

In accordance with the synthetic route of Example 50, the starting material 50a used in step 1 was replaced with 4-ethylaniline, accordingly, the title compound 52 (58 mg, a yellow solid) was prepared.

MS m/z (ESI): 478.5[M+1]

$^1$H NMR (400 MHz, CDCl$_3$) δ 7.77 (s, 1H), 7.60 (s, 1H), 7.45-7.36 (m, 4H), 7.33-7.28 (m, 2H), 7.18 (s, 1H), 7.10-7.04 (m, 3H), 6.83 (d, 2H), 6.40 (d, 1H), 5.62 (s, 1H), 3.96 (s, 3H), 3.83-3.80 (m, 1H), 2.88-2.85 (m, 1H), 2.67-2.54 (m, 3H), 1.32 (d, 3H), 1.20 (t, 3H).

Example 53

(E)-3-(4-(2-(4-Fluorophenyl)-6-(1-methyl-1H-pyrazol-4-yl)-1,2,3,4-tetrahydroisoquinolin-1-yl)phenyl)acrylic acid 53

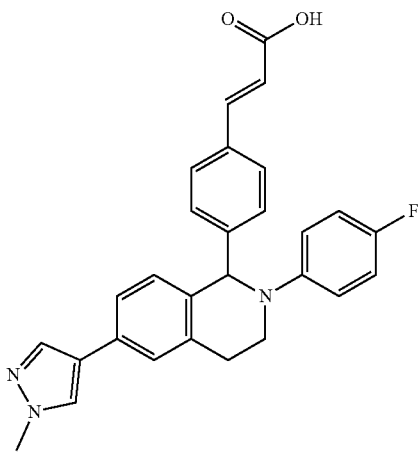

In accordance with the synthetic route of Example 51, the starting material 1b used in step 1 was replaced with 4-fluoroaniline, accordingly, the title compound 53 (108 mg, a yellow solid) was prepared.

MS m/z (ESI): 453.5 [M+1]

$^1$H NMR (400 MHz, CD$_3$OD) δ 7.92 (s, 1H), 7.80 (s, 1H), 7.60 (d, 1H), 7.46 (d, 2H), 7.39-7.36 (m, 2H), 7.25-7.18 (m, 3H), 6.94-6.84 (m, 4H), 6.41 (d, 1H), 5.76 (s, 1H), 3.91 (s, 3H), 3.66-3.60 (m, 1H), 3.45-3.39 (m, 1H), 3.03-2.97 (m, 2H).

Biological Assay

The present invention will be further described with reference to the following test examples, but the examples should not be considered as limiting the scope of the invention.

Test Example 1. Inhibition Effect of the Compound of the Present Invention on the Binding of Estrogen (E) to Estrogen Receptor (ER)

1. Experimental Object

The compounds of the present invention have an inhibition effect on the binding of E (estrogen) to ER (estrogen receptor), thereby blocking the binding of a complex of E and ER complex to ERE (estrogen responsive element), and subsequently blocking the expression of downstream luciferase protein.

The inhibition effect of the compounds on the binding of E to ER in vitro was tested by the following method.

The object of this experiment was to determine the inhibition effect of the compounds on the binding of E to ER, and the in vitro activity of the compounds was evaluated according to the IC$_{50}$ values.

2. Experimental Materials and Instruments 2.1 Experimental Instruments

| Instrument name | Supply company | Model |
| --- | --- | --- |
| Victor3 | PE | 1420-012 |
| Micro-oscillator | Haimen Kylin-Bell | MH-I |
| 96-well plate | Corning | 3599 |
| Votex | Corning | LSE |
| Reinin | Mettler Toledo | EDP3-plus |
| 50 ml Centrifuge tube | Corning | 430828 |

2.2 Experimental Materials

| Reagent name | Supply company | Item number |
| --- | --- | --- |
| ONE-Glo ™ Luciferase assay system | Promega | E6110 |
| Steady-Glo Luciferase assay system | Promega | E2510 |
| Estradiol | Sigma | E2758 |
| MEM | Hyclone | SH30024.01B |
| Fetal bovine serum (FBS) | Corning | 35-076-CV |
| Fetal bovine serum-Sterile filtration | Moregate | FBSF |
| G418, Sulfate | Enzo | ALX-380-013-G005 |
| Sodium pyruvate solution | Sigma | S8636-100ML |
| Non-essential amino acid solution | Sigma | M7145-100ML |
| Penicillin - streptomycin solution | Hyclone | SV30010 |
| DMSO | Shanghai Titanchem Co., Ltd | G75927B |
| Deionized water | Shanghai Hengrui Phamaceutical Co., Ltd | Self-made |
| ERE-pGL4.17 | GENEWIZ Biological Technology Co., Ltd | Synthesis |

3. Experimental Method

ERE was cloned into the upstream of the luciferase gene, and MCF-7/ERE-luciferase monoclonal cells were selected by transfection of MCF-7 (Cell Bank of Chinese Academy of Sciences typical culture preservation Committee, TCHu74). MCF-7/ERE-luciferase cells were inoculated into the MEM medium (hyclone, SH30024.01B) containing 10% charcoal stripped FBS (Moregate, FBSF), 1% sodium pyruvate (Sigma, S8636), 1% nonessential amino acids (Sigma, M7145) and 500 µg/ml G418 in a 96-well plates with a density of 30,000 cells/well, and the cells were incubated under the conditions of 37° C., and 5% $CO_2$. The drug was prepared as a 20 mM stock solution that was later diluted with 100% DMSO in 10 fold concentration gradient, and then diluted 20-fold with the medium DMEM. After incubation for 24 hours, the medium was removed, then 0.1 nM estradiol (Sigma, E2758) and 10 µl of the drug diluted with the medium were added to each well, and the control group was added with DMSO. The plate was gently shaken and incubated in a incubator at 37° C., 5% $CO_2$. After 24 hours, the cell culture medium was discarded, Then, 50 µl of the prepared luciferase substrate (Promega, E6110) was added to each well, and the plate was placed in the dark at room temperature for 10-15 minutes, then the chemiluminescence signal value was determined.

4. Test Result

The inhibition effect of the compounds of the present invention on the binding of E to ER was tested by the experiment described above. The values of the chemiluminescence signal vs the logarithmic concentrations of the compounds were plotted using Graphpad Prism, and the measured $IC_{50}$ values are shown in Table 1.

TABLE 1

$IC_{50}$ value of inhibition effect of the compounds of the present invention on the binding of E to ER

| Example No. | $IC_{50}$ (nM) |
|---|---|
| 1 | 2.11 |
| 2 | 1.71 |
| 4 | 0.27 |
| 7 | 1.79 |
| 8 | 0.39 |
| 10 | 1.07 |
| 11 | 0.32 |
| 13 | 0.27 |
| 14 | 0.25 |
| 16 | 2.15 |
| 17 | 3.32 |
| 22 | 1 |
| 23 | 0.85 |
| 24 | 1.81 |
| 25 | 1.62 |
| 26 | 6.76 |
| 28 | 0.42 |
| 29 | 1.26 |
| 30 | 0.34 |
| 32 | 0.74 |
| 34 | 5.42 |
| 35 | 1 |
| 36 | 5.63 |
| 37 | 0.84 |
| 38 | 0.18 |
| 39 | 0.17 |
| 40 | 0.6 |
| 41 | 8.08 |
| 42 | 0.52 |
| 43 | 31.7 |
| 44 | 7.57 |
| 45 | 4.06 |
| 46 | 1.42 |
| 47 | 5.39 |
| 48 | 0.71 |
| 49 | 3.46 |

Conclusion: The compounds of the present invention have a significant inhibition effect on the binding of E to ER.

Test Example 2. Inhibition Effect of the Compounds in the Present Invention on the Proliferation of MCF7 Cells 1. Experimental Object The object of this experiment was to determine the inhibition effect of the compounds on the proliferation activity of MCF7 cells, and the in vitro activity of the compounds was evaluated according to the $IC_{50}$ values.

2. Experimental Reagents and Materials

| Instrument and material name | Supply Company | Type (Item number) |
|---|---|---|
| Microplate reader | PerkinElmer | VICTOR3 |
| Micro-oscillator | IKA | MTS2/4 S25 |
| Bravo Liquid Workstation | Agilent Technologies | SGS120TH34702 |
| Cell count kit | Dojindo Chemical Technology Co., Ltd. | CK04 |
| Cell Titer-Glo Luminescence Cell Activity Detection Kit | Promega | G7571 |
| MEM | Hyclone | SH30024.01B |
| Sodium pyruvate solution | Sigma | S8636-100ML |
| MEM Non-essential amino acid solution | Sigma | M7145-100ML |
| MCF7 | Cell bank of Chinese Academy of Sciences | |
| Inverted microscope | Nikon | ELWD0.3 T1-SNCP |
| Cell count plate | Sigma | Z359629-1EA |
| Centrifuge | Xiangyi Centrifuge Equipment Co., Ltd. | L-530 |
| 0.25% trypsin-EDTA (1x), phenol red | Gibco | 25200-072 |
| Fetal bovine serum | Gibco | 10099-141 |
| 96-well cell culture plate | Corning | 3599 |
| 96-well plate with U-shaped bottom | Corning | 3975 |
| Constant temperature incubator | Thermo | NAPCO 6500 TC |
| Biosafety Cabinet | NUAIRE | NU-425-400E |
| 75 $cm^2$ Flask | Corning | 430641 |

3. Experimental Method

MCF-7 cells (Cell Bank of Chinese Academy of Sciences typical culture preservation Committee, TChu 74) were inoculated into the MEM medium (Hyclone, SH30024.01B) containing 10% FBS (Gibco, 10099-141), 1% sodium pyruvate (Sigma, S8636), and 1% nonessential amino acids (Sigma, M7145) in a 96-well plate with a density of 40,000 cells/well, and the cells were incubated under the conditions of 37° C., and 5% $CO_2$. The compound was prepared as a 20 mM stock solution that was later diluted to 1000× final concentration with 100% DMSO, and then diluted with 20-fold medium containing 2% FBS. After incubation for 24 hours, the medium was removed and 90 µl of the medium containing 2% FBS and 10 µl of the drug were added to each well, 10 ∝l of DMSO was added to the control group, and the blank group contained only 100 µl medium containing 2% FBS. The plate was gently shaken and incubated in a incubator at 37° C., 5% $CO_2$. After 72 hours later, 50 µl of mixed Cell Titer-Glo (Promega, G7571) was added to each well. The plate was shaken until the ingredients were mixed uniformly, and placed at room temperature for 10 minutes, then the chemiluminescence signal value was determined. The inhibition effect of the compound AZD9496 at 100 nM on the proliferation of MCF-7 cells was set to 100%, the maximum inhibition rate of other compounds=(chemiluminescence signal value$_{negative\ control}$−chemiluminescence signal value$_{compound\ 100\ nm}$)/(chemiluminescence signal value$_{negative\ control}$−chemiluminescence signal value$_{AZD9496\ 100\ nm}$)×100%, and the negative control was a well with 0.5% DMSO.

4. Result analysis

The values of the chemiluminescence signals vs the logarithmic concentrations of the compounds were plotted using Graghpad Prism to obtain the IC$_{50}$ values. The results were shown in Table 2.

TABLE 2

IC$_{50}$ value of inhibition effect of the compounds of the present invention on the proliferation of MCF7 cells

| Example No. | IC$_{50}$ (nM) |
|---|---|
| 1 | 0.37 |
| 2 | 0.4 |
| 4 | 0.42 |
| 7 | 0.86 |
| 8 | 0.17 |
| 10 | 0.3 |
| 11 | 1.47 |
| 13 | 1.12 |
| 14 | 0.53 |
| 16 | 0.93 |
| 17 | 0.65 |
| 20 | 4.53 |
| 22 | 0.57 |
| 23 | 0.81 |
| 24 | 0.9 |
| 25 | 0.89 |
| 28 | 0.31 |
| 29 | 2.36 |
| 30 | 2.7 |
| 32 | 0.42 |
| 35 | 1.03 |
| 36 | 2.8 |
| 37 | 1.74 |
| 38 | 0.38 |
| 39 | 0.42 |
| 40 | 0.23 |
| 42 | 0.34 |
| 46 | 0.65 |
| 47 | 4.9 |
| 48 | 0.59 |
| 49 | 1.04 |

Conclusion: The compounds of the present invention have a significant inhibition effect on the proliferation of MCF7 cells.

Test Example 3. Degradation Effect of the Compounds of the Present Invention on ERα

1. Experimental Object

In order to determine the degradation effect on ER induced by the compound of present invention, the following method was used to determine the degradation effect of the compounds of the present invention on ER.

2. Materials and Instruments

BioTek Synergy HT Flatbed reader

MCF-7 cell line (TChu 74, Cell Bank of Chinese Academy of Sciences typical culture preservation Committee)

ERα Duoset Kit (#DYC5715E, R&D System)

3. Experimental Method

MCF-7 cells well incubated in DMEM/F-12 medium containing 10% FBS.

On the first day of the experiment, MCF-7 cells were resuspended in DMEM/F-12 medium containing 10% FBS treated by activated carbon, then inoculated into a 48-well plate with a density of 50,000 cells/well and incubated for 22-24 hours.

On the second day of the experiment, the test compound was diluted with medium and added to a 48-well plate. The ERα-capture antibody was diluted to 1 µg/ml with PBS, and added with 100 µl/well to a 96-well plate at 100 µl/well. The plate was sealed and coated overnight at room temperature.

On the third day of the experiment, the coated 96-well plate was washed twice with PBS, added with with a sealing solution (1% BSA in PBS) at 110 µl/well and sealed for 1 hour at room temperature. The 48-well plate was washed once and the residual liquid was removed. Then, 60 µl of lysis buffer (6 M urea, 1 mM EDTA, 0.5% Triton X-100, 1 mM PMSF, Protease Inhibitor cocktail) was added to each well. After lysis on ice for 15 minutes, the diluent (1 mM EDTA, 0.5% TritonX-100 dissolved in PBS) was added. The cell-diluted lysate was transferred to a 96-well plate at 100 µl/well, then the plate was incubated at room temperature for 2 hours. The diluted primary antibody was added after the plate was washed 4 times with a washing liquid (PBST). After incubation for 1 hour, the 96-well plate was washed 4 times, and the second antibody was added, then the plate was incubated for 30 minutes. After the plate was washed with a washing liquid, TMB chromogenic solution was added and incubated for 15 minutes. The reaction was stopped by the addition of 1 M H$_2$SO$_4$, then the light absorption at a wavelength of 450 nm was read. The degradation effect of the compound AZD9496 at 3 µM was set to 100%, the Emax of other compounds=(OD$_{negative\ control}$−OD$_{compound\ 3\ \mu M}$)/(OD$_{negative\ control}$−OD$_{AZD9496\ 3\ \mu M}$)×100%, and the negative control was a well with DMSO.

4. Test Result

The EC$_{50}$ values measured for the degradation effect of the compounds of the present invention on ERα are shown in Table 3.

TABLE 3

EC$_{50}$ value of the degradation effect of the compounds of the present invention on ERα, Emax being 100% for positive control AZD-9496

| Example No. | EC$_{50}$ (nM) | Emax (%) |
|---|---|---|
| 1 | 2.72 | 115 |
| 2 | 18.2 | 114 |
| 4 | 0.37 | 136 |
| 7 | 15.9 | 118 |
| 8 | 4.85 | 129 |
| 11 | 19.1 | 134 |
| 14 | 4.61 | 147 |
| 40 | 27.3 | 115 |
| 42 | 7.51 | 112 |
| 46 | 8.5 | 111 |

Conclusion: The compounds of the present invention have a significant degradation effect on ERα, and the Emax (%) value of the degradation effect of the compounds of the present invention on ERα is significantly higher than that of the positive control AZD-9496.

Pharmacokinetics Assay

Test Example 4. Pharmacokinetics Assay of the Compounds of Examples 1, 7, 8, 10, 11, 14, 16, 39 and 42 of the Present Invention 1. Abstract BALB/C nude mice were used as test animals. The drug concentration in plasma at different time points was determined by LC/MS/MS after intragastrical administration of the compounds of Examples 1, 7, 8, 10, 11, 14, 16, 39 and 42 to BALB/C nude mice. The pharmacokinetic behavior of the compounds of the compounds of the present invention was studied and evaluated in BALB/C nude mice.

2. Protocol 2.1 Samples

Compounds of Examples 1, 7, 8, 10, 11, 14, 16, 39 and 42

2.2 Test Animals

Eighty-one (81) female BALB/C nude mice, were equally divided into 9 groups, which were purchased from SINO-BRITSH SIPPR/BK LAB. ANIMAL LTD., CO, with Certificate No.: SOCK (Shanghai) 2008-0016.

2.3 Preparation of the Test Compounds

The appropriate amount of each test compound was weighed, and successively added with 9% PEG400+0.5% tween 80+0.5% PVP+90% aqueous solution of 0.5% CMC.

2.4 Administration

After an overnight fasting, 81 female BALB/C nude mice were equally divided into 9 groups; and administered the test compounds intragastrically at an administration volume of 0.2 mL/10 g.

3. Process 81 female Balb/C nude mice were administered the test compounds intragastrically after an overnight fasting. Blood (0.1 mL) was taken (3 animals at each time point) at 0.5, 1.0, 2.0, 4.0, 6.0, 8.0, 11.0, and 24.0 h after administration. The samples were stored in heparinized test tubes, and centrifuged for 10 minutes at 3,500 rpm to separate the blood plasma. The plasma samples were stored at −20° C.

The concentration of the prototype drug in the plasma and in the solution to be administered was determined by liquid chromatography tandem mass spectrometry (LC/MS MS).

4. Results of Pharmacokinetic Parameters in BALB/C Nude Mice

Pharmacokinetic parameters of the compounds of Examples 1, 7, 8, 10, 11, 14, 16, 39 and 42 of the present invention are shown below.

Conclusion: The compounds of the present invention are well absorbed and have a significant pharmacological absorption effect.

What is claimed is:

1. A compound of formula (I):

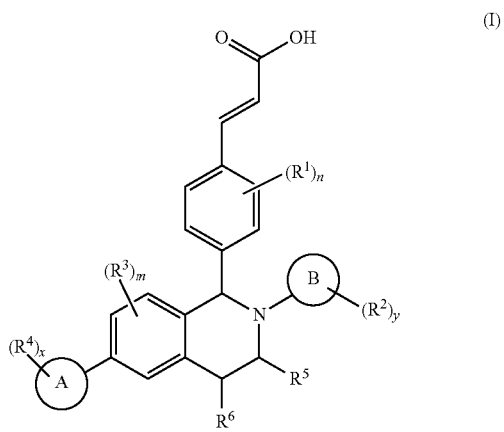

or a tautomer, mesomer, racemate, enantiomer, diastereomer, or mixture thereof, or a pharmaceutically acceptable salt thereof, wherein:

ring A is selected from the group consisting of cycloalkyl, heterocyclyl, aryl and heteroaryl;

ring B is aryl or heteroaryl;

each $R^1$ is identical or different and each is independently selected from the group consisting of hydrogen, alkyl, haloalkyl, hydroxyalkyl, alkoxy, amino, cycloalkyl, halogen, cyano, carboxy, aldehyde, hydroxy, and nitro,

| | Pharmacokinetics Assay (3 mg/kg) | | | | | |
|---|---|---|---|---|---|---|
| Example No. | Plasma Conc. Cmax (ng/mL) | Area Under Curve AUC (ng/mL*hour) | Half-Life $t_{1/2}$ (hour) | Mean Residence Time MRT (hour) | Clearance CL/F (l/hour/kg) | Apparent Distribution Volume Vz/F (l/kg) |
| 1 | 3444 | 14369 | 2.87 | 4.53 | 3.48 | 865 |
| 7 | 1279 | 12886 | 3.67 | 6.80 | 3.88 | 1233 |
| 8 | 1617 | 9378 | 3.27 | 5.26 | 5.33 | 1509 |
| 10 | 1068 | 6281 | 4.61 | 7.08 | 7.96 | 3179 |
| 11 | 1893 | 16352 | 5.58 | 7.90 | 3.06 | 1477 |
| 14 | 2480 | 14754 | 4.29 | 6.73 | 3.39 | 1257 |
| 16 | 1557 | 9122 | 3.01 | 4.87 | 5.48 | 1427 |
| 39 | 1763 | 10165 | 3.6 | 7.02 | 4.92 | 1534 |
| 42 | 1267 | 11211 | 8.04 | 9.21 | 4.46 | 3103 | wherein the alkyl cycloalkyl are each optionally substituted by one or more groups selected from the group consisting of alkyl, halogen, amino, nitro, cyano, hydroxy, hydroxyalkyl, alkoxy, cycloalkyl, heterocyclyl, aryl and heteroaryl;

each $R^2$ is identical or different and each is independently selected from the group consisting of hydrogen, alkyl, haloalkyl, hydroxyalkyl, alkoxy, amino, cycloalkyl, halogen, cyano, carboxy, aldehyde, hydroxy, nitro, aryl and heteroaryl, wherein the alkyl, cycloalkyl, aryl and heteroaryl are each optionally substituted by one or more groups selected from the group consisting of alkyl, halogen, amino, nitro, cyano, hydroxy, hydroxyalkyl, alkoxy, cycloalkyl, heterocyclyl, aryl and heteroaryl;

each $R^3$ is identical or different and each is independently selected from the group consisting of hydrogen, alkyl, haloalkyl, hydroxyalkyl, alkoxy, amino, cycloalkyl, halogen, cyano, carboxy, aldehyde, hydroxy, and nitro wherein the alkyl and cycloalkyl are each optionally substituted by one or more groups selected from the group consisting of alkyl, halogen, amino, nitro, cyano, hydroxy, hydroxyalkyl, alkoxy, cycloalkyl, heterocyclyl, aryl and heteroaryl;

each $R^4$ is identical or different and each is independently selected from the group consisting of hydrogen, alkyl, deuteroalkyl, haloalkyl, hydroxyalkyl, alkoxy, amino, cycloalkyl, halogen, cyano, carboxy, aldehyde, hydroxy, and nitro wherein the alkyl and cycloalkyl are each optionally substituted by one or more groups selected from the group consisting of alkyl, halogen, amino, nitro, cyano, hydroxy, hydroxyalkyl, alkoxy, cycloalkyl, heterocyclyl, aryl and heteroaryl;

$R^5$ is selected from the group consisting of hydrogen, alkyl, cycloalkyl, heterocyclyl, aryl and heteroaryl, wherein the alkyl, cycloalkyl, heterocyclyl, aryl and heteroaryl are each optionally substituted by one or more groups selected from the group consisting of alkyl, halogen, hydroxy, amino, nitro, cyano, alkoxy, hydroxyalkyl, cycloalkyl, heterocyclyl, aryl and heteroaryl;

$R^6$ is selected from the group consisting of hydrogen, alkyl, hydroxy, halogen, cyano, amino, nitro, and alkoxy;

m is 0, 1, 2 or 3;

n is 0, 1, 2, 3 or 4;

x is 0, 1, 2 or 3; and y is 0, 1, 2, 3, 4 or 5.

2. The compound of formula (I) or the tautomer, mesomer, racemate, enantiomer, diastereomer, or mixture thereof, or the pharmaceutically acceptable salt thereof according to claim 1, wherein ring A is heteroaryl.

3. The compound of formula (I) or the tautomer, mesomer, racemate, enantiomer, diastereomer, or mixture thereof, or the pharmaceutically acceptable salt thereof according to claim 1, being a compound of formula (II):

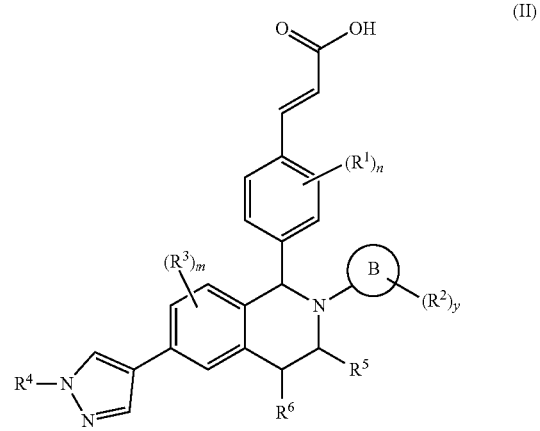

or a tautomer, mesomer, racemate, enantiomer, diastereomer, or mixture thereof, or a pharmaceutically acceptable salt thereof, wherein:

ring B, $R^1$ to $R^6$, m, n and y are as defined in claim 1.

4. The compound of formula (I) or the tautomer, mesomer, racemate, enantiomer, diastereomer, or mixture thereof, or the pharmaceutically acceptable salt thereof according to claim 1, wherein ring B is aryl.

5. The compound of formula (I) or the tautomer, mesomer, racemate, enantiomer, diastereomer, or mixture thereof, or the pharmaceutically acceptable salt thereof according to claim 3, being a compound of formula (III):

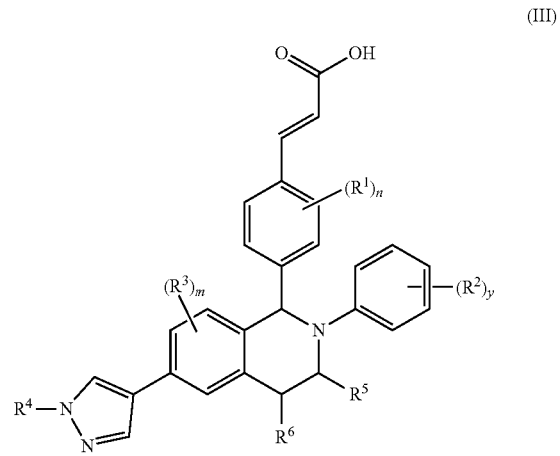

or a tautomer, mesomer, racemate, enantiomer, diastereomer, or mixture thereof, or a pharmaceutically acceptable salt thereof, wherein:

$R^1$ to $R^6$, m, n and y are as defined in claim 3.

6. The compound of formula (III) or the tautomer, mesomer, racemate, enantiomer, diastereomer, or mixture thereof, or the pharmaceutically acceptable salt thereof according to claim 5, being a compound of formula (III-1):

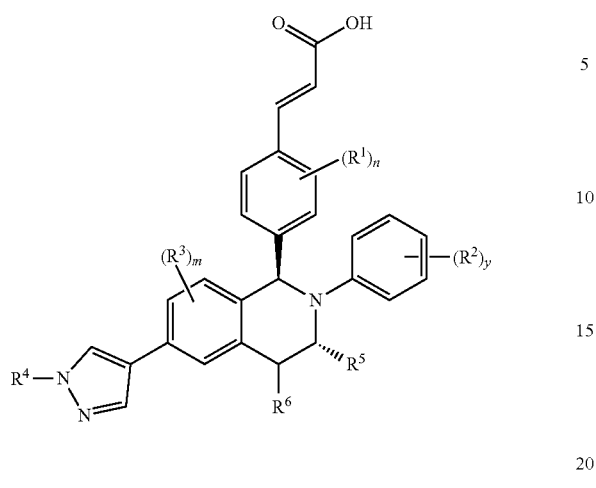

(III-1)

or a tautomer, mesomer, racemate, enantiomer, diastereomer, or mixture thereof, or a pharmaceutically acceptable salt thereof, wherein:

$R^1$ to $R^6$, m, n and y are as defined in claim 5.

7. The compound of formula (I) or the tautomer, mesomer, racemate, enantiomer, diastereomer, or mixture thereof, or the pharmaceutically acceptable salt thereof according to claim 1, wherein $R^1$ is hydrogen or halogen.

8. The compound of formula (I) or the tautomer, mesomer, racemate, enantiomer, diastereomer, or mixture thereof, or the pharmaceutically acceptable salt thereof according to claim 1, wherein $R^2$ is selected from the group consisting of hydrogen, halogen, alkyl, haloalkyl, alkoxy and cycloalkyl, wherein the alkyl is optionally substituted by one or more groups selected from the group consisting of halogen, alkoxy and cycloalkyl.

9. The compound of formula (I) or the tautomer, mesomer, racemate, enantiomer, diastereomer, or mixture thereof, or the pharmaceutically acceptable salt thereof according to claim 1, wherein $R^3$ is hydrogen.

10. The compound of formula (I) or the tautomer, mesomer, racemate, enantiomer, diastereomer, or mixture thereof, or the pharmaceutically acceptable salt thereof according to claim 1, wherein $R^4$ is selected from the group consisting of hydrogen, deuteroalkyl, haloalkyl and alkyl.

11. The compound of formula (I) or the tautomer, mesomer, racemate, enantiomer, diastereomer, or mixture thereof, or the pharmaceutically acceptable salt thereof according to claim 1, wherein $R^5$ is hydrogen or alkyl.

12. The compound of formula (I) or the tautomer, mesomer, racemate, enantiomer, diastereomer, or mixture thereof, or the pharmaceutically acceptable salt thereof according to claim 1, wherein $R^6$ is hydrogen.

13. A compound selected from the group consisting of:

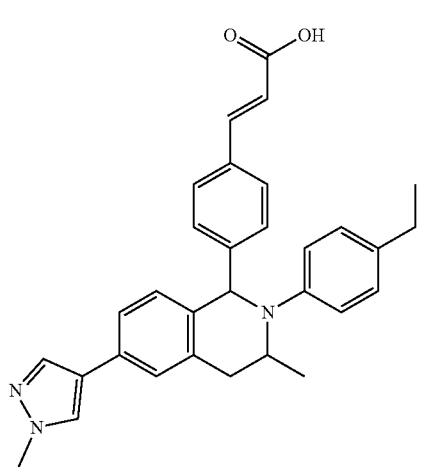

1

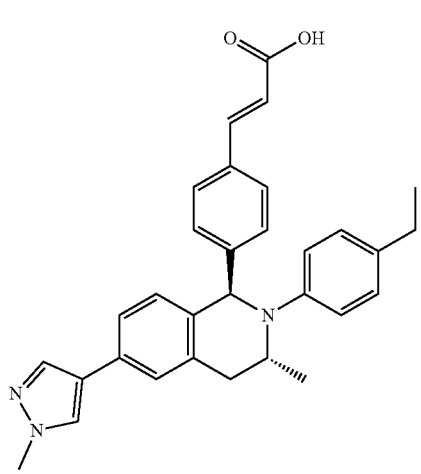

2

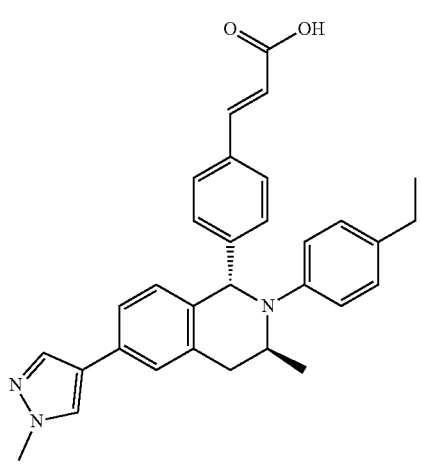

3

179
-continued
4
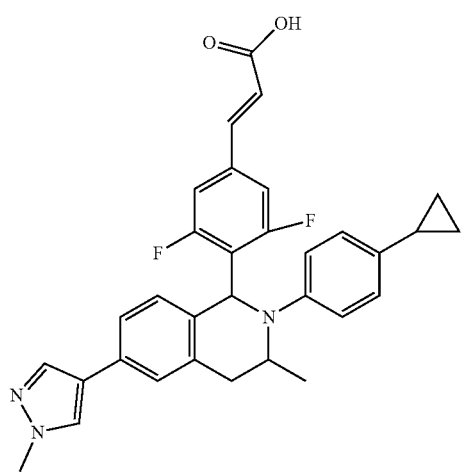
5
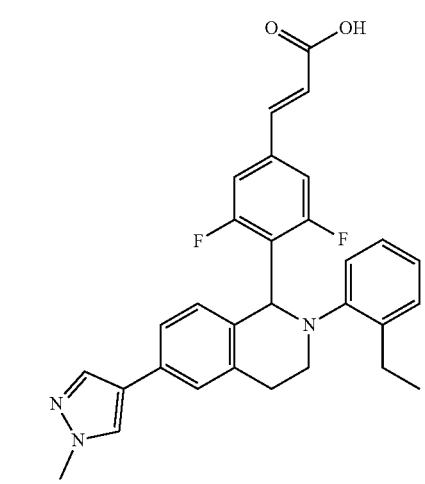
6
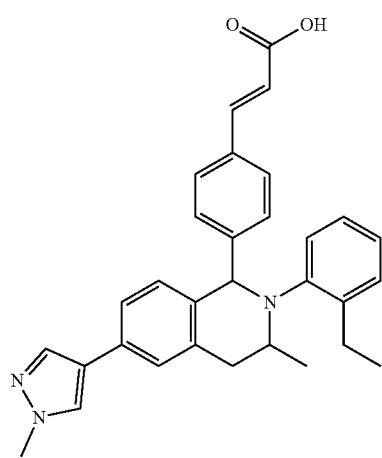
180
-continued
7
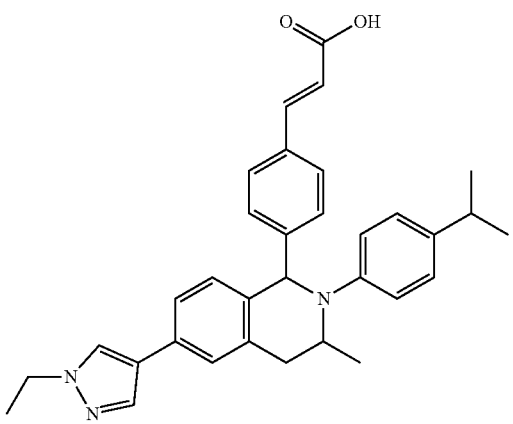
8
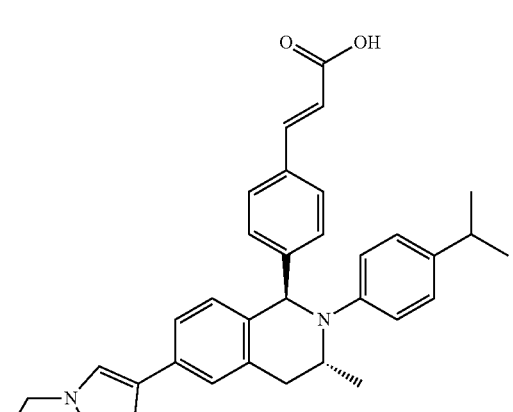
9
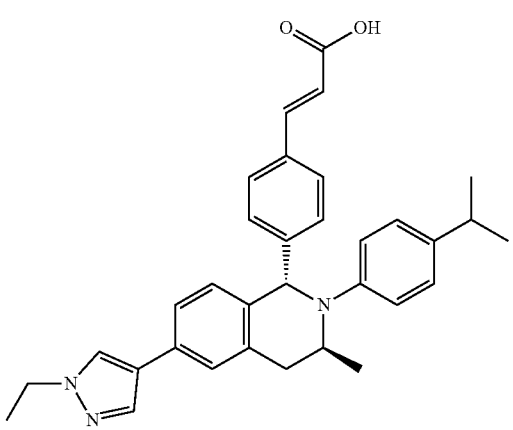

10
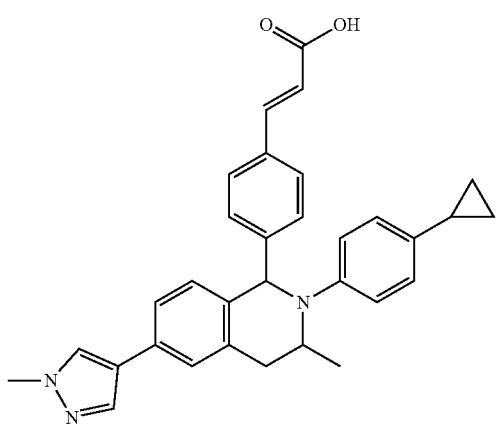
11
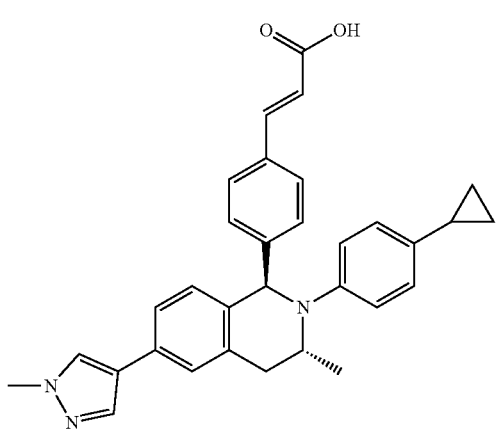
12
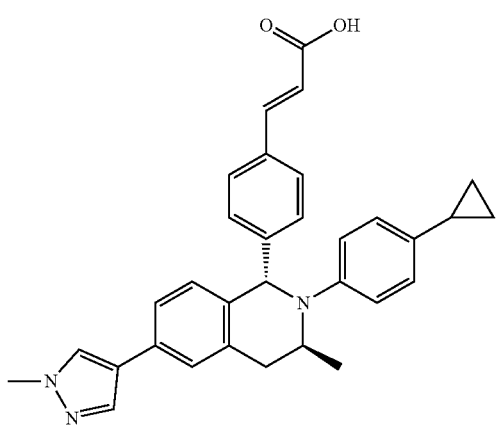
13
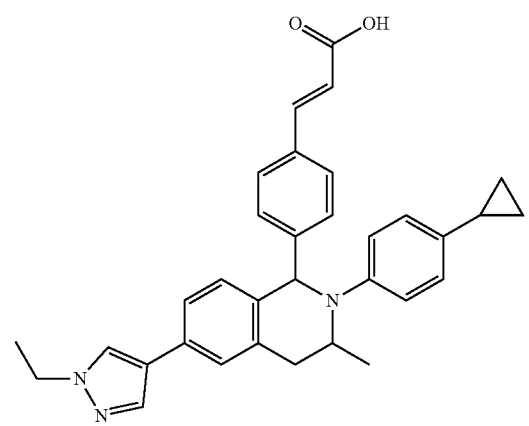
14
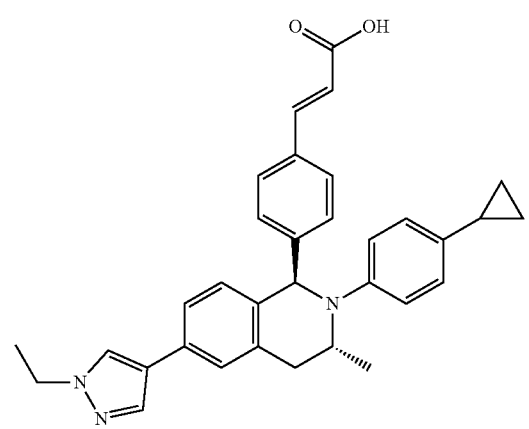
15
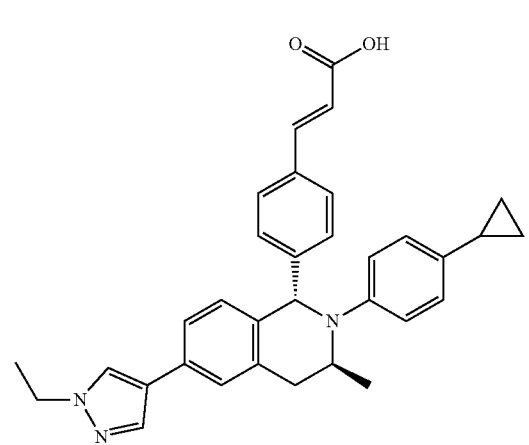

16
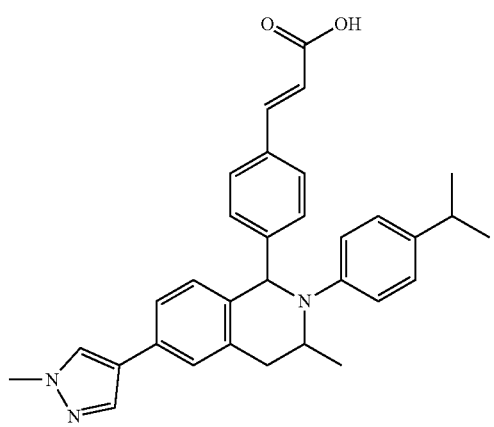
19
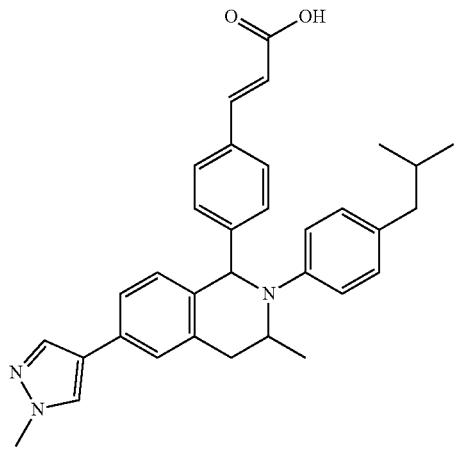
17
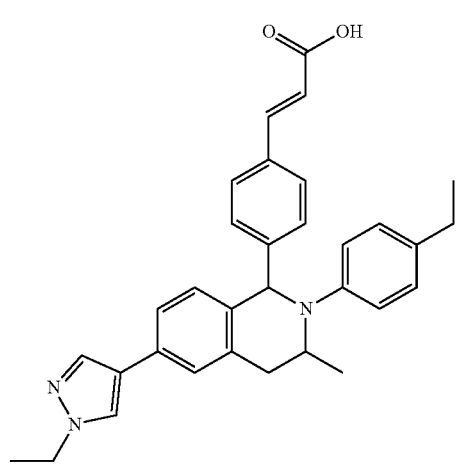
20
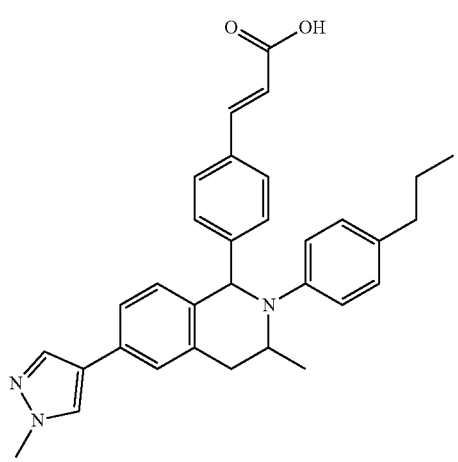
18
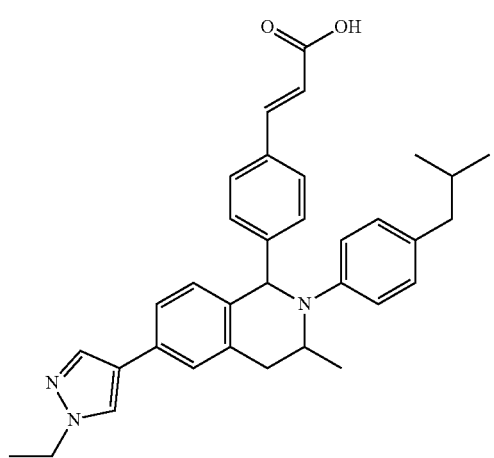
21
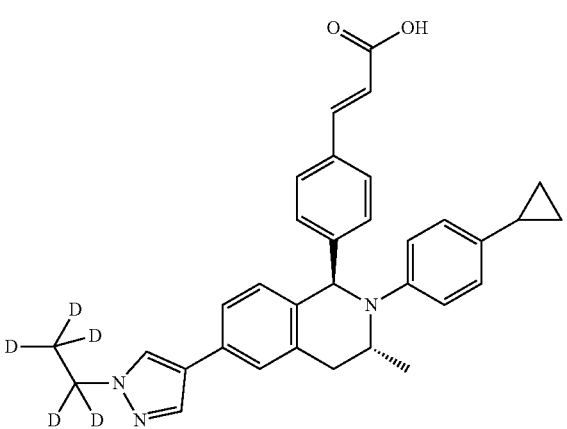

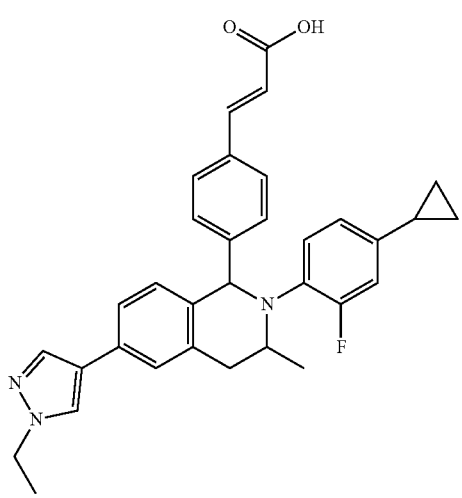
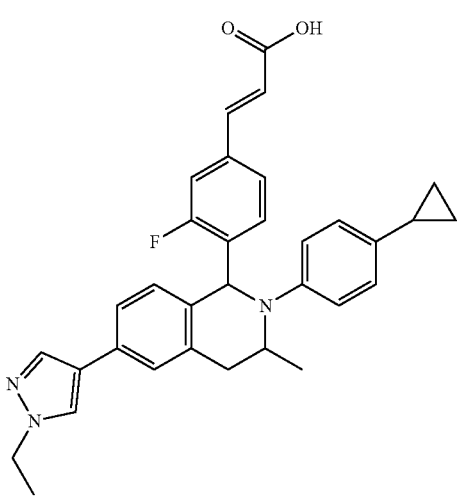

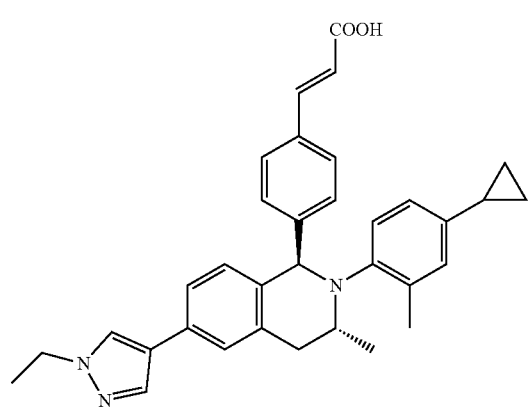
28
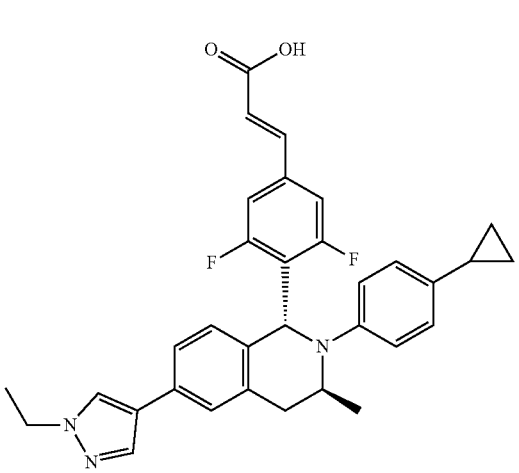
31
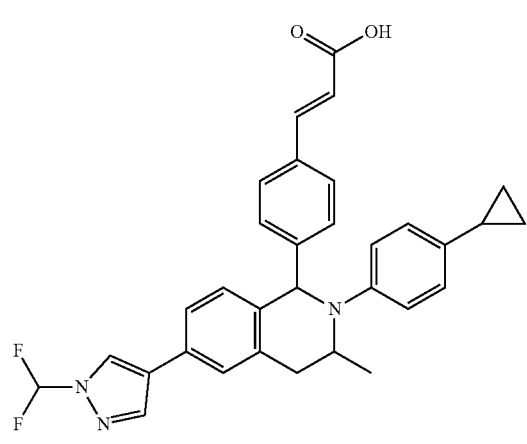
29
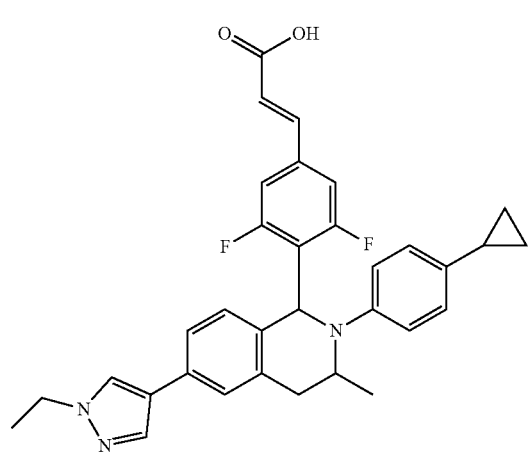
30
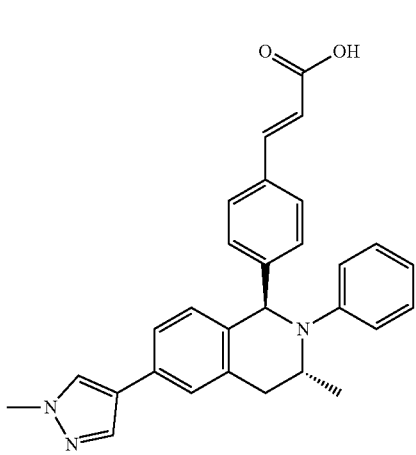
33

34
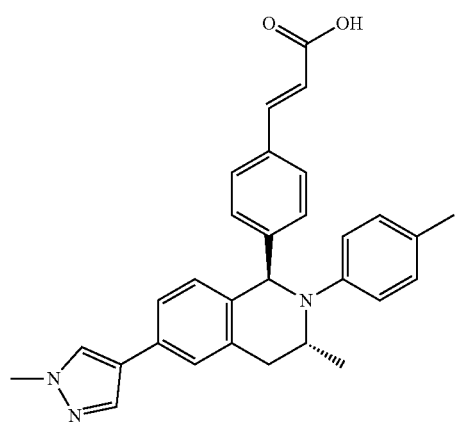
37
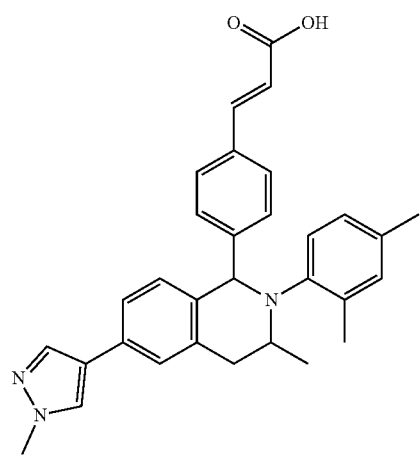
35
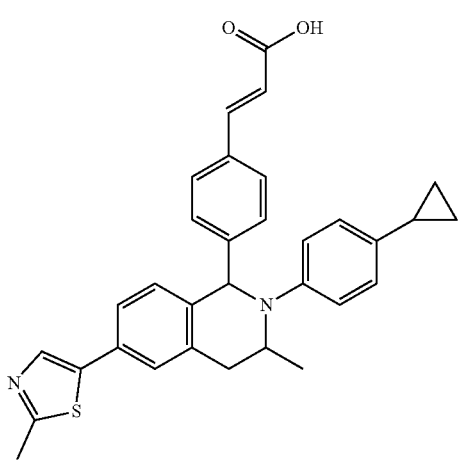
38
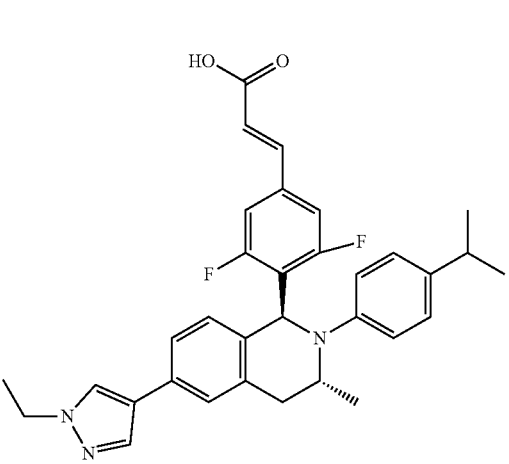
36
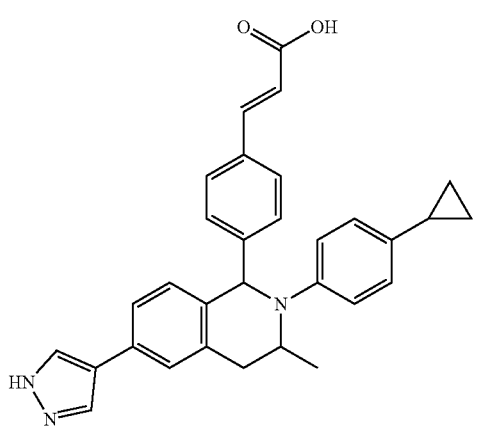
39
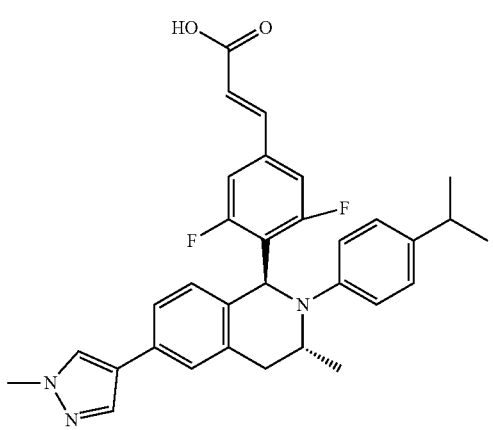

40
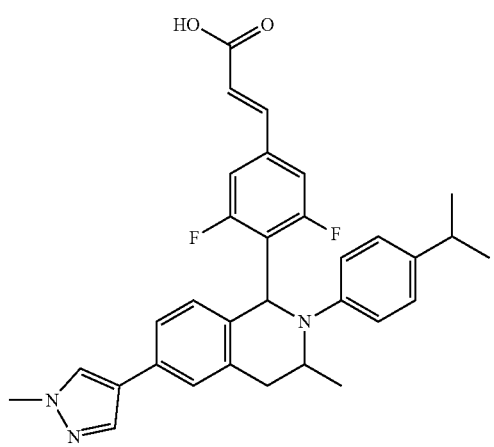
41
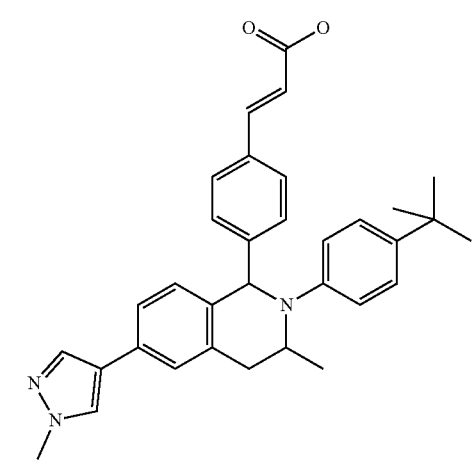
42
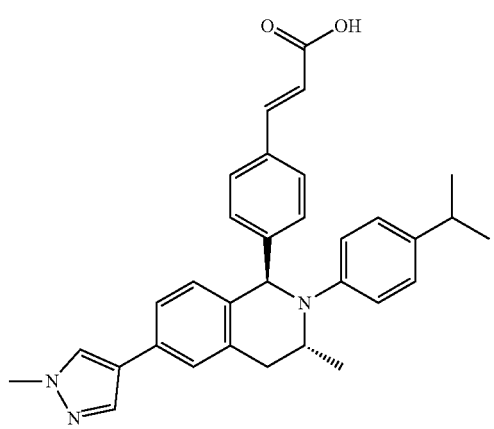
43
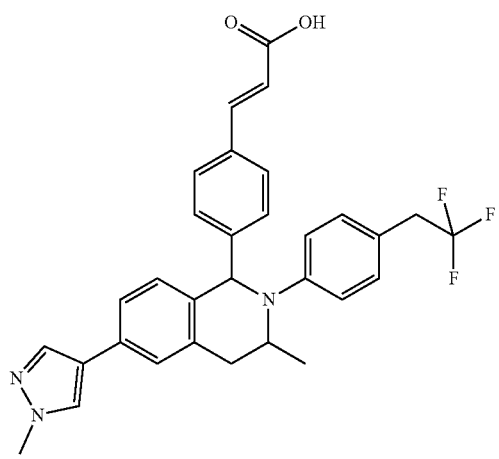
44
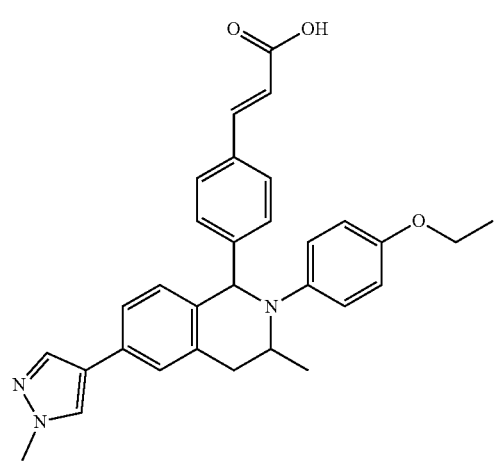
45
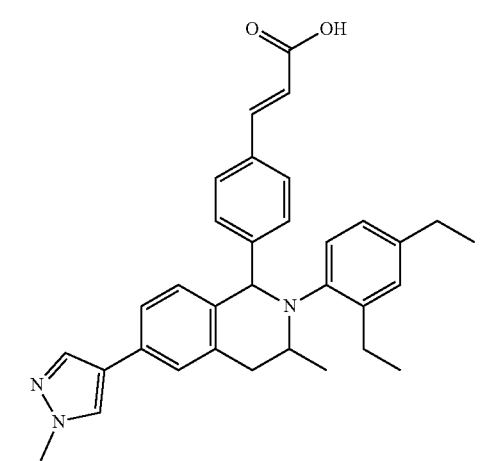

| 193 | 194 |
|---|---|
| -continued | -continued |
| 46 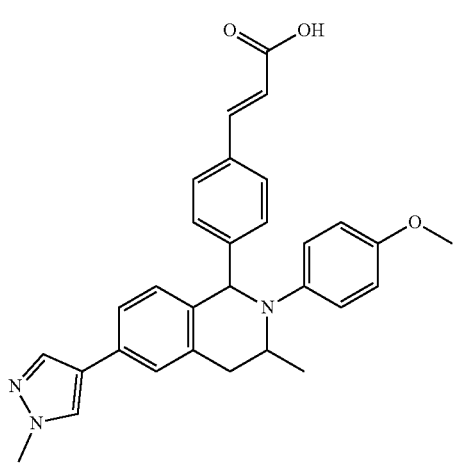 | 49 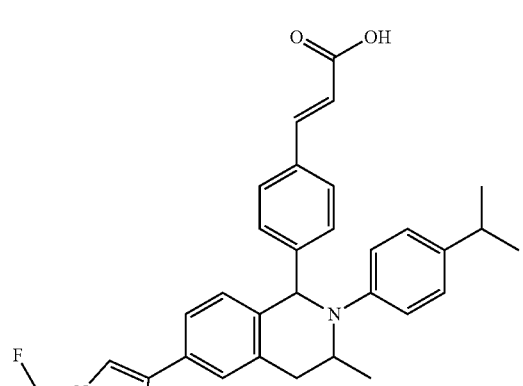 |
| 47 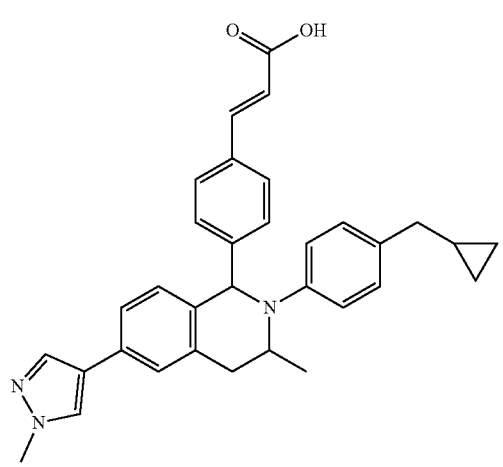 | 50 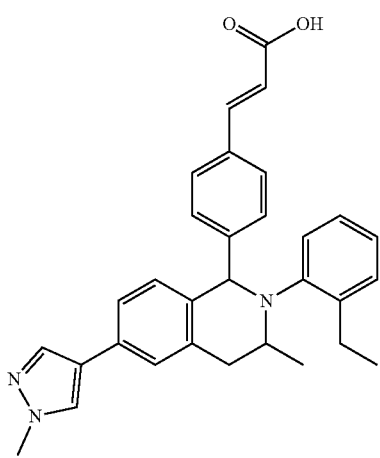 |
| 48 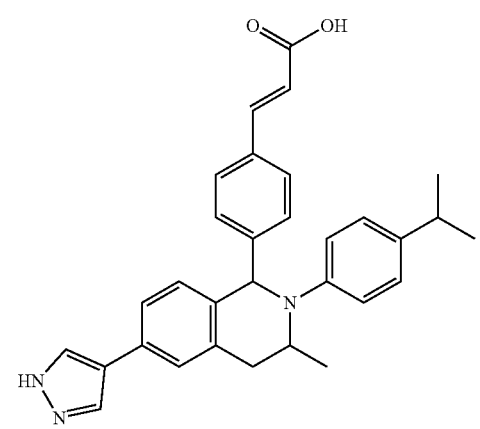 | 51 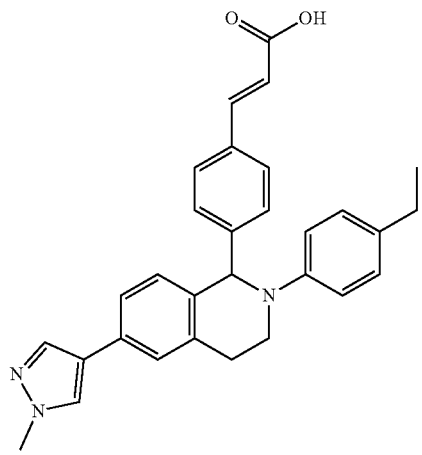 |

-continued

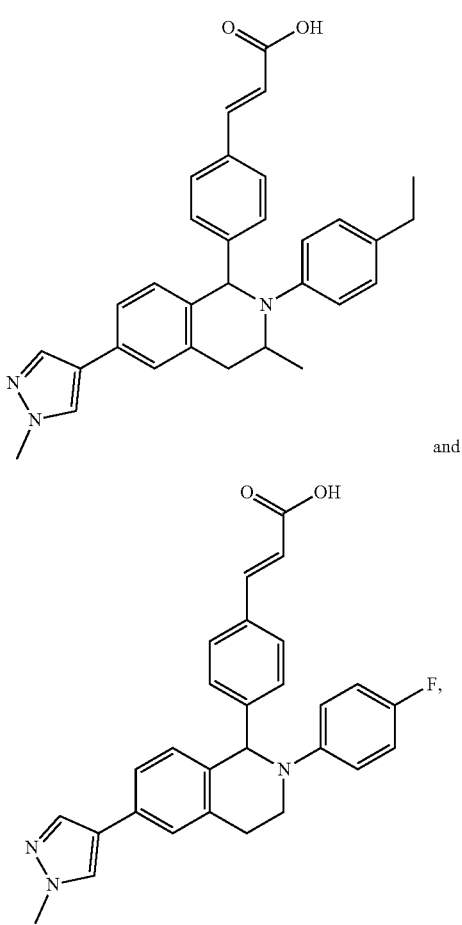

or a tautomer, mesomer, racemate, enantiomer, diastereomer, or mixture thereof, or a pharmaceutically acceptable salt thereof.

14. A compound of formula (IV):

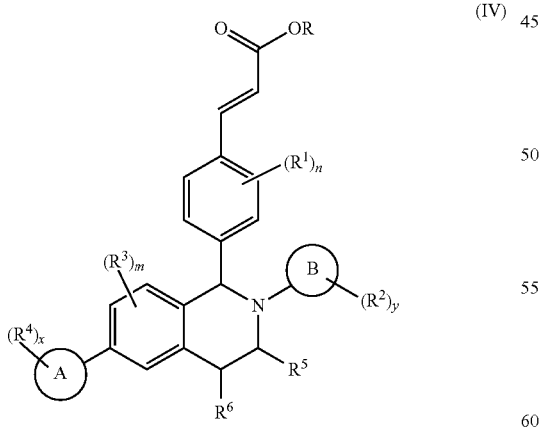

(IV)

or a tautomer, mesomer, racemate, enantiomer, diastereomer, or mixture thereof, or a pharmaceutically acceptable salt thereof,
wherein:
R is alkyl or cycloalkyl, wherein the alkyl and cycloalkyl are each optionally substituted by one or more groups selected from the group consisting of alkyl, halogen, amino, cyano, hydroxy, alkoxy, carboxy and cycloalkyl; and ring A is selected from the group consisting of cycloalkyl, heterocyclyl, aryl and heteroaryl;

ring B is aryl or heteroaryl;

each $R^1$ is identical or different and each is independently selected from the group consisting of hydrogen, alkyl, haloalkyl, hydroxyalkyl, alkoxy, amino, cycloalkyl, halogen, cyano, carboxy, aldehyde, hydroxy, and nitro, wherein the alkyl and cycloalkyl are each optionally substituted by one or more groups selected from the group consisting of alkyl, halogen, amino, nitro, cyano, hydroxy, hydroxyalkyl, alkoxy, cycloalkyl, heterocyclyl, aryl and heteroaryl;

each $R^2$ is identical or different and each is independently selected from the group consisting of hydrogen, alkyl, haloalkyl, hydroxyalkyl, alkoxy, amino, cycloalkyl, halogen, cyano, carboxy, aldehyde, hydroxy, nitro, aryl and heteroaryl, wherein the alkyl, cycloalkyl, aryl and heteroaryl are each optionally substituted by one or more groups selected from the group consisting of alkyl, halogen, amino, nitro, cyano, hydroxy, hydroxyalkyl, alkoxy, cycloalkyl, heterocyclyl, aryl and heteroaryl;

each $R^3$ is identical or different and each is independently selected from the group consisting of hydrogen, alkyl, haloalkyl, hydroxyalkyl, alkoxy, amino, cycloalkyl, halogen, cyano, carboxy, aldehyde, hydroxy, and nitro, wherein the alkyl and cycloalkyl are each optionally substituted by one or more groups selected from the group consisting of alkyl, halogen, amino, nitro, cyano, hydroxy, hydroxyalkyl, alkoxy, cycloalkyl, heterocyclyl, aryl and heteroaryl;

each $R^4$ is identical or different and each is independently selected from the group consisting of hydrogen, alkyl, deuteroalkyl, haloalkyl, hydroxyalkyl, alkoxy, amino, cycloalkyl, halogen, cyano, carboxy, aldehyde, hydroxy, and nitro, wherein the alkyl and cycloalkyl are each optionally substituted by one or more groups selected from the group consisting of alkyl, halogen, amino, nitro, cyano, hydroxy, hydroxyalkyl, alkoxy, cycloalkyl, heterocyclyl, aryl and heteroaryl;

$R^5$ is selected from the group consisting of hydrogen, alkyl, cycloalkyl, heterocyclyl, aryl and heteroaryl, wherein the alkyl, cycloalkyl, heterocyclyl, aryl and heteroaryl are each optionally substituted by one or more groups selected from the group consisting of alkyl, halogen, hydroxy, amino, nitro, cyano, alkoxy, hydroxyalkyl, cycloalkyl, heterocyclyl, aryl and heteroaryl;

$R^6$ is selected from the group consisting of hydrogen, alkyl, hydroxy, halogen, cyano, amino, nitro, and alkoxy;

n is 0, 1, 2, 3 or 4;

x is 0, 1, 2 or 3; and y is 0, 1, 2, 3, 4 or 5.

15. A process for preparing a compound of formula (I) or a tautomer, mesomer, racemate, enantiomer, diastereomer, or mixture thereof, or a pharmaceutically acceptable salt thereof according to claim 1, comprising:

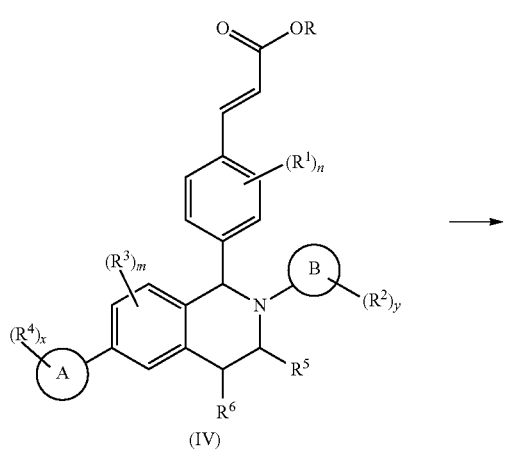

(IV)

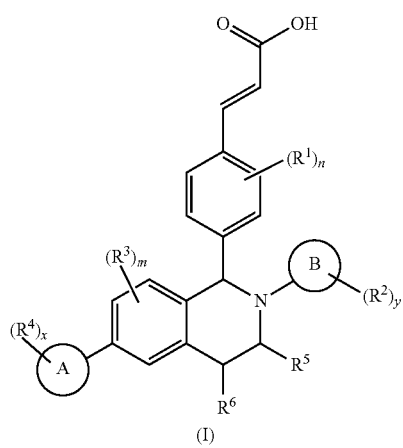

(I)

hydrolyzing a compound of formula (IV) under an alkaline condition to obtain the compound of formula (I);
wherein:
R is alkyl or cycloalkyl, wherein the alkyl and cycloalkyl are each optionally substituted by one or more groups selected from the group consisting of alkyl, halogen, amino, cyano, hydroxy, alkoxy, carboxy and cycloalkyl; and
ring A, ring B, $R^1$ to $R^6$, m, n, x and y are as defined in claim 1.

16. A pharmaceutical composition comprising a therapeutically effective amount of the compound of formula (I) or the tautomer, mesomer, racemate, enantiomer, diastereomer, or mixture thereof, or the pharmaceutically acceptable salt thereof according to claim 1, and one or more pharmaceutically acceptable carriers, diluents or excipients.

17. A method for treating bone cancer, breast cancer, colorectal cancer, endometrial cancer, prostate cancer, ovarian cancer, uterine cancer, cervical cancer, lung cancer, leiomyomata, uterine leiomyomas, alcoholism, migraine, aortic aneurysm, susceptibility to myocardial infarction, aortic valve sclerosis, cardiovascular disease, coronary artery disease, hypertension, deep vein thrombosis, Grave's disease, arthritis, multiple sclerosis, cirrhosis, hepatitis B, chronic liver disease, cholestasis, hypospadias, obesity, osteoarthritis, osteopenia, osteoporosis, Alzheimer's disease, Parkinson's disease, migraine, dizziness, anorexia nervosa, attention deficit hyperactivity disorder (ADHD), dementia, severe depressive disorder, psychosis, endometriosis or infertility in mammals, comprising administering to a patient in need thereof the pharmaceutical composition according to claim 16.

18. A method for treating an estrogen receptor mediated or dependent disease or condition, comprising administering to a patient in need thereof the pharmaceutical composition according to claim 16, wherein the estrogen receptor mediated or dependent disease or condition is selected from the group consisting of cancer, central nervous system diseases, cardiovascular system diseases, hematological system diseases, immune and inflammation diseases, susceptibility to infection, metabolic diseases, neurological diseases, psychiatric diseases and reproductive diseases.

19. The method according to claim 18, wherein the cancer is selected from the group consisting of breast cancer, endometrial cancer, uterine cancer, cervical cancer, skin cancer, prostate cancer, ovarian cancer, fallopian tube tumor, ovarioncus, hemophilia and leukemia; preferably breast cancer, ovarian cancer, endometrial cancer, prostate cancer or uterine cancer.

20. The method according to claim 19, wherein the cancer is breast cancer.

21. A method of modulating an estrogen receptor in a patient in need thereof, the method comprising administering to the patient the pharmaceutical composition of claim 16.

22. The compound according to claim 13, wherein the compound is

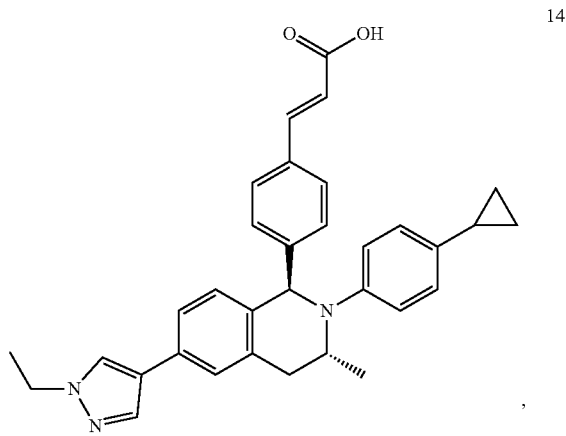 [SMILES: CCn1cc(-c2ccc3c(c2)C[C@@H](C)N(c2ccc(C4CC4)cc2)[C@@H]3c2ccc(/C=C/C(=O)O)cc2)cn1]

14 or a pharmaceutically acceptable salt thereof.

23. The compound according to claim 13, wherein the compound is
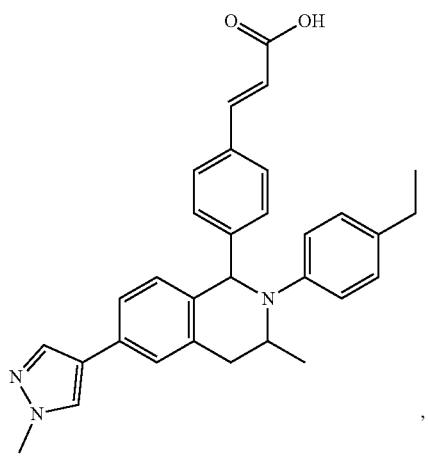
,
or a pharmaceutically acceptable salt thereof.
24. The compound according to claim 13, wherein the compound is
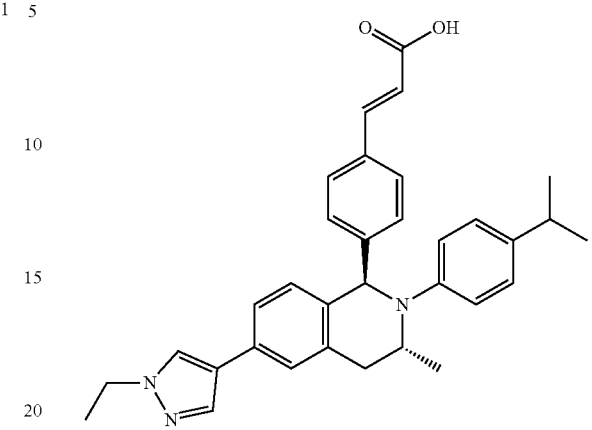
,
or a pharmaceutically acceptable salt thereof.
* * * * *